United States Patent
Burkholder et al.

(10) Patent No.: US 6,329,392 B1
(45) Date of Patent: Dec. 11, 2001

(54) SUBSTITUTED PIPERIDINES USEFUL FOR THE TREATMENT OF ALLERGIC DISEASES

(75) Inventors: Timothy P. Burkholder, Carmel, IN (US); Larry D. Bratton, Whitmore Lake, MI (US); Elizabeth M. Kudlacz, Groton; George P. Maynard, Westbrook, both of CT (US); John M. Kane, Cincinnati, OH (US); Braulio Santiago, San Juan, PR (US)

(73) Assignee: Aventis Pharmaceuticals, Inc., Bridgewater, NJ (US)

( * ) Notice: Subject to any disclaimer, the term of this patent is extended or adjusted under 35 U.S.C. 154(b) by 32 days.

(21) Appl. No.: 09/079,924

(22) Filed: May 15, 1998

Related U.S. Application Data

(63) Continuation-in-part of application No. 08/501,914, filed on Jul. 13, 1995, now abandoned, which is a continuation-in-part of application No. 08/295,960, filed on Aug. 25, 1994, now abandoned.

(51) Int. Cl.$^7$ .................................................. A61K 31/445
(52) U.S. Cl. .......................... 514/322; 514/321; 514/326; 546/198; 546/199; 546/208
(58) Field of Search .................................... 546/198, 199, 546/208; 514/321, 322, 326

(56) References Cited

U.S. PATENT DOCUMENTS

| | | | |
|---|---|---|---|
| 3,282,947 | 11/1966 | Grogan | 514/255 |
| 3,862,173 | 1/1975 | Carr | 546/213 |
| 4,254,129 | 3/1981 | Carr | 546/237 |
| 4,254,130 | 3/1981 | Carr | 546/238 |
| 4,285,958 | 8/1981 | Carr | 546/237 |
| 4,550,116 | 10/1985 | Soto | 514/327 |
| 4,598,079 | 7/1986 | Beyerle | 514/252 |
| 4,666,905 | 5/1987 | Downs | 514/222 |
| 4,908,372 | 3/1990 | Carr | 514/322 |
| 5,166,136 | 11/1992 | Ward | 514/15 |
| 5,212,187 | 5/1993 | Alisch | 514/342 |
| 5,236,921 | 8/1993 | Edmonds-Alt | 514/255 |
| 5,317,020 | 5/1994 | Emonds-Alt | 514/255 |
| 5,322,850 | 6/1994 | Orjales-Venero | 514/322 |

FOREIGN PATENT DOCUMENTS

| | | |
|---|---|---|
| 1591692 | 5/1991 | (AU). |
| 2601262 | 7/1976 | (DE). |
| 0428434 | 11/1990 | (EP). |
| 0512902 | 5/1991 | (EP). |
| 0474561 | 9/1991 | (EP). |
| 0482539 | 10/1991 | (EP). |
| 0512901 | 4/1992 | (EP). |
| 053344 | 8/1992 | (EP). |
| 0559538 | 3/1993 | (EP). |
| 517589 | 6/1991 | (FR). |
| 4297492 | 2/1991 | (JP). |
| 9206086 | 10/1990 | (WO). |
| 9222569 | 6/1991 | (WO). |
| 9314113 | 1/1992 | (WO). |
| 9300330 | 1/1993 | (WO). |
| 9426735 | 11/1994 | (WO). |

OTHER PUBLICATIONS

Barnes, et al., TIPS 11:185–189 (May 1990).

Ichinose, et al., The Lancet 340:1248–1251 (Nov. 21, 1992).

Hagiwara, et al., Studies on Neurokinin Antagonists 2., Journal of Medicinal Chemistry, vol. 35, No. 17, 3184–3191, 1992.

Hagiwara, et al., Studies on Nerokinin Antagonists 1., J. Med. Chem, 35, 2015–2025, 1992.

Van Parys, et al., Bull. Soc. Chim. Beig. 90(7):757–65 (1981).

Kametani, et al., Chemical Abstracts 72:55212n (1970).

Clark, et al., J. Med. Chem. 26(6):855–861 (1983).

Somers, et al., J. Med. Chem. 7:784–89 (1964).

Van Parys, et al. Bull Soc. Chim Beig 90(7):749–55 (1981).

Kametani, e tal., Yakugaku Zasshi 89(11)1482–7 (1969).

Borch, J. American Chemical So., 99:5, (1977).

Maynard, Biorganic and Medicinal Chemistry Letters, vol. 3 (4), 753–756, 1993.

Wahlgren, J. Heterocyclic Chem., 26, 541–543, 1989.

Iemura, Chem. Pharm. Bull. 37(4), 967–972, 1989.

Iemura, J. Heterocyclic Che., 24, 31–37, 1987.

Daijiro Hagiwara et al., Design of a Novel Dipeptide Substance P Antagonist FK888 and Its Pharmacological Profile, Fujisawa Pharmacetucial Co., Ltd. (1995).

(List continued on next page.)

*Primary Examiner*—Ceila Chang

(57) ABSTRACT

The present invention relates to novel substituted piperidine derivatives of the formula

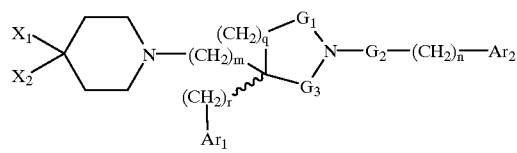

stereoisomers thereof, and pharmaceutically acceptable salts thereof which are useful as histamine receptor antagonists and tachykinin receptor antagonist. Such antagonists are useful in the treatment of allergic diseases including: seasonal rhinitis, allergic rhinitis, and sinusitis.

77 Claims, No Drawings

OTHER PUBLICATIONS

T. Yamashita, et al., Preparations and enantioface–differen-tiating abilities of 27–and 36–membered ring peptides containing N,N–ethylene–bridged dipeptides and glycine, Makromol, Chem. 191, 1261–1268 (1990).

J. DiMaio, et al., Synthesis of Chiral Piperazin–2–ones as Model Peptidomimetics, J. Chem. Soc. Perkin Trans, 1989.

CA 107(23)::217900f, Takase, et al., Tetrahedron, 42(21), 5887–5894, 1986.

CA 103(3):22829z, Takase, et al, Tetrahedron Lett., 26(7), 847–850, (1982).

Schilling, et al., C. 2., Approaches towards the Design and Synthesis of Nonpeptidic Substance–P Antagonis Ciba Geigy Ltd. (15) 207–220 (1993).

Logan, et al., Recent Advances in Neurokinin Receptor Antagonists, Annual Reports in Medicinal Chemistry (26) 43–51. (1983).

Hagiwara, et al., The Discovery of a Tripeptide Substance P Antagonist and its Structure–Activity Relations J. Pharmacobio–Dyn. 14, 5–104 (1991).

Roubini, et al., 1,4–Piperazine–derived, partially nonpeptidic analogs of Substance P, Hebrew University of Jerusalem, 161–162. (1991).

Chorev, et al., Toward Nonpeptidal Substance P Mimetic Analogues; Design, Synthesis, and Biological Activity, Hebrew University of Jerusalem, 725–732. (1991).

Hagiwara, et al., Studies on Neurokinin Antagonists 3., J. Med. Chem, 36, 2266–2278, 1993.

Edmonds–Alt, et al., Life Sciences, 56(1):27–32, (1995).

Melloni, et al., Eur. J. Med. Chem., 26, 207–213 (1991).

Burger et al, "A guide to the chemical basis of drug design" Wiley Intersci. Pubs. p. 15 (1983).

Bundgaard "Design of prodrugs" Elsevier, p. 29 (1985).

Jannsens, et al., J. Med. Chem. 28:1934–1943, (1985).

Janssens, et al., Drug Development Research 8:27–36, (1986).

Janssens, et al., J. Med. Chem., 28(12): 1925–1933, (1985).

Iemura, et al., Chem. Pharm. Bull., 37(4):967–972, (1989).

Janssens, et al., J. Med. Chem., 28(12):1943–1947, (1985).

Carr et al., The J. Organic Chem., 55(4): 1399–1401, (1990).

Iemura, et al., Chem. Pharm. Bull.,37(4):962–966, (1989).

Iemura, et al., J. Med. Chem., 29(7): 1178–1183, (1986).

SUBSTITUTED PIPERIDINES USEFUL FOR THE TREATMENT OF ALLERGIC DISEASES

This application is a continuation-in-part of application Ser. No. 08/501,914, filed Jul. 13, 1995, now abandoned, which is hereby incorporated by reference, which is a continuation-in-part of application Ser. No. 08/295,960, filed Aug. 25, 1994, now abandoned, which is hereby incorporated by reference.

The present invention relates to novel substituted piperidine derivatives (herein referred to as a compound or compounds of formula (1)) and their use as histamine receptor antagonists and tachykinin receptor antagonists. Such antagonists are useful in the treatment of allergic diseases disclosed herein including: seasonal rhinitis, allergic rhinitis, and sinusitis.

The compounds of the present invention are useful in their pharmacological activities, such as histamine receptor antagonism and tachykinin receptor antagonism. Antagonism of histamine responses can be elicited through blocking of histamine receptors. Antagonism of tachykinin responses can be elicited through blocking of tachykinin receptors. One object of the present invention is to provide new and useful antagonists of histamine. A further object of the present invention is to provide new and useful antagonists of tachykinins. A particular object of the present invention are those compounds that exhibit both $H_1$ and $NK_1$ receptor antagonism.

SUMMARY OF THE INVENTION

The present invention provides novel substituted piperidine derivatives of the formula:

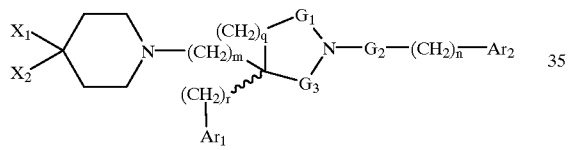

wherein
$G_1$ is —$CH_2$— or —$C(O)$—;
$G_2$ is —$CH_2$— or —$C(O)$—;
$G_3$ is —$CH_2$— or —$C(O)$—;
m is 2 or 3;
n is 0 or 1;
q is 1 or 2;
r is 0 or 1;
$Ar_1$ is a radical chosen from the group consisting of

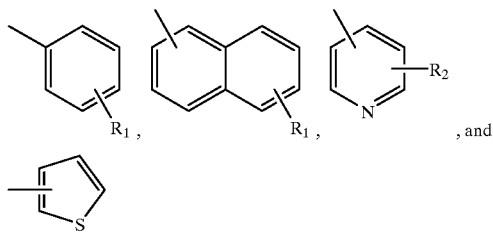

wherein
$R_1$ is from 1 to 3 substituents each independently chosen from the group consisting of hydrogen, halogen, hydroxy, $CF_3$, $C_1$–$C_6$ alkyl, and $C_1$–$C_6$ alkoxy;
$R_2$ is from 1 to 2 substituents each independently chosen from the group consisting of hydrogen, halogen, $C_1$–$C_6$ alkyl, and $C_1$–$C_6$ alkoxy;

$Ar_2$ is a radical chosen from the group consisting of

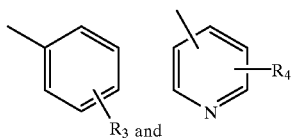

wherein $R_3$ is from 1 to 3 substituents each independently chosen from the group consisting of hydrogen, halogen, $C_3$–$C_6$ alkyl, $C_1$–$C_6$ alkoxy, and —$OCH_2CO_2R_2$ wherein R is chosen from the group consisting of hydrogen and $C_1$–$C_4$ alkyl;
$R_4$ is from 1 to 2 substituents each independently chosen from the group consisting of hydrogen, halogen, $C_1$–$C_6$ alkyl, and $C_1$–$C_6$ alkoxy; and
$X_1$ and $X_2$ are as defined in one of parts A), B), or C):
A) $X_1$ is hydrogen;
$X_2$ is a radical chosen from the group consisting of

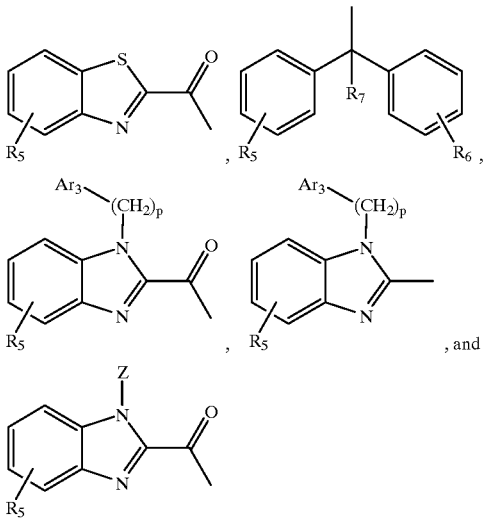

wherein p is 1 or 2

$R_5$ is from 1 to 3 substituents each independently chosen from the group consisting of hydrogen, halogen, $CF_3$, $C_1$–$C_6$ alkyl, and $C_1$–$C_6$ alkoxy;

$R_6$ is from 1 to 3 substituents each independently chosen from the group consisting of hydrogen, halogen, $CF_3$, $C_1$–$C_6$ alkyl, and $C_1$–$C_6$ alkoxy, $R_7$ is hydrogen or hydroxy;

$Ar_3$ is a radical chosen from the group consisting of

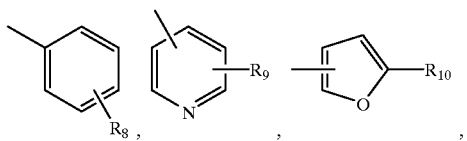

-continued

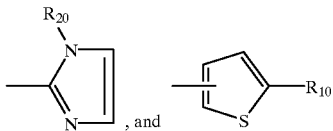
, and wherein $R_8$ is from 1 to 3 substituents each independently chosen from the group consisting of hydrogen, halogen, $CF_3$, $C_1-C_6$ alkyl, $C_1-C_6$ alkoxy, and $-CO_2R_{19}$ wherein $R_{19}$ is chosen from the group consisting of hydrogen and $C_1-C_4$ alkyl;

$R_9$ is from 1 to 2 substituents each independently chosen from the group consisting of hydrogen, halogen, $C_1-C_6$ alkyl, and $C_1-C_6$ alkoxy;

$R_{10}$ is chosen from the group consisting of hydrogen, $-CH_3$, and $-CH_2OH$;

$R_{20}$ is chosen from the group consisting of hydrogen, $C_1-C_4$ alkyl, and benzyl;

Z is chosen from the group consisting of hydrogen, $C_1-C_4$ alkyl, $-(CH_2)_w-O-(CH_2)_t-Y$, $-(CH_2)_fA$, $-(CH_2)_u CO_2R_{11}$, $-(CH_2)_uC(O)NR_{12}R_{13}$, $-(CH_2)_gC(O)(CH_2)_h CH_3$, $-(CH_2)_w-O-Ar_4$, and $-CH_2OCH_2CH_2Si(CH_3)_3$
wherein w is an integer from 2 to 5;

t is an integer from 1 to 3;

f is 2 or 3;

u is an integer from 1 to 4;

g is an integer from 1 to 3;

h is an integer from 0 to 3;

w is an integer from 2 to 4;

Y is chosen from the group consisting of hydrogen, $-CH=OH_2$, $-CH=C(CH_3)_2$ and $-CO_2R_{14}$ wherein $R_{14}$ is chosen from the group consisting of hydrogen and $C_1-C_4$ alkyl;

A is chosen from the group consisting of $-NR_{17}R_{18}$, acetylamino, and morpholino wherein $R_{17}$ is chosen from the group consisting of hydrogen and $C_1-C_4$ alkyl and $R_{18}$ is $C_1-C_4$ alkyl;

$R_{11}$ is chosen from the group consisting of hydrogen and $C_1-C_4$ alkyl;

$R_{12}$ is chosen from the group consisting of hydrogen, $C_1-C_4$ alkyl, and benzyl;

$R_{13}$ is chosen from the group consisting of hydrogen and $C_1-C_4$ alkyl;

$Ar_4$ is a radical chosen from the group consisting of

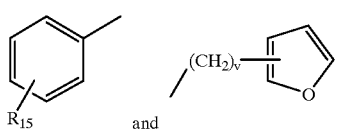
and wherein v is an integer from 1 to 3;

$R_{15}$ is chosen from the group consisting of hydrogen and $-CO_2R_{16}$ wherein $R_{16}$ is chosen from the group consisting of hydrogen and $C_1-C_4$ alkyl;

B) $X_1$ is hydroxy; and $X_2$ is a radical chosen from the group consisting of

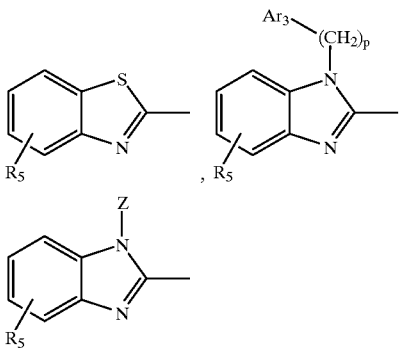

wherein p, $R_5$, Z, and $Ar_3$ are as previously defined;

C) $X_2$ is a radical of the formula;

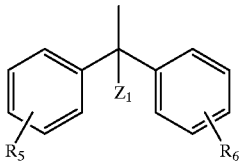

wherein $R_5$ and $R_6$ are as previously defined; and $X_1$ and $Z_1$ taken together form a second bond between the carbon atoms bearing $X_1$ and $Z_1$;

provided that when $G_1$ is $-C(O)-$ then $G_2$ and $G_3$ are $-CH_2-$;

further provided that when $G_2$ is $-C(O)-$ then $G_1$ and $G_3$ are $-CH_2-$;

still further provided that when $G_3$ is $-C(O)-$ then $G_1$ and $G_2$ are $-CH_2-$;

or stereoisomers, or pharmaceutically acceptable salt thereof.

As is appreciated by one of ordinary skill in the art the compounds of the formula (1) may exist as stereoisomers depending on the nature of the substituents present. Any reference in this application to one of the compounds of the formula (1) is meant to encompass either specific stereoisomers or a mixture of stereoisomers. Where indicated, the compounds follow the designation of (+)- and (−)- for the stereochemistry of compounds represented by formula (1). It is specifically recognized that in the substituted 3-aryl-3-[(piperidin-1-yl)-alkyl]-pyrrolidines and substituted 3-arylmethyl-3-[(piperidin-1-yl)-alkyl]-pyrrolidines, and substituted 3-aryl-3-[(piperidin-1-yl)-alkyl]-piperidines and substituted 3-arylmethyl-3-[(piperidin-1-yl)-alkyl]-piperidines; the 3-position of the pyrrolidine or piperidine is asymmetric, and may be in the (+)- or (−)- configuration, or may be a mixture thereof.

The specific stereoisomers can be prepared by stereospecific synthesis using enantiomerically pure or enantiomerically enriched starting materials. The specific stereoisomers can also be resolved and recovered by techniques known in the art, such as chromatography on chiral stationary phases, enzymatic resolution, or fractional recrystallization of addition salts formed by reagents used for that purpose, as described in "Enantiomers, Racemates, and Resolutions", J. Jacques, A. Collet, and S. H. Wilen, Wiley (1981).

As used in this application:

a) the term "halogen" refers to a fluorine atom, chlorine atom, bromine atom, or iodine atom;

b) the term "$C_1-C_6$ alkyl" refers to a branched or straight chained alkyl radical containing from 1 to 6 carbon atoms, such as methyl, ethyl, n-propyl, isopropyl, n-butyl, isobutyl, t-butyl, pentyl, hexyl, cyclopentyl, cyclohexyl, etc;

c) the term "$C_1$–$C_6$ alkoxy" refers to a straight or branched alkoxy group containing from 1 to 6 carbon atoms, such as methoxy, ethoxy, n-propoxy, isopropoxy, n-butoxy, isobutoxy, t-butoxy, pentoxy, hexoxy, cyclopentoxy, cyclohexoxy, etc;

d) the designations —C(O)— or —(O)C— refer to a carbonyl group of the formula:

e) the designation "〰〰" refers to a bond for which the stereochemistry is not designated;

f) as used in the examples and preparations, the following terms have the meanings indicated: "kg" refers to kilograms, "g" refers to grams, "mg" refers to milligrams, "mol" refers to moles, "mmol" refers to millimoles, "L" refers to liters, "mL" refers to milliliters, "μL" refers to microliters, "° C." refers to degrees Celsius, "$R_f$" refers to retention factor, "mp" refers to melting point, "dec" refers to decomposition, "bp" refers to boiling point, "mm of Hg" refers to millimeters of mercury, "cm" refers to centimeters, "nm" refers to nanometers, "$[\alpha]_D^{20}$" refers to specific rotation of the D line of sodium at 20° C. obtained in a 1 decimeter cell, "c" refers to concentration in g/mL, "THF" refers to tetrahydrofuran, "DMF" refers to dimethylformamide, "M" refers to molar, "mM" refers to millimolar, "μM" refers to micromolar, "nM" refers to nanomolar, "TLC" refers to thin layer chromatography, "HPLC" refers to high performance liquid chromatography, "HRMS" refers to high resolution mass spectrum, "μCi" refers to microcuries;

g) the designation

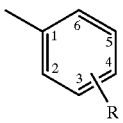

refers to a phenyl or a substituted phenyl and it is understood that the radical is attached at the 1-position and the substituent or substituents represented by R can be attached in any of the 2, 3, 4, 5, or 6 positions;

h) the designation

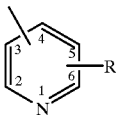

refers to a pyridine, substituted pyridine, pyridinyl, substituted pyridinyl, pyridyl or substituted pyridyl and it is understood that the radical can be attached at either the 2-position, the 3-position, or the 4-position, it is further understood that when the radical is attached at the 2-position the substituent or substituents represented by R can be attached in any of the 3, 4, 5, or 6 positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;

i) the designation

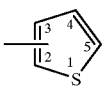

refers to a thienyl, thiophene, or thiophenyl and it is understood that the radical is attached at the 2 or 3-positions;

j) the designation

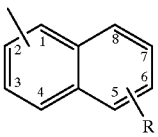

refers to a naphthyl, substituted naphthyl, naphthalenyl, or substituted naphthalenyl and it is understood that the radical can be attached at either the 1-position or the 2-position, it is further understood that when the radical is attached at the 1-position the substituent or substituents represented by R can be attached in any of the 2, 3, 4, 5, 6, 7, or 8 positions and that when the radical is attached at the 2-position the substituent or substituents represented by R can be attached in any of the 1, 3, 4, 5, 6, 7, or 8 positions;

k) the term "enantiomeric excess" or "ee" refers to the percent by which one enantiomer, E1, is in excess in a mixture of the two enantiomers, E1 plus E2, such that $$\{(E1-E2) \div (E1+E2)\} \times 100\% = ee,$$

with the designation "(+)-" refers to the plus enantiomer, "(−)-" refers to the minus enantiomer;

l) the term "$C_1$–$C_4$alkyl" refers to a saturated straight or branched chain alkyl group containing from 1–4 carbon atoms and includes methyl, ethyl, propyl, isopropyl, n-butyl, isobutyl, and t-butyl;

m) the designations —$CO_2R$ and —C(O)OR refer to a group of the formula:

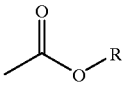

n) the designation —C(O)NRR refer to a group of the formula:

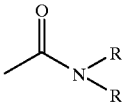

o) the designation

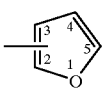

refers to a furyl, furanyl, or furan and it is understood that the radical is attached at either the 2- or 3-position;

p) the term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

Preferred embodiments of formula (1) are given below:

1) Compounds wherein m is 2 are preferred;

2) Compounds wherein $G_1$ is —$CH_2$— are preferred;

3) Compounds wherein $G_2$ is —C(O)— are preferred;

4) Compounds wherein $X_1$ is hydrogen are preferred;

5) Compounds wherein $X_2$ is a radical of the formula

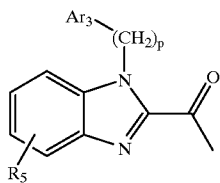

are preferred;

6) Compounds wherein $X_2$ is a radical of the formula

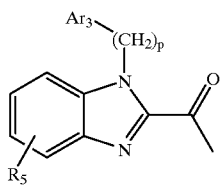

wherein p is 1 and $Ar_3$ is 4-fluorophenyl, pyrid-2-yl, or fur-2-yl are more preferred;

7) Compounds wherein $X_2$ is a radical of the formula

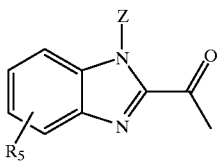

are preferred; and

8) Compounds wherein $X_2$ is a radical of the formula

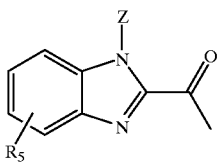

wherein Z is 2-ethoxy-ethyl or 3-fur-2-ylmethoxy-ethyl are more preferred.

It is understood that further preferred embodiments of formula (1) can be selected by requiring one or more of the preferred embodiments 1 through 8 of formula (1) or by reference to examples given herein.

Examples of compounds encompassed by the present invention include the following. It is understood that the examples encompass both the (+)-isomer and the (−)-isomer of the compound and mixtures thereof. This list is meant to be representative only and is not intended to limit the scope of the invention in any way:

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine;

1-Benzoyl-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine;

1-Benzoyl-3-[2-[4-[1-(4-fluoro-benzyl)-1H-benzoimidazol-2-yl]-4-hydroxy-piperidin-1-yl]-ethyl]-3-(3,4-dimethoxy-phenyl)-pyrrolidine;

1-Benzoyl-3-[2-[4-(benzothiazol-2-yl)-piperidin-1-yl]-ethyl]-3-(3,4-dimethoxy-phenyl)-pyrrolidine;

1-(3,4,5-Trimethoxy-benzoyl)-3-[2-[4-[1-(4-fluoro-benzyl)-1H-benzoimidazol-2-yl]-4-hydroxy-piperidin-1-yl]-ethyl]-3-(3,4-dimethoxy-phenyl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dichloro-phenyl)-pyrrolidine;

1-(3,4,5-Trimethoxy-benzoyl)-3-[2-[4-[1-(4-fluoro-benzyl)-1H-benzoimidazol-2-yl]-4-hydroxy-piperidin-1-yl]-ethyl]-3-(3,4-dichloro-phenyl)-pyrrolidine;

1-Benzoyl-3-[2-[4-(benzothiazole-2-carbonyl)-piperidin-1-yl]-ethyl]-3-(3,4-dimethoxy-phenyl)-pyrrolidine;

1-(3,4,5-Trimethoxy-benzoyl)-3-[2-[4-(hydroxy-diphenyl-methyl)-piperidin-1-yl]-ethyl]-3-(3,4-dimethoxy-phenyl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(benzo[1,3]dioxol-5-yl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-phenyl-pyrrolidine;

1-Benzoyl-3-[2-[4-[1-(4-fluoro-benzyl)-1H-benzoimidazole-2-carbonyl]-piperidin-1-yl]-ethyl]-3-(naphth-2-yl)-pyrrolidine;

1-Benzyl-3-[2-[4-[1-(4-fluoro-benzyl)-1H-benzoimidazole-2-carbonyl]-piperidin-1-yl]-ethyl]-3-(3,4-dichloro-phenyl)-5-oxo-pyrrolidine;

1-[3,5-Bis-(trifluoromethyl)-benzoyl]-3-[2-[4-[1-(4-fluorobenzyl)-1H-benzoimidazole-2-carbonyl]-piperidin-1-yl]-ethyl]-3-(3,4-dichloro-phenyl)-pyrrolidine;

1-(4-t-Butyl-benzoyl)-3-[2-[4-[1-(4-fluoro-benzyl)-1H-benzoimidazole-2-carbonyl]-piperidin-1-yl]-ethyl]-3-(3,4-dichloro-phenyl)-pyrrolidine;

1-(3,4,5-Trimethoxyphenyl-acetyl)-3-[2-[4-[1-(4-fluorobenzyl)-1H-benzoimidazole-2-carbonyl]-piperidin-1-yl]-ethyl]-3-(3,4-dimethoxy-phenyl)-pyrrolidine;

1-(Pyridine-2-carbonyl)-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3-trifluoromethyl-phenyl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(4-trifluoromethyl-phenyl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(thiophen-2-yl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(4-hydroxyphenyl)-pyrrolidine;

1-(3,4,5-Trimethoxy-benzoyl)-3-[3-[4-[1-(4-fluoro-benzyl)-1H-benzoimidazole-2-carbonyl]-piperidin-1-yl]-propyl]-3-(3,4-dichloro-phenyl)-pyrrolidine;

1-(3,4,5-Trimethoxy-benzyl)-3-[3-[4-[1-(4-fluoro-benzyl)-1H-benzoimidazole-2-carbonyl]-piperidin-1-yl]-propyl]-3-(3,4-dichloro-phenyl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(2,4-difluoro-phenyl)-pyrrolidine;

1-(3-Isopropoxy-phenyl-acetyl)-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine;

1-(3-Isopropoxy-phenyl-acetyl)-3-[2-[4-[1-(4-fluoro-benzyl)-1H-benzoimidazole-2-carbonyl]-piperidin-1-yl]-ethyl]-3-(benzo[1,3]dioxol-5-yl)-pyrrolidine;

1-(3,4,5-Trimethoxy-benzoyl)-3-[2-[4-benzhydrylidene-piperidin-1-yl]-ethyl]-3-(3,4-dichloro-phenyl)-pyrrolidine;

1-(2,3,4-Trimethoxy-benzoyl)-3-[2-[4-[1-(4-fluoro-benzyl)-1H-benzoimidazole-2-carbonyl]-piperidin-1-yl]-ethyl]-3-(benzo[1,3]dioxol-5-yl)-pyrrolidine;

1-(3,4,5-Triethoxy-benzoyl)-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine;

1-(2,4-Dichloro-benzoyl)-3-[2-[4-[1-(4-fluoro-benzyl)-1H-benzoimidazole-2-carbonyl]-piperidin-1-yl]-ethyl]-3-(benzo [1,3]dioxol-5-yl)-pyrrolidine;

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(pyridin-3-yl)-pyrrolidine;

1-(3,4,5-Trimethoxy-benzoyl)-3-[2-[4-[1-(2-(morpholin-4-yl)ethyl)-1H-benzoimidazole-2-carbonyl]-piperidin-1-yl]-ethyl]-3-(3,4-dichloro-phenyl)-pyrrolidine;

1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine;

1-(3,4,5-Trimethoxy-benzoyl)-3-[2-[4-[1-(3-ethoxycarbonyl-propyl)-1H-benzoimidazole-2-carbonyl]-piperidin-1-yl]-ethyl]-3-(3,4-dichloro-phenyl)-pyrrolidine;

1-(3,4,5-Trimethoxy-benzoyl)-3-[2-[4-[1-(3-carboxy-propyl)-1H-benzoimidazole-2-carbonyl]-piperidin-1-yl]-ethyl]-3-(3,4-dichloro-phenyl)-pyrrolidine;

1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(4-methoxycarbonyl-benzyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(4-carboxy-benzyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(4-carbomethoxy-phenylmethyl)-1H-benzoimidazole-2-carbonyl]-piperidin-1-yl]-ethyl]-3-(3,4-dimethoxy-phenyl)-pyrrolidine;

1-(3,4,5-Trimethoxy-benzoyl)-3-[2-[4-[1-(4-carboxy-phenylmethyl)-1H-benzoimidazole-2-carbonyl]-piperidin-1-yl]-ethyl]-3-(3,4-dimethoxy-phenyl)-pyrrolidine;

1-(3,4,5-Trimethoxy-benzoyl)-3-[2-[4-[1-(fur-2-ylmethyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(2-fur-2-ylmethoxy-ethyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(2-allyloxy-ethyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(2-(3,3-dimethylallyloxy)-ethyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(3-trifluormethyl-benzyl)-1H-benzoimidazole-2-carbonyl]-piperidin-1-yl]-ethyl]-3-phenyl-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3-chloro-phenyl)-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(4-chloro-phenyl)-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-piperidine;

1-(3-Isopropoxy-phenyl-acetyl)-3-[2-[4-[1-(2-ethoxy-ethyl)-1H-benzoimidazole-2-carbonyl]-piperidin-1-yl]-ethyl]-3-(3,4-dichloro-phenyl)-piperidine;

1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine;

1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(3,4-dichloro-phenylmethyl)-2-oxo-pyrrolidine;

1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(3,4-dimethoxy-phenylmethyl)-2-oxo-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(3,4-dimethoxy-phenylmethyl)-2-oxo-pyrrolidine;

1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(4-fluoro-phenylmethyl)-2-oxo-pyrrolidine;

1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(2,4-difluoro-phenylmethyl)-2-oxo-pyrrolidine;

1-Benzyl-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(phenylmethyl)-2-oxo-pyrrolidine;
1-(3,4,5-Trimethoxy-benzyl)-3-[2-[4-[1-(2-ethoxy-ethyl)-1H-benzoimidazole-2-carbonyl]-piperidin-1-yl]-ethyl]-3-phenyl-2-oxo-pyrrolidine;
1-Benzyl-3-[2-[4-[1-(4-fluoro-benzyl)-1H-benzoimidazol-2-yl]-4-hydroxy-piperidin-1-yl]-ethyl]-3-(phenylmethyl)-2-oxo-piperidine;
1-(3-Isopropoxy-phenyl-acetyl)-3-[2-[4-[1-(4-fluoro-benzyl)-1H-benzoimidazole-2-carbonyl]-piperidin-1-yl]-ethyl]-3-(3,4-dichloro-phenyl)-piperidine;
1-(4-Ethyl acetoxy-3,5-dimethoxy-benzoyl)-3-[2-[4-[1-(2-ethoxy-30 ethyl)-1H-benzoimidazole-2-carbonyl]-piperidin-1-yl]-ethyl]-3-phenyl-pyrrolidine;
1-(4-Acetoxy-3,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-dimethyl-phenyl)-pyrrolidine;
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(4-fluoro-phenyl)-pyrrolidine;
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(pyridin-2-yl)-pyrrolidine;
1-(3,4,5-Trimethoxy-benzoyl)-3-[2-[4-[1-(3-(2-carbomethoxy-phenoxy)-propyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(3-(2-carboxy-phenoxy)-propyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(2-oxo-propyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(N,N-dimethylacetamido)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(2-acetamido-ethyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(4-methoxy-phenyl)-pyrrolidine;
1-(3,4,5-Trimethoxy-benzyl)-3-[3-[4-[1-(2-ethoxy-ethyl)-1H-benzoimidazole-2-carbonyl]-piperidin-1-yl]-propyl]-3-(4-fluoro-phenylmethyl)-2-oxo-pyrrolidine;
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-difluoro-phenyl)-pyrrolidine;
1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dichloro-phenyl)-piperidine;
1-(3,4,5-Trimethoxy-benzoyl)-3-[2-[4-[1H-benzoimidazole-2-carbonyl]-piperidin-1-yl]-ethyl]-3-(3,4-dimethoxy-phenyl)-pyrrolidine;
1-Benzoyl-3-[2-[4-[1H-benzoimidazole-2-carbonyl]-piperidin-1-yl]-ethyl]-3-(3,4-dimethoxy-phenyl)-pyrrolidine;
1-(3,4,5-Trimethoxy-benzoyl)-3-[2-[4-[1H-benzoimidazole-2-carbonyl]-piperidin-1-yl]-ethyl]-3-(3,4-dichloro-phenyl)-pyrrolidine;
1-Benzyl-3-[2-[4-[1H-benzoimidazole-2-carbonyl]-piperidin-1-yl]-ethyl]-3-(3,4-dichloro-phenyl)-5-oxo-pyrrolidine;
1-(3,4,5-Trimethoxy-benzoyl)-3-[2-[4-[1-(imidazol-2-ylmethyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(2-ethoxy-ethyl)-1H-benzoimidazole]-4-hydroxy-piperidin-1-yl]-ethyl]-3-(3,4-dichloro-phenyl)-pyrrolidine
1-(3,4,5-Trimethoxy-benzoyl)-3-[2-[4-[1-(4-fluoro-benzyl)-1H-benzoimidazol-2-yl]-4-hydroxy-piperidin-1-yl]-ethyl]-3-(3,4-methoxy-phenylmethyl)-2-oxo-pyrrolidine;
1-Benzyl-3-[2-[4-[1-(4-fluoro-benzyl)-1H-benzoimidazol-2-yl]-4-hydroxy-piperidin-1-yl]-ethyl]-3-phenylmethyl-2-oxo-pyrrolidine;
1-(3,4,5-Trimethoxy-benzyl)-3-[2-[4-[1-(pryid-2-ylmethyl)-1H-benzoimidazole-2-carbonyl]-piperidin-1-yl]-ethyl]-3-(4-fluoro-phenylmethyl)-2-oxo-pyrrolidine;
1-(3,4,5-Trimethoxy-benzoyl)-3-[2-[4-[1-(5-methylfur-2-ylmethyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(5-hydroxymethylfur-2-ylmethyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-(3,4-dichloro-phenyl)-piperidine;
1-(3,4,5-Trimethoxy-benzoyl)-3-[2-[4-[1-(3-ethoxycarbonyl-propyl)-1H-benzoimidazole-2-carbonyl]-piperidin-1-yl]-ethyl]-3-(3,4-dichloro-phenyl)-piperidine;
1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-phenyl-piperidine;
1-(3,4,5-Trimethoxy-benzoyl)-3-[2-[4-[1-(fur-2-ylmethyl)-1H-benzoimidazole-2-carbonyl]-piperidin-1-yl]-ethyl]-3-phenyl-piperidine;
1-(3,4,5-Trimethoxy-benzoyl)-3-[2-[4-[1-(2-fur-2-ylmethoxy-ethyl)-1H-benzoimidazole-2-carbonyl]-piperidin-1-yl]-ethyl]-3-phenyl-piperidine;
1-(3,4,5-Trimethoxy-benzoyl)-3-[2-[4-[1-(4-carbomethoxy-phenylmethyl)-1H-benzoimidazole-2-carbonyl]-piperidin-1-yl]-ethyl]-3-(3,4-dimethoxy-phenyl)-pyrrolidine;
1-(3,4,5-Trimethoxy-benzoyl)-3-[2-[4-[1-(fur-2-ylmethyl)-1H-benzoimidazole-2-carbonyl]-piperidin-1-yl]-ethyl]-3-phenyl-2-oxo-pyrrolidine;
1-(3,4,5-Trimethoxy-benzyl)-3-[2-[4-[1-(2-fur-2-ylmethoxy-ethyl)-1H-benzoimidazole-2-carbonyl]-piperidin-1-yl]-ethyl]-3-phenyl-2-oxo-pyrrolidine;
1-(3,4,5-Trimethoxy-benzoyl)-3-[2-[4-[1-(2-allyloxy-ethyl)-1H-benzoimidazole-2-carbonyl]-piperidin-1-yl]-ethyl]-3-phenyl-piperidine;
1-(2,4-Dichloro-benzyl)-3-[2-[4-[1-(4-fluoro-benzyl)-1H-benzoimidazole-2-carbonyl]-piperidin-1-yl]-ethyl]-3-(benzo[1,3]dioxol-5-yl)-2-oxo-pyrrolidine;
1-(3,4,5-Trimethoxy-benzyl)-3-[2-[4-[1-(2-ethoxy-ethyl)-1H-benzoimidazole-2-carbonyl]-piperidin-1-yl]-ethyl]-3-(4-chloro-phenyl)-pyrrolidine;
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-2-oxo-piperidine;
1-(3-Isopropoxy-phenyl-acetyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine;
1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(phenylmethyl)-pyrrolidine;
1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(3,4-dichloro-phenylmethyl)-pyrrolidine;
1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(3,4-dimethoxy-phenylmethyl)-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(3,4-dimethoxy-phenylmethyl)-pyrrolidine;
1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(4-fluoro-phenylmethyl)-pyrrolidine;
1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(2,4-difluoro-phenylmethyl)-pyrrolidine;
1-Benzyl-3-[2-[4-[1-(4-fluoro-benzyl)-1H-benzoimidazol-2-yl]-4-hydroxy-piperidin-1-yl]-ethyl]-3-(phenylmethyl)-pyrrolidine;
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(phenylmethyl)-pyrrolidine;
1-(3,4,5-Trimethoxy-benzyl)-3-[2-[4-[1-(2-ethoxy-ethyl)-1H-benzoimidazole-2-carbonyl]-piperidin-1-yl]-ethyl]-3-phenyl-pyrrolidine;
1-Benzyl-3-[2-[4-[1-(4-fluoro-benzyl)-1H-benzoimidazol-2-yl]-4-hydroxy-piperidin-1-yl]-ethyl]-3-(phenylmethyl)-piperidine; 1-(3,4,5-Trimethoxy-benzyl)-3-[2-[4-[1-(2-ethoxy-ethyl)-1H-benzoimidazole-2-carbonyl]-piperidin-1-yl]-ethyl]-3-(3,4-dimethyl-phenyl)-2-oxo-pyrrolidine;
1-(3,4,5-Trimethoxy-benzyl)-3-[2-[4-[1-(2-ethoxy-ethyl)-1H-benzoimidazole-2-carbonyl]-piperidin-1-yl]-ethyl]-3-(4-fluoro-phenyl)-2-oxo-pyrrolidine;
1-(3,4,5-Trimethoxy-benzoyl)-3-[2-[4-[1-(2-oxo-butyl)-1H-benzoimidazole-2-carbonyl]-piperidin-1-yl]-ethyl]-3-(3,4-dichloro-phenyl)-pyrrolidine;
1-(3,4,5-Trimethoxy-benzoyl)-3-[2-[4-[1-(fur-3-ylmethyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(3-(4-carbomethoxy-phenoxy)-propyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(3-(4-carboxy-phenoxy)-propyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(thien-2-ylmethyl)-1H-benzoimidazole-2-carbonyl]-piperidin-1-yl]-ethyl]-3-(3,4-dichloro-phenyl)-pyrrolidine;
1-(3,4,5-Trimethoxy-benzoyl)-3-[2-[4-[1-(thien-2-ylmethyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(N-butylacetamido)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(2-acetoxy-ethyl)-1H-benzoimidazole-2-carbonyl]-piperidin-1-yl]-ethyl]-3-phenyl-pyrrolidine;
1-(3,4,5-Trimethoxy-benzoyl)-3-[2-[4-[1-(4-oxo-pentyl)-1H-benzoimidazole-2-carbonyl]-piperidin-1-yl]-ethyl]-3-(4-methoxy-phenyl)-pyrrolidine;
1-(3,4,5-Trimethoxy-benzyl)-3-[3-[4-[1-(pyrid-2-ylmethyl)-1H-benzoimidazole-2-carbonyl]-piperidin-1-yl]-propyl]-3-(4-fluoro-phenylmethyl)-2-oxo-pyrrolidine;
1-(3,4,5-Trimethoxy-benzoyl)-3-[2-[4-[1-(imidazol-2-ylmethyl)-1H-benzoimidazole-2-carbonyl]-piperidin-1-yl]-ethyl]-3-(3,4-difluoro-phenyl)-pyrrolidine;
1-(3,4,5-Trimethoxy-benzoyl)-3-[2-[4-[1-(pyrid-4-ylmethyl)-1H-benzoimidazole-2-carbonyl]-piperidin-1-yl]-ethyl]-3-(3,4-dichloro-phenyl)-piperidine;
1-(3,4,5-Trimethoxy-benzoyl)-3-[2-[4-[1-(pyrid-3-ylmethyl)-1H-benzoimidazole-2-carbonyl]-piperidin-1-yl]-ethyl]-3-(3,4-dimethoxy-phenyl)-pyrrolidine;
1-(3,4,5-Trimethoxy-benzoyl)-3-[2-[4-[1-(thien-3-ylmethyl)-1H-benzoimidazole-2-carbonyl]-piperidin-1-yl]-ethyl]-3-phenyl-pyrrolidine;
1-Benzoyl-3-[2-[4-[1H-benzoimidazole-2-carbonyl]-piperidin-1-yl]-ethyl]-3-(3,4-dichloro-phenyl)-pyrrolidine;
1-(3,5-Bis(trifluoromethyl)-benzoyl)-3-[2-[4-[1H-benzoimidazole-2-carbonyl]-piperidin-1-yl]-ethyl]-3-(3,4-dichloro-phenyl)-pyrrolidine;
1-(3,4,5-Trimethoxy-benzoyl)-3-[2-[4-[1H-benzoimidazole-2-carbonyl]-piperidin-1-yl]-ethyl]-3-(3-trifluoromethyl-phenyl)-pyrrolidine;
1-(3,4,5-Trimethoxy-benzoyl)-3-[2-[4-[1H-benzoimidazole-2-carbonyl]-piperidin-1-yl]-ethyl]-3-(4-trifluoromethyl-phenyl)-pyrrolidine;
1-(3,4,5-Trimethoxy-benzoyl)-3-[2-[4-[1H-benzoimidazole-2-carbonyl]-piperidin-1-yl]-ethyl]-3-(2,4-difluoro-phenyl)-pyrrolidine;
1-(3-Isopropoxy-phenyl-acetyl)-3-[2-[4-[1H-benzoimidazole-2-carbonyl]-piperidin-1-yl]-ethyl]-3-(3,4-dimethoxy-phenyl)-pyrrolidine;
1-(3-Isopropoxy-phenyl-acetyl)-3-[2-[4-[1H-benzoimidazole-2-carbonyl]-piperidin-1-yl]-ethyl]-3-(benzo[1,3]dioxol-5-yl)-pyrrolidine;
1-(3-Isopropoxy-phenyl-acetyl)-3-[2-[4-[1H-benzoimidazole-2-carbonyl]-piperidin-1-yl]-ethyl]-3-(3,4-dichloro-phenyl)-pyrrolidine;
1-(2,4-Dichloro-benzoyl)-3-[2-[4-[1H-benzoimidazole-2-carbonyl]-piperidin-1-yl]-ethyl]-3-(benzo[1,3]dioxol-5-yl)-pyrrolidine;
1-(3,4,5-Trimethoxy-benzoyl)-3-[2-[4-[1H-benzoimidazole-2-carbonyl]-piperidin-1-yl]-ethyl]-3-phenyl-pyrrolidine;
1-(4-Ethyl acetoxy-3,5-dimethoxy-benzoyl)-3-[2-[4-[1H-benzoimidazole-2-carbonyl]-piperidin-1-yl]-ethyl]-3-(3,4-dichloro-phenyl)-pyrrolidine;
1-(4-Ethyl acetoxy-3,5-dimethoxy-benzoyl)-3-[2-[4-[1H-benzoimidazole-2-carbonyl]-piperidin-1-yl]-ethyl]-3-(3,4-dimethoxy-phenyl)-pyrrolidine;
1-(4-Ethyl acetoxy-3,5-dimethoxy-benzoyl)-3-[2-[4-[1H-benzoimidazole-2-carbonyl]-piperidin-1-yl]-ethyl]-3-phenyl-pyrrolidine;
1-(3-Ethyl acetoxy-4,5-dimethoxy-benzoyl)-3-[2-[4-[1H-benzoimidazole-2-carbonyl]-piperidin-1-yl]-ethyl]-3-(3,4-dichloro-phenyl)-pyrrolidine;
1-(3-Ethyl acetoxy-4,5-dimethoxy-benzoyl)-3-[2-[4-[1H-benzoimidazole-2-carbonyl]-piperidin-1-yl]-ethyl]-3-phenyl-pyrrolidine;
1-(4-Acetoxy-3,5-dimethoxy-benzoyl)-3-[2-[4-[1H-benzoimidazole-2-carbonyl]-piperidin-1-yl]-ethyl]-3-(3,4-dichloro-phenyl)-pyrrolidine;
1-(4-Acetoxy-3,5-dimethoxy-benzoyl)-3-[2-[4-[1H-benzoimidazole-2-carbonyl]-piperidin-1-yl]-ethyl]-3-(3,4-dimethoxy-phenyl)-pyrrolidine;
1-(4-Acetoxy-3,5-dimethoxy-benzoyl)-3-[2-[4-[1H-benzoimidazole-2-carbonyl]-piperidin-1-yl]-ethyl]-3-phenyl-pyrrolidine;
1-(3-Acetoxy-4,5-dimethoxy-benzoyl)-3-[2-[4-[1H-benzoimidazole-2-carbonyl]-piperidin-1-yl]-ethyl]-3-(3,4-dichloro-phenyl)-pyrrolidine;
1-(3-Acetoxy-4,5-dimethoxy-benzoyl)-3-[2-[4-[1H-benzoimidazole-2-carbonyl]-piperidin-1-yl]-ethyl]-3-phenyl-pyrrolidine;
1-(3,4,5-Trimethoxy-benzyl)-3-[2-[4-[1H-benzoimidazole-2-carbonyl]-piperidin-1-yl]-ethyl]-3-(phenylmethyl)-2-oxo-pyrrolidine;
1-(3,4,5-Trimethoxy-benzyl)-3-[2-[4-[1H-benzoimidazole-2-carbonyl]-piperidin-1-yl]-ethyl]-3-(3,4-dimethoxy-phenylmethyl)-2-oxo-pyrrolidine;
1-(3,4,5-Trimethoxy-benzyl)-3-[2-[4-[1H-benzoimidazole-2-carbonyl]-piperidin-1-yl]-ethyl]-3-(3,4-dichloro-phenylmethyl)-2-oxo-pyrrolidine;

1-(3,4,5-Trimethoxy-benzyl)-3-[2-[4-[1H-benzoimidazole-2-carbonyl]-piperidin-1-yl]-ethyl]-3-(4-fluoro-phenylmethyl)-2-oxo-pyrrolidine;

1-(3,4,5-Trimethoxy-benzyl)-3-[2-[4-[1H-benzoimidazole-2-carbonyl]-piperidin-1-yl]-ethyl]-3-(4-methoxy-phenylmethyl)-2-oxo-pyrrolidine;

1-(3,4,5-Trimethoxy-benzyl)-3-[2-[4-[1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1H-benzoimidazole-2-carbonyl]-piperidin-1-yl]-ethyl]-3-(2,4-difluoro-phenylmethyl)-2-oxo-pyrrolidine;

1-Benzyl-3-[2-[4-[1H-benzoimidazole-2-carbonyl]-piperidin-1-yl]-ethyl]-3-(phenylmethyl)-2-oxo-pyrrolidine;

1-Benzyl-3-[2-[4-[1H-benzoimidazole-2-carbonyl]-piperidin-1-yl]-ethyl]-3-(phenylmethyl)-2-oxo-piperidine;

1-Benzyl-3-[2-[4-[1H-benzoimidazole-2-carbonyl]-piperidin-1-yl]-ethyl]-3-(4-fluoro-phenylmethyl)-2-oxo-piperidine;

1-Benzyl-3-[2-[4-[1H-benzoimidazole-2-carbonyl]-piperidin-1-yl]-ethyl]-3-(4-methoxy-phenylmethyl)-2-oxo-piperidine;

1-Benzyl-3-[2-[4-[1-(4-fluoro-benzyl)-1H-benzoimidazole-2-carbonyl]-piperidin-yl]-ethyl]-3-phenylmethyl-2-oxo-pyrrolidine;

1-(3,4,5-Trimethoxy-benzoyl)-3-[2-[4-[1H-benzoimidazole-2-carbonyl]-piperidin-1-yl]-ethyl]-3-(2,4-difluoro-phenyl)-pyrrolidine;

1-(3,4,5-Trimethoxy-benzyl)-3-[2-[4-[1H-benzoimidazole-2-carbonyl]-piperidin-1-yl]-ethyl]-3-(4-fluoro-phenylmethyl)-2-oxo-pyrrolidine;

1-Benzoyl-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine;

1-(3,5-Bis(trifluoromethyl)-benzoyl)-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine;

1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-(3-trifluoromethyl-phenyl)-pyrrolidine;

1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-(4-trifluoromethyl-phenyl)-pyrrolidine;

1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-(2,4-difluoro-phenyl)-pyrrolidine;

1-(3-Isopropoxy-phenyl-acetyl)-3-[2-[4-[1-(pyrid-2-ylmethyl)-1H-benzoimidazole-2-carbonyl]-piperidin-1-yl]-ethyl]-3-(3,4-dimethoxy-phenyl)-pyrrolidine;

1-(3-Isopropoxy-phenyl-acetyl)-3-[2-[4-[1-(pyrid-2-ylmethyl)-1H-benzoimidazole-2-carbonyl]-piperidin-1-yl]-ethyl]-3-(benzo[1,3]dioxol-5-yl)-pyrrolidine;

1-(3-Isopropoxy-phenyl-acetyl)-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine;

1-(2,4-Dichloro-benzoyl)-3-[2-[4-[1-(pyrid-2-ylmethyl)-1H-benzoimidazole-2-carbonyl]-piperidin-1-yl]-ethyl]-3-(benzo[1,3]dioxol-5-yl)-pyrrolidine;

1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-phenyl-pyrrolidine;

1-(4-Ethyl acetoxy-3,5-dimethoxy-benzoyl)-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine;

1-(4-Ethyl acetoxy-3,5-dimethoxy-benzoyl)-3-[2-[4-[1-(pyrid-2-ylmethyl)-1H-benzoimidazole-2-carbonyl]-piperidin-1-yl]-ethyl]-3-(3,4-dimethoxy-phenyl)-pyrrolidine;

1-(4-Ethyl acetoxy-3,5-dimethoxy-benzoyl)-3-[2-[4-[1-(pyrid-2-ylmethyl)-1H-benzoimidazole-2-carbonyl]-piperidin-1-yl]-ethyl]-3-phenyl-pyrrolidine;

1-(3-Ethyl acetoxy-4,5-dimethoxy-benzoyl)-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine;

1-(3-Ethyl acetoxy-4,5-dimethoxy-benzoyl)-3-[2-[4-[1-(pyrid-2-ylmethyl)-1H-benzoimidazole-2-carbonyl]-piperidin-1-yl]-ethyl]-3-phenyl-pyrrolidine;

1-(4-Acetoxy-3,5-dimethoxy-benzoyl)-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine;

1-(4-Acetoxy-3,5-dimethoxy-benzoyl)-3-[2-[4-[1-(pyrid-2-ylmethyl)-1H-benzoimidazole-2-carbonyl]-piperidin-1-yl]-ethyl]-3-(3,4-dimethoxy-phenyl)-pyrrolidine;

1-(4-Acetoxy-3,5-dimethoxy-benzoyl)-3-[2-[4-[1-(pyrid-2-ylmethyl)-1H-benzoimidazole-2-carbonyl]-piperidin-1-yl]-ethyl]-3-phenyl-pyrrolidine;

1-(3-Acetoxy-4,5-dimethoxy-benzoyl)-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine;

1-(3-Acetoxy-4,5-dimethoxy-benzoyl)-3-[2-[4-[1-(pyrid-2-ylmethyl)-1H-benzoimidazole-2-carbonyl]-piperidin-1-yl]-ethyl]-3-phenyl-pyrrolidine;

1-(3,4,5-Trimethoxy-benzyl)-3-[2-[4-[1-(pyrid-2-ylmethyl)-1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1-(pyrid-2-ylmethyl)-1H-benzoimidazole-2-carbonyl]-piperidin-1-yl]-ethyl]-3-(3,4-dimethoxy-phenylmethyl)-2-oxo-pyrrolidine;

1-(3,4,5-Trimethoxy-benzyl)-3-[2-[4-[1-(pyrid-2-ylmethyl)-1H-benzoimidazole-2-carbonyl]-piperidin-1-yl]-ethyl]-3-(3,4-dichloro-phenylmethyl)-2-oxo-pyrrolidine;

1-(3,4,5-Trimethoxy-benzyl)-3-[2-[4-[1-(pyrid-2-ylmethyl)-1H-benzoimidazole-2-carbonyl]-piperidin-1-yl]-ethyl]-3-(4-fluoro-phenylmethyl)-2-oxo-pyrrolidine;

1-(3,4,5-Trimethoxy-benzyl)-3-[2-[4-[1-(pyrid-2-ylmethyl)-1H-benzoimidazole-2-carbonyl]-piperidin-1-yl]-ethyl]-3-(4-methoxy-phenylmethyl)-2-oxo-pyrrolidine;

1-(3,4,5-Trimethoxy-benzyl)-3-[2-[4-[1-(pyrid-2-ylmethyl)-1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1-(pyrid-2-ylmethyl)-1H-benzoimidazole-2-carbonyl]-piperidin-1-yl]-ethyl]-3-(2,4-difluoro-phenylmethyl)-2-oxo-pyrrolidine;

1-Benzyl-3-[2-[4-[1-(pyrid-2-ylmethyl)-1H-benzoimidazole-2-carbonyl]-piperidin-1-yl]-ethyl]-3-(phenylmethyl)-2-oxo-pyrrolidine;

1-Benzyl-3-[2-[4-[1-(pyrid-2-ylmethyl)-1H-benzoimidazole-2-carbonyl]-piperidin-1-yl]-ethyl]-3-(phenylmethyl)-2-oxo-piperidine;

1-Benzyl-3-[2-[4-[1-(pyrid-2-ylmethyl)-1H-benzoimidazole-2-carbonyl]-piperidin-1-yl]-ethyl]-3-(4-fluoro-phenylmethyl)-2-oxo-piperidine;

1-Benzyl-3-[2-[4-[1-(pyrid-2-ylmethyl)-1H-benzoimidazole-2-carbonyl]-piperidin-1-yl]-ethyl]-3-(4-methoxy-phenylmethyl)-2-oxo-piperidine;

1-Benzyl-3-[2-[4-[1-(4-fluoro-benzyl)-1H-benzoimidazole-2-carbonyl]-piperidin-1-yl]-ethyl]-3-phenyl methyl-2-oxo-pyrrolidine;

1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-(2,4-difluoro-phenyl)-pyrrolidine;

1-(3,4,5-Trimethoxy-benzyl)-3-[2-[4-[1-(pyrid-2-ylmethyl)-1H-benzoimidazole-2-carbonyl]-piperidin-1-yl]-ethyl]-3-(4-fluoro-phenylmethyl)-2-oxo-pyrrolidine;

1-Benzoyl-3-[2-[4-[1-(2-fur-2-ylmethoxy-ethyl)-1H-benzoimidazole-2-carbonyl]-piperidin-1-yl]-ethyl]-3-(3,4-dichloro-phenyl)-pyrrolidine;

1-(3,5-Bis(trifluoromethyl)-benzoyl)-3-[2-[4-[1-(2-fur-2-ylmethoxy-ethyl)-1H-benzoimidazole-2-carbonyl]-piperidin-1-yl]-ethyl]-3-(3,4-dichloro-phenyl)-pyrrolidine;

1-(3,4,5-Trimethoxy-benzoyl)-3-[2-[4-[1-(2-fur-2-ylmethoxy-ethyl)-1H-benzoimidazole-2-carbonyl]-piperidin-1-yl]-ethyl]-3-(3-trifluoromethyl-phenyl)-pyrrolidine;

1-(3,4,5-Trimethoxy-benzoyl)-3-[2-[4-[1-(2-fur-2-ylmethoxy-ethyl)-1H-benzoimidazole-2-carbonyl]-piperidin-1-yl]-ethyl]-3-(4-trifluoromethyl-phenyl)-pyrrolidine;

1-(3,4,5-Trimethoxy-benzoyl)-3-[2-[4-[1-(2-fur-2-ylmethoxy-ethyl)-1H-benzoimidazole-2-carbonyl]-piperidin-1-yl]-ethyl]-3-(2,4-difluoro-phenyl)-pyrrolidine;

1-(3-Isopropoxy-phenyl-acetyl)-3-[2-[4-[1-(2-fur-2-ylmethoxy-ethyl)-1H-benzoimidazole-2-carbonyl]-piperidin-1-yl]-ethyl]-3-(3,4-dimethoxy-phenyl)-pyrrolidine;

1-(3-Isopropoxy-phenyl-acetyl)-3-[2-[4-[1-(2-fur-2-ylmethoxy-ethyl)-1H-benzoimidazole-2-carbonyl]-piperidin-1-yl]-ethyl]-3-(benzo[1,3]dioxol-5-yl)-pyrrolidine;

1-(3-Isopropoxy-phenyl-acetyl)-3-[2-[4-[1-(2-fur-2-ylmethoxy-ethyl)-1H-benzoimidazole-2-carbonyl]-piperidin-1-yl]-ethyl]-3-(3,4-dichloro-phenyl)-pyrrolidine;

1-(2,4-Dichloro-benzoyl)-3-[2-[4-[1-(2-fur-2-ylmethoxy-ethyl)-1H-benzoimidazole-2-carbonyl]-piperidin-1-yl]-ethyl]-3-(benzo[1,3]dioxol-5-yl)-pyrrolidine;

1-(3,4,5-Trimethoxy-benzoyl)-3-[2-[4-[1-(2-fur-2-ylmethoxy-ethyl)-1H-benzoimidazole-2-carbonyl]-piperidin-1-yl]-ethyl]-3-phenyl-pyrrolidine;

1-(4-Ethyl acetoxy-3,5-dimethoxy-benzoyl)-3-[2-[4-[1-(2-fur-2-ylmethoxy-ethyl)-1H-benzoimidazole-2-carbonyl]-piperidin-1-yl]-ethyl]-3-(3,4-dichloro-phenyl)-pyrrolidine;

1-(4-Ethyl acetoxy-3,5-dimethoxy-benzoyl)-3-[2-[4-[1-(2-fur-2-ylmethoxy-ethyl)-1H-benzoimidazole-2-carbonyl]-piperidin-1-yl]-ethyl]-3-(3,4-dimethoxy-phenyl)-pyrrolidine;

1-(4-Ethyl acetoxy-3,5-dimethoxy-benzoyl)-3-[2-[4-[1-(2-fur-2-ylmethoxy-ethyl)-1H-benzoimidazole-2-carbonyl]-piperidin-1-yl]-ethyl]-3-phenyl-pyrrolidine;

1-(3-Ethyl acetoxy-4,5-dimethoxy-benzoyl)-3-[2-[4-[1-(2-fur-2-ylmethoxy-ethyl)-1H-benzoimidazole-2-carbonyl]-piperidin-1-yl]-ethyl]-3-(3,4-dichloro-phenyl)-pyrrolidine;

1-(3-Ethyl acetoxy-4,5-dimethoxy-benzoyl)-3-[2-[4-[1-(2-fur-2-ylmethoxy-ethyl)-1H-benzoimidazole-2-carbonyl]-piperidin-1-yl]-ethyl]-3-phenyl-pyrrolidine;

1-(4-Acetoxy-3,5-dimethoxy-benzoyl)-3-[2-[4-[1-(2-fur-2-ylmethoxy-ethyl)-1H-benzoimidazole-2-carbonyl]-piperidin-1-yl]-ethyl]-3-(3,4-dichloro-phenyl)-pyrrolidine;

1-(4-Acetoxy-3,5-dimethoxy-benzoyl)-3-[2-[4-[1-(2-fur-2-ylmethoxy-ethyl)-1H-benzoimidazole-2-carbonyl]-piperidin-1-yl]-ethyl]-3-(3,4-dimethoxy-phenyl)-pyrrolidine;

1-(4-Acetoxy-3,5-dimethoxy-benzoyl)-3-[2-[4-[1-(2-fur-2-ylmethoxy-ethyl)-1H-benzoimidazole-2-carbonyl]-piperidin-1-yl]-ethyl]-3-phenyl-pyrrolidine;

1-(3-Acetoxy-4,5-dimethoxy-benzoyl)-3-[2-[4-[1-(2-fur-2-ylmethoxy-ethyl)-1H-benzoimidazole-2-carbonyl]-piperidin-1-yl]-ethyl]-3-(3,4-dichloro-phenyl)-pyrrolidine;

1-(3-Acetoxy-4,5-dimethoxy-benzoyl)-3-[2-[4-[1-(2-fur-2-ylmethoxy-ethyl)-1H-benzoimidazole-2-carbonyl]-piperidin-1-yl]-ethyl]-3-phenyl-pyrrolidine;

1-(3,4,5-Trimethoxy-benzyl)-3-[2-[4-[1-(2-fur-2-ylmethoxy-ethyl)-1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1-(2-fur-2-ylmethoxy-ethyl)-1H-benzoimidazole-2-carbonyl]-piperidin-1-yl]-ethyl]-3-(3,4-dimethoxy-phenylmethyl)-2-oxo-pyrrolidine;

1-(3,4,5-Trimethoxy-benzyl)-3-[2-[4-[1-(2-fur-2-ylmethoxy-ethyl)-1H-benzoimidazole-2-carbonyl]-piperidin-1-yl]-ethyl]-3-(3,4-dichloro-phenylmethyl)-2-oxo-pyrrolidine;

1-(3,4,5-Trimethoxy-benzyl)-3-[2-[4-[1-(2-fur-2-ylmethoxyethyl)-1H-benzoimidazole-2-carbonyl]-piperidin-1-yl]-ethyl]-3-(4-fluoro-phenylmethyl)-2-oxo-pyrrolidine;

1-(3,4,5-Trimethoxy-benzyl)-3-[2-[4-[1-(2-fur-2-ylmethoxy-ethyl)-1H-benzoimidazole-2-carbonyl]-piperidin-1-yl]-ethyl]-3-(4-methoxy-phenylmethyl)-2-oxo-pyrrolidine;

1-(3,4,5-Trimethoxy-benzyl)-3-[2-[4-[1-(2-fur-2-ylmethoxy-ethyl)-1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1-(2-fur-2-ylmethoxy-ethyl)-1H-benzoimidazole-2-carbonyl]-piperidin-1-yl]-ethyl]-3-(2,4-difluoro-phenylmethyl)-2-oxo-pyrrolidine;

1-Benzyl-3-[2-[4-[1-(2-fur-2-ylmethoxy-ethyl)-1H-benzoimidazole-2-carbonyl]-piperidin-1-yl]-ethyl]-3-(phenylmethyl)-2-oxo-pyrrolidine;

1-Benzyl-3-[2-[4-[1-(2-fur-2-ylmethoxy-ethyl)-1H-benzoimidazole-2-carbonyl]-piperidin-1-yl]-ethyl]-3-(phenylmethyl)-2-oxo-piperidine;

1-Benzyl-3-[2-[4-[1-(2-fur-2-ylmethoxy-ethyl)-1H-benzoimidazole-2-carbonyl]-piperidin-1-yl]-ethyl]-3-(4-fluoro-phenylmethyl)-2-oxo-piperidine;

1-Benzyl-3-[2-[4-[1-(2-fur-2-ylmethoxy-ethyl)-1H-benzoimidazole-2-carbonyl]-piperidin-1-yl]-ethyl]-3-(4-methoxy-phenylmethyl)-2-oxo-piperidine;

1-Benzyl-3-[2-[4-[1-(4-fluoro-benzyl)-1H-benzoimidazole-2-carbonyl]-piperidin-1-yl]-ethyl]-3-phenylmethyl-2-oxo-pyrrolidine;

1-(3,4,5-Trimethoxy-benzoyl)-3-[2-[4-[1-(2-fur-2-ylmethoxy-ethyl)-1H-benzoimidazole-2-carbonyl]-piperidin-1-yl]-ethyl]-3-(2,4-difluoro-phenyl)-pyrrolidine;

1-(3,4,5-Trimethoxy-benzyl)-3-[2-[4-[1-(2-fur-2-ylmethoxy-ethyl)-1H-benzoimidazole-2-carbonyl]-piperidin-1-yl]-ethyl]-3-(4-fluoro-phenylmethyl)-2-oxo-pyrrolidine;

1-Benzoyl-3-[2-[4-[1-(fur-2-ylmethyl)-1H-benzoimidazole-2-carbonyl]-piperidin-1-yl]-ethyl]-3-(3,4-dichloro-phenyl)-pyrrolidine;

1-(3,5-Bis(trifluoromethyl)-benzoyl)-3-[2-[4-[1-(fur-2-ylmethyl)-1H-benzoimidazole-2-carbonyl]-piperidin-1-yl]-ethyl-]-3-(3,4-dichloro-phenyl)-pyrrolidine;

1-(3,4,5-Trimethoxy-benzoyl)-3-[2-[4-[1-(fur-2-ylmethyl)-1H-benzoimidazole-2-carbonyl]-piperidin-1-yl]-ethyl]-3-(3-trifluoromethyl-phenyl)-pyrrolidine;

1-(3,4,5-Trimethoxy-benzoyl)-3-[2-[4-[1-(fur-2-ylmethyl)-1H-benzoimidazole-2-carbonyl]-piperidin-1-yl]-ethyl]-3-(4-trifluoromethyl-phenyl)-pyrrolidine;

1-(3,4,5-Trimethoxy-benzoyl)-3-[2-[4-[1-(fur-2-ylmethyl)-1H-benzoimidazole-2-carbonyl]-piperidin-1-yl]-ethyl]-3-(2,4-difluoro-phenyl)-pyrrolidine;

1-(3-Isopropoxy-phenyl-acetyl)-3-[2-[4-[1-(fur-2-ylmethyl)-1H-benzoimidazole-2-carbonyl]-piperidin-1-yl]-ethyl]-3-(3,4-dimethoxy-phenyl)-pyrrolidine;

1-(3-Isopropoxy-phenyl-acetyl)-3-[2-[4-[1-(fur-2-ylmethyl)-1H-benzoimidazole-2-carbonyl]-piperidin-1-yl]-ethyl]-3-(benzo[1,3]dioxol-5-yl)-pyrrolidine;

1-(3-Isopropoxy-phenyl-acetyl)-3-[2-[4-[1-(fur-2-ylmethyl)-1H-benzoimidazole-2-carbonyl]-piperidin-1-yl]-ethyl]-3-(3,4-dichloro-phenyl)-pyrrolidine;

1-(2,4-Dichloro-benzoyl)-3-[2-[4-[1-(fur-2-ylmethyl)-1H-benzoimidazole-2-carbonyl]-piperidin-1-yl]-ethyl]-3-(benzo[1,3]dioxol-5-yl)-pyrrolidine;

1-(3,4,5-Trimethoxy-benzoyl)-3-[2-[4-[1-(fur-2-ylmethyl)-1H-benzoimidazole-2-carbonyl]-piperidin-1-yl]-ethyl]-3-phenyl-pyrrolidine;

1-(4-Ethyl acetoxy-3,5-dimethoxy-benzoyl)-3-[2-[4-[1-(fur-2-ylmethyl)-1H-benzoimidazole-2-carbonyl]-piperidin-1-yl]-ethyl]-3-(3,4-dichloro-phenyl)-pyrrolidine;

1-(4-Ethyl acetoxy-3,5-dimethoxy-benzoyl)-3-[2-[4-[1-(fur-2-ylmethyl)-1H-benzoimidazole-2-carbonyl]-piperidin-1-yl]-ethyl]-3-(3,4-dimethoxy-phenyl)-pyrrolidine;

1-(4-Ethyl acetoxy-3,5-dimethoxy-benzoyl)-3-[2-[4-[1-(fur-2-ylmethyl)-1H-benzoimidazole-2-carbonyl]-piperidin-1-yl]-ethyl]-3-phenyl-pyrrolidine;

1-(3-Ethyl acetoxy-4,5-dimethoxy-benzoyl)-3-[2-[4-[1-(fur-2-ylmethyl)-1H-benzoimidazole-2-carbonyl]-piperidin-1-yl]-ethyl]-3-(3,4-dichloro-phenyl)-pyrrolidine;

1-(3-Ethyl acetoxy-4,5-dimethoxy-benzoyl)-3-[2-[4-[1-(fur-2-ylmethyl)-1H-benzoimidazole-2-carbonyl]-piperidin-1-yl]-ethyl]-3-phenyl-pyrrolidine;

1-(4-Acetoxy-3,5-dimethoxy-benzoyl)-3-[2-[4-[1-(fur-2-ylmethyl)-1H-benzoimidazole-2-carbonyl]-piperidin-1-yl]-ethyl]-3-(3,4-dichloro-phenyl)-pyrrolidine;

1-(4-Acetoxy-3,5-dimethoxy-benzoyl)-3-[2-[4-[1-(fur-2-ylmethyl)-1H-benzoimidazole-2-carbonyl]-piperidin-1-yl]-ethyl]-3-(3, 4-dimethoxy-phenyl)-pyrrolidine;

1-(4-Acetoxy-3,5-dimethoxy-benzoyl)-3-[2-[4-[1-(fur-2-ylmethyl)-1H-benzoimidazole-2-carbonyl]-piperidin-1-yl]-ethyl]-3-phenyl)-pyrrolidine;

1-(3-Acetoxy-4,5-dimethoxy-benzoyl)-3-[2-[4-[1-(fur-2-ylmethyl)-1H-benzoimidazole-2-carbonyl]-piperidin-1-yl]-ethyl]-3-(3,4-dichloro-phenyl)-pyrrolidine;

1-(3-Acetoxy-4,5-dimethoxy-benzoyl)-3-[2-[4-[1-(fur-2-ylmethyl)-1H-benzoimidazole-2-carbonyl]-piperidin-1-yl]-ethyl]-3-phenyl-pyrrolidine;

1-(3,4,5-Trimethoxy-benzyl)-3-[2-[4-[1-(fur-2-ylmethyl)-1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1-(fur-2-ylmethyl)-1H-benzoimidazole-2-carbonyl]-piperidin-1-yl]-ethyl]-3-(3,4-dimethoxy-phenylmethyl)-2-oxo-pyrrolidine;

1-(3,4,5-Trimethoxy-benzyl)-3-[2-[4-[1-(fur-2-ylmethyl)-1H-benzoimidazole-2-carbonyl]-piperidin-1-yl]-ethyl]-3-(3,4-dichloro-phenylmethyl)-2-oxo-pyrrolidine;

1-(3,4,5-Trimethoxy-benzyl)-3-[2-[4-[1-(fur-2-ylmethyl)-1H-benzoimidazole-2-carbonyl]-piperidin-1-yl]-ethyl]-3-(4-fluoro-phenylmethyl)-2-oxo-pyrrolidine;

1-(3,4,5-Trimethoxy-benzyl)-3-[2-[4-[1-(fur-2-ylmethyl)-1H-benzoimidazole-2-carbonyl]-piperidin-1-yl]-ethyl]-3-(4-methoxy-phenylmethyl)-2-oxo-pyrrolidine;

1-(3,4,5-Trimethoxy-benzyl)-3-[2-[4-[1-(fur-2-ylmethyl)-1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1-(fur-2-ylmethyl)-1H-benzoimidazole-2-carbonyl]-piperidin-1-yl]-ethyl]-3-(2,4-difluoro-phenylmethyl)-2-oxo-pyrrolidine;

1-Benzyl-3-[2-[4-[1-(fur-2-ylmethyl)-1H-benzoimidazole-2-carbonyl]-piperidin-1-yl]-ethyl]-3-(phenylmethyl)-2-oxo-pyrrolidine;

1-Benzyl-3-[2-[4-[1-(fur-2-ylmethyl)-1H-benzoimidazole-2-carbonyl]-piperidin-1-yl]-ethyl]-3-(phenylmethyl)-2-oxo-piperidine;

1-Benzyl-3-[2-[4-[1-(fur-2-ylmethyl)-1H-benzoimidazole-2-carbonyl]-piperidin-1-yl]-ethyl]-3-(4-fluoro-phenylmethyl)-2-oxo-piperidine;

1-Benzyl-3-[2-[4-[1-(fur-2-ylmethyl)-1H-benzoimidazole-2-carbonyl]-piperidin-1-yl]-ethyl]-3-(4-methoxy-phenylmethyl)-2-oxo-piperidine;

1-Benzoyl-3-[2-[4-[1-(2-ethoxy-ethyl)-1H-benzoimidazole-2-carbonyl]-piperidin-1-yl]-ethyl]-3-(3,4-dichloro-phenyl)-pyrrolidine;

1-(3,5-Bis(trifluoromethyl)-benzoyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3-trifluoromethyl-phenyl)-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(4-trifluoromethyl-phenyl)-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(2,4-difluoro-phenyl)-pyrrolidine;

1-(3-Isopropoxy-phenyl-acetyl)-3-[2-[4-[1-(2-ethoxy-ethyl)-1H-benzoimidazole-2-carbonyl]-piperidin-1-yl]-ethyl]-3-(3,4-dimethoxy-phenyl)-pyrrolidine;

1-(3-Isopropoxy-phenyl-acetyl)-3-[2-[4-[1-(2-ethoxy-ethyl)-1H-benzoimidazole-2-carbonyl]-piperidin-1-yl]-ethyl]-3-(benzo[1,3]dioxol-5-yl)-pyrrolidine;

1-(3-Isopropoxy-phenyl-acetyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine;

1-(2,4-Dichloro-benzoyl)-3-[2-[4-[1-(2-ethoxy-ethyl)-1H-benzoimidazole-2-carbonyl]-piperidin-1-yl]-ethyl]-3-(benzo[1,3]dioxol-5-yl)-pyrrolidine;

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine;

1-(4-Ethyl acetoxy-3,5-dimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine;

1-(4-Ethyl acetoxy-3,5-dimethoxy-benzoyl)-3-[2-[4-[1-(2-ethoxy-ethyl)-1H-benzoimidazole-2-carbonyl]-piperidin-1-yl]-ethyl]-3-(3,4-dimethoxy-phenyl)-pyrrolidine;

1-(4-Ethyl acetoxy-3,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine;

1-(3-Ethyl acetoxy-4,5-dimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine;

1-(3-Ethyl acetoxy-4,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine;

1-(4-Acetoxy-3,5-dimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine;

1-(4-Acetoxy-3,5-dimethoxy-benzoyl)-3-[2-[4-[1-(2-ethoxy-ethyl)-1H-benzoimidazole-2-carbonyl]-piperidin-1-yl]-ethyl]-3-(3,4-dimethoxy-phenyl)-pyrrolidine;

1-(4-Acetoxy-3,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine;

1-(3-Acetoxy-4,5-dimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine;

1-(3-Acetoxy-4,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(3,4-dimethoxy-phenylmethyl)-2-oxo-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(3,4-dichloro-phenylmethyl)-2-oxo-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(4-fluoro-phenylmethyl)-2-oxo-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(4-methoxy-phenylmethyl)-2-oxo-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(phenylmethyl)-2-oxo-pyrrolidine;

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(2,4-difluoro-phenylmethyl)-2-oxo-pyrrolidine;

1-Benzyl-3-[2-[4-[1-(2-ethoxy-ethyl)-1H-benzoimidazole-2-carbonyl]-piperidin-1-yl]-ethyl]-3-(phenylmethyl)-2-oxo-pyrrolidine;

1-Benzyl-3-[2-[4-[1-(2-ethoxy-ethyl)-1H-benzoimidazole-2-carbonyl]-piperidin-1-yl]-ethyl]-3-(phenylmethyl)-2-oxo-piperidine;

1-Benzyl-3-[2-[4-[1-(2-ethoxy-ethyl)-1H-benzoimidazole-2-carbonyl]-piperidin-1-yl]-ethyl]-3-(4-fluoro-phenylmethyl)-2-oxo-piperidine;

1-Benzyl-3-[2-[4-[1-(2-ethoxy-ethyl)-1H-benzoimidazole-2-carbonyl]-piperidin-1-yl]-ethyl]-3-(4-methoxy-phenylmethyl)-2-oxo-piperidine.

The compounds of formula (1) may be synthesized by use of the following synthetic procedures to produce intermediates or final compounds of the invention:

Reaction Scheme A.1 relates to the synthesis of compounds of formula (1) by alkylation of intermediates derived from alcohols of structure 2.

Reaction Scheme A.2 relates to the synthesis of compounds of formula (1) by reductive amination of aldehydes derived from alcohols of structure 2.

Reaction Scheme B relates to the synthesis of alcohols of structure 2 in which $G_3$ is —$CH_2$— used as a starting material in Reaction Schemes A.1 and A.2.

Reaction Scheme C relates to a synthesis of alcohols of structure 2 in which m is 2, q is 1, r is 0, and $G_3$ is —$CH_2$— and relates to the synthesis of intermediates of structure 8 used to prepare alcohols of structure 2 in Reaction Scheme B.

Reaction Scheme D relates to a synthesis of alcohols of structure 2 in which r is 1 and $G_1$ is —$CH_2$— used as a starting material in Reaction Scheme A.1 and A.2.

Reaction Scheme E relates to a synthesis of alcohols of structure 2 in which r is 0 and $G_1$ is —$CH_2$— used as a starting material in Reaction Scheme A.1 and A.2.

A general synthetic procedure for preparing these compounds of formula (1) is set forth in Reaction Scheme A.1.

The reagents and starting materials are readily available to one of ordinary skill in the art. In Reaction Scheme A.1, all substituents, unless otherwise indicated, are as previously defined

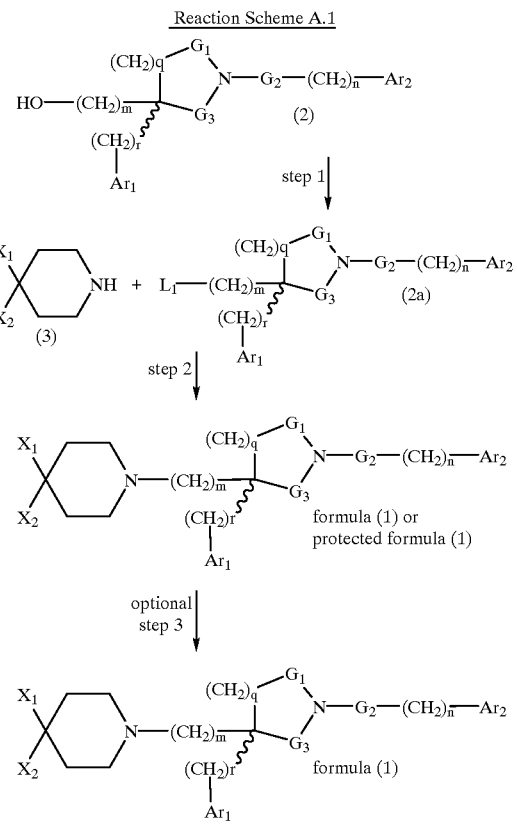

In Reaction Scheme A.1, step 1, the hydroxy group of an appropriate alcohol of structure 2 is converted to an appropriate leaving group to give a compound of structure 2a. An appropriate alcohol of structure 2 is one in which the stereochemistry is as desired in the final product of formula (1) and m, n, q, r, $G_1$, $G_2$, $G_3$, $Ar_1$ and $Ar_2$ are as desired in the final product of formula (1). Alternately, an appropriate alcohol of structure 2 can be one in which the stereochemistry gives rise after resolution to stereochemistry as desired in the final product of formula (1) and m, n, q, r, $G_1$, $G_2$, $G_3$, $Ar_1$ and $Ar_2$ are as desired in the final product of formula (1). An appropriate alcohol of structure 2 can also be one in which the stereochemistry is as desired in the final product of formula (1); and m, n, q, r, $G_1$, $G_2$, and $G_3$ are as desired in the final product of formula (1); and $Ar_1$ and/or $Ar_2$ gives rise upon deprotection to $Ar_1$ and/or $Ar_2$ as desired in the final product of formula (1). Alternately, an appropriate alcohol of structure 2 can also be one in which the stereochemistry gives rise after resolution to stereochemistry as desired in the final product of formula (1); and m, n, q, r, $G_1$, $G_2$, and $G_3$ are as desired in the final product of formula (1); and $Ar_1$ and/or $Ar_2$ gives rise upon deprotection to $Ar_1$ and/or $Ar_2$ as desired in the final product of formula (1). An appropriate leaving group, $L_1$, is one which can be displaced by a piperidine of structure 3 to give rise to a compound of formula (1). Appropriate leaving groups, $L_1$, include but are not limited to chloro, bromo, iodo, mesylate, tosylate, benzenesulfonate, trifluoromethanesulfonate, and the like. The conversion of hydroxy groups to leaving groups such as chloro, bromo, iodo, mesylate, tosylate, benzenesulfonate, and trifluoromethanesulfonate is well known and appreciated in the art.

For example, compounds in which $L_1$ is bromo are formed by contacting an appropriate alcohol of structure 2 with 1.0 to 1.5 molar equivalents of carbon tetrabromide and 1.0 to 1.75 molar equivalents triphenylphosphine. (P. J. Kocienski et al. *JOC* 42, 353–355 (1977)). The reaction is carried out by combining the alcohol of structure 2 with carbon tetrabromide in a suitable solvent, such as dichloromethane or chloroform and then adding a solution of triphenylphosphine in a suitable solvent, such as dichloromethane or chloroform. Generally the reaction is carried out at temperatures of from −10° C. to ambient temperature. Generally, the reactions require from 5 minutes to 24 hours. The product can be isolated and purified by techniques well known in the art, such as extraction, evaporation, trituration, chromatography, and recrystallization.

Compounds in which $L_1$ is bromo are also formed by contacting an appropriate alcohol of structure 2 with a slight molar excess of triphenylphosphine dibromide. (R. F Borch et al. *JACS* 99, 1612–1619 (1977)). The reaction may be carried out by contacting an appropriate alcohol of structure 2 with preformed triphenylphosphine dibromide. The reaction is carried out in a suitable solvent, such as tetrahydrofuran and diethyl ether. The reaction is carried out in the presence of a suitable base, such as pyridine. Generally the reaction is carried out at temperatures of from 0° C. to 50° C. Generally, the reactions require from 5 minutes to 24 hours. The product can be isolated and purified by techniques well known in the art, such as extraction, evaporation, trituration, chromatography, and recrystallization.

Alternately, for example, compounds in which $L_1$ is mesylate are formed by contacting an appropriate alcohol of structure 2 with a molar excess of methanesulfonyl chloride. The reaction is carried out in a suitable solvent, such as dichloromethane, chloroform, toluene, benzene, or pyridine. The reaction is carried out in the presence of a suitable base, such as triethylamine, diisopropylethylamine, or pyridine. Generally the reaction is carried out at temperatures of from −20° C. to 50° C. Generally, the reactions require from 1 hour to 24 hours. The product can be isolated and purified by techniques well known in the art, such as extraction, evaporation, trituration, chromatography, and recrystallization.

Compounds of structure 2a in which $L_1$ is iodo can be prepared from compounds of structure 2a in which $L_1$ is mesylate, chloro, or bromo by an exchange reaction, such as the Finkelstein reaction.

For example, a compound of structure 2a in which $L_1$ is mesylate, chloro, or bromo is contacted with from 1.0 to 10.0 molar equivalents of an iodide salt, such as sodium iodide or potassium iodide. The reaction is carried out in a suitable solvent, such as acetone, butanone, tetrahydrofuran, tetrahydrofuran/water mixtures, toluene, and acetonitrile. Generally, the reaction is carried out at temperatures of from ambient temperature to the refluxing temperature of the solvent. Generally, the reactions require from 1 hour to 24 hours. The product can be isolated and purified by techniques well known in the art, such as extraction, evaporation, trituration, chromatography, and recrystallization.

In Reaction Scheme A.1, step 2, the compound of structure 2a reacts with an appropriate piperidine compound of structure 3 or a salt thereof to give a protected compound of formula (1) or a compound of formula (1).

An appropriate piperidine of structure 3 or salt thereof is one in which $X_1$ and $X_2$ are as desired in the final product of formula (1) or $X_1$ and $X_2$ give rise after deprotection to $X_1$ and $X_2$ are as desired in the final product of formula (1). Appropriate piperidines of structure 3 are well known and appreciated in the art and are described in International Patent Application (PCT) No. WO 92/06086, U.S. Pat. No. 4,908,372, Mar. 13, 1990, U.S. Pat. No. 4,254,129, Mar. 3, 1981, U.S. Pat. No. 4,254,130, Mar. 3, 1981, U.S. Pat. No. 4,285,958, Apr. 25, 1981, U.S. Pat. No. 4,550,116, Oct. 29, 1985, and European Patent Application No. 0 533 344, published Mar. 24, 1993. Appropriate piperidines of structure 3 wherein $X_1$ and $Z_1$ taken together form a second bond between the carbon atoms bearing $X_1$ and $Z_1$ may be prepared by dehydration of the corresponding compound wherein $X_1$ is hydroxy by procedures generally known in the art, such as refluxing in strongly acidic solution. Appropriate piperidines of structure 3 may also be prepared by addition of readily available organometallic reagents to suitably protected 4-piperidinones or suitably protected isonipecotic acid derivatives, by methods known in the art such as described by G. D. Maynard et al., *Bioorg. and Med. Chem. Lets.*, 3, 753–756 (1993). Appropriate piperidines of structure 3 may also be prepared from readily available starting materials or by methods known analogously in the art, such as described by C. G. Wahlgren and A. W. Addison, *J. Heterocyclic Chem.*, 26, 541 (1989), R. Iemura and H. Ohtka, *Chem. Pharm. Bull.*, 37, 967–972 (1989), and K. Ito and G. Tsukamoto, *J. Heterocyclic Chem.*, 24, 31 (1987), by carrying out suitable deprotections, protections, and alkylations, as are well known in the art, in the order and number required for formation of an appropriate piperidine of structure 3.

For example, the compound of structure 2a is contacted with an appropriate piperidine compound of structure 3 or salt thereof to give a protected compound of formula (1) or a compound of formula (1). The reaction is carried out in a suitable solvent, such as dioxane, tetrahydrofuran, tetrahydrofuran/water mixtures, acetone, acetone/water mixtures, ethyl acetate, ethyl acetate/water mixtures, pyridine, acetonitrile, toluene, toluene/water mixtures, chlorobenzene, or dimethylformamide. The reaction is carried out in the presence of from 1.0 to 6.0 molar equivalents of a suitable base, such as sodium carbonate, sodium bicarbonate, potassium carbonate, potassium bicarbonate, triethylamine, pyridine, or diisopropylethylamine. When a salt of an appropriate piperidine of structure 3 is used, an additional molar excess of a suitable base may be required. The reaction may be facilitated by the addition of a catalytic amount, 0.1 to 0.5 molar equivalents, of an iodide salt, such as sodium iodide, potassium iodide, or tetrabutyl ammonium iodide. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme A.1, optional step 3, a compound of formula (1) or a protected compound of formula (1) in which Z is hydrogen is modified to give a compound of formula (1) or a protected compound of formula (1) in which Z is not hydrogen. Also encompassed by Reaction Scheme A.1, optional step 3, a protected compound of formula (1) is deprotected to give a compound of formula (1).

A modification reaction, encompasses the formation of amides and the alkylation of the benzoimidazole nitrogen. The formation of amides from esters and acids is well known and appreciated in the art. The alkylation of a benzoimidazole nitrogen using a suitable alkylating agent is well known and appreciated in the art. The reaction is carried out in a suitable solvent, such as dioxane, tetrahydrofuran, tetrahydrofuran/water mixtures, acetone, or acetonitrile. A suitable alkylating agent is one which transfers the group Z as desired in the final product of formula (1) or a protected group Z which gives rise after protection to Z as desired in the final product of formula (1). The reaction is carried out in the presence of from 1.0 to 6.0 molar equivalents of a suitable base, such as sodium carbonate, sodium bicarbonate, potassium carbonate, potassium bicarbonate, triethylamine, 1,8-diazabicyclo[5.4.0]undec-7-ene, 1,5-diazabicyclo[4.3.0]non-5-ene, potassium bis-(trimethylsilyl)amide, lithium bis-(trimethylsilyl)amide, or diusopropylethylamine. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization. Alternately, the compounds of formula (1) or a protected compound of formula (1) in which Z is hydrogen and having a benzoimidazole-2-carbonyl can be alkylated by the Mitsunobu reaction using a suitable alcohol. A suitable alcohol is one which transfers the group Z as desired in the final product of formula (1) or a protected group Z which gives rise after deprotection to Z as desired in the final product of formula (1).

A deprotection reaction, such as the removal of hydroxy protecting groups or hydrolysis of an ester, utilizing suitable protecting groups such as those described in *Protecting Groups in Organic Synthesis* by T. Greene is well known and appreciated in the art.

A general synthetic procedure for preparing the compounds of formula (1) by reductive amination is set forth in Reaction Scheme A.2. The reagents and starting materials are readily available to one of ordinary skill in the art. In Scheme A.2, all substituents, unless otherwise indicated, are as previously defined. For the preparation of compounds of formula (1) in which $Ar_1$ is pyridyl the reductive amination as set forth in Reaction Scheme A.2 is preferred.

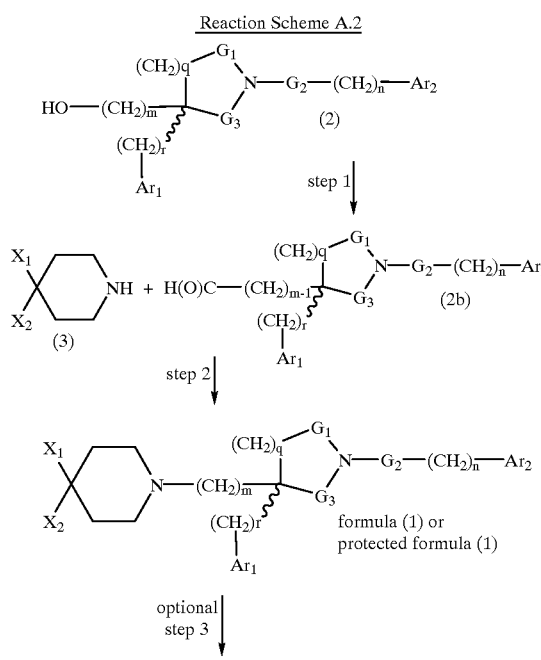

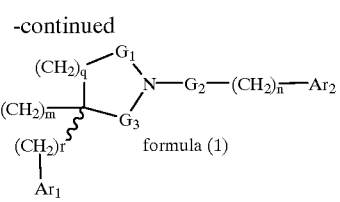

In Reaction Scheme A.2, step 1, an appropriate alcohol of structure 2 is oxidized to an aldehyde of structure 2b. An appropriate alcohol of structure 2 is as described in Reaction Scheme A.1

For example, about two molar equivalents of dimethyl sulfoxide are added dropwise to a solution of oxalyl chloride, pyridine sulfur trioxide complex, or trifluoroacetic anhydride in dichloromethane, at approximately −60° C. After the addition is complete, the reaction is stirred for approximately two minutes. A molar equivalent of the alcohol of structure 2 either neat or as a solution in dichloromethane is added. After the addition is complete the reaction mixture is stirred for 5 to 45 minutes, then a 3 to 5 molar equivalents of triethylamine is added. The reaction mixture is allowed to stir with warming to ambient temperature over 30 minutes to 2 hours. The product can be isolated and purified by techniques well known in the art, such as extraction, evaporation, chromatography, and recrystallization.

In Reaction Scheme A.2, step 2, the compound of structure 2b is contacted with an appropriate piperidine of structure 3 or salt thereof in a reductive amination to give a protected compound of formula (1) or a compound of formula (1). An appropriate piperidine of structure 3 or salt thereof is as defined in Reaction Scheme A.1.

For example, the compound of structure 2b is contacted with an appropriate piperidine compound of structure 3 or salt thereof. The reaction is carried out using a molar excess of a suitable reducing agent such as sodium borohydride or sodium cyanoborohydride with sodium cyanoborohydride being preferred. The reaction is carried out in a suitable solvent, such as ethanol, methanol, dichloromethane, or dimethylformamide. Generally, the reaction is carried out at temperatures of from 0° C. to 50° C. Generally, the reactions require 1 to 72 hours. The product can be isolated and purified by techniques well known in the art, such as extraction, evaporation, chromatography, and recrystallization.

In Reaction Scheme A.2, optional step 3, a compound of formula (1) or a protected compound of formula (1) in which Z is hydrogen is modified to give a compound of formula (1) or a protected compound of formula (1) in which Z is not hydrogen and/or a protected compound of formula (1) is deprotected to give a compound of formula (1) as described in Reaction Scheme A.1, optional step 3.

Reaction Scheme B is a general scheme for preparing alcohols of structure 2 in which $G_3$ is —$CH_2$— used as a starting material in Reaction Schemes A.1 and A.2. The reagents and starting materials are readily available to one of ordinary skill in the art. In Reaction Scheme B, all substituents, unless otherwise indicated, are as previously defined.

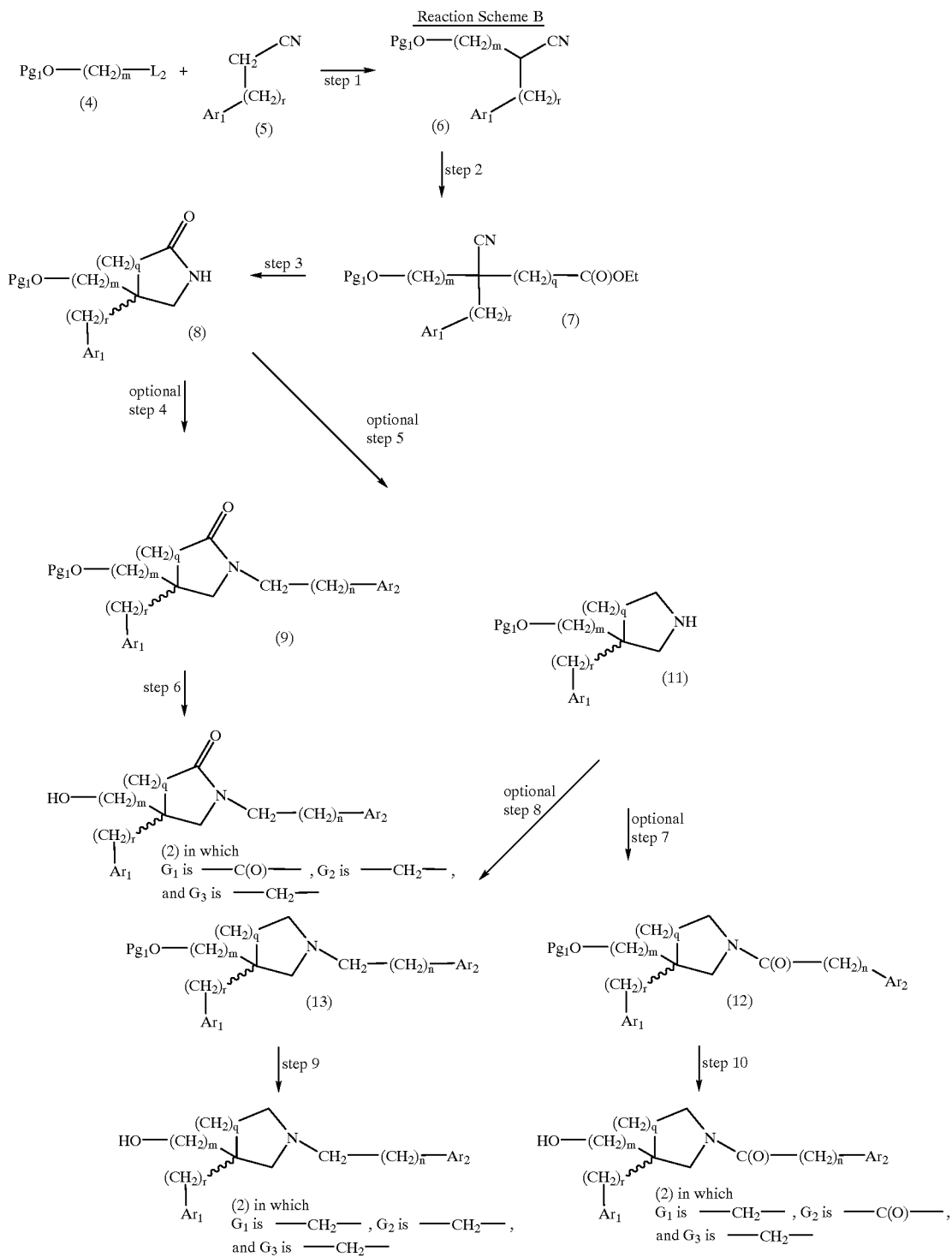

Reaction Scheme B

In Reaction Scheme B, step 1, an appropriate nitrile of structure 5 is alkylated with an appropriate protected alcohol of structure 4 to give an ω-protected-hydroxyalkyl-nitrile of structure 6.

An appropriate nitrile of structure 5 is one in which r and $Ar_1$ are as desired in the final product of formula (1) or $Ar_1$ gives rise after deprotection to an $Ar_1$ as desired in the final product of formula (1). An appropriate protected alcohol of structure 4 is one in which m is as desired in the final product of formula (1) and the leaving group, $L_2$, is one which can be displaced by an anion derived from an appropriate nitrile of structure 5. Suitable leaving groups include but are not limited to chloro, bromo, iodo, and mesylate with chloro and bromo being preferred. The selection and use of a suitable hydroxy protecting group, $Pg_1$, such as those described in *Protecting Groups in Organic Synthesis* by T. Greene are well known and appreciated in the art. The use of tetrahyropyran-2-yl and t-butyldimethylsilyl are generally preferred.

For example, the appropriate nitrile of structure 5 is contacted with 1.0 to 1.2 molar equivalents of the appropriate protected alcohol of structure 4. The reaction is carried out in the presence of an equimolar amount of a suitable base, such as sodium hydride, sodium bis-(trimethylsilyl) amide, potassium t-butoxide, and lithium diisopropylamide with sodium hydride and sodium bis-(trimethylsilyl)amide being preferred. The reaction is carried out in a solvent, such as dimethylformamide or tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme B, step 2, the ω-protected-hydroxyalkyl-nitrile of structure 6 is alkylated with ethyl bromoacetate or ethyl bromopropionate to give a nitrile ester compound of structure 7.

For example, the ω-protected-hydroxyalkyl-nitrile of structure 6 is contacted with approximately a molar equivalent of ethyl bromoacetate or ethyl bromopropionate. The reaction is carried out in the presence a approximately a molar equivalent of a suitable base, such as sodium bis-(trimethylsilyl)amide or lithium diisopropylamide. The reaction is carried out in a suitable solvent, such as tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, chromatography, and recrystallization.

In Reaction Scheme B, step 3, the nitrile ester compound of structure 7 is reduced and cyclized to give an oxo-3-(ω-protected-hydroxyalkyl) compound of structure 8. The cyclization may occur spontaneously after the reduction or may be carried out in a separate step after the isolation of the intermediate amine.

For example, the nitrile ester compound of structure 7 is contacted with an excess of an appropriate reducing agent, such as sodium borohydride in the presence of cobalt (II) chloride hexahydrate or hydrogen in the presence of a suitable catalyst, such as Raney nickel or platinum oxide. For compounds of structure 7 in which $Ar_1$ is thienyl, sodium borohydride in the presence of cobalt (II) chloride hexahydrate is preferred.

When sodium borohydride in the presence of cobalt chloride is used, the reaction is carried out in a suitable solvent, such as methanol, or ethanol. The reaction is generally carried out at temperatures of from 0° C. to 50° C. Generally, the reactions require 1 to 72 hours. Generally, the cyclization occurs spontaneously under these conditions. The product can be isolated and purified by techniques well known in the art, such as extraction with aqueous acid, evaporation, trituration, chromatography, and recrystallization.

When Raney nickel is used, the reaction is carried out in a suitable solvent containing ammonia, such as ethanol/aqueous ammonium hydroxide or methanol/aqueous. ammonium hydroxide. The reaction is generally carried out at temperatures of from ambient temperature to 70° C. The reaction is carried out with hydrogen at pressures of from 15 psi to 120 psi in an apparatus designed for carrying out reactions under pressure, such as a Parr hydrogenation apparatus. Generally, the cyclization occurs spontaneously under these conditions. The product can be isolated by carefully removing the catalyst by filtration and evaporation. The product can be purified by extraction, evaporation, trituration, chromatography, and recrystallization.

When platinum oxide is used, the reaction is carried out in a suitable solvent such as ethanol, methanol, chloroform, ethanol/chloroform mixtures, or methanol/chloroform mixtures. The reaction is generally carried out at temperatures of from ambient temperature to 50° C. The reaction is carried out with hydrogen at pressures of from 15 psi to 120 psi in an apparatus designed for carrying out reactions under pressure, such as a Parr hydrogenation apparatus. Generally, an amine intermediate is obtained under these conditions and is isolated by carefully removing the catalyst by filtration and evaporation. The amine intermediate is cyclized by heating in a suitable solvent, such as ethanol, methanol, toluene, or chlorobenzene. The reaction is generally carried out at temperatures of from 50° C. to the refluxing temperature of the solvent. Generally, the reaction requires 8 to 48 hours. The product can be purified by extraction, evaporation, trituration, chromatography, and recrystallization.

In Reaction Scheme B, optional step 4, the oxo-3-(ω-protected-hydroxyalkyl) compound of structure 8 is alkylated with an appropriate alkylating agent, X—$CH_2$—$(CH_2)_n$—$Ar_2$, to an 1-arylaklyl-oxo compound of structure 9. An appropriate alkylating agent, X—$CH_2$—$(CH_2)_n$—$Ar_2$, is one in which X is methanesulfonyl, chloro, bromo, or iodo; n is as desired in the final product of formula (1), and $Ar_2$ is as desired in formula (1) or gives rise after deprotection to $Ar_2$ as desired in formula (1).

For example, the oxo-3-(ω-protected-hydroxyalkyl) compound of structure 8 is contacted with from 1 to 5 molar equivalents of an appropriate alkylating agent, X—$CH_2$-$(CH_2)_n$—$Ar_2$. The reaction is carried out in a suitable solvent, such as tetrahydrofuran, dimethyl sulfoxide, or dimethylformamide. The reaction is carried out in the presence of a base, such as sodium hydride, potassium t-butoxide, potassium bis(trimethylsilyl)amide, or lithium diisopropylamide with sodium hydride and potassium bis (trimethylsilyl)amide being preferred. The reaction is generally carried out at temperatures of from 0° C. to 50° C. Generally, the reactions require 1 to 72 hours. The product can be isolated and purified by techniques well known in the art, such as extraction, evaporation, trituration, chromatography, and recrystallization.

In Reaction Scheme B, step 6, the 1-arylaklyl-oxo-3-(ω-protected-hydroxyalkyl) compound of structure 9 is deprotected to give an alcohol of structure 2 in which $G_1$ is —C(O)—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme B, optional step 5, the oxo-3-(ω-protected-hydroxyalkyl) compound of structure 8 is reduced to give a 3-(ω-protected-hydroxyalkyl) compound of structure 11.

For example, the oxo-3-(ω-protected-hydroxyalkyl) compound of structure 8 is contacted with an excess of a suitable reducing agent, such as lithium aluminum hydride, aluminum hydride, or borane dimethyl sulfide complex. The reaction is carried out in a suitable solvent, such as tetrahydrofuran. The reaction is generally carried out at temperature of from 0° C. to the refluxing temperature of the solvent. Generally, the reactions require 1 to 72 hours. The product can be isolated and purified by techniques well known in the art, such as quenching of borane or aluminum complexes, extraction, evaporation, trituration, chromatography, and recrystallization.

In Reaction Scheme B, optional step 7, the 3-(ω-protected-hydroxyalkyl) compound of structure 11 is aroylated with an appropriate aroyl acid, aroyl ester, aroyl halide, aryl anhydride, or aryl mixed anhydride, A—C(O)—(CH$_2$)$_n$—Ar$_2$, to give an 1-aroyl-3-(ω-protected-hydroxyalkyl) compound of structure 12. An appropriate aroyl acid, aroyl ester, aroyl halide, aryl anhydride, or aryl mixed anhydride, A—C(O)—(CH$_2$)$_n$—Ar$_2$, is one in which A is hydrogen; an activated ester, such as O-hydroxysuccinimide, O-hydroxybenzotriazole; an activated leaving group, such as chloro, bromo; or an acyl group which forms an anhydride; or mixed anhydride, n is as desired in the final product of formula (1), and Ar$_2$ is as desired in formula (1) or give rise after deprotection to Ar$_2$ as desired in formula (1).

For example, the 3-(ω-protected-hydroxyalkyl) compound of structure 11 is contacted with 1 to 1.5 molar equivalents of an appropriate aroyl acid, aroyl ester, aroyl halide, aryl anhydride, or aryl mixed anhydride, A—C(O)—(CH$_2$)$_n$—Ar$_2$. The reaction is carried out in a suitable solvent, such as dichloromethane, tetrahydrofuran, acetonitrile, dimethylformamide, or pyridine. The reaction is carried out in the presence of a base, such as sodium carbonate, sodium bicarbonate, triethylamine, N-methylmorpholine, diisopropylethylamine, or pyridine. The reaction is generally carried out at temperatures of from −20° C. to 50° C. Generally, the reactions require 1 to 6 hours. The product can be isolated and purified by techniques well known in the art, such as extraction, evaporation, trituration, chromatography, and recrystallization.

In Reaction Scheme B, optional step 8, the 3-(ω-protected-hydroxyalkyl) compound of structure 11 is alkylated with an appropriate alkyl halide, X$_3$—CH$_2$—(CH$_2$)$_n$—Ar$_2$, to give an 1-arylalkyl-3-(ω-protected-hydroxyalkyl) compound of structure 13. An appropriate alkyl halide, X$_3$—CH$_2$—(CH$_2$)$_n$—Ar$_2$, is one in which X$_3$ is chloro or bromo, n is as desired in the final product of formula (1), and Ar$_2$ is as desired in formula (1) or gives rise after deprotection to Ar$_2$ as desired in formula (1).

For example, the 3-(ω-protected-hydroxyalkyl) compound of structure 11 is contacted with from 1.0 to 1.2 molar equivalents of an appropriate alkyl halide, X$_3$—CH$_2$—(CH$_2$)$_n$—Ar$_2$. The reaction is carried out in a suitable solvent, such as tetrahydrofuran, dimethyl sulfoxide, acetonitrile, tetrahydrofuran/water, toluene, toluene/water, or dimethylformamide. The reaction is carried out in the presence of a base, such as sodium carbonate, sodium bicarbonate, potassium carbonate, triethylamine, diisopropylethylamine, or pyridine. The reaction is generally carried out at temperatures of from 0° C. to reflux temperature of solvent. Generally, the reactions require 1 to 72 hours. The product can be isolated and purified by techniques well known in the art, such as extraction, evaporation, trituration, chromatography, and recrystallization.

In Reaction Scheme B, step 9, the 1-arylaklyl-3-(ω-protected-hydroxyalkyl) compound of structure 13 is deprotected to give an alcohol of structure 2 in which G$_3$, G$_2$, and G$_3$ are —CH$_2$—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme B, step 10, the 1-aroyl-3-(ω-protected-hydroxyalkyl) compound of structure 12 is deprotected to give an alcohol of structure 2 in which G$_1$ is —CH$_2$—, G$_2$ is —C(O)—, and G$_3$ is —CH—.

Reaction Scheme C is a general scheme for preparing intermediates of structure 8 in which m is 2, r is 0, and q is 1 used in Reaction Scheme B to prepare alcohols of structure 2; and for preparing alcohols of structure 2 in which q is 1, r is 0, m is 2, and G$_3$ is —CH$_2$— used as a starting material in Reaction Schemes A.1 and A.2. The reagents and starting materials are readily available to one of ordinary skill in the art. In Reaction Scheme C, all substituents, unless otherwise indicated, are as previously defined.

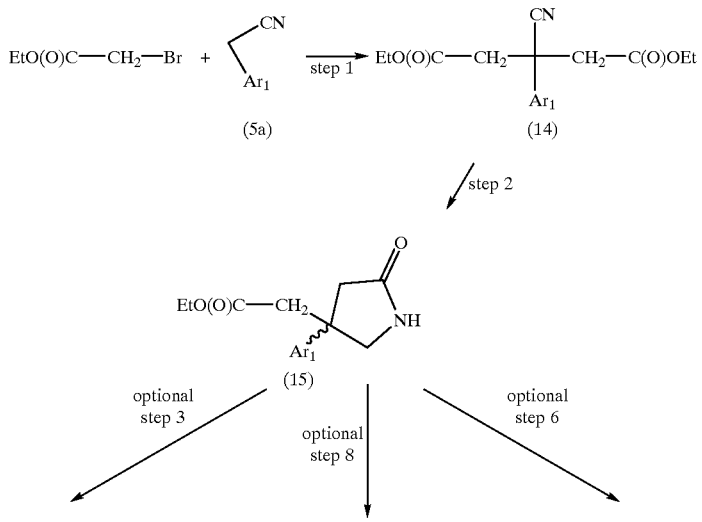

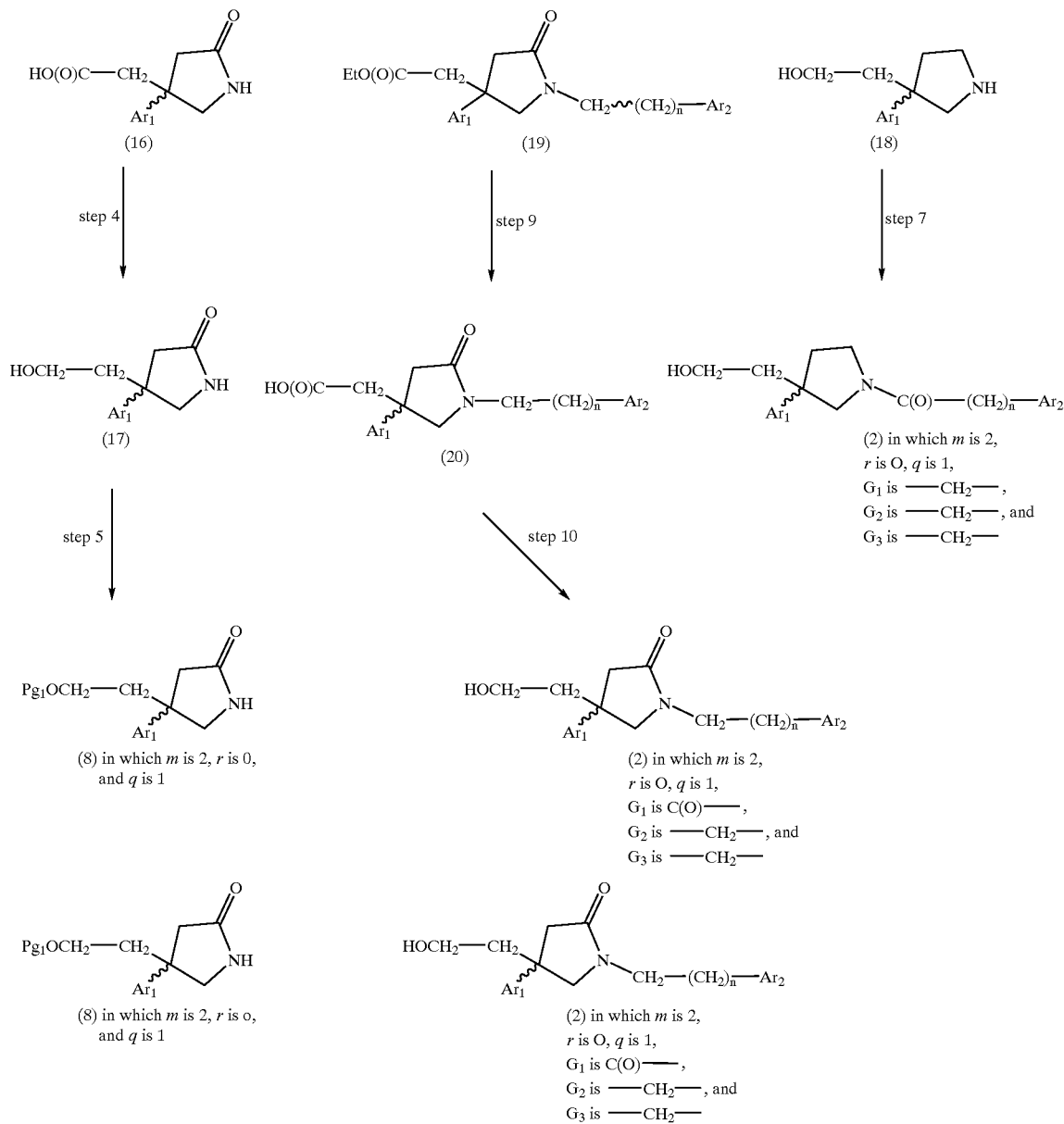

In Reaction Scheme C, step 1, an appropriate aryl-acetonitrile of structure 5a is bis-alkylated with ethyl bromoacetate to give a nitrile bis-ester compound of structure 14. An appropriate aryl-acetonitrile of structure 5a is one in which $Ar_1$ is as desired in the final product of formula (1) or gives rise after deprotection to an $Ar_1$ as desired in the final product of formula (1).

For example, an appropriate aryl-acetonitrile of structure 5a is contacted with 2.0 to 3.0 molar equivalents of ethyl bromoacetate. The reaction is carried out in the presence of approximately 2.0 to 3.0 molar equilvalents of a suitable base, such as sodium bis-(trimethylsilyl)amide or lithium diisopropylamide. The reaction is carried out in a suitable solvent, such as tetrahydrofuran. The reaction is generally carried out at temperatures of from −78° C. to 0° C. Generally, the reactions require 1 to 72 hours. The product can be isolated and purified by techniques well known in the art, such as extraction, evaporation, trituration, distillation, chromatography, and recrystallization.

In Reaction Scheme C, step 2, the nitrile bis-ester compound of structure 14 is reduced and cyclized to give a 5-oxo-3-acetic acid ester pyrrolidine of structure 15.

For example, the nitrile bis-ester compound of structure 14 is contacted with a suitable reducing agent, such as sodium borohydride in the presence of cobalt II chloride hexahydrate or hydrogen in the presence of a suitable catalyst, such as Raney nickel or platinum oxide as taught in Reaction Scheme B, step 3. For compounds of structure 14 in which $Ar_1$ is thienyl, sodium borohydride in the presence of cobalt II chloride hexahydrate is preferred.

In Reaction Scheme C, optional step 3, the 5-oxo-3-acetic acid ester pyrrolidine of structure 15 is hydrolyzed to give a 5-oxo-3-acetic acid pyrrolidine of structure 16.

For example, the 5-oxo-3-acetic acid ester pyrrolidine of structure 15 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme C, step 4, the 5-oxo-3-acetic acid pyrrolidine of structure 16 is reduced to give a 5-oxo-3-(2-hydroxyethyl)-pyrrolidine of structure 17.

For example, the 5-oxo-3-acetic acid pyrrolidine of structure 16 is contacted with a suitable borane reagent, such as borane dimethyl sulfide complex. The reaction is carried out in a suitable solvent, such as tetrahydrofuran. The reaction is generally carried out at a temperature of from 0° C. to the refluxing temperature of the solvent. When complete the reaction is quenched by the careful addition of a suitable aqueous acid solution, such as 1 M hydrochloric acid solution. The product can be isolated and purified by techniques well known in the art, such as extraction, evaporation, trituration, chromatography, and recrystallization.

Alternately, the 5-oxo-3-acetic acid pyrrolidine of structure 16 can be reduced by formation of a mixed anhydride intermediate and contacting the mixed anhydride intermediate with a suitable mild reducing agent, such as sodium borohydride.

For example, the 5-oxo-3-acetic acid pyrrolidine of structure 16 is contacted with 1.2 to 1.7 equivalents of a suitable base, such as N-methylmorpholine, in a suitable solvent, such as tetrahydrofuran or diethyl ether. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 3 hours to allow for the formation of the mixed anhydride. After the formation of the mixed anhydride is complete, sodium borohydride is added. The product can be isolated and purified by techniques well known in the art, such as extraction, evaporation, chromatography, and recrystallization.

In Reaction Scheme C, step 5, the 5-oxo-3-(2-hydroxyethyl)-pyrrolidine of structure 17 is protected to give a 5-oxo-3-(ω-protected-hydroxyethyl)-pyrrolidine of structure 8 in which m is 2, r is 0, and q is 1 used in Reaction Scheme B for preparing compounds of structure 2. The selection and use of suitable protecting groups such as those described in *Protecting Groups in Organic Synthesis* by T. Greene is well known and appreciated in the art.

In Reaction Scheme C optional step 6, the 5-oxo-3-acetic acid ester pyrrolidine of structure 15 is reduced to give a 3-(ω-hydroxyethyl)-pyrrolidine of structure 18 as taught in Reaction Scheme B, optional step 5.

In Reaction Scheme C, step 7, the 3-(ω-hydroxyethyl)-pyrrolidine of structure 18 is aroylated with an appropriate aroyl halide, aryl anhydride, or aryl mixed anhydride, $A_1$—C(O)—$(CH_2)_n$—$Ar_2$, to give an alcohol of structure 2. An appropriate aroyl halide, aryl anhydride, or aryl mixed anhydride, $A_1$—C(O)—$(CH_2)_n$—$Ar_2$, is one in which $A_1$ is an activated leaving group, such as chloro, bromo, or an acyl group which forms an anhydride or mixed anhydride, n is as desired in the final product of formula (1), and $Ar_2$ is as desired in formula (1) or gives rise after deprotection to $Ar_2$ as desired in formula (1).

For example, the 3-(ω-hydroxyethyl)-pyrrolidine of structure 18 is contacted with 1 to 1.1 molar equivalents of an appropriate aroyl halide, aryl anhydride, or aryl mixed anhydride, $A_1$—C(O)—$(CH_2)_n$—$Ar_2$. The reaction is carried out in a suitable solvent, such as tetrahydrofuran, dichloromethane, acetone, ethyl acetate, or diethyl ether. The reaction is carried out in the presence of a base, such as N-methylmorpholine, sodium carbonate, triethylamine, diisopropylethylamine, potassium carbonate or sodium bicarbonate. The reaction is generally carried out at temperatures of from −78° C. to ambient temperature. Generally, the reactions require 1 to 24 hours. The product can be isolated and purified by techniques well known in the art, such as extraction, evaporation, trituration, chromatography, and recrystallization.

Alternately, for example, the 3-(ω-hydroxyethyl)-pyrrolidine of structure 18 is contacted with 1 to 1.1 molar equivalents of an appropriate aroyl halide, aryl anhydride, or aryl mixed anhydride, Al—C(O)—$(CH_2)_n$—$Ar_2$ under Schotten-Baumann conditions. The reaction is carried out in a suitable solvent mixture, such as acetone/water, tetrahydrofuran/water, or ethyl acetate/water. The reaction is carried out in the presence of a base, such as potassium carbonate, potassium bicarbonate, sodium bicarbonate, or sodium carbonate. The reaction is generally carried out at temperatures of from −20° C. to 50° C. Generally, the reactions require 15 minutes to 24 hours. The product can be isolated and purified by techniques well known in the art, such as extraction, evaporation, trituration, chromatography, and recrystallization.

In Reaction Scheme C, optional step 8 the 5-oxo-3-acetic acid ester pyrrolidine of structure 15 is alkylated with an appropriate alkyl halide, $X_4$—$CH_2$—$(CH_2)_n$—$Ar_2$, to give an 1-arylalkyl-5-oxo-3-acetic acid ester pyrrolidine of structure 19. An appropriate alkyl halide, $X_4$—$CH_2$—$(CH_2)$—$Ar_2$, is one in which $X_4$ is chloro, bromo, or iodo; n is as desired in the final product of formula (1), and $Ar_2$ is as desired in formula (1).

For example, the 5-oxo-3-acetic acid ester pyrrolidine of structure 15 is contacted with from 1.0 to 1.2 molar equivalents of an appropriate alkyl halide, $X_4$—$CH_2$—$(CH_2)_n$—$Ar_2$. The reaction is carried out in a suitable solvent, such as tetrahydrofuran, dimethyl sulfoxide, acetonitrile, or dimethylformamide. The reaction is carried out in the presence of a base, such as sodium hydride, sodium bis-(trimethylsilyl) amide, potassium t-butoxide. The reaction is generally carried out at temperatures of from 0° C. to 50° C. Generally, the reactions require 1 to 72 hours. The product can be isolated and purified by techniques well known in the art, such as extraction, evaporation, trituration, chromatography, and recrystallization.

In Reaction Scheme C, step 9, the 1-arylalkyl-5-oxo-3-acetic acid ester pyrrolidine of structure 19 is hydrolyzed to give an 1-arylalkyl-5-oxo-3-acetic acid pyrrolidine of structure 20.

For example, the 1-arylalkyl-5-oxo-3-acetic acid ester pyrrolidine of structure 19 is contacted with a suitable hydrolyzing agent, such as sodium hydroxide, potassium hydroxide, or lithium hydroxide. The reaction is carried out in a suitable solvent such as water, tetrahydrofuran/water mixtures, methanol, methanol/water mixtures, or ethanol/water mixtures. The reaction is generally carried out at temperatures of from 0° C. to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme C, step 10, the 1-arylalkyl-5-oxo-3-acetic acid pyrrolidine of structure 20 is reduced as taught in Reaction Scheme C, step 4, above, to give an alcohol of structure 2 in which r is 0, q is 1, m is 2, $G_1$ is —C(O)—, and $G_2$ and $G_3$ are —$CH_2$—.

Reaction Scheme D sets forth a synthetic procedure for preparing alcohols of structure 2 in which $G_1$ is —$CH_2$— used as a starting material in Reaction Scheme A.1 and A.2. The reagents and starting materials used in Reaction Scheme D are readily available to one of ordinary skill in the art. In Reaction Scheme D, all substituents, unless otherwise indicated, are as previously defined.

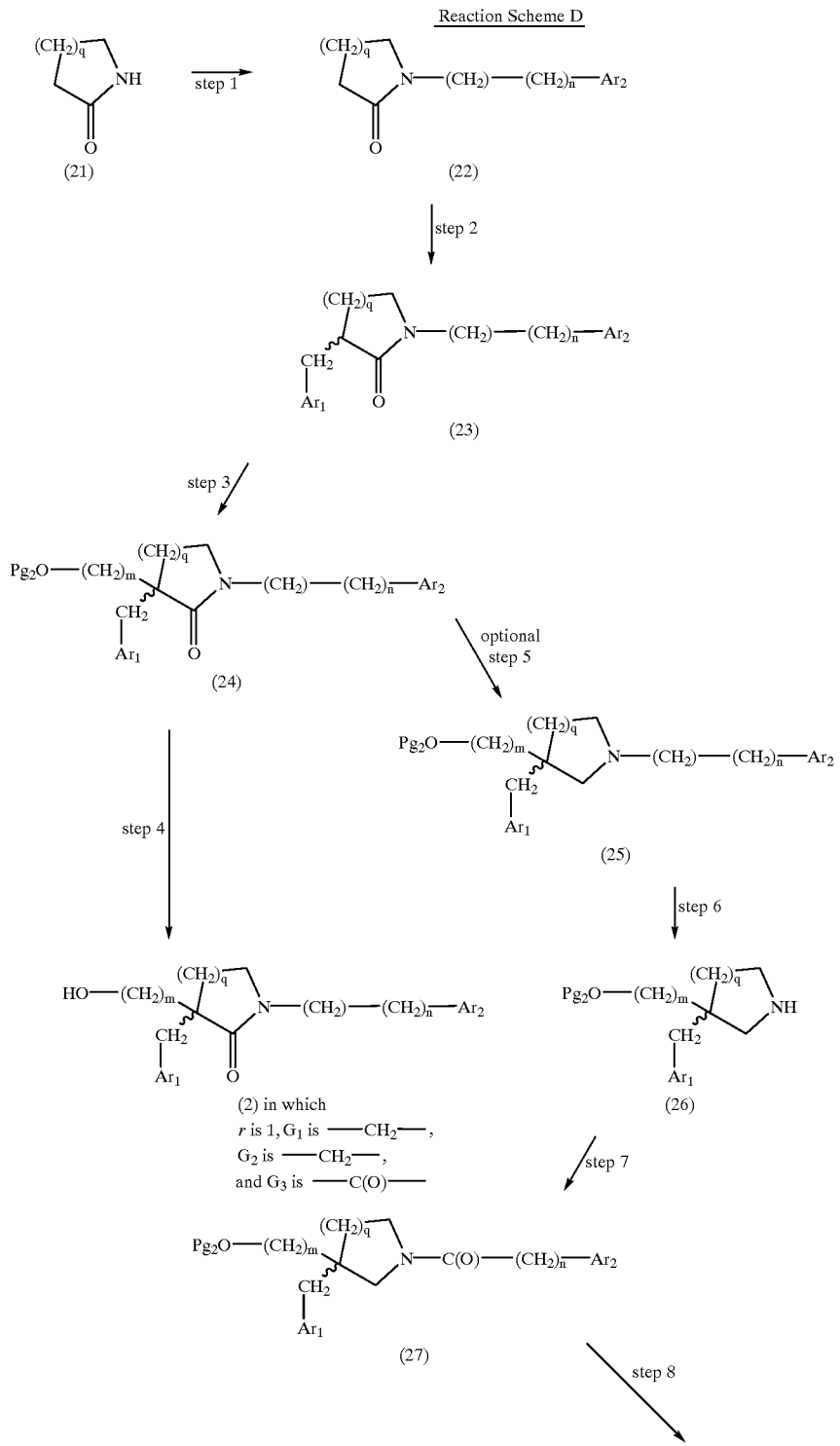

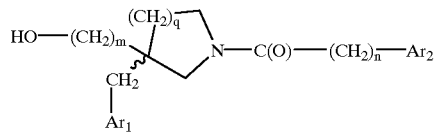

(2) in which
r is 1, G$_1$ is —CH$_2$—,
G$_2$ is —C(O),
and G$_3$ is —CH$_2$—

In Reaction Scheme D, step 1, an appropriate compound of structure 21 is alkylated with an appropriate alkylating agent to give an 1-arylalkyl-2-oxo compound of structure 22. An appropriate compound of structure 21 is one in which q is as desired in formula (1). An appropriate alkylating agent, X—CH$_2$—(CH$_2$)$_n$—Ar$_2$, is as defined in Reaction Scheme B, optional step 4.

For example, an appropriate compound structure 21 is contacted with from 1 to 5 molar equivalents of an appropriate alkylating agent, X—CH$_2$—(CH$_2$)$_n$—Ar$_2$. The reaction is carried out in a suitable solvent, such as tetrahydrofuran. The reaction is carried out in the presence of a base, such as sodium hydride, potassium t-butoxide, potassium bis(trimethylsilyl)amide with potassium bis(trimethylsilyl) amide being preferred. The reaction is generally carried out at temperatures of from 0° C. to –78° C. Generally, the reactions require 1 to 72 hours. The product can be isolated and purified by techniques well known in the art, such as extraction, evaporation, trituration, chromatography, and recrystallization.

In Reaction Scheme D, step 2, the 1-arylalkyl-2-oxo compound of structure 22 is arylmethylated with an appropriate arylmethylating agent to give an 1-arylalkyl-2-oxo-3-arylmethyl compound of structure 23. An appropriate arylmethylating agent, X$_5$—CH$_2$—Ar$_1$, is one in which X$_5$ is methanesulfonyl, chloro, bromo, or iodo and Ar$_1$ is as desired in formula (1) or gives rise after deprotection to Ar$_1$ as desired in formula (1). Examples of appropriate arylmethylating agents include, but are not limited to benzyl bromide, benzyl chloride, 3,4,5-trimethoxybenzyl methanesulfonate, 4-fluorobenzyl bromide, 4-fluorobenzyl chloride, 3,4-difluorobenzyl bromide, 3,4-difluorobenzyl chloride, 4-methoxybenzyl chloride, 3,4-dimethoxybenzyl bromide, 3,4-dimethoxybenzyl chloride, 3,4-dichlorobenzyl bromide, 3,4-dichlorobenzyl chloride, 3-chlorobenzyl bromide, 4-chlorobenzyl chloride, 2,4-difluorobenzyl bromide, 2,4-difluorobenzyl chloride, and the like.

For example, the 1-arylalkyl-2-oxo compound of structure 22 is contacted with from 1 to 5 molar equivalents of an appropriate arylmethylating agent. The reaction is carried out in a suitable solvent, such as tetrahydrofuran. The reaction is carried out in the presence of a base, such as lithium bis(trimethylsilyl)amide. The reaction is generally carried out at temperatures of from 0° C. to –78° C. Generally, the reactions require 1 to 72 hours. The product can be isolated and purified by techniques well known in the art, such as extraction, evaporation, trituration, chromatography, and recrystallization.

In Reaction Scheme D, step 3, the 1-arylalkyl-2-oxo-3-arylmethyl compound of structure 23 is alkylated with an appropriate protected alcohol, Pg$_2$O—(CH$_2$)$_m$—L$_3$, to give an 1-arylalkyl-2-oxo-3-arylmethyl-3-(ω-protected-hydroxyalkyl) compound of structure 24.

An appropriate protected alcohol, Pg$_2$O—(CH$_2$)$_m$—L$_3$, is one in which m is as desired in the final product of formula (1) and the leaving group, L$_3$, is one which can be displaced by an anion derived from an appropriate 1-arylalkyl-2-oxo-3-arylmethyl compound of structure 23. Suitable leaving groups, L$_3$, include but are not limited to methanesulfonyl, chloro, bromo, and iodo. Suitable hydroxy protecting groups such as those described in *Protecting Groups in Organic Synthesis* by T. Greene are well known and appreciated in the art. In Reaction Scheme D, the use of t-butyldimethylsilyl is generally preferred.

For example, the 1-arylalkyl-2-oxo-3-arylmethyl compound of structure 23 is contacted with 1.0 to 1.2 molar equivalents of an appropriate protected alcohol, Pg$_2$O—(CH$_2$)$_m$—L$_3$. The reaction is carried out in the presence of an equimolar amount of a suitable base, such as lithium bis(trimethylsilyl)amide. The reaction is carried out in a solvent, such as tetrahydrofuran. The reaction is generally carried out at temperatures of from –78° C. to 0° C. Generally, the reactions require 1 to 72 hours. The product can be isolated and purified by techniques well known in the art, such as extraction, evaporation, trituration, chromatography, and recrystallization.

In Reaction Scheme D, step 4, the 1-arylalkyl-2-oxo-3-arylmethyl-3-(ω-protected-hydroxyalkyl) compound of structure 24 is deprotected to give an alcohol of structure 2 in which r is 1 and G$_3$ is —C(O)—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme D, optional step 5, the 1-arylalkyl-2-oxo-3-arylmethyl-3-(ω-protected-hydroxyalkyl) compound of structure 24 is reduced to give an 1-arylalkyl-3-arylmethyl-3-(ω-protected-hydroxyalkyl) compound of structure 25.

This reaction is carried out as taught in reaction Scheme B, optional step 5 and may result in the removal of the protecting group Pg$_2$. when the protection group Pg$_2$ is removed the same or another protecting group Pg$_2$ may be introduced or, alternately, the steps that follow may be carried out on the unprotected hydroxy compound.

In Reaction Scheme D, step 6, an appropriate 1-arylalkyl-3-arylmethyl-3-(ω-protected-hydroxyalkyl) compound of structure 25 is debenzylated to give a 3-arylmethyl-3-(ω-protected-hydroxyalkyl) compound of structure 26. An appropriate 1-arylalkyl-3-arylmethyl-37-(ω-protected-hydroxyalkyl) compound of structure 25 is one in which n is 0 and Ar$_2$ is phenyl or 4-methoxyphenyl; and m, q, and Ar$_1$ are as desired in the final product of formula (1) or Ar$_1$ gives rise after deprotection to an Ar$_1$ as desired in the final product of formula (1).

For example, and an appropriate 1-arylalkyl-3-arylmethyl-3-(ω-protected-hydroxyalkyl) compound of structure 25 is hydrogenated. The reaction is carried out in a suitable solvent, such as ethanol, methanol, or water. The reaction is carried out in the presence of a suitable catalyst, such as 20% palladium hydroxide-on-carbon. The reaction is generally carried out at temperatures of from 50° C. to 0° C. Generally, the reactions require 1 to 72 hours. The product can be isolated and purified by techniques well known in the art, such as filtration, evaporation, trituration, chromatography, and recrystallization.

In Reaction Scheme D, step 7, the 3-arylmethyl-3-(ω-protected-hydroxyalkyl) compound of structure 26 is aroylated as taught in Reaction Scheme B, optional step 7 to give an 1-aroyl-3-arylmethyl-3-(ω-protected-hydroxyalkyl) compound of structure 27.

In Reaction Scheme D, step 8, the 1-aroyl-3-arylmethyl-3-(ω-protected-hydroxyalkyl) compound of structure 27 is deprotected, if required, to give an alcohol of structure 2 in which r is 1, $G_3$ is —$CH_2$—, and $G_2$ is —C(O)—. A deprotection reaction, such as the removal of hydroxy protecting groups utilizing suitable protecting groups such as those described in *Protecting Groups in Organic Synthesis* by T. Greene is well known and appreciated in the art.

Reaction Scheme E sets forth the preparation of alcohols of structure 2 in which r is 0 and $G_1$ is —$CH_2$— used as a starting material in Reaction Scheme A.1 and A.2. The reagents and starting materials are readily available to one of ordinary skill in the art. In Reaction Scheme E, all substituents, unless otherwise indicated, are as previously defined.

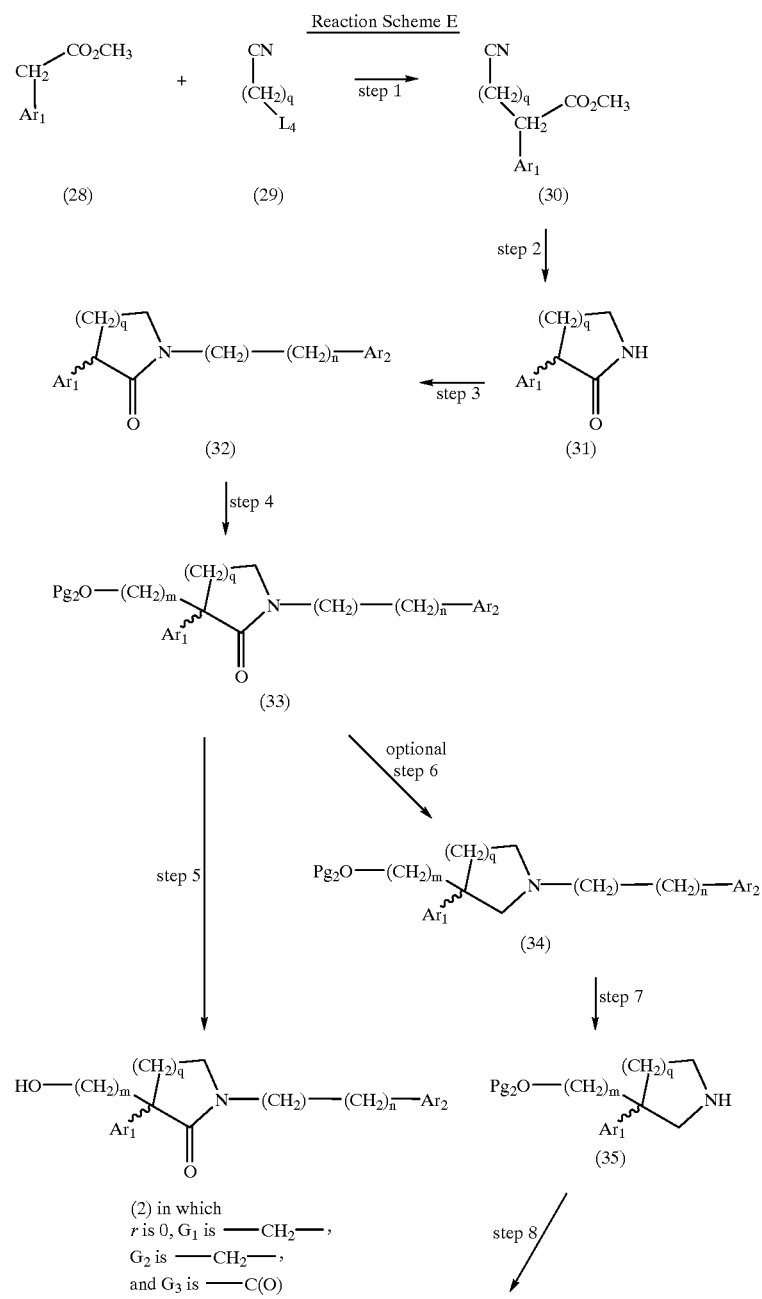

-continued

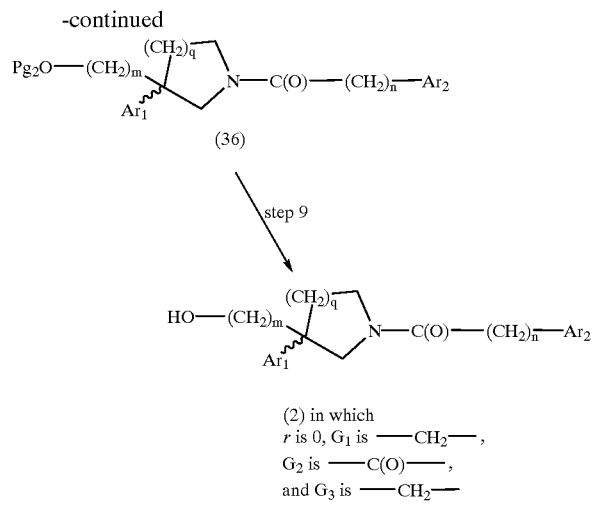

(2) in which
r is 0, $G_1$ is —$CH_2$—,
$G_2$ is —C(O)—,
and $G_3$ is —$CH_2$—

In Reaction Scheme E, step 1, an appropriate methyl arylacetate of structure 28 is alkylated with an appropriate ω-cyano alkylating agent of structure 29 to give a cyano ester of structure 30.

An appropriate methyl arylacetate of structure 28 is one in which $Ar_1$ is as desired in formula (1) or gives rise after deprotection to $Ar_1$ as desired in formula (1). An appropriate ω-cyano alkylating agent of structure 29 is one in which q is as desired in formula (1) and $L_4$ is chloro or bromo. Examples of appropriate ω-cyano alkylating agent of structure 29 include α-chloroacetonitrile, α-bromoacetonitrile, β-chloropropionitrile, and β-bromopropionitrile.

For example, an appropriate methyl arylacetate of structure 28 is contacted with from 0.8 to 1.2 molar equivalents of an appropriate ω-cyano alkylating agent of structure 29. The reaction is carried out in a suitable solvent, such as tetrahydrofuran. The reaction is carried out in the presence of a base, such as sodium hydride, lithium bis(trimethylsilyl)amide, or potassium bis(trimethylsilyl)amide. The reaction is generally carried out at temperatures of from 0° C. to −78° C. Generally, the reactions require 1 to 72 hours. The product can be isolated and purified by techniques well known in the art, such as extraction, evaporation, trituration, chromatography, and recrystallization.

In Reaction Scheme E, step 2, the cyano ester of structure 30 is reduced and cyclized to give a 2-oxo-3-aryl compound of structure 31 as taught in Reaction Scheme B, step 3.

In Reaction Scheme E, step 3, the 2-oxo-3-aryl compound of structure 31 is alkylated with an appropriate alkylating agent as taught in Reaction Scheme D, step 1, to give an 1-arylalkyl-2-oxo-3-aryl compound of structure 32.

In Reaction Scheme E, step 4, the 1-arylalkyl-2-oxo-3-aryl compound of structure 32 is alkylated with an appropriate protected alcohol, $Pg_2O$—$(CH_2)_m$—$L_3$, as taught in Reaction Scheme D, step 3, to give a 3-(ω-protected-hydroxyalkyl) 1-arylalkyl-2-oxo-3-aryl compound of structure 33.

In Reaction Scheme E, step 5, the 3-(ω-protected-hydroxyalkyl) 1-arylalkyl-2-oxo-3-aryl compound of structure 33 is deprotected to give an alcohol of structure 2 in which r is 0 and $G_3$ is —C(O)—. A deprotection reaction, such as the removal of hydroxy protecting groups utilizing suitable protecting groups such as those described in *Protecting Groups in Organic Synthesis* by T. Greene is well known and appreciated in the art.

In Reaction Scheme E, optional step 6, the 3-(ω-protected-hydroxyalkyl) 1-arylalkyl-2-oxo-3-aryl compound of structure 33 is reduced to give a 3-(ω-protected-hydroxyalkyl) 1-arylalkyl-3-aryl compound of structure 34.

This reaction is carried out as taught in reaction Scheme B, optional step 5 and may result in the removal of the protecting group $Pg_2$. When the protection group $Pg_2$ is removed the same or another protecting group $Pg_2$ may be introduced or, alternately, the steps that follow may be carried out on the unprotected hydroxy compound.

In Reaction Scheme E, step 7, an appropriate 3-(ω-protected-hydroxyalkyl) 1-arylalkyl-3-aryl compound of structure 34 is debenzylated as taught in Reaction Scheme D, step 6, to give a 3-(ω-protected-hydroxyalkyl) 3-aryl compound of structure 35. An appropriate 3-(ω-protected-hydroxyalkyl) 1-arylalkyl-3-aryl compound of structure 34 is one in which n is 0 and $Ar_2$ is phenyl or 4-methoxyphenyl; and m, q, and $Ar_1$ are as desired in the final product of formula (1) or Ar, gives rise after deprotection to an $Ar_1$ as desired in the final product of formula (1).

In Reaction Scheme E, step 8, a 3-(ω-protected-hydroxyalkyl)-3-aryl compound of structure 35 is aroylated as taught in Reaction Scheme B, optional step 7 to give an 1-aroyl-3-(ω-protected-hydroxyalkyl)-3-aryl compound of structure 36.

In Reaction Scheme E, step 9, the 1-aroyl-3-(ω-protected-hydroxyalkyl)-3-aryl compound of structure 36 is deprotected, if required, to give an alcohol of structure 2 in which r is 0, $G_3$ is —$CH_2$—, and $G_2$ is —C(O)—. A deprotection reaction, such as the removal of hydroxy protecting groups utilizing suitable protecting groups such as those described in *Protecting Groups in Organic Synthesis* by T. Greene is well known and appreciated in the art.

The following examples and preparations present typical syntheses of the compounds of formula (1). These examples are understood to be illustrative only and are not intended to limit the scope of the invention in any way.

Preparation A

Synthesis of 4-(1-(4-Fluoro-benzyl)-1H-benzoimidazole-2-carbonyl)-piperidine trifluoroacetic acid salt Combine 1-(t-butoxycarbonyl)-4-(1H-benzoimidazole-2-carbonyl)-piperidine (1.50 g, 4.57 mmol), 4-fluorobenzyl alcohol (0.50 mL, 4.58 mmol) and triphenylphosphine (1.44 g, 5.50 mmol) in tetrahydrofuran (15 mL). Add diethylazodicarboxylate (0.87 mL, 5.50 mmol) dropwise at room temperature. After 23 hours, evaporate the reaction mixture in vacuo to give a residue. Chromatograph the residue on silica gel eluting with 25% ethyl acetate/hexane to give 1-(t-butoxycarbonyl)-4-(1-(4-fluoro-benzyl)-1H-benzoimidazole-2-carbonyl)-piperidine.

Cool the 1-(t-butoxycarbonyl)-4-(1-(4-fluoro-benzyl)-1H-benzoimidazole-2-carbonyl)-piperidine in an ice bath. Add trifluoroacetic acid and mix. After 15 minutes, add diethyl ether. Collect the residue by filtration and dried under vacuum. Recrystallize from ethanol/ether and dry resulting solid under vacuum to give the title compound.

EXAMPLE 1
1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine

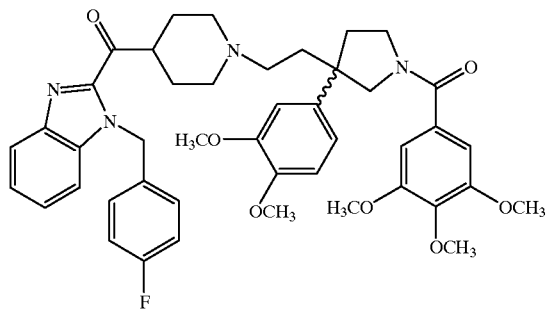

1.1 Synthesis of 3-cyano-3-(3,4-dimethoxy-phenyl) pentanedioic diethyl ester

Combine 3,4-dimethoxy-phenyl-acetonitrile (20 g, 113 mmol) and anhydrous tetrahydrofuran (100 mL). Cool in a dry-ice/acetone bath. Add dropwise a solution of sodium bis-(trimethylsilyl)amide (226 mL, 1 M in THF, 226 mmol). When the addition is complete warm the reaction mixture to 10° C. and allow to stir for 15 minutes. Cool in a dry-ice/acetone bath, add dropwise ethyl bromoacetate (37.7 g, 226 mmol). When the addition of ethyl bromoacetate is complete, warm the reaction mixture to ambient temperature. After 18 hours, partition the reaction mixture between diethyl ether and water. Extract the organic layer with water and saturated aqueous solution of ammonium chloride. Separate the organic layer, dry over $MgSO_4$, filter, and concentrate in vacuo to obtain a residue. Chromatograph the residue on silica gel eluting with 33% ethyl acetate/hexane remove residual solvent in vacuo at 82° C to give the title compound: $R_f$=0.37 (silica gel, 33% ethyl acetate/hexane). Elemental Analysis calculated for $C_{18}H_{23}NO_6$: C 61.88; H 6.64; N 4.01; Found: C 61.79; H 6.62; N 3.91.

1.2 Synthesis of 3-(3,4-dimethoxy-phenyl)-5-oxo-pyrrolidin-3-yl]-acetic acid ethyl ester Combine 3-cyano-3-(3,4-dimethoxy-phenyl)-pentanedioic diethyl ester (1.3 g, 3.24 mmol) and cobalt(II) chloride hexahydrate (1.54 g, 6.48 mmol) in methanol (50 mL). While maintaining the temperature at or below 20° C. with an ice-bath, add portionwise sodium borohydride (2.17 g, 57 mmol). After the addition is complete, allow the reaction mixture to stand at ambient temperature for 18 hours. Evaporate the reaction mixture in vacuo to obtain a residue. Partition the residue between dichloromethane and 1 M hydrochloric acid solution. Extract the aqueous layer several times with dichloromethane, combine the organic layers, dry over $Na_2SO_4$, filter, and concentrate in vacuo to obtain a residue. Chromatograph the residue on silica gel eluting with 20/1 ethyl acetate/methanol remove residual solvent in vacuo at 82° C. to give the title compound: $R_f$=0.74 (silica gel, 5/1 ethyl acetate/methanol); mp; 116–118° C. Elemental Analysis calculated for $C_{16}H_{21}NO_5$: C 62.53; H 6.89; N 4.56; Found: C 62.52; H 6.85; N 4.50.

1.3 Synthesis of 3-(3,4-dimethoxy-phenyl)-3-(2-hydroxy-ethyl)-pyrrolidine

Combine lithium aluminum hydride (0.99 g, 26.0 mmol) and anhydrous tetrahydrofuran (20 mL). Slowly, add [3-(3,4-dimethoxy-phenyl)-5-oxo-pyrrolidin-3-yl]-acetic acid ethyl ester (2.0 g, 6.5 mmol) as a solution in anhydrous tetrahydrofuran (40 mL). After the addition is complete. heat to reflux. After 18 hours, cool in an ice-bath. Add water (1 mL) dropwise at such a rate that the temperature of the reaction mixture does not rise above 20° C. Cool to 10° C., add 15% sodium hydroxide solution (1.0 mL). Add water (3 mL). After 15 minutes, filter the reaction mixture and concentrate the filtrate in vacuo to give the title compound: $R_f$=0.68 (silica gel, 5/1 ethyl acetate/methanol). Prepare an analytical sample as follows: Combine 3-(3,4-dimethoxy-phenyl)-3-(2-hydroxy-ethyl)-pyrrolidine (0.51 g, 2.02 mmol) and oxalic acid (0.18 g, 2.00 mmol) in tetrahydrofuran (70 mL). After 18 hours, filter and dry. Triturate with diethyl ether (100 mL), filter and dry in vacuo at 81° C. to give the title compound as its oxalate salt: mp; 140–142° C. Elemental Analysis calculated for $C_{14}H_{21}NO_3 \cdot C_2H_2O_4$: C 56.30; H 6.79; N 4.10; Found: C 56.15; H 6.76; N 4.13.

1.4.1 Synthesis of 1-(3,4,5-trimethoxy-benzoyl)-3-(3,4-dimethoxy-phenyl)-3-(2-hydroxy-ethyl)-pyrrolidine Combine 3-(3,4-dimethoxy-phenyl)-3-(2-hydroxy-ethyl)-pyrrolidine (2.27 g, 9.03 mmol) and N-methylmorpholine (2.48 mL, 22.6 mmol) in anhydrous dichloromethane (100 mL). Cool the reaction mixture to −5° C. with an salt-ice bath. Slowly, add 3,4,5-trimethoxy-benzoyl chloride (2.2 g, 9.5 mmol) as a solution in dichloromethane (30 mL). Warm to ambient temperature. After 18 hours, extract the reaction mixture with a saturated solution of potassium carbonate. Dry the organic layer over $Na_2SO_4$, filter, and concentrate in vacuo to obtain a residue. Chromatograph the residue on silica gel eluting with 95% dichloromethane/methanol to obtain a residue. Combine the residue and dichloromethane (100 mL), and extract 3 times with 1 M hydrochloric acid solution and saturated solution of potassium carbonate. Dry the organic layer over $Na_2SO_4$, filter, and concentrate in vacuo to obtain a residue. Chromatograph the residue on silica gel eluting with 20/1 ethyl acetate/methanol to obtain an oil: $R_f$=0.14 (silica gel, 20/1 ethyl acetate/methanol). Dry in vacuo at 110° C. to obtain the title compound as a glass: mp; 60–62° C. Elemental Analysis calculated for $C_{24}H_{31}NO_7$: C 64.70; H 7.01; N 3.14; Found C 64.40; H 7.21; N 2.85.

1.4.2 Synthesis of 1-(3,4,5-trimethoxy-benzoyl)-3-(3,4-dimethoxy-phenyl)-3-(2-hydroxy-ethyl)-pyrrolidine Combine 3-(3,4-dimethoxy-phenyl)-3-(2-hydroxy-ethyl)-pyrrolidine (5.34 g, 21.23 mmol) and sodium carbonate (1.24 g, 11.68 mmol) in ethyl acetate/water (4/1) (120 mL). Cool the reaction mixture to −5° C. with an salt-ice bath. Slowly, add 3,4,5-trimethoxy-benzoyl chloride (5.14 g, 22.3 mmol) as a solution in ethyl acetate (60 mL) at a rate such that the temperature of the reaction mixture does not rise above 0° C. Maintain the reaction temperature at about 0° C. After 18 hours, separate the organic layer. Extract the organic layer twice with 1 M aqueous hydrochloric acid solution, saturated solution of sodium bicarbonate, water and a saturated solution of sodium chloride. Dry the organic layer over $Na_2SO_4$, filter, and concentrate in vacuo to obtain a residue. Combine the aqueous layers and neutralize with a saturated solution of sodium bicarbonate. Extract the neutralized aqueous layers with dichloromethane. Dry the organic layer over $Na_2SO_4$, filter, and concentrate in vacuo to obtain another residue. Combine the residues and chromatograph on silica gel eluting with 10/1 dichloromethane/methanol to obtain a residue. Combine the residue and dichloromethane (100 mL), and extract 3 times with 1 M hydrochloric acid solution and saturated solution of potassium carbonate. Dry the organic layer over $Na_2SO_4$, filter, and concentrate in vacuo to obtain the title compound: $R_f$=0.23 (silica gel, 10/1 ethyl acetate/methanol).

1.5 Synthesis of 1-(3,4,5-trimethoxy-benzoyl)-3-(3,4-dimethoxy-phenyl)-3-(2-methanesulfonyl-ethyl)-pyrrolidine Combine 1-(3,4,5-trimethoxy-benzoyl)-3-(3,4-dimethoxy-phenyl)-3-(2-hydroxy-ethyl)-pyrrolidine (0.43 g, 0.97 mmol), trimethylamine (3.3 mL, 2.4 mmol), and anhydrous dichloromethane (30 mL). Cool the reaction mixture to −5° C. with an salt-ice bath. Slowly, add methanesulfonyl chloride (0.082 mL, 1.06 mmol) at such a rate that the temperature of the reaction mixture does not rise above 2° C. Warm to ambient temperature. After 18 hours, quench the reaction by the addition of ice. Separate the organic layer and extract 3 times with 1 M hydrochloric acid solution and 2 times with a saturated solution of sodium bicarbonate. Dry the organic layer over $Na_2SO_4$, filter, and concentrate in vacuo to obtain the title compound: $R_f$=0.48 (silica gel, 20/1 ethyl acetate/methanol).

1.6.1 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine Combine 1-(3,4,5-trimethoxy-benzoyl)-3-(3,4-dimethoxy-phenyl)-3-(2-methanesulfonyl-ethyl)-pyrrolidine (0.69 g, 1.32 mmol) and 4-[1-(4-fluoro-benzyl)-1 H-benzoimidazole-2-carbonyl]-piperidine (0.49 g, 1.42 mmol), and sodium bicarbonate (0.223 g, 2.64 mmol) in tetrahydrofuran/water (15/4) (30 mL). Heat to reflux. After 72 hours, cool and evaporate in vacuo to obtain a residue. Partition the residue between dichloromethane and 5% sodium bicarbonate solution. Dry the organic layer over $MgSO_4$, filter, and concentrate in vacuo to obtain a residue. Chromatograph the residue on silica gel eluting with 5/1 ethyl acetate/methanol to give an oil. Combine the oil with dichloromethane and extract with 5% sodium bicarbonate solution. Dry the organic layer over $Na_2SO_4$, filter, and concentrate in vacuo to obtain a residue. Dry the residue in vacuo at 82° C. to give the title compound: $R_f$=0.27 (silica gel, 5/1 ethyl acetate/methanol); mp; 80–83° C. Elemental Analysis calculated for $C_{44}H_{49}FN_4O_7$: C 69.09; H 6.46; N 7.32; Found: C 68.82; H 6.44; N 7.42.

1.6.2 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine Combine 1-(3,4,5-trimethoxy-benzoyl)-3-(3,4-dimethoxy-phenyl)-3-(2-methanesulfonyl-ethyl)-pyrrolidine (0.5 g, 0.96 mmol) and 4-[1-(4-fluoro-benzyl)-1 H-benzoimidazole-2-carbonyl]-piperidine (0.49 g, 1.44 mmol), and diisopropylethylamine (0.33 mL, 1.92 mmol) in acetonitrile (5 mL). Heat to reflux. After 18 hours, cool and dilute with ethyl acetate. Extract twice with 5% sodium bicarbonate solution, twice with water, and with saturated sodium chloride solution. Dry the organic layer over $Na_2SO_4$, filter, and concentrate in vacuo to obtain a residue. Chromatograph the residue on silica gel eluting with 5/1 ethyl acetate/methanol to give an oil. Combine the oil with dichloromethane and extract with 5% sodium bicarbonate solution. Dry the organic layer over $Na_2SO_4$, filter, and concentrate in vacuo to obtain a residue. Dry the residue in vacuo at 65° C. to give the title compound: $R_f$=0.27 (silica gel, 5/1 ethyl acetate/methanol).

1.7 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine maleic acid salt Combine 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine (0.32 g, 0.418 mmol) and maleic acid (0.048 g, 0.414 mmol) in tetrahydrofuran (30 mL). Heat to reflux. After 15 minutes, cool to ambient temperature. After 18 hours, evaporate in vacuo to give a residue. Triturate the residue with diethyl ether (100 ml) to give a solid. Filter and dry in vacuo at 110° C. to give the title compound: mp; 119–122° C. Elemental Analysis calculated for $C_{44}H_{49}FN_4O_7 \cdot C_4H_4O_4$: C 65.44; H 6.06; N 6.36; Found: C 65.08; H 6.20; N 6.30.

EXAMPLE 2

1-Benzoyl-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine

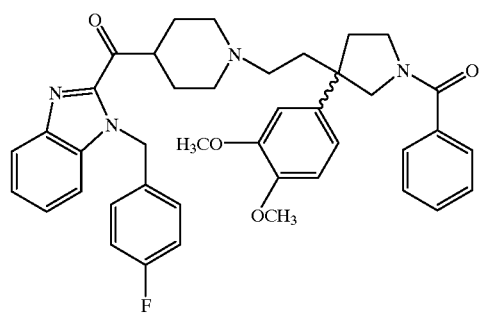

2.1 Synthesis of 1-benzoyl-3-(3,4-dimethoxy-phenyl)-3-(2-hydroxy-ethyl)-pyrrolidine Combine 3-(3,4-dimethoxy-phenyl)-3-(2-hydroxy-ethyl)-pyrrolidine (0.79 g, 3.14 mmol) and dichloromethane (20 mL). Add triethylamine (10.8 mL, 7.9 mmol). Cool in a salt-ice bath. Add trimethylsilyl chloride (0.40 mL, 3.14 mmol) at such a rate that the temperature of the reaction mixture does not rise above 0° C. After 1 hour, add dichloromethane (10 mL). Add benzoyl chloride (0.38 mL, 3.3 mmol) at such a rate that the temperature of the reaction mixture does not rise above 0° C. After 2 hours, extract the reaction mixture with 1 M hydrochloric acid solution and a saturated aqueous solution of sodium carbonate. Separate the organic layer, dry over $MgSO_4$, filter, and concentrate in vacuo to obtain a residue. Chromatograph the residue on silica gel eluting sequentially with 66% ethyl acetate/hexane to obtain a fast eluting residue; $R_f$=0.79 (silica gel, 20:1 ethyl acetate/methanol) and ethyl acetate/methanol (20:1) to obtain a slow eluting residue; $R_f$=0.26 (silica gel, 20:1 ethyl acetate/methanol). Combine the fast eluting residue, dichloromethane (100 mL), and 1 M hydrochloric acid solution and stir vigorously. After 2 days, separate the organic layer, dry over $MgSO_4$, filter, and concentrate in vacuo to obtain a residue; combine this residue with the slow eluting residue obtained above. Chromatograph the combined residues on silica gel eluting with 20:1 ethyl acetate/methanol. Remove residual solvent at 82° C. to obtain the title compound as a foam: mp; 42–44° C. $R_f$=0.26 (silica gel, 20:1 ethyl acetate/methanol). Elemental Analysis calculated for $C_{21}H_{25}NO_4 \cdot 0.20\ H_2O$: C 70.25; H 7.13; N 3.90; Found: C 69.95; H 7.27; N 3.81.

2.2 Synthesis of 1-benzoyl-3-(3,4-dimethoxy-phenyl)-3-(2-methanesulfonyl-ethyl)-pyrrolidine Prepared by the method of Example 1.5 using 1-benzoyl-3-(3,4-dimethoxy-phenyl)-3-(2-hydroxy-ethyl)-pyrrolidine (0.58 g, 1.63 mmol) and methanesulfonyl chloride (0.56 g, 4.89 mmol) to give the title compound: $R_f$=0.52 (silica gel, 20/1 ethyl acetate/methanol).

2.3 Synthesis of 1-benzoyl-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine Combine 1-benzoyl-3-(3,4-dimethoxy-phenyl)-3-(2-methanesulfonyl-ethyl)-pyrrolidine (0.54 g, 1.3 mmol) and 4-[1-(4-fluoro-benzyl)-1 H-benzoimidazole-2-carbonyl]-piperidine (0.46 g, 1.4 mmol), and sodium bicarbonate (0.2 g, 2.5 mmol) in tetrahydrofuran/water (15/4) (30 mL). Heat to reflux. After 48 hours, cool to ambient temperature. After 72 hours, evaporate in vacuo to obtain a residue. Partition the residue between dichloromethane/chloroform and 5% sodium bicarbonate solution. Dry the organic layer over $Na_2SO_4$, filter, and concentrate in vacuo to obtain a residue. Chromatograph the residue on silica gel eluting with 5/1 ethyl acetate/methanol to give a solid. Combine the solid with dichloromethane and extract with 5% sodium bicarbonate solution. Dry the organic layer over $Na_2SO_4$, filter, and concentrate in vacuo to obtain a residue. Dry the residue in vacuo at 82° C. to give the title compound: $R_f$=0.28 (silica gel, 5/1 ethyl acetate/methanol); mp; 88–90° C. Elemental Analysis calculated for $C_{41}H_{43}FN_4O_4$: C 72.20; H 6.47; N 8.21; Found: C 71.96; H 6.38; N 8.17.

2.4 Resolution of (+)-1-benzoyl-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine and (−)-1-benzoyl-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine Inject repeatedly, samples of (+/−)-1-benzoyl-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine (2.0 mg in 200 μL of 15% methanol/pentane) onto a CHIRALPAK AS HPLC column, 25 cm×4.6 mm (10 μm) eluting with 15% methanol/pentane at a flow rate of 1.5 mL/minute. Collect the separated enantiomers and evaporate in vacuo. Analytical HPLC analysis using a CHIRALPAK AS HPLC column, 25 cm×4.6 mm (10 μm) eluting with 15% methanol/pentane at a flow rate of 2.0 mL/minute shows that the faster eluting isomer (retention time; 26.5 minutes) is obtained in 95% ee and the slower eluting isomer (retention time; 33.0 minutes) is obtained in 93% ee.

EXAMPLE 3

1-Benzoyl-3-[2-[4-[1-(4-fluoro-benzyl)-1 H-benzoimidazol-2-yl]-4-hydroxy-piperidin-1-yl]-ethyl]-3-(3,4-dimethoxy-phenyl)-pyrrolidine

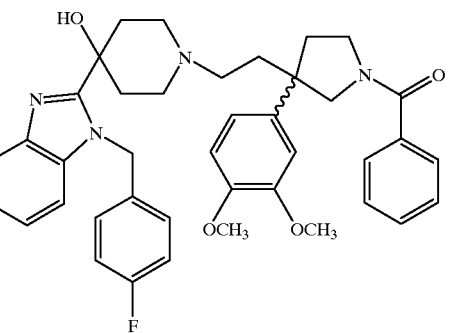

3.1 Synthesis of 1-benzoyl-3-[2-[4-[1-(4-fluoro-benzyl)-1 H-benzoimidazol-2-yl]-4-hydroxy-piperidin-1-yl]-ethyl]-3-(3,4-dimethoxy-phenyl)-pyrrolidine Combine 1-benzoyl-3-(3,4-dimethoxy-phenyl)-3-(2-methanesulfonyl-ethyl)-pyrrolidine (0.48 g, 1.1 mmol) and 4-[1-(4-fluoro-benzyl)-1 H-benzoimidazol-2-yl]-4-hydroxy-piperidine (0.54 g, 1.7 mmol), and sodium bicarbonate (0.235 g, 2.22 mmol) in tetrahydrofuran/water (15/4) (50 mL). Heat to reflux. After 72 hours, cool to ambient temperature and evaporate in vacuo to obtain a residue. Partition the residue between dichloromethane and 5% sodium bicarbonate solution. Dry the organic layer over $Na_2SO_4$, filter, and concentrate in vacuo to obtain a residue. Chromatograph the residue on silica gel eluting with 5/1 ethyl acetate/methanol to give a solid. Combine the solid with dichloromethane and extract with 5% sodium bicarbonate solution. Dry the organic layer over $Na_2SO_4$, filter, and concentrate in vacuo to obtain a solid residue. Dry the residue in vacuo at 82° C. to give the title compound: $R_f$=0.32 (silica gel, 5/1 ethyl acetate/methanol); mp; 111–114° C. HRMS (FAB+): calculated 663.334502. Found 663.334660.

EXAMPLE 4

1-Benzoyl-3-[2-[4-(benzothiazol-2-yl)-piperidin-1-yl]-ethyl]-3-(3,4-dimethoxy-phenyl)-pyrrolidine

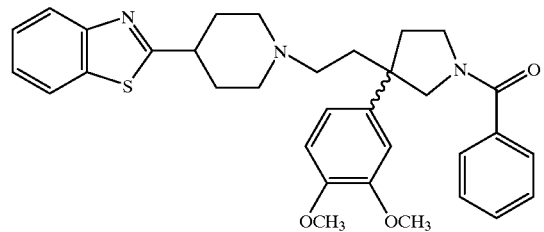

4.1 Synthesis of 1-benzoyl-3-[2-[4-(benzothiazol-2-yl)-piperidin-1-yl]-ethyl]-3-(3,4-dimethoxy-phenyl)-pyrrolidine Combine 1-benzoyl-3-(3,4-dimethoxy-phenyl)-3-(2-methanesulfonyl-ethyl)-pyrrolidine (0.63 g, 1.45 mmol) and 4-(benzothiazol-2-yl)-piperidine (0.35 g, 1.60 mmol), and sodium bicarbonate (0.24 g, 2.9 mmol) in tetrahydrofuran/water (15/4) (30 mL). Heat to reflux. After 48 hours, cool to ambient temperature and evaporate in vacuo to obtain a residue. Partition the residue between dichloromethane and 5% sodium bicarbonate solution. Dry the organic layer over $Na_2SO_4$, filter, and concentrate in vacuo to obtain a residue. Chromatograph the residue on silica gel eluting with 5/1 ethyl acetate/methanol to give a solid. Combine the solid with dichloromethane and extract with 5% sodium bicarbonate solution. Dry the organic layer over $Na_2SO_4$, filter, and concentrate in vacuo to obtain a residue. Dry the residue in vacuo at 65° C. to give the title compound: $R_f$=0.24 (silica gel, 5/1 ethyl acetate/methanol); mp; 60–62° C. Elemental Analysis calculated for $C_{33}H_{37}N_3O_3S·0.25\ H_1O$: C 70.75; H 6.75; N 7.50; Found: C 70.79; H 6.70; N 7.39.

EXAMPLE 5

1-(3,4,5-Trimethoxy-benzoyl)-3-[2-[4-[1-(4-fluoro-benzyl)-1 H-benzoimidazol-2-yl]-4-hydroxy-piperidin-1-yl]-ethyl]-3-(3,4-dimethoxy-phenyl)-pyrrolidine

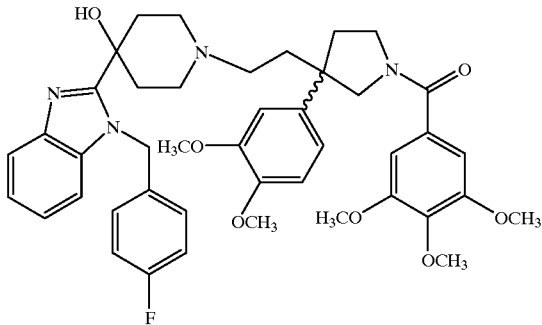

5.1 Synthesis of 1-(3,4,5-trimethoxy-benzoyl)-3-[2-[4-[1-(4-fluoro-benzyl)-1 H-benzoimidazol-2-yl]-4-hydroxy-piperidin-1-yl]-ethyl]-3-(3,4-dimethoxy-phenyl)-pyrrolidine Combine 1-(3,4,5-trimethoxy-benzoyl)-3-(3,4-dimethoxy-phenyl)-3-(2-methanesulfonyl-ethyl)-pyrrolidine (0.70 g, 1.3 mmol) and 4-[1-(4-fluoro-benzyl)-1 H-benzoimidazol-2-yl]-4-hydroxy-piperidine (0.58 g, 1.8 mmol), and potassium carbonate (0.37 g, 2.7 mmol) in dimethylformamide (22 mL). Heat to 70–75° C. After 4 days, cool and evaporate in vacuo to obtain a residue. Partition the residue between ethyl acetate and water. Extract the organic layer with water and a saturated solution of potassium carbonate. Dry the organic layer over $Na_2SO_4$, filter, and concentrate in vacuo to obtain a residue. Chromatograph the residue on silica gel eluting with 2/1 ethyl acetate/methanol to give a foam. Combine the foam with dichloromethane and extract with 5% sodium bicarbonate solution. Dry the organic layer over $Na_2SO_4$, filter, and concentrate in vacuo to obtain the title compound: $R_f$=0.37 (silica gel, 2/1 ethyl acetate/methanol); mp; 110–120° C.

5.2 Synthesis of 1-(3,4,5-trimethoxy-benzoyl)-3-[2-[4-[1-(4-fluoro-benzyl)-1 H-benzoimidazol-2-yl]-4-hydroxy-piperidin-1-yl]-ethyl]-3-(3,4-dimethoxy-phenyl)-pyrrolidine maleic acid salt Combine 1-(3,4,5-trimethoxy-benzoyl)-3-[2-[4-[1-(4-fluoro-benzyl)-1 H-benzoimidazol-2-yl]-4-hydroxy-piperidin-1-yl]-ethyl]-3-(3,4-dimethoxy-phenyl)-pyrrolidine (0.52 g, 0.69 mmol) and maleic acid (0.081 g, 0.69 mmol) in tetrahydrofuran (25 mL). Heat the reflux. After 15 minutes, cool to ambient temperature and evaporate in vacuo to give a residue. Triturate the residue with diethyl ether (100 ml) to give a solid. Filter and dry in vacuo at 82° C. to give the title compound: mp; 125–127° C. HRMS (FAB+): calculated 753.366354. Found 753.364711.

EXAMPLE 6

1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine

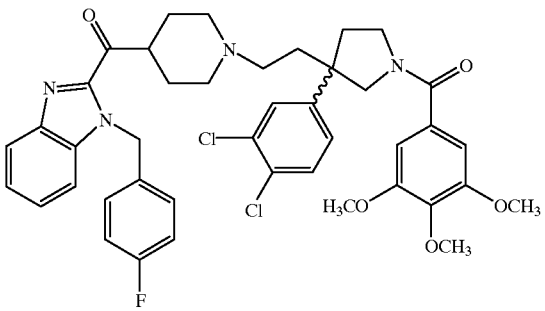

6.1 Synthesis of 3-cyano-3-(3,4-dichloro-phenyl)-pentanedioic acid diethyl ester Prepare by the method of Example 1.1 using 3,4-dichlorophenylacetonitrile (30.0 g, 0.161 mol). Purify by recrystallization from diethyl ether to give the title compound: $R_f$=0.28 (silica gel, 20% ethyl acetate/hexane), mp; 68–69° C. Elemental Analysis calculated for $C_{16}H_{17}Cl_2NO_4$: C 53.65; H 4.78; N 3.91; Found: C 53.69; H 4.79; N 3.93.

6.2.1 Synthesis of [3-(3,4-dichloro-phenyl)-5-oxo-pyrrolidin-3-yl]-acetic acid ethyl ester Prepare by the method of Example 1.2 using 3-cyano-3-(3,4-dichloro-phenyl)-pentanedioic acid diethyl ester (10 g, 28 mmol). To purify chromatograph on silica gel eluting sequentially with 3% methanol/dichloromethane 6% methanol/dichloromethane to give the title compound.

6.2.2 Synthesis of [3-(3,4-dichloro-phenyl)-5-oxo-pyrrolidin-3-yl]-acetic acid ethyl ester Combine 3-cyano-3-(3,4-dichloro-phenyl)-pentanedioic acid diethyl ester (32 g, 89 mmol) and ethanol (150 mL) in a Parr bottle. Add Raney nickel (100 g) and an aqueous concentrated ammonia solution (40 mL). Hydrogenate at 50 psi for 24 h. Filter through a celite pad and rinse the solids with ethanol. Evaporate the filtrate in vacuo to obtain a residue. Chromatograph the residue on silica gel eluting with 6% methanol/dichloromethane to give the title compound: $R_f$=0.34 (silica gel, 6% methanol/dichloromethane); mp; 87–90° C. Elemental Analysis calculated for $C_{14}H_{15}Cl_2NO_3$: C 53.18; H 4.78; N 4.43; Found: C 53.34; H 4.71; N 4.51.

6.3 Synthesis of [3-(3,4-dichloro-phenyl)-3-(2-hydroxy-ethyl)-pyrrolidine

Cool a solution of lithium aluminum hydride (450 mL, 1 M in THF, 450 mmol) to −10° C. in a ice/acetone bath. Add dropwise, a solution of sulfuric acid (12 mL, 99.999%, 225.3 mmol) in THF (35 mL). (Use caution when adding the sulfuric acid to the THF and also when adding the sulfuric acid/THF solution to the lithium aluminum hydride solution). After the addition is complete, stir for 1 hour. Warm to ambient temperature and stir for 2 hours. Add dropwise, a solution of [3-(3,4-dichloro-phenyl)-5-oxo-pyrrolidin-3-yl]-acetic acid ethyl ester (23.2 g, 73.4 mmol) in THF (70 mL). Heat to 45–50° C. for 36 hours. Cool in an ice bath. Add dropwise, a solution of THF/water (1/1, 70 mL). Filter and rinse the filter cake with THF and dichloromethane, retain the filtrate. Combine the filter cake with THF/water/15% sodium hydroxide solution (1 L/70 mL/20 mL) and vigorously stir for 2 hours. Filter and combine the filtrate with the filtrate obtained above. Concentrate the combined filtrates in vacuo to obtain a residue. Dissolve the residue in dichloromethane and dry over $MgSO_4$, filter, and concentrate in vacuo to obtain a residue. Recrystallize the residue from diethyl ether to give the title compound: $R_f$=0.27 (silica gel, 9:1:0.2; dichloromethane:methanol:ammonium hydroxide); mp; 91–94° C. Elemental Analysis calculated for $C_{12}H_{15}Cl_2NO$: C 55.40; H 5.81; N 5.38; Found: C 55.64; H 5.88; N 5.20.

6.4 Synthesis of 1-(3,4,5-trimethoxy-benzoyl)-[3-(3,4-dichloro-phenyl)-3-(2-hydroxy-ethyl)-pyrrolidine Combine 3-(3,4-dichloro-phenyl)-3-(2-hydroxy-ethyl)-pyrrolidine (288 mg, 1.1 mmol) and 4-methylmorpholine (0.25 mL, 2.27 mmol) in dichloromethane (10 mL). Cool to −78° C. in a dry-ice/acetone bath. Add a solution of 3,4,5-trimethoxy-benzoyl chloride (250 mg, 1.1 mmol) in dichloromethane (3 mL). Warm the reaction mixture to 0° C. After 1 hour, extract the reaction mixture with 1 M hydrochloric acid solution and 5% sodium bicarbonate solution. Dry the organic layer over $MgSO_4$, filter, and concentrate in vacuo to give a residue. Chromatograph the residue on silica gel eluting sequentially with 50% ethyl acetate/hexane and 6% methanol/dichloromethane to give the title compound: $R_f$=0.38 (silica gel, 6% methanol/dichloromethane).

6.5.1 Synthesis of 1-(3,4,5-trimethoxy-benzoyl)-[3-(3,4-(dichloro-phenyl)-3-(2-methanesulfonyl-ethyl)-pyrrolidine Prepare by the method of Example 1.5 using 1-(3,4,5-trimethoxy-benzoyl)-3-(3,4-dichloro-phenyl)-3-(2-hydroxy-ethyl)-pyrrolidine to give the title compound: $R_f$=0.65 (silica gel, 6% methanol/dichloromethane).

6.5.2 Synthesis of 1-(3,4,5-trimethoxy-benzoyl)-3-(3,4-dichloro-phenyl)-3-(2-methanesulfonyl-ethyl)-pyrrolidine Combine 1-(3,4,5-trimethoxy-benzoyl)-3-(3,4-dichloro-phenyl)-3-(2-hydroxy-ethyl)-pyrrolidine (200 mg, 0.44 mmol) and diisopropylethylamine (0.169 mL, 0.968 mmol) in dichloromethane (25 mL). Cool in a ice-bath. Add dropwise, methanesulfonyl chloride (0.066 g, 0.57 mmol). After 2 hours, extract with 1 M hydrochloric acid solution and 5% sodium bicarbonate solution. Dry the organic layer over $MgSO_4$, filter, and concentrate in vacuo to give the title compound: $R_f$=0.42 (silica gel, 6% methanol/dichloromethane); mp; 64.0–66.0° C.

6.6.1 Synthesis of 1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine Combine 1-(3,4,5-trimethoxy-benzoyl)-3-(3,4-dichloro-phenyl)-3-(2-methanesulfonyl-ethyl)-pyrrolidine (0.26 g, 0.488 mmol) and 4-[1-(4-fluoro-benzyl)-1 H-benzoimidazole-2-carbonyl]-piperidine (0.25 g, 0.73 mmol), and potassium carbonate (0.20 g, 1.46 mmol) in toluene/water (10/1)(5 mL). Heat to reflux. After 3 days, cool and evaporate in vacuo to obtain a residue. Partition the residue between dichloromethane and water. Dry the organic layer over $Na_2SO_4$, filter, and concentrate in vacuo to obtain a residue. Chromatograph the residue on silica gel eluting with 10/1 ethyl acetate/methanol to give the title compound: $R_f$=0.28 (silica gel, 10/1 ethyl acetate/methanol).

6.6.2 Synthesis of 1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine Combine 1-(3,4,5-trimethoxy-benzoyl)-3-(3,4-dichloro-phenyl)-3-(2-methanesulfonyl-ethyl)-pyrrolidine (0.48 g, 1.41 mmol), diisopropylethylamine (0.24 g, 1.9 mmol), 4-[1-(4-fluoro-benzyl)-1 H-benzoimidazole-2-carbonyl]-piperidine (0.50 g, 0.94 mmol), and acetonitrile (15 mL). Heat to reflux. After 18 hours, cool and partition the reaction mixture between ethyl acetate and water. Extract the organic layer with a saturated sodium bicarbonate solution and a saturated sodium chloride solution. Dry the organic layer over $Na_2SO_4$, filter, and concentrate in vacuo to obtain a residue. Chromatograph the residue on silica gel eluting with 12% methanol/ethyl acetate containing 0.1% concentrated aqueous ammonia solution to give the title compound: $R_f$=0.35 (silica gel, 12% methanol/ethyl acetate containing 0.1% concentrated aqueous ammonia solution).

6.6.3 Synthesis of 1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine Combine 1-(3,4,5-trimethoxy-benzoyl)-3-(3,4-dichloro-phenyl)-3-(2-methanesulfonyl-ethyl)-pyrrolidine (0.50 g, 0.94 mmol), diisopropylethylamine (0.24 g, 1.9 mmol), 4-[1-(4-fluoro-benzyl)-1 H-benzoimidazole-2-carbonyl]-piperidine (0.47 g, 1.91 mmol), and dioxane (7 mL). Heat to reflux. After 14 hours, cool and partition the reaction mixture between ethyl acetate and water. Extract the organic layer with a saturated sodium bicarbonate solution and a saturated sodium chloride solution. Dry the organic layer over $Na_2SO_4$, filter, and concentrate in vacuo to obtain a residue. Chromatograph the residue on silica gel eluting with 12% methanol/ethyl acetate containing 0.1% a concentrated aqueous ammonia solution to give the title compound: $R_f$=0.35 (silica gel, 12% methanol/ethyl acetate containing 0.1% concentrated aqueous ammonia solution).

6.6.4 Synthesis of 1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine Combine 1-(3,4,5-trimethoxy-benzoyl)-3-(3,4-dichloro-phenyl)-3-(2-methanesulfonyl-ethyl)-pyrrolidine (0.50 g, 0.94 mmol), diisopropylethylamine (0.24 g, 1.9 mmol), 4-[1-(4-fluoro-benzyl)-1 H-benzoimidazole-2-carbonyl]-piperidine (0.48 g, 1.41 mmol), and chlorobenzene (10 mL). Heat to reflux. After 14 hours, cool and partition the reaction mixture between ethyl acetate and water. Extract the organic layer with 5% sodium bicarbonate solution and a saturated sodium chloride solution. Dry the organic layer over $Na_2SO_4$, filter, and concentrate in vacuo to obtain a residue. Chromatograph the residue on silica gel eluting with 10% methanol/ethyl acetate to give the title compound.

6.7.1 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine maleic acid salt Prepare by the method of Example 1.7 using (3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine (0.12 g, 0.16 mmol) and maleic acid (0.16 mmol) to give the title compound: mp; 167–169° C. Elemental Analysis calculated for $C_{42}H_{43}Cl_2FN_4O_5 \cdot C_4H_4O_4$: C 62.09; H 5.32; N 6.30; Found: C 62.22; H 5.20; N 6.19.

6.7.2 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine sulfuric acid salt Combine (3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine (0.16 g, 0.21 mmol) and sulfuric acid (3 drops) in 16/1 diethyl ether/dichloromethane (170 mL). After 18 hours, filter and dry at 82° C. to give the title compound: mp; 145–150° C.

6.7.3 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine methanesulfonic acid salt Combine (3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine (0.56 g) and ethyl acetate (10 mL). Add 0.77 M methanesulfonic acid in ethyl acetate (1.41 mL). Heat gently for 5 minutes. Add diethyl ether (40 mL) and stir for 1.5 hours. Filter under a blanket of nitrogen, wash with diethyl ether, and dry in vacuo at 82° C. to give the title compound: mp; 140–143° C. Elemental Analysis calculated for $C_{42}H_{43}Cl_2FN_4O_5 \cdot 1.4$ $CH_3SO_3H$: C 55.62; H 5.57; N 5.98; Found: C 55.32; H 5.84; N 5.90.

EXAMPLE 7

1-(3,4,5-Trimethoxy-benzoyl)-3-[2-[4-[1-(4-fluoro-benzyl)-1 H-benzoimidazol-2-yl]-4-hydroxy-piperidin-1-yl]-ethyl]-3-(3,4-dichloro-phenyl)-pyrrolidine

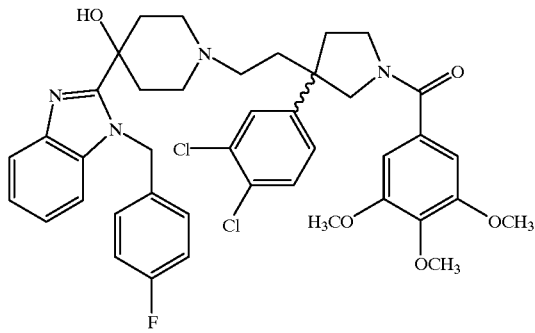

7.1 Synthesis of 1-(3,4,5-Trimethoxy-benzoyl)-3-[2-[4-[1-(4-fluoro-benzyl)-1 H-benzoimidazol-2-yl]-4-hydroxy-piperidin-1-yl]-ethyl]-3-(3,4-dichloro-phenyl)-pyrrolidine Combine 1-(3,4,5-trimethoxy-benzoyl)-3-(3,4-dichloro-phenyl)-3-(2-methanesulfonyl-ethyl)-pyrrolidine (0.20 g, 0.38 mmol) and 4-[1-(4-fluoro-benzyl)-1 H-benzoimidazol-2-yl]-4-hydroxy-piperidine (0.15 g, 0.46 mmol), and potassium carbonate (0.16 g, 1.13 mmol) in tetrahydrofuran/water (3/1) (40 mL). Heat to reflux. After 6 days, cool and evaporate in vacuo to obtain a residue. Partition the residue between dichloromethane and water. Extract the organic layer with 1 M hydrochloric acid solution, a 5% sodium bicarbonate solution, and water. Dry the organic layer over $Na_2SO_4$, filter, and concentrate in vacuo to obtain a residue. Chromatograph the residue on silica gel eluting sequentially with 10/1 ethyl acetate/methanol and 2/1 ethyl acetate/methanol to give the title compound: $R_f$=0.57 (silica gel, 2/1 ethyl acetate/methanol).

7.2 Synthesis of 1-(3,4,5-Trimethoxy-benzoyl)-3-[2-[4- [1-(4-fluoro-benzyl)-1 H-benzoimidazol-2-yl]-4-hydroxy-piperidin-1-yl]-ethyl]-3-(3,4-dichloro-phenyl)-pyrrolidine oxalic acid salt Combine 1-(3,4,5-Trimethoxy-benzoyl)-3-[2-[4-[1-(4-fluoro-benzyl)-1 H-benzoimidazol-2-yl]-4-hydroxy-piperidin-1-yl]-ethyl]-3-(3,4-dichloro-phenyl)-pyrrolidine (0.11 g, 0.14 mmol) and oxalic acid (0.013 g, 0.14 mmol) in tetrahydrofuran (25 mL). Heat to reflux. After 1 hour, cool to ambient temperature and evaporate in vacuo to obtain a residue. Triturate with diethyl ether (40 mL) and stir for 18 hours. Filter and dry at 82° C. in vacuo to give the title compound: mp; 130–150° C. HRMS (FAB+): calculated 761.267280. Found 761.267480.

EXAMPLE 8

1-Benzoyl-3-[2-[4-(benzothiazole-2-carbonyl)-piperidin-1-yl]-ethyl]-3-(3,4-dimethoxy-phenyl)-pyrrolidine

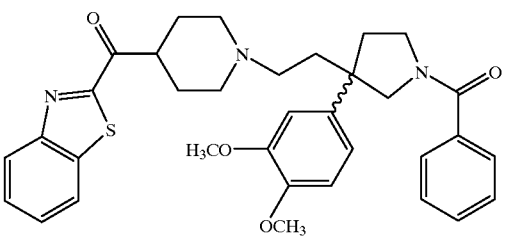

8.1 Synthesis of 1-benzoyl-3-[2-[4-(benzothiazole-2-carbonyl) -piperidin-1-yl]-ethyl]-3-(3,4-dimethoxy-phenyl)-pyrrolidine Combine 1-benzoyl-3-(3,4-dimethoxy-phenyl)-3-(2-methanesulfonyl-ethyl)-pyrrolidine (0.20 g, 0.46 mmol) and 4-(benzothiazole-2-carbonyl)-piperidine (0.11 g, 0.46 mmol), and sodium carbonate (0.098 g, 0.92 mmol) in tetrahydrofuran/water (15/4) (30 mL). Heat to reflux. After 4 days, cool to ambient temperature and evaporate in vacuo to obtain a residue. Partition the residue between dichloromethane and 5% sodium bicarbonate solution. Dry the organic layer over $Na_2SO_4$, filter, and concentrate in vacuo to obtain a residue. Chromatograph the residue on silica gel eluting with 10/1 ethyl acetate/methanol to give a residue. Combine the solid with dichloromethane and extract with 5% sodium bicarbonate solution. Dry the organic layer over $Na_2SO_4$, filter, and concentrate in vacuo to obtain a residue. Dry the residue in vacuo at 82° C. to give the title compound: $R_f$=0.21 (silica gel, 10/1 ethyl acetate/methanol); mp; 74–76° C.

EXAMPLE 9

1-(3,4,5-Trimethoxy-benzoyl)-3-[2-[4-(hydroxy-diphenyl-methyl)-piperidin-1-yl]-ethyl]-3-(3,4-dimethoxy-phenyl)-pyrrolidine

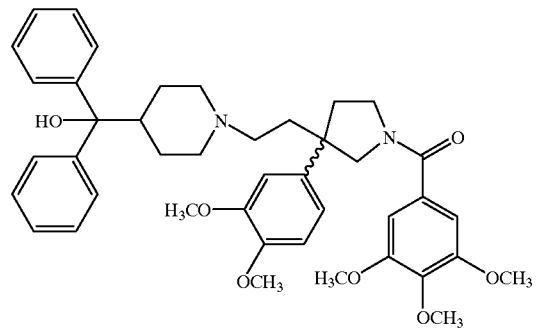

9.1 Synthesis of 1-(3,4,5-trimethoxy-benzoyl)-3-[2-[4-(hydroxy-diphenyl-methyl)-piperidin-1-yl]-ethyl]-3-(3,4-dimethoxy-phenyl)-pyrrolidine Combine 1-(3,4,5-trimethoxy-benzoyl)-3-(3,4-dimethoxy-phenyl)-3-(2-methanesulfonyl-ethyl)-pyrrolidine (0.50 g, 0.96 mmol), 4-(hydroxy-diphenyl-methyl)-piperidine (0.39 g, 1.44 mmol), and potassium carbonate (0.60 g, 4.34 mmol) in dimethylformamide (30 mL). Heat to 80° C. After 48 hours, cool and evaporate in vacuo to obtain a residue. Partition the residue between ethyl acetate and water. Extract the organic layer with water and a saturated solution of potassium carbonate. Dry the organic layer over $Na_2SO_4$, filter, and concentrate in vacuo to obtain a residue. Chromatograph the residue on silica gel eluting with 5/1 ethyl acetate/methanol to give a foam. Combine the foam with dichloromethane and extract with 5% sodium bicarbonate solution. Dry the organic layer over Na$_2$SO$_4$, filter, and concentrate in vacuo at 65° C. to obtain the title compound: R$_f$=0.21 (silica gel, 5/1 ethyl acetate/methanol); mp; 95–97° C.

9.2 Synthesis of 1-(3,4,5-trimethoxybenzoyl)-3-[2-[4-(hydroxy-diphenyl-methyl)-piperidin-1-yl]-ethyl]-3-(3,4-dimethoxy-phenyl)-pyrrolidine maleic acid salt Prepare by the method of Example 1.7 using 1-(3,4,5-trimethoxybenzoyl)-3-[2-[4-(hydroxy-diphenyl-methyl)-piperidin-1-yl]-ethyl]-3-(3,4-dimethoxy-phenyl)-pyrrolidine (0.33 g, 0.48 mmol) and maleic acid (0.055 g, 0.47 mmol) to give a solid. Filter and dry to give the title compound: mp; 169–170° C. Elemental Analysis calculated for C$_{42}$H$_{50}$N$_2$O$_7$·C$_4$H$_4$O$_4$·0.4 H$_2$O: C 67.48; H 6.75; N 3.42; Found: C 67.46; H 6.74; N 3.36.

EXAMPLE 10

1-(3,4,5-Trimethoxy-benzoyl)-3-[2- [4- [1- (4-fluoro-benzyl)-1 H-benzoimidazole-2-carbonyl]-piperidin-1-yl]-ethyl]-3-(benzo[1,3]dioxol-5-yl)-pyrrolidine

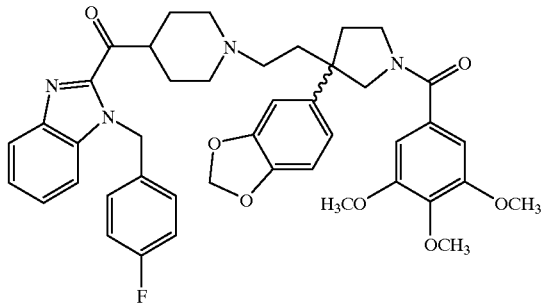

10.1 Synthesis of 3-cyano-3-(benzo[1,3]dioxol-5-yl)-pentanedioic diethyl ester

Prepare by the method of Example 1.1 using 3-(benzo[1,3]dioxol-5-yl)-phenyl-acetonitrile to obtain the title compound: R$_f$=0.32 (silica gel, 25% ethyl acetate/hexane). Elemental Analysis calculated for C$_{17}$H$_{19}$NO$_6$: C 61.25; H 5.75; N 4.20; Found: C 61.51; H 5.88; N 4.18.

10.2 Synthesis of 3-(benzo[1,3]dioxol-5-yl)-5-oxo-pyrrolidin-3-yl]-acetic acid ethyl ester Prepare by the method of Example 1.2 using 3-cyano-3-(benzo[1,3]dioxol-5-yl)-pentanedioic diethyl ester to obtain the title compound: R$_f$=0.40 (silica gel, ethyl acetate); mp; 120–121° C. Elemental Analysis calculated for C$_{15}$H$_{17}$NO$_5$: C 61.85; H 5.88; N 4.81; Found: C 61.60; H 5.89; N 4.72.

10.3 Synthesis of 3-(benzo[1,3]dioxol-5-yl)-3-(2-hydroxy-ethyl)-pyrrolidine

Prepare by the method of Example 1.3 using 3-(benzo[1,3]dioxol-5-yl)-5-oxo-pyrrolidin-3-yl]-acetic acid ethyl ester to obtain the title compound: mp; 112.0–114.5° C. Elemental Analysis calculated for C$_{13}$H$_{17}$NO$_3$: C 66.36; H 7.28; N 5.95; Found: C 66.38; H 7.29; N 5.74.

10.4 Synthesis of 1-(3,4,5-trimethoxy-benzoyl)-3-(benzo[1,3]dioxol-5-yl)-3-(2-hydroxy-ethyl)-pyrrolidine Prepare by the method of Example 1.4.1 using 3-(benzo[1,3]dioxol-5-yl)-3-(2-hydroxy-ethyl)-pyrrolidine to obtain the title compound: R$_f$=0.34 (silica gel, 20/1 ethyl acetate/methanol); mp; 63–65° C. Elemental Analysis calculated for C$_{23}$H$_{27}$NO$_7$: C 64.32; H 6.34; N 3.26; Found: C 64.30; H 6.55; N 3.04.

10.5 Synthesis of 1-(3,4,5-trimethoxy-benzoyl)-3-(benzo[1,3]dioxol-5-yl)-3-(2-methanesulfonyl-ethyl)-pyrrolidine Combine 1-(3,4,5-trimethoxy-benzoyl)-3-(benzo[1,3]dioxol-5-yl)-3-(2-hydroxy-ethyl)-pyrrolidine (0.5 g, 1.2 mmol), diisopropylethylamine (0.33 g, 2.6 mmol), and dichloromethane (15 mL). Cool to −5° C. using a salt-ice bath. Add dropwise, methanesulfonyl chloride (0.19 g, 1.62 mmol) at such a rate as to maintain the reaction temperature below 0° C. After 1 hour, the reaction mixture is extracted with 1 M hydrochloric acid solution and then a 5% sodium bicarbonate solution. Dry the organic layer over Na$_2$SO$_4$, filter and evaporate in vacuo to give the title compound: R$_f$=0.48 (silica gel, ethyl acetate).

10.6 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine Combine 1-(3,4,5-trimethoxy-benzoyl)-3-(benzo[1,3]dioxol-5-yl)-3-(2-methanesulfonyl-ethyl)-pyrrolidine (0.64 g, 1.26 mmol), diisopropylethylamine (0.33 g, 2.6 mmol), acetonitrile (14 mL), and 4-[1-(4-fluoro-benzyl)-1 H-benzoimidazole-2-carbonyl]-piperidine (0.64 g, 1.9 mmol). Heat to reflux. After 48 hours, partition the reaction mixture between ethyl acetate and water. Extract 2 times with water, a saturated sodium bicarbonate solution, and a saturated sodium chloride solution. Dry the organic layer over Na$_2$SO$_4$, filter, and evaporate in vacuo to give a residue. Chromatograph the residue on silica gel eluting with 10/1 ethyl acetate/methanol to give a residue. Partition the residue between dichloromethane and water. Dry the organic layer over Na$_2$SO$_4$, filter, and evaporate in vacuo at 70° C. to give the title compound: R$_f$=0.54 (silica gel, 10/1 ethyl acetate/methanol); mp; 94–97° C.

10.7 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine methanesulfonate salt Prepare by the method of Example 6.7.3 using 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine (0.50 g, 0.67 mmol) and methanesulfonic acid (1.36 mL, 0.77 M in ethyl acetate, 1.05 mmol) to give the title compound: mp; 129–131° C. Elemental Analysis calculated for C$_{43}$H$_{45}$FN$_4$O$_7$·1.6 CH$_3$SO$_3$H·2.2 H$_2$O: C 56.81; H 5.97; N 5.94; Found: C 56.84; H 5.88; N 6.02.

EXAMPLE 11

1-(3,4,5-Trimethoxy-benzoyl)-3-[2-[4-[1-(4-fluoro-benzyl)-1 H-benzoimidazole-2-carbonyl]-piperidin-1-yl]-ethyl]-3-phenyl-pyrrolidine

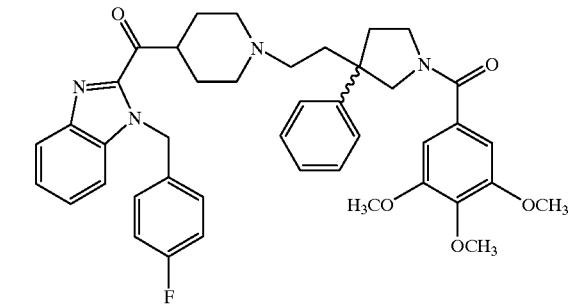

11.1.1 Synthesis of 3-cyano-3-phenyl-pentanedioic acid diethyl ester

Prepare by the method of Example 1.1 using phenyl-acetonitrile (5.85 g, 50.0 mmol). Purify by chromatography on silica gel eluting with 20% ethyl acetate in hexane to obtain the title compound: R$_f$=0.23 (silica gel, 20% ethyl acetate in hexane).

11.1.2 Synthesis of 3-cyano-3-phenyl-pentanedioic acid diethyl ester

Combine phenyl-acetonitrile (5.85 g, 50.0 mmol) and tetrahydrofuran (140 mL). Cool to about 5° C. Add dropwise a solution of sodium bis-(trimethylsilyl)amide (800 mL, 1 M in tetrahydrofuran, 800 mmol). When the addition is complete, warm the reaction mixture to ambient temperature and allow to stir for 1 hour. Transfer the above solution via cannula into a cooled (−8° C.) solution of ethyl bromoacetate (84.5 mL, 762 mmol) in tetrahydrofuran (500 mL) at such a rate that the temperature of the reaction mixture does not rise above about 20° C. Allow to stir at ambient temperature. After 18 hours, dilute with diethyl ether (1.5 L) and extract with saturated aqueous solution of ammonium chloride, then water, and then saturated aqueous solution of sodium chloride. Dry the organic layer over MgSO$_4$, filter, and concentrate in vacuo to obtain a residue. Distill the residue by bulb-to-bulb distillation to give the title compound: bp; 140–150° C. at 0.2 mm Hg.

11.2.1 Synthesis of [3-phenyl-5-oxo-pyrrolidin-3-yl]-acetic acid ethyl ester

Prepared by the method of Example 6.2.2 using 3-cyano-3-phenyl-pentanedioic acid diethyl ester to give the title compound: $R_f$=0.60 (silica gel, 6% methanol/dichloromethane).

11.2.2 Synthesis of [3-phenyl-5-oxo-pyrrolidin-3-yl]-acetic acid ethyl ester

Combine 3-cyano-3-phenyl-pentanedioic acid diethyl ester (93 g, 321 mmol) and ethanol (400 mL) in a 2 gallon pressure reactor. Add Raney nickel (280 g). Heat to 50° C. and charge with 200 psi of hydrogen. After 15 minutes, vent the reactor and add aqueous concentrated ammonia solution (120 mL). Charge the reactor with 200 psi of hydrogen. After 7 hours, vent the reactor and allow to stand for 18 hours. Filter through a celite pad and rinse the solids with ethanol. Evaporate the filtrate in vacuo to obtain a residue. Combine the residue and 1/5 diethyl ether/hexane (500 mL) and cool to −20° C. After 18 hours, decant and add 1/5 diethyl ether/hexane (500 mL) and cool to −20° C. to give a solid. Collect the solid by filtration and triturate with 1/5 diethyl ether/hexane (500 mL). Filter and dissolve in diethyl ether (300 mL) and add hexane (700 mL) to give a solid. Collect the solid by filtration and dry to give the title compound. Elemental Analysis calculated for $C_{14}H_{17}NO_3$: C 68.00; H 6.93; N 5.66; Found: C 67.63; H 6.99; N 5.81.

11.3 Synthesis of 3-phenyl-3-(2-hydroxy-ethyl)-pyrrolidine

Prepare by the method of Example 1.3 using [3-phenyl-5-oxo-pyrrolidin-3-yl]-acetic acid ethyl ester (8.7 g, 35 mmol) to give, after recrystallization from dichloromethane/diethyl ether, the title compound: mp; 115.0–117.0° C.; $R_f$=0.03 (silica gel, 6% methanol/dichloromethane). Elemental Analysis calculated for $C_{12}H_{17}NO$: C 75.36; H 8.96; N 7.32; Found: C 75.78; H 8.96; N 7.45.

11.4.1 Synthesis of 1-(3,4,5-trimethoxy-benzoyl)-3-phenyl-3-(2-hydroxy-ethyl)-pyrrolidine Prepared by the method of Example 1.4.1 using 3-phenyl-3-(2-hydroxy-ethyl)-pyrrolidine to give the title compound: $R_f$=0.38 (silica gel, 6% methanol/dichloromethane).

11.4.2 Synthesis of 1-(3,4,5-trimethoxy-benzoyl)-3-phenyl-3-(2-hydroxy-ethyl)-pyrrolidine Prepared by the method of Example 1.4.2 using 3-phenyl-3-(2-hydroxy-ethyl)-pyrrolidine to give the title compound: $R_f$=0.05 (silica gel, ethyl acetate).

11.5 Synthesis of 1-(3,4,5-trimethoxy-benzoyl)-3-phenyl-3-(2-methanesulfonyl-ethyl)-pyrrolidine Combine 1-(3,4,5-trimethoxy-benzoyl)-3-phenyl-3-(2-hydroxy-ethyl)-pyrrolidine (0.5 g, 1.3 mmol), diisopropylethylamine (0.5 mL, 2.9 mmol), and anhydrous dichloromethane (17 mL). Cool to 0° C. using an ice bath. Add methanesulfonyl chloride (201 mg, 1.36 mmol). After 2 hours, dilute the reaction mixture with dichloromethane and extract with a saturated solution of sodium bicarbonate. Dry the organic layer over Na$_2$So$_4$, filter, and concentrate in vacuo to give the title compound: $R_f$=0.26 (silica gel, ethyl acetate).

11.6 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-phenyl-pyrrolidine Combine 1-(3,4,5-trimethoxy-benzoyl)-3-phenyl-3-(2-methanesulfonyl-ethyl)-pyrrolidine (0.60 g, 1.30 mmol) and 4-[1-(4-fluoro-benzyl)-1 H-benzoimidazole-2-carbonyl]-piperidine (0.66 g, 1.95 mmol), and diisopropylethylamine (0.453 mL, 2.60 mmol) in chlorobenzene (8 mL). Heat to reflux. After 18 hours, partition the residue between ethyl acetate and water. Extract the organic layer 3 times with water and 1 time with saturated sodium chloride solution. Dry the organic layer over Na$_2$So$_4$, filter, and concentrate in vacuo to obtain a residue. Chromatograph the residue on silica gel eluting with 10/1/0.1 ethyl acetate/methanol/concentrated aqueous ammonium hydroxide to give the title compound: $R_f$=0.15 (silica gel, 10/1/0.1 ethyl acetate/methanol/concentrated aqueous ammonium hydroxide).

11.7 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-phenyl-pyrrolidine maleic acid salt Prepare by the method of Example 1.7 using 1-(3,4,5-trimethoxy-benzoyl)-3-[2-[4-[1-(4-fluoro-benzyl)-1 H-benzoimidazole-2-carbonyl]-piperidin-1-yl]-ethyl]-3-phenyl-pyrrolidine (0.55 g, 0.78 mmol) and maleic acid (91 mg, 0.79 mmol) to give the title compound: mp; 107–109° C.

EXAMPLE 12

1-Benzoyl-3-[2- [4-[1-(4-fluoro-benzyl)-1 H-benzoimidazole-2-carbonyl]-piperidin-1-yl]-ethyl]-3-(naphth-2-yl)-pyrrolidine

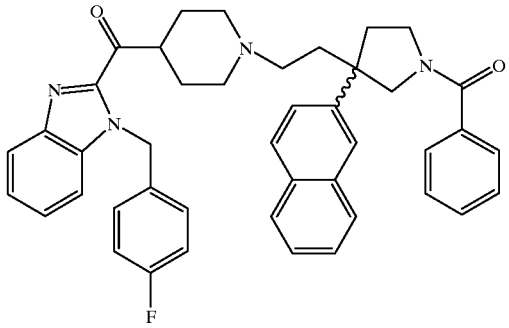

12.1 Synthesis of 3-cyano-3-(naphth-2-yl)-pentanedioic acid diethyl ester

Prepare by the method of Example 1.1 using 2-naphthylacetonitrile (1.67 g, 10 mmol) to obtain a residue. Chromatograph the residue on silica gel eluting sequentially with 5% ethyl acetate/hexane and then with 20% ethyl acetate/hexane to give of the title compound.

12.2 Synthesis of [3-(naphth-2-yl)-5-oxo-pyrrolidin-3-yl]-acetic acid ethyl ester Prepare by the method of Example 6.2.2 using 3-cyano-3-(naphth-2-yl)-pentanedioic acid diethyl ester (3.2 g, 9.5 mmol) to obtain a residue. Chromatograph the residue on silica gel eluting sequentially with 30% ethyl acetate/hexane then 2% methanol/dichloromethane to give the title compound.

12.3 Synthesis of 3-(naphth-2-yl)-3-(2-hydroxy-ethyl)-pyrrolidine

Prepare by the method of Example 1.3 using [3-(naphth-2-yl)-5-oxo-pyrrolidin-3-yl]-acetic acid ethyl ester (1.3 g, 4.25 mmol) to give the title compound.

12.4 Synthesis of 1-benzoyl-3-(naphth-2-yl)-3-(2-hydroxy-ethyl)-pyrrolidine

Combine 3-(naphth-2-yl)-3-(2-hydroxy-ethyl)-pyrrolidine (0.12 g, 0.5 mmol) and dichloromethane (10 mL). Cool to 0° C. in an ice bath. Add benzoyl chloride (0.06 mL, 0.5 mmol) and diisopropylethylamine (0.09 mL, 0.50 mmol). After 4 hours, dilute with ethyl acetate and extract with 1 M hydrochloric acid solution, saturated sodium bicarbonate solution, and saturated sodium chloride solution. Dry the organic layer over $MgSO_4$, filter, and concentrate in vacuo to give a residue. Chromatograph the residue on silica gel eluting sequentially with 35% ethyl acetate/hexane and then 4% methanol/chloroform to give the title compound.

12.5 Synthesis of 1-benzoyl-3-(naphth-2-yl)-3-(2-methanesulfonyl-ethyl)-pyrrolidine Combine 1-benzoyl-3-(naphth-2-yl)-3-(2-hydroxy-ethyl)-pyrrolidine (1.05 g, 3.0 mmol) and diisopropylethylamine (0.93 mL, 4.0 mmol) in dichloromethane (30 mL). Cool to 0° C. in an ice bath. Add methanesulfonyl chloride (0.28 mL, 3.65 mmol). After 2 hours, add diisopropylethylamine (0.93 mL, 4.0 mmol) and methanesulfonyl chloride (0.28 mL, 3.7 mmol). After 2 hours, concentrate in vacuo to obtain a residue. Chromatograph the residue on silica gel eluting with 1% methanol/dichloromethane to give the title compound.

12.6 Synthesis of 1-benzoyl-3-[2-[4-[1-(4-fluoro-benzyl)-1 H-benzoimidazole-2-carbonyl]-piperidin-1-yl]-ethyl]-3-(naphth-2-yl)-pyrrolidine Prepare by the method of Example 6.6.2 using 1-benzoyl-3-(naphth-2-yl)-3-(2-methanesulfonyl-ethyl)-pyrrolidine (2 mmol) to give the title compound.

EXAMPLE 13

1-Benzyl-3-[2-[4-[1-(4-fluoro-benzyl)-1 H-benzoimidazole-2-carbonyl]-piperidin-1-yl]-ethyl]-3-(3,4-dichloro-phenyl)-5-oxo-pyrrolidine

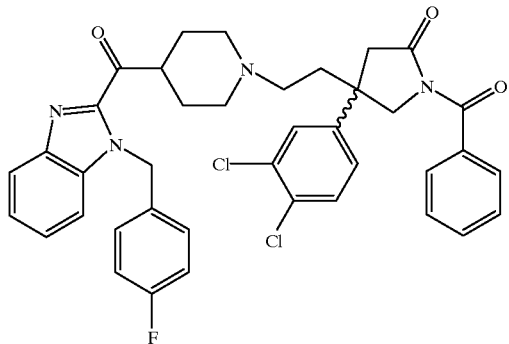

13.1 Synthesis of 2-(3,4-dichloro-phenyl)-4-(tetrahydro-pyran-2-yl-oxy)-butyronitrile Combine sodium hydride (1.4 g, 59.2 mmol) and THF (25 mL). Cool in a dry-ice/acetone bath. Add a solution of 3,4-dichlorophenylacetonitrile (10 g, 53.8 mmol) in THF (60 mL). After the addition is complete, warm to ambient temperature. After 2.5 hours, cool to 0° C. Add dropwise, a solution of 2-(2-bromo-ethoxy)-tetrahydro-pyran (55 mmol) in THF (25 mL). Warm to 20° C. and stir for 16 hours. Pour the reaction mixture into saturated ammonium chloride solution and extract with diethyl ether. Extract the organic layer with water and saturated sodium chloride solution. Dry the organic layer over $MgSO_4$, filter, and concentrate in vacuo to give a residue. Chromatograph the residue on silica gel eluting sequentially with 5% ethyl acetate/hexane then 20% ethyl acetate/hexane to give the title compound.

13.2 Synthesis of 3-cyano-3-(3,4-dichloro-phenyl)-5-(tetrahydro-pyran-2-yl-oxy) pentanoic acid ethyl ester Combine 2-(3,4-dichloro-phenyl)-4-(tetrahydro-pyran-2-yl-oxy)-butyronitrile (10.8 g, 34.6 mmol) and THF (20 mL). Cool to −78° C. in a dry-ice/acetone bath. Add dropwise over 30 minutes, a solution of lithium diisopropylamide (27.2 mL, 40.8 mmol). After 30 minutes, add ethyl bromoacetate (4.2 mL, 37.9 mmol) Warm to ambient temperature and stir for 4 hours. Partition the reaction mixture between ammonium chloride solution and diethyl ether. Extract with water and a saturated sodium chloride solution. Dry the organic layer over $MgSO_4$, filter, and concentrate in vacuo to give a residue. Chromatograph the residue on silica gel eluting sequentially with 20% ethyl acetate/hexane then 30% ethyl acetate/hexane to give of the title compound.

13.3 Synthesis of 4-(3,4-dichloro-phenyl)-4-(tetrahydro-pyran-2-yl-oxy)ethyl)-pyrrolidin-2-one Combine 3-cyano-3-(3,4-dichloro-phenyl)-5-(tetrahydro-pyran-2-yl-oxy)pentanoic acid ethyl ester (9.5 g, 23.8 mmol) and ethanol/aqueous concentrated ammonium hydroxide (190 mL/38 mL). Hydrogenate in a Parr shaker at 45 psi for 7 hours over Raney nickel (30 g). Filter to remove the catalyst. Concentrate the filtrate in vacuo to obtain a residue. Chromatograph the residue on silica gel eluting sequentially with 30% ethyl acetate/hexane then 10% methanol/dichloromethane to give the title compound.

13.4 Synthesis of 1-benzyl-4-(3,4-dichloro-phenyl)-4-[2-(tetrahydro-pyran-2-yl-oxy)ethyl]-pyrrolidin-2-one Combine 3-(3,4-dichloro-phenyl)-4-(tetrahydro-pyran-2-yl-oxy)ethyl)-pyrrolidin-2-one (1.0 g, 2.79 mmol) and sodium hydride (80 mg) in THF (10 mL) and allow to stir until gas evolution ceases. Add benzyl bromide (0.7 mL, 5.89 mmol). After 7.5 hours, partition the reaction mixture between diethyl ether and a saturated ammonium chloride solution. Extract the organic layer with water and saturated sodium chloride solution. Dry the organic layer over $MgSO_4$, filter, and concentrate in vacuo to give a residue. Chromatograph the residue on silica gel eluting with 50% ethyl acetate in hexane to give the title compound.

13.5 Synthesis of 1-benzyl-4-(3,4-dichloro-phenyl)-4-(2-hydroxy-ethyl)-pyrrolidin-2-one Combine 1-benzyl-4-(3,4-dichloro-phenyl)-4-[2-(tetrahydro-pyran-2-yl-oxy)ethyl]-pyrrolidin-2-one (1.0 g, 2.8 mmol) and p-toluenesulfonic acid (200 mg) in methanol (6 mL). After 5 hours, concentrate in vacuo to obtain a residue. Dissolve the residue in dichloromethane and extract with 5% sodium bicarbonate solution and water. Dry the organic layer over $MgSO_4$, filter, and concentrate in vacuo to give a residue. Chromatograph the residue on silica gel eluting sequentially with 50% ethyl acetate/hexane then 10% methanol/dichloromethane to give the title compound.

13.6 Synthesis of 1-benzyl-4-(3,4-dichloro-phenyl)-4-(2-methanesulfonyl-ethyl)-pyrrolidin-2-one Combine 1-benzyl-4-(3,4-dichloro-phenyl)-4-(2-hydroxy-ethyl)-pyrrolidin-2-one (779 mg, 2.14 mmol) and diisopropylethylamine (0.5 mL, 2.87 mmol) in dichloromethane (10 mL). Cool to 0° C. using an ice bath. Add methanesulfonyl chloride (0.2 mL, 2.6 mmol). After 2 hours, extract the reaction mixture with 1 M hydrochloric acid solution, 5% sodium bicarbonate solution, and water. Dry the organic layer over $MgSO_4$, filter, and concentrate in vacuo to give a residue. Chromatograph the residue on silica gel eluting sequentially with 50% ethyl acetate/hexane then ethyl acetate to give the title compound.

13.7 Synthesis of 1-benzyl-3-[2-[4-[1-(4-fluoro-benzyl)-1 H-benzoimidazole-2-carbonyl]-piperidin-1-yl]-ethyl]-3-(3, 4-dichloro-phenyl)-5-oxo-pyrrolidine Prepare by the method of Example 6.6.2 using 1-benzyl-4-(3,4-dichloro-phenyl)-4-(2-methanesulfonyl-ethyl)-pyrrolidin-2-one to give the title compound.

EXAMPLE 14

(+)-1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine

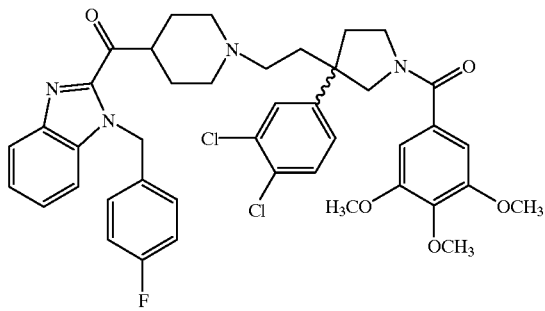

14.1 Synthesis of 1-(3,4,5-trimethoxy-benzoyl)-3-(3,4-dichloro-phenyl)-3-(2-acetoxy-ethyl)-pyrrolidine Combine 3-(3,4-dichloro-phenyl)-3-(2-hydroxy-ethyl)-pyrrolidine (4.5 g, 9.9 mmol) and dichloromethane/pyridine (70 mL, 6/1). Add acetic anhydride (1.04 mL, 11.0 mmol) and 4-dimethylaminopyridine (50 mg, 0.41 mmol). After 2 hours, concentrate the reaction mixture in vacuo to obtain a residue. Dissolve the residue in ethyl acetate and extract with 1 M hydrochloric acid solution (2×200 mL), saturated sodium bicarbonate solution, and saturated sodium chloride solution. Dry the organic layer over $MgSO_4$, filter, and concentrate in vacuo to obtain a residue. Chromatograph the residue on silica gel eluting with ethyl acetate to give the title compound: $R_f$=0.38 (silica gel, ethyl acetate). Elemental Analysis calculated for $C_{24}H_{27}Cl_2NO_6$: C 58.07; H 5.48; N 2.82; Found: C 57.67; H 5.46; N 2.84.

14.2 Resolution to dive (+)-1-(3,4,5-trimethoxy-benzoyl)-3-(3,4-dichloro-phenyl)-3-(2-acetoxy-ethyl)-pyrrolidine.

Combine 1-(3,4,5-trimethoxy-benzoyl)-3-(3,4-dichloro-phenyl)-3-(2-acetoxy-ethyl)-pyrrolidine (6.6 g, 13.31 mmol) and dichloromethane (100 mL). Add silica gel (32 g). Concentrate the slurry in vacuo to give a residue. Suspend the residue in phosphate buffer (800 mL, 0.1 M, pH=7.5, the buffer was prepared with 11.5 g $H_3PO_4$ (85%) diluted to 1 L with deionized water and then adjusting the pH with solid potassium hydroxide pellets to 7.5) to obtain a slurry. Treat the slurry with Lipase (13 g, EC 3.1.1.3, Type VII, from Candida cylindracea). Monitor the reaction by HPLC on a CHIRALPAK AD 25 cm×0.46 cm column eluting with pentane/ethanol/methanol (80/15/5) with a flow rate of 1.0 mL/minute. Prepare an aliquot for analysis as follows: centrifuge the solution for 10 minutes at 14000 $cm^{-1}$, remove the supernatant and concentrate under a nitrogen stream to obtain a residue, dissolve the residue in dichloromethane (ca. 1 mL) and inject on the column for analysis. When the enantiomeric excess (ee) is satisfactory (>95% ee) for the (+)-acetate, filter the reaction. Rinse the solids with dichloromethane (8×500 mL). Extract the filtrate with dichloromethane (8×500 mL). Chromatograph the solids on silica gel eluting with 6% methanol/dichloromethane. Concentrate the combined eluant and extracts in vacuo to obtain a residue. Dissolve the residue in dichloromethane, dry over $MgSO_4$, filter, and concentrate in vacuo to give a residue. Chromatograph the residue on silica gel eluting with ethyl acetate to give the title compound: $R_f$=0.38 (silica gel, ethyl acetate). Elemental Analysis calculated for $C_{24}H_{27}Cl_2NO_6·0.5 H_2O$: C 57.14; H 5.59; N 2.78; Found: C 57.37; H 5.45; N 2.87.

$[\alpha]^{20}$=+36.4° (c=0.894, $CHCl_3$).

14.3 Synthesis of (+)-1-(3,4,5-trimethoxy-benzoyl)-3-(3,4-dichloro-phenyl)-3-(2-hydroxy-ethyl)-pyrrolidine Combine (+)-1-(3,4,5-trimethoxy-benzoyl)-3-(3,4-dichloro-phenyl)-3-(2-acetoxy-ethyl)-pyrrolidine (670 mg, 1.35 mmol) and aqueous lithium hydroxide solution (4.2 mL, 1 M) in methanol (15 mL). After 3.5 hours, concentrate in vacuo to give a residue. Dissolve the residue in dichloromethane and extract with 1 M hydrochloric acid solution and saturated sodium bicarbonate solution. Dry the organic layer over $MgSO_4$, filter, and concentrate in vacuo to obtain a residue. The residue was dried under high vacuum for 18 hours to give the title compound: $R_f$=0.11 (silica gel, ethyl acetate).

14.4.1 Resolution of (+)-3-(3,4-dichloro-phenyl)-3-(2-hydroxy-ethyl)-pyrrolidine (R, R)-di-p-anisoyltartaric acid salt and (−)-3-(3,4-dichloro-phenyl)-3-(2-hydroxy-ethyl)-pyrrolidine (R, R)-di-p-anisoyltartaric acid salt Combine 3-(3,4-dichloro-phenyl)-3-(2-hydroxy-ethyl)-pyrrolidine (1.0 g, 38.5 mmol) and butanone. Add a solution of (R, R)-di-p-anisoyltartaric acid (1.6 g, 38.0 mmol) in butanone (80 mL). Heat to reflux. After 15 minutes, cool to ambient temperature and then cool further in an salt-ice bath. Filter the solid that forms and rinse with butanone. Recrystallize the solid from water/methanol to give (+)-3-(3,4-dichloro-phenyl)-3-(2-hydroxy-ethyl)-pyrrolidine (R, R)-di-p-anisoyltartaric acid salt: mp; 201–204° C. (dec). Analysis on HPLC, on an analytical sample of the free amine obtained by extraction, using a CHIRALPAK AD 25 cm×0.46 cm column eluting with pentane/methanol/triethylamine (80/10/0.1) with a flow rate of 1.0 mL/minute indicates an enantiomeric excess of 96%, (96% ee), retention time of the (+)-isomer 11.2 minutes, retention time of the (−)-isomer 14.5 minutes.

14.4.2 Resolution of (+)-3-(3,4-dichloro-phenyl)-3-(2-hydroxy-ethyl)-pyrrolidine (R, R)-di-p-anisoyltartaric acid-hydrochloric acid salt and (−)-3-(3,4-dichloro-phenyl)-3-(2-hydroxy-ethyl)-pyrrolidine (R, R)-di-p-anisoyltartaric acid-hydrochloric acid salt Combine (R, R)-di-p-anisoyltartaric acid (0.8 g, 19 mmol) and aqueous 12 M hydrochloric acid solution (0.16 mL, 19 mmol) in water (10 mL)/(10 mL). Heat to reflux.

Add dropwise, a solution of 3-(3,4-dichloro-phenyl)-3-(2-hydroxy-ethyl)-pyrrolidine (1.0 g, 38.5 mmol) in methanol (10 mL). After 15 minutes, slowly cool to ambient temperature. Filter the solid that forms and rinse with water to give (+)-3-(3,4-dichloro-phenyl)-3-(2-hydroxy-ethyl)-pyrrolidine (R, R)-di-p-anisoyltartaric acid-hydrochloric acid salt: mp; 201–204° C. (dec). Analysis by HPLC, as described in Example 14.1.1 indicates an enantiomeric excess of 97%, (97% ee).

14.5 Synthesis of (+)-1-(3,4,5-trimethoxy-benzoyl)-3-(3,4-dichloro-phenyl)-3-(2-hydroxy-ethyl)-pyrrolidine Combine (+)-3-(3,4-dichloro-phenyl)-3-(2-hydroxy-ethyl)-pyrrolidine (R, R)-di-p-anisoyltartaric acid salt (0.14 g, 0.21 mmol) ethyl acetate (15 mL, acetonitrile (6 mL), water, (6 mL) and sodium bicarbonate (0.09 g, 1.03 mmol). Cool to 0° C. in an salt-ice bath. Add 3,4,5-trimethoxy-benzoyl chloride (0.048 g, 0.21 mmol). After 30 minutes, warm to ambient temperature. After 30 minutes at ambient temperature, partition the reaction mixture between ethyl acetate and saturated aqueous sodium chloride solution. Extract the organic layer with 1 M hydrochloric acid solution, then saturated aqueous sodium bicarbonate solution. Dry the organic layer over $MgSO_4$, filter, and evaporate in vacuo to give the title compound: $R_f$=0.11 (silica gel, ethyl acetate).

14.6 Synthesis of (+)-1-(3,4,5-trimethoxy-benzoyl)-3-(3,4-dichloro-phenyl)-3-(2-methanesulfonyl-ethyl)-pyrrolidine Prepare by the method of Example 6.5.2 using (+)-1-(3,4,5-trimethoxy-benzoyl)-3-(3,4-dichloro-phenyl)-3-(2-hydroxy-ethyl)-pyrrolidine (1.351 mmol) and methanesulfonyl chloride (0.14 mL, 1.81 mmol) to give the title compound: $R_f$=0.27 (silica gel, ethyl acetate)

14.7 Synthesis of (+)-1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine Prepare by the method of Example 6.6.2 using (+)-1-(3,4,5-trimethoxy-benzoyl)-3-(3,4-dichloro-phenyl)-3-(2-methanesulfonyl-ethyl)-pyrrolidine to give the title compound: mp; 85–92° C. Elemental Analysis calculated for $C_{42}H_{43}Cl_2FN_4O_5$: C 65.20; H 5.60; N 7.24; Found: C 64.80; H 5.60; N 7.11.

EXAMPLE 15
1-[3,5-Bis-(trifluoromethyl)-benzoyl]-3-[2-[4-[1-(4-fluoro-benzyl)-1 H-benzoimidazole-2-carbonyl]-piperidin-1-yl]-ethyl]-3-(3,4-dichloro-phenyl)-pyrrolidine

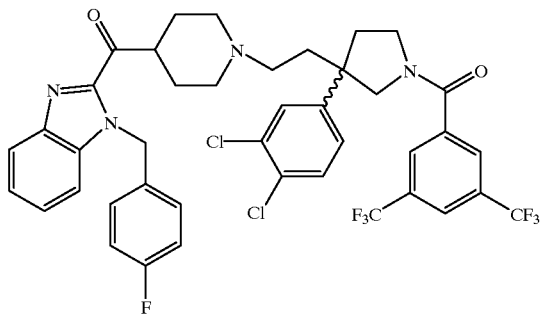

15.1 Synthesis of 1-[3,5-bis-(trifluoromethyl)-benzoyl]-3-(3,4-dichloro-phenyl)-3-(2-hydroxy-ethyl)-pyrrolidine Prepare by the method of Example 6.4 using 3,5-bis (trifluoromethyl)-benzoyl chloride to give the title compound: $R_f$=0.53 (silica gel, 10% methanol/ dichloromethane).

15.2 Synthesis of 1-[3,5-Bis-(trifluoromethyl)-benzoyl]-[3-(3,4-(dichloro-phenyl)-3-(2-methanesulfonyl-ethyl)-pyrrolidine Prepare by the method of Example 1.5 using 1-[3,5-bis-(trifluoromethyl)-benzoyl]-3-(3,4-dichloro-phenyl)-3-(2-hydroxy-ethyl)-pyrrolidine to give the title compound: $R_f$=0.68 (silica gel, 10% methanol/dichloromethane).

15.3 Synthesis of 1-[3,5-Bis-(trifluoromethyl)-benzoyl]-3-[2-[4-[1-(4-fluoro-benzyl)-1 H-benzoimidazole-2-carbonyl]-piperidin-1-yl]-ethyl]-3-(3,4-dichloro-phenyl)-pyrrolidine Prepare by the method of Example 6.6.2 using 1-[3,5-bis-(trifluoromethyl)-benzoyl]-[3-(3,4-(dichloro-phenyl)-3-(2-methanesulfonyl-ethyl)-pyrrolidine to give the title compound.

EXAMPLE 16
1-(4-t-Butyl-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine

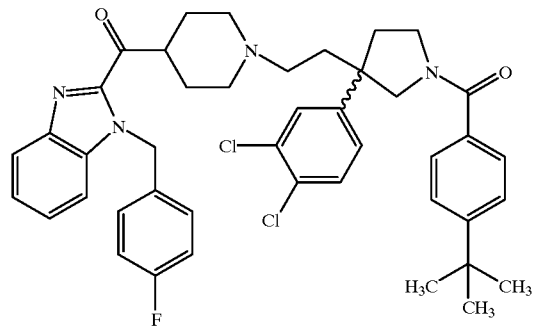

16.1 Synthesis of 1-(4-t-butyl-benzoyl)-3-(3,4-dichloro-phenyl)-3-(2-hydroxy-ethyl)-pyrrolidine Prepare by the method of Example 6.4 using 4-t-butyl-benzoyl chloride to give the title compound.

16.2 Synthesis of 1-(4-t-butyl-benzoyl)-3-(3,4-dichloro-phenyl)-3-(2-methanesulfonyl-ethyl)-pyrrolidine Prepare by the method of Example 1.5 using 1-(4-t-butyl-benzoyl)-3-(3,4-dichloro-phenyl)-3-(2-hydroxy-ethyl)-pyrrolidine to give the title compound.

16.3 Synthesis of 1-(4-t-butyl-benzoyl)-3-[2-[4-[1-(4-fluoro-benzyl)-1 H-benzoimidazole-2-carbonyl]-piperidin-1-yl]-ethyl]-3-(3,4-dichloro-phenyl)-pyrrolidine Prepare by the method of Example 6.6.2 using 1-(4-t-butyl-benzoyl)-3-(3,4-dichloro-phenyl)-3-(2-methanesulfonyl-ethyl)-pyrrolidine to give the title compound.

EXAMPLE 17
1-(3,4,5-Trimethoxyophenyl-acetyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine

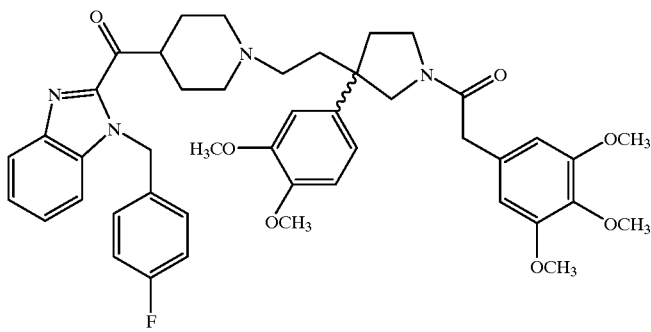

17.1 Synthesis of 1-(3,4,5-trimethoxy-acetyl)-3-(3,4-dimethoxy-phenyl)-3-(2-hydroxy-ethyl)-pyrrolidine Prepare by the method of Example 1.4.1 using 3,4,5-trimethoxyphenyl-acetyl chloride to give the title compound.

17.2 Synthesis of 1-(3,4,5-trimethoxy-acetyl)-3-(3,4-dimethoxy-phenyl)-3-(2-methanesulfonyl-ethyl)-pyrrolidine Prepare by the method of Example 1.5 using 1-(3,4,5-trimethoxy-acetyl)-3-(3,4-dimethoxy-phenyl)-3-(2-hydroxy-ethyl)-pyrrolidine to give the title compound.

17.3 Synthesis of 1-(3,4,5-trimethoxylphenyl-acetyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine Prepare by the method of Example 6.6.2 using 1-(3,4,5-trimethoxy-acetyl)-3-(3,4-dimethoxy-phenyl)-3-(2-methanesulfonyl-ethyl)-pyrrolidine to give the title compound.

EXAMPLE 18

1-(Pyridine-2-carbonyl)-3- [2- [4-[1- (4-fluoro-benzyl)-1 H-benzoimidazole-2-carbonyl]-piperidin-1-yl]-ethyl]-3-(3,4-dimethoxy-phenyl)-pyrrolidine

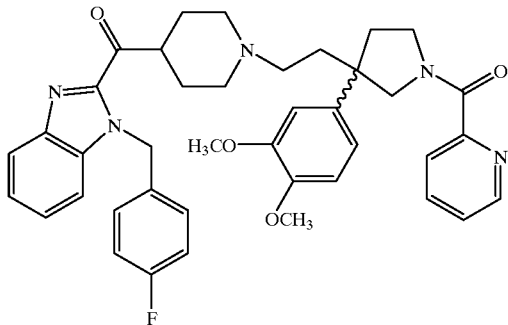

18.1 Synthesis of 1-(pyridine-2-carbonyl)-3-(3,4-dimethoxy-phenyl)-3-(2-hydroxy-ethyl)-pyrrolidine Prepare by the method of Example 1.4.1 using 2-pyridinecarbonyl chloride hydrochloride and an additional equivalent of N-methylmorpholine to give the title compound.

18.2 Synthesis of 1-(pyridine-2-carbonyl)-3-(3,4-dimethoxy-phenyl)-3-(2-methanesulfonyl-ethyl)-pyrrolidine Prepare by the method of Example 1.5 using 1-(pyridine-2-carbonyl)-3-(3,4-dimethoxy-phenyl)-3-(2-hydroxy-ethyl)-pyrrolidine to give the title compound.

18.3 Synthesis of 1-(pyridine-2-carbonyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine Prepare by the method of Example 6.6.2 using 1-(pyridine-2-carbonyl)-3-(3,4-dimethoxy-phenyl)-3-(2-methanesulfonyl-ethyl)-pyrrolidine to give the title compound.

EXAMPLE 19

1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(3-trifluoromethyl-phenyl)-pyrrolidine

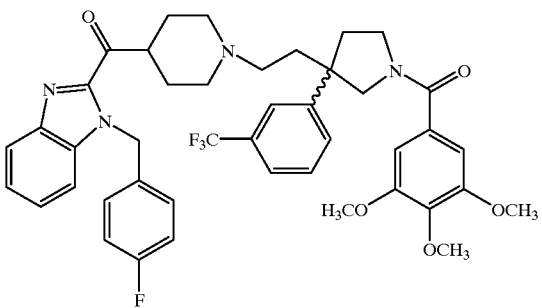

19.1 Synthesis of 3-cyano-3-(3-trifluoromethyl-phenyl)-pentanedioic acid diethyl ester Prepare by the method of Example 1.1 using 3-trifluoromethyl-phenylacetonitrile to give the title compound.

19.2 Synthesis of [3-(3-trifluoromethyl-phenyl)-5-oxo-pyrrolidin-3-yl]-acetic acid ethyl ester Prepare by the method of Example 1.2 using 3-cyano-3-(3-trifluoromethyl-phenyl)-pentanedioic acid diethyl ester to give the title compound.

19.3 Synthesis of 3-(3-trifluoromethyl-phenyl)-3-(2-hydroxy-ethyl)-pyrrolidine

Prepare by the method of Example 1.3 using [3-(3-trifluoromethyl-phenyl)-5-oxo-pyrrolidin-3-yl]-acetic acid ethyl ester to give the title compound.

19.4 Synthesis of 1-(3,4,5-trimethoxy-benzoyl)-3-(3-trifluoromethyl-phenyl)-3-(2-hydroxy-ethyl)-pyrrolidine Prepare by the method of Example 1.4.1 using 3-(3-trifluoromethyl-phenyl)-3-(2-hydroxy-ethyl)-pyrrolidine to give the title compound.

19.5 Synthesis of 1-(3.4,5-trimethoxy-benzoyl)-3-(3-trifluoromethyl-phenyl)-3-(2-methanesulfonyl-ethyl)-pyrrolidine Prepare by the method of example 1.5 using 1-(3,4,5-trimethoxy-benzoyl)-3-(3-trifluoromethyl-phenyl)-3-(2-hydroxy-ethyl)-pyrrolidine to give the title compound.

19.6 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(3-trifluoromethyl-phenyl)-pyrrolidine Prepare by the method of Example 6.6.2 using 1-(3,4,5-trimethoxy-benzoyl)-3-(3-trifluoromethyl-phenyl)-3-(2-methanesulfonyl-ethyl)-pyrrolidine to give the title compound.

EXAMPLE 20

1-(3,4,5-Trimethoxy-benzoyl)-3-[2- [4- [1- (4-fluoro-benzyl)-1 H-benzoimidazole-2-carbonyl]-piperidin-1-yl]-ethyl]-3-(4-trifluoromethyl-phenyl)-pyrrolidine

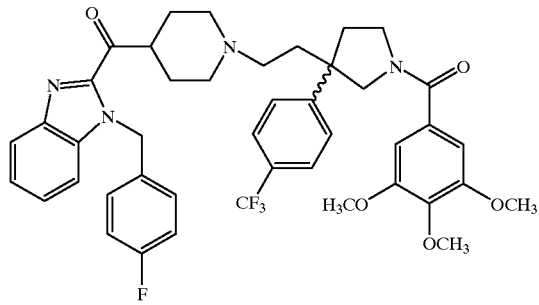

20.1 Synthesis of 3-cyano-3-(4-trifluoromethyl-phenyl)-pentanedioic acid diethyl ester Prepare by the method of Example 1.1 using 4-trifluoromethyl-phenylacetonitrile to give the title compound: $R_f$=0.46 (silica gel, 25% ethyl acetate/hexane). Elemental Analysis calculated for $C_{17}H_{18}F_3NO_4$: C 57.14; H 5.08; N 3.92; Found: C 57.29; H 5.13; N 3.93.

20.2 Synthesis of [3-(4-trifluoromethyl-phenyl)-5-oxo-pyrrolidin-3-yl]-acetic acid ethyl ester Prepare by the method of Example 1.2 using 3-cyano-3-(4-trifluoromethyl-phenyl)-pentanedioic acid diethyl ester to give the title compound: $R_f$=0.34 (silica gel, 5 ethyl acetate); mp; 104–105.5° C. Elemental Analysis calculated for $C_{15}H_{16}F_3NO_3$: C 57.14; H 5.11; N 4.44; Found: C 57.15; H 5.10; N 4.40.

20.3 Synthesis of 3-(4-trifluoromethyl-phenyl)-3-(2-hydroxy-ethyl)-pyrrolidine

Prepare by the method of Example 1.3 using [3-(4-trifluoromethyl-phenyl)-5-oxo-pyrrolidin-3-yl]-acetic acid ethyl ester to give the title compound.

20.4.1 Synthesis of 1-(3,4,5-trimethoxy-benzoyl)-3-(4-trifluoromethyl-phenyl)-3-(2-hydroxy-ethyl)-pyrrolidine Prepare by the method of Example 1.4.1 using 3-(4-trifluoromethyl-phenyl)-3-(2-hydroxy-ethyl)-pyrrolidine to give the title compound.

20.4.2 Synthesis of 1-(3,4,5-trimethoxy-benzoyl)-3-(4-trifluoromethyl-phenyl)-3-(2-hydroxy-ethyl)-pyrrolidine Combine 3-(4-trifluoromethyl-phenyl)-3-(2-hydroxy-ethyl)-pyrrolidine (0.791 g, 3.06 mmol), diisopropylethylamine (0.59 mL, 3.37 mmol), 1-ethyl-3-(3-dimethylaminopropyl)carbodiimide hydrochloride salt (0.65 g, 3.0 mmol), 1-hydroxybenzotriazole hydrate (0.56 g, 3.37 mmol) and 3,4,5-trimethoxy-benzoic acid (0.65 g, 3.06 mmol) in dichloromethane (40 mL). After 18 hours, extract the reaction mixture twice with 1 M hydrochloric acid solution and then with 5% sodium bicarbonate solution. Dry the organic layer over $Na_2SO_4$, filter, and concentrate in vacuo to obtain a residue. Chromatograph the residue on silica gel eluting sequentially with ethyl acetate and then 20/1 ethyl acetate/methanol to give a solid. Combine the solid with dichloromethane and extract with 5% sodium bicarbonate solution. Dry the organic layer over $Na_2SO_4$, filter, and concentrate in vacuo to obtain a solid residue. Dry the residue in vacuo at 90° C. to give the title compound: $R_f$=0.48 (silica gel, 20/1 ethyl acetate/methanol); mp; 55–57° C. Elemental Analysis calculated for $C_{23}H_{26}F_3NO_5$: C 60.92; H 5.78; N 3.09; Found: C 60.58; H 5.84; N 3.07.

20.5.1 Synthesis of 1-(3,4,5-trimethoxy-benzoyl)-3-(4-trifluoromethyl-phenyl)-3-(2-methanesulfonyl-ethyl)-pyrrolidine Prepare by the method of example 1.5 using 1-(3,4,5-trimethoxy-benzoyl)-3-(4-trifluoromethyl-phenyl)-3-(2-hydroxy-ethyl)-pyrrolidine to give the title compound.

20.5.2 Synthesis of 1-(3,4,5-trimethoxy-benzoyl)-3-(4-trifluoromethyl-phenyl)-3-(2-methanesulfonyl-ethyl)-pyrrolidine Combine 1-(3,4,5-trimethoxy-benzoyl)-3-(4-trifluoromethyl-phenyl)-3-(2-hydroxy-ethyl)-pyrrolidine (0.49 g, 1.1 mmol), diisopropylethylamine (0.41 mL, 2.4 mmol), and dichloromethane (15 mL). Cool to –5° C. using a salt-ice bath. Add dropwise, methanesulfonyl chloride (0.17 g, 1.5 mmol) at such a rate as to maintain the reaction temperature below 0° C. After 2 hour, extract twice with 1 M hydrochloric acid solution and then a 5% sodium bicarbonate solution. Dry the organic layer over $Na_2SO_4$, filter and evaporate in vacuo to give the title compound: $R_f$=0.63 (silica gel, 20/1 ethyl acetate/methanol); mp; 49–55° C.

20.6 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(4-trifluoromethyl-phenyl)-pyrrolidine Prepare by the method of Example 6.6.2 using 1-(3,4,5-trimethoxy-benzoyl)-3-(4-trifluoromethyl-phenyl)-3-(2-methanesulfonyl-ethyl)-pyrrolidine to give, after chromatography on silica gel eluting with 10/1 ethyl acetate/methanol and drying in vacuo at 70° C., the title compound: $R_f$=0.24 (silica gel, 10/1 ethyl acetate/methanol); mp; 85–88° C. Elemental Analysis calculated for $C_{43}H_{44}F_4N_4O_5$: C 66.67; H 5.76; N 7.20; Found: C 66.83; H 5.74; N 7.25. HRMS (FAB+): calculated 773.332609. Found 773.328709.

EXAMPLE 21

1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(thiophen-2-yl)-pyrrolidine

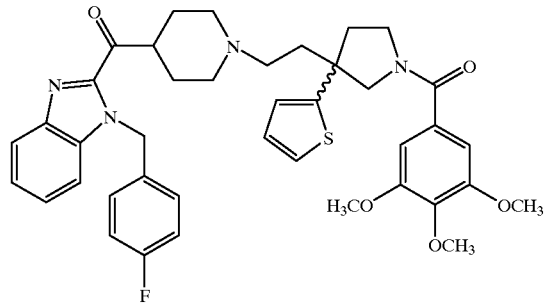

21.1 Synthesis of 3-cyano-3-(thiophen-2-yl)-pentanedioic acid diethyl ester

Prepare by the method of Example 1.1 using 2-thiophenacetonitrile to give the title compound.

21.2 Synthesis of [3-(thiophen-2-yl)-5-oxo-pyrrolidin-3-yl]-acetic acid ethyl ester Prepare by the method of Example 1.2 using 3-cyano-3-(thiophen-2-yl)-pentanedioic acid diethyl ester to give the title compound.

21.3 Synthesis of 3-(thiophen-2-yl)-3-(2-hydroxy-ethyl)-pyrrolidine

Prepare by the method of Example 1.3 using [3-(thiophen-2-yl)-5-oxo-pyrrolidin-3-yl]-acetic acid ethyl ester to give the title compound.

21.4 Synthesis of 1-(3,4,5-trimethoxy-benzoyl)-3-(thiophen-2-yl)-3-(2-hydroxy-ethyl)-pyrrolidine Prepare by the method of Example 1.4.1 using 3-(thiophen-2-yl)-3-(2-hydroxy-ethyl)-pyrrolidine to give the title compound.

21.5 Synthesis of 1-(3,4,5-trimethoxy-benzoyl)-3-(thiophen-2-yl)-3-(2-methanesulfonyl-ethyl)-pyrrolidine Prepare by the method of example 1.5 using 1-(3,4,5-trimethoxy-benzoyl)-3-(thiophen-2-yl)-3-(2-hydroxy-ethyl)-pyrrolidine to give the title compound.

21.6 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(thiophen-2-yl)-pyrrolidine Prepare by the method of Example 6.6.2 using 1-(3,4,5-trimethoxy-benzoyl)-3-(thiophen-2-yl)-3-(2-methanesulfonyl-ethyl)-pyrrolidine to give the title compound.

EXAMPLE 22

1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(4-hydroxy-phenyl)-pyrrolidine

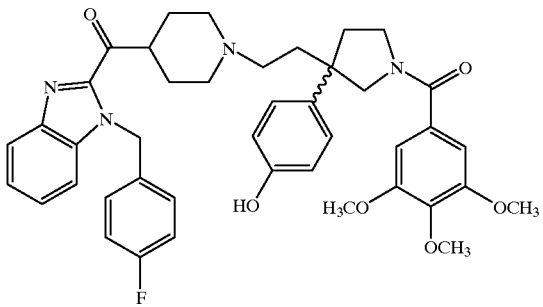

22.1 Synthesis of 4-(t-butyldimethylsilyloxy)-phenyl-acetonitrile

Combine t-butyldimethylsilyl chloride (0.460 mol), imidazole (0.600 mol) and DMF (125 mL). Add 4-hydroxyphenylacetonitrile (0.400 mol). After 16 hours, dilute the reaction mixture with diethyl ether, extract with water saturated sodium chloride solution, dry over $MgSO_4$, filter, and concentrate in vacuo to obtain a residue. Chromatograph on silica gel to obtain the title compound.

22.2 Synthesis of 3-cyano-3-(4-(t-butyldimethylsilyloxy)-phenyl)-pentanedioic acid diethyl ester Prepare by the method of Example 1.1 using 4-(t-butyldimethylsilyloxy)-phenyl-acetonitrile to give the title compound.

22.3 Synthesis of [3-(4-(t-butyldimethylsilyloxy)-phenyl)-5-oxo-pyrrolidin-3-yl]-acetic acid ethyl ester Prepare by the method of Example 1.2 using 3-cyano-3-(4-(t-butyldimethylsilyloxy)-phenyl)-pentanedioic acid diethyl ester to give the title compound.

22.4 Synthesis of 3-(4-(t-butyldimethylsilyloxy)-phenyl)-3-(2-hydroxy-ethyl)-pyrrolidine Prepare by the method of Example 1.3 using [3-(4-(t-butyldimethylsilyloxy)-phenyl)-5-oxo-pyrrolidin-3-yl]-acetic acid ethyl ester to give the title compound.

22.5 Synthesis of 1-(3,4,5-trimethoxy-benzoyl)-3-(4-(t-butyldimethylsilyloxy)-phenyl)-3-(2-hydroxy-ethyl)-pyrrolidine Prepare by the method of Example 1.4.1 using 3-(4-(t-butyldimethylsilyloxy)-phenyl)-3-(2-hydroxy-ethyl)-pyrrolidine to give the title compound.

22.6 Synthesis of 1-(3,4,5-trimethoxy-benzoyl)-3-(4-(t-butyldimethylsilyloxy)-phenyl)-3-(2-methanesulfonyl-ethyl)-pyrrolidine Prepare by the method of example 1.5 using 1-(3,4,5-trimethoxy-benzoyl)-3-(4-(t-butyldimethylsilyloxy)-phenyl)-3-(2-hydroxy-ethyl)-pyrrolidine to give the title compound.

22.7 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(4-(t-butyldimethylsilyloxy)-phenyl)-pyrrolidine Prepare by the method of Example 6.6.2 using 1-(3,4,5-trimethoxy-benzoyl)-3-(4-(t-butyldimethylsilyloxy)-phenyl)-3-(2-methanesulfonyl-ethyl)-pyrrolidine to give the title compound.

22.8 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(4-hydroxy-phenyl)-pyrrolidine Combine 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(4-(t-butyldimethylsilyloxy)-phenyl)-pyrrolidine (6 mmol) and THF (20 mL). Cool using an ice bath. Add dropwise, a 1 M THF solution of tetrabutylammonium fluoride (7 mL). After 30 minutes, concentrate in vacuo to obtain a residue. Combine dichloromethane (50 mL) and the residue. Extract with water (3×15 mL), dry the organic layer over $Na_2SO_4$, filter, and concentrate in vacuo to obtain a residue. Chromatograph on silica gel to obtain the title compound.

EXAMPLE 23

1-(3,4,5-Trimethoxy-benzoyl)-3-[3-[4-[1-(4-fluoro-benzyl)-1 H-benzoimidazole-2-carbonyl]-piperidin-1-yl]-propyl]-3-(3,4-dichloro-phenyl)-pyrrolidine

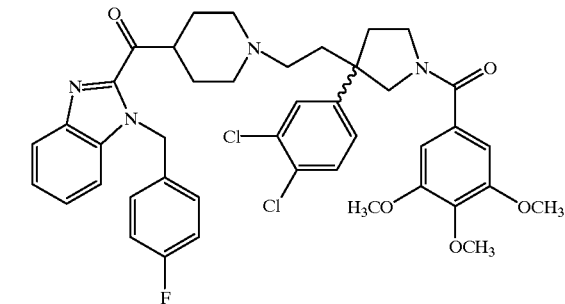

23.1 Synthesis of 2-(3,4-dichloro-phenyl)-5-(tetrahydro-pyran-2-yl-oxy)-pentanenitrile Prepare according to the method of example 13.1 using 3,4-dichlorophenylacetonitrile (50 mmol) and 2-(3-bromo-propoxy)-tetrahydro-pyran (50 mmol). Chromatograph on silica gel to give the title compound.

23.2 Synthesis of ethyl [3-cyano-3-(3,4-dichloro-phenyl)-6-(tetrahydro-pyran-2-yl-oxy)]-hexanoate Prepare according to the method of example 13.2 using 2-(3,4-dichloro-phenyl)-5-(tetrahydro-pyran-2-yl-oxy)-pentane nitrile (34 mmol) and ethyl bromoacetate (38 mmol). Chromatograph on silica gel to give the title compound.

23.3 Synthesis of 4-(3,4-dichloro-phenyl)-4-[3-(tetrahydro-pyran-2-yl-oxy)-propyl]-pyrrolidin-2-one Prepare according to the method of example 13.3 using ethyl-[3-cyano-3-(3,4-dichloro-phenyl)-6-(tetrahydro-pyran-2-yl-oxy)]-hexanoate (24 mmol) and Raney nickel (30 g). Chromatograph on silica gel to give the title compound.

23.4 Synthesis of 4-(3,4-dichloro-phenyl)-4-[3-(tetrahydro-pyran-2-yl-oxy)-propyl]-pyrrolidine Prepare according to the method of example 6.3 using 4-(3,4-dichloro-phenyl)-4-[3-(tetrahydro-pyran-2-yl-oxy)-propyl]-pyrrolidin-2-one (3 mmol), lithium aluminum hydride (18 mmol), and sulfuric acid (99.999%) (9 mmol). Purify to give the title compound.

23.5 Synthesis of 1-(3,4,5-trimethoxy-benzyl)-3-(3,4-dichloro-phenyl)-3-[3-(tetrahydro-pyran-2-yl-oxy)-propyl]-pyrrolidine Prepare by the method of example 6.4 using 3-(3,4-dichloro-phenyl)-3-[3-(tetrahydro-pyran-2-yl-oxy)-propyl]-pyrrolidine (2 mmol) and 3,4,5-trimethoxy-benzoyl chloride (2 mmol). Chromatograph on silica gel to give the title compound.

23.6 Synthesis of of 1-(3,4,5-trimethoxy-benzoyl)-3(3,4-dichloro-phenyl)-4-(3-hdroxy-propyl)-pyrrolidine Prepare according to the method of example 13.5 using 1-(3,4,5-trimethoxy-benzoyl)-3-(3,4-dichloro-phenyl)-3-[3-(tetrahydro-pyran-2-yl-oxy)-propyl]-pyrrolidine (3 mmol) and p-toluenesulfonic acid (200 mg). Chromatograph on silica gel to give the title compound.

23.7 Synthesis of 1(3,4,5-trimethoxy-benzoyl)-3-(3,4-dichloro- phenyl)-4-(3-methanesulfonyl-propyl)-pyrrolidine Prepare according to the method of example 6.5.2 using 1-(3,4,5-trimethoxy-benzoyl)-3-(3,4-dichloro-phenyl)-4-(3-hydroxy-propyl)-pyrrolidine (5 mmol) and methanesulfonyl chloride (6 mmol) to give the title compound.

23.8 Synthesis of 1-(3,4,5-trimethoxy-benzoyl)-3-[3-[4-[1-(4-fluoro-benzyl)-1 H-benzoimidazole-2-carbonyl]-piperidin-1-yl]-propyl]-3-(3,4-dichloro-phenyl)-pyrrolidine Prepare by the method of Example 6.6.2 using 1-(3,4,5-trimethoxy-benzoyl)-3-(3,4-dichloro-phenyl)-4-(3-methanesulfonyl-propyl)-pyrrolidine to give the title compound.

EXAMPLE 24

1-(3,4,5-Trimethoxy-benzyl-3[-3-[4-[1-(4-fluoro-benzyl)-1 H-benzoimidazole-2-carbonyl]-piperidin-1-yl]-proyl]-3-(3,4-dichloro-phenyl)-pyrrolidine

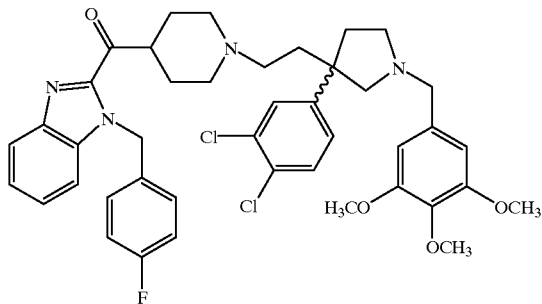

24.1 Synthesis of 1-(3,4,5-trimethoxy-benzyl)-3-(3,4-dichloro-phenyl)-3-[3-(tetrahydro-pyran-2-yl-oxy)-propyl]-pyrrolidine Combine 3-(3,4-dichloro-phenyl)-3-[3-(tetrahydro-pyran-2-yl-oxy)-propyl]-pyrrolidine (10 mmol), potassium carbonate (30 mmol), and 3,4,5-trimethoxy-benzyl bromide (10 mmol) in THF/H$_2$O (4/1, 200 mL). Heat to reflux and stir for 16 h. Concentrate in vacuo to obtain a residue. Dilute the residue with ethyl acetate and extract with water. Separate the layers, dry the organiclayer over MgSO$_4$, filter, and concentrate in vacuo to obtain a residue. Chromatograph the residue on silica gel to give the title compound.

24.2 Synthesis of 1-(3,4,5-trimethoxy-benzyl)-3-(3,4-dichloro-phenyl)-3-(3-hydroxy-prolyl)-pyrrolidine Prepare according to the method of example 13.5 using 1-(3,4,5-trimethoxy-benzyl)-3-(3,4-dichloro-phenyl)-3-[3-(tetrahydro-pyran-2-yl-oxy)-propyl]-pyrrolidine (3 mmol) and p-toluenesulfonic acid (200 mg). Chromatograph on silica gel to give the title compound.

24.3 Synthesis of 1-(3,4,5-trimethoxy-benzyl)-3-(3,4-dichloro-phenyl)-3-(3-bromo-propyl)-pyrrolidine Combine 1-(3,4,5-trimethoxy-benzyl)-3-(3,4-dichloro-phenyl)-4-(3-hydroxy-propyl)-pyrrolidine (5 mmol), carbon tetrabromide (6.3 mmol), and dichloromethane (8 mL). Add portionwise, triphenylphosphine (7.5 mmol). After 1 hour, concentrate in vacuo to obtain a residue. Purify to obtain the title compound.

24.4 Synthesis of 1-(3,4,5-trimethoxy-benzyl)-3-[3-[4-[1-(4-fluoro-benzyl)-1 H-benzoimidazole-2-carbonyl]-piperidin-1-yl]-propyl]-3-(3,4-dichloro-phenyl)-pyrrolidine Prepare by the method of Example 6.6.2 using 1-(3,4,5-trimethoxy-benzyl)-3-(3,4-dichloro-phenyl)-3-(3-bromo-propyl)-pyrrolidine (5 mmol) to give the title compound.

EXAMPLE 25

1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(2,4-difluoro-phenyl)-pyrrolidine

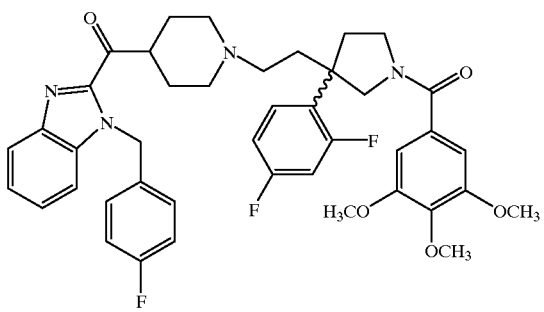

25.1 Synthesis of 3-cyano-3-(2,4-difluoro-phenyl)-pentanedioic acid diethyl ester Prepare by the method of Example 1.1 using 2,4-difluoro-phenylacetonitrile to give, after bulb-to-bulb distillation the title compound: $R_f$=0.43 (silica gel, 25% ethyl acetate/hexane); bp; 190–200° C. at 0.60 mm Hg. Elemental Analysis calculated for $C_{16}H_{17}F_2NO_4$: C 59.07; H 5.27; N 4.31; Found: C 59.27; H 5.34; N 4.29.

25.2 Synthesis of [3-(2,4-difluoro-phenyl)-5-oxo-pyrrolidin-3-yl]-acetic acid ethyl ester Prepare by the method of Example 1.2 using 3-cyano-3-(2,4-difluoro-phenyl)-pentanedioic acid diethyl ester to give the title compound: $R_f$=0.46 (silica gel, ethyl acetate); mp; 89.0–91.0° C. Elemental Analysis calculated for $C_{14}H_{15}F_2NO_3$: C 59.36; H 5.34; N 4.94; Found: C 59.34; H 5.36; N 4.91.

25.3 Synthesis of 3-(2,4-difluoro-phenyl)-3-(2-hydroxy-ethyl)-pyrrolidine

Prepare by the method of Example 1.3 using [3-(2,4-difluoro-phenyl)-5-oxo-pyrrolidin-3-yl]-acetic acid ethyl ester to give the title compound: mp; 90–100° C.

25.4.1 Synthesis of 1-(3,4,5-trimethoxy-benzoyl)-3-(2,4-difluoro-phenyl)-3-(2-hydroxy-ethyl)-pyrrolidine Prepare by the method of Example 1.4.1 using 3-(2,4-difluoro-phenyl)-3-(2-hydroxy-ethyl)-pyrrolidine to give the title compound.

25.4.2 Synthesis of 1-(3,4,5-trimethoxy-benzoyl)-3-(2,4-difluoro-phenyl)-3-(2-hydroxy-ethyl)-pyrrolidine Prepare by the method of Example 1.4.2 using 3-(2,4-difluoro-phenyl)-3-(2-hydroxy-ethyl)-pyrrolidine to give the title compound: $R_f$=0.43 (silica gel, 20/1 ethyl acetate/methanol); mp; 58–60° C. Elemental Analysis Calculated for $C_{22}H_{25}F_2NO_5$: C 62.70; H 5.98; N 3.32; Found: C 62.53; H 6.06; N 3.42.

25.5.1 Synthesis of 1-(3,4,5-trimethoxy-benzoyl)-3-(2,4-difluoro-phenyl)-3-(2-methanesulfonyl-ethyl)-pyrrolidine Prepare by the method of Example 1.5 using 1-(3,4,5-trimethoxy-benzoyl)-3-(2,4-difluoro-phenyl)-3-(2-hydroxy-ethyl)-pyrrolidine to give the title compound.

25.5.2 Synthesis of 1-(3,4,5-trimethoxy-benzoyl)-3-(2,4-difluoro-phenyl)-3-(2-methanesulfonyl-ethyl)-pyrrolidine Prepare by the method of Example 10.5 using 1-(3,4,5-trimethoxy-benzoyl)-3-(2,4-difluoro-phenyl)-3-(2-hydroxy-ethyl)-pyrrolidine to give the title compound: $R_f$=0.62 (silica gel, 20/1 ethyl acetate/methanol); mp; 43.0–45.0° C.

25.6 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(2,4-difluoro-phenyl)-pyrrolidine Prepare by the method of Example 6.6.2 using 1-(3,4,5-trimethoxy-benzoyl)-3-(2,4-difluoro-phenyl)-3-(2-methanesulfonyl-ethyl)-pyrrolidine to give the title compound: $R_f$=0.46 (silica gel, 10/1 ethyl acetate/methanol); mp; 84.0–86.0° C. Elemental Analysis calculated for $C_{42}H_{43}F_3N_4O_{5\cdot 0.30}H_2O$: C 67.50; H 5.89; N 7.51; Found: C 67.53; H 5.97; N 7.56.

PREPARATION 1

Synthesis of 3-Isopropoxy-phenyl-acetyl chloride

Combine 3-hydroxy-phenylacetic acid (9.26 g, 60.9 mmol), isopropyl iodide (42.6 g, 250 mmol), and acetone (80 mL). Add portionwise, potassium carbonate (16.9 g, 122 mmol). Heat to reflux with vigorous mechanical stirring. After 20 hours, cool to ambient temperature and evaporate in vacuo to give a residue. Partition the residue between diethyl ether and 5% sodium hydroxide solution. Extract the organic layer with water and a saturated sodium chloride solution. Dry the organic layer over $MgSO_4$, filter and evaporate in vacuo to obtain a liquid. Bulb-to-bulb distillation gives 3-isopropoxy-phenyl-acetic acid isopropyl ester: bp; 125° C. at 0.2 mm of Hg.

Combine 3-isopropoxy-phenyl-acetic acid isopropyl ester 10.2 g, 43.2 mmol) and sodium hydroxide (2.08 g, 51.8 mmol) in 1/1 ethanol/water (80 mL). Heat to reflux. After 18 hours, remove the ethanol by evaporation in vacuo and acidify to pH=1 using an aqueous solution with 1 M hydrochloric acid solution. Extract the aqueous solution 3 times with ethyl acetate. Extract the combined organic layers with water and saturated sodium chloride solution. Dry the organic layer over $MgSO_4$, filter, and evaporate in vacuo to obtain 3-isopropoxy-phenyl-acetic acid.

Combine 3-isopropoxy-phenyl-acetic acid (0.5 g, 2.6 mmol) and dichloromethane (5 mL). Cool to −5° C. using a salt-ice bath. Add 2 drops of dimethylformamide followed by dropwise addition of oxalyl chloride (0.34 g, 2.7 mmol). After 1 hour, warm the reaction mixture to ambient temperature. After 2 hours, evaporate the reaction mixture in vacuo to give the title compound as a liquid.

EXAMPLE 26

1-(3-Isopropoxy-phenyl-acetyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine

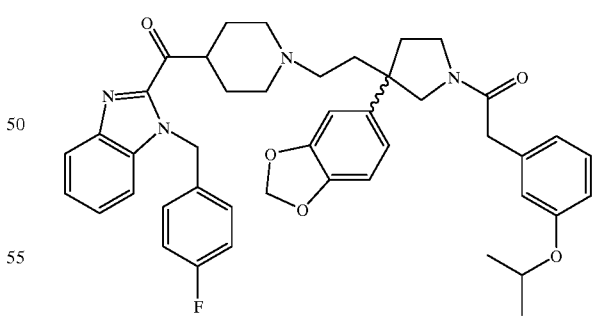

26.1 Synthesis of 1-(3-isopropoxy-phenyl-acetyl)-3-(benzo[1,3]dioxol-5-yl)-3-(2-hydroxy-ethyl)-pyrrolidine Combine 3-(benzo[1,3]dioxol-5-yl)-3-(2-hydroxy-ethyl)-pyrrolidine (0.53.g, 2.3 mmol) and sodium carbonate in ethyl acetate/water (9 mL/2 mL). Warm to dissolve the starting material. Cool to −5° C. using a salt-ice bath. With vigorous stirring add dropwise, a solution of 3-isopropoxy-phenyl-acetyl chloride (0.5 g, 2.4 mmol) in ethyl acetate (2 mL). After 30 minutes, dilute the reaction mixture with ethyl acetate (40 mL) and extract the organic layer with 1 M hydrochloric acid solution, a 5% sodium bicarbonate solution, water, and a saturated sodium chloride solution. Dry the organic layer over $Na_2SO_4$, filter, and evaporate in vacuo at 80° C. to give the title compound: $R_f$=0.34 (silica gel, ethyl acetate). Elemental Analysis calculated for $C_{24}H_{29}NO_5$: C 70.05; H 7.10; N 3.40; Found: C 70.28; H 7.18; N 3.18.

26.2 Synthesis of 1-(3-isopropoxy-phenyl-acetyl)-3-(benzo[1,3]dioxol-5-yl)-3-(2-methanesulfonyl-ethyl)-pyrrolidine Prepare by the method of Example 1.5 using 1-(3-isopropoxy-phenyl-acetyl)-3-(benzo[1,3]dioxol-5-yl)-3-(2-hydroxy-ethyl)-pyrrolidine to give the title compound: $R_f$=0.70 (silica gel, ethyl acetate).

26.3 Synthesis of 1-(3-isopropoxy-phenyl-acetyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine Prepare by the method of Example 6.6.2 using 1-(3-isopropoxy-phenyl-acetyl)-3-(benzo[1,3]dioxol-5-yl)-3-(2-methanesulfonyl-ethyl)-pyrrolidine to give the title compound: $R_f$=0.49 (silica gel, 10% methanol/ethyl acetate); mp; 73–76° C. Elemental Analysis calculated for $C_{44}H_{47}FN_4O_5$·0.38 $H_2O$: C 71.64; H 6.53; N 7.60; Found: C 71.50; H 6.49; N 8.28.

26.4 Synthesis of 1-(3-isopropoxy-phenyl-acetyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine methane sulfonate salt Prepare by the method of 6.7.3 using 1-(3-isopropoxy-phenyl-acetyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine (0.59 g, 0.81 mmol) and a solution of methanesulfonic acid (0.12 g, 1.58 mL, 0.77 M in ethyl acetate, 1.21 mmol) to give the title compound: mp; 137–140° C. HRMS (FAB+): calculated 731.357113. Found 731.360874.

EXAMPLE 27

1-(2,3,4-Trimethoxy-benzoyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine

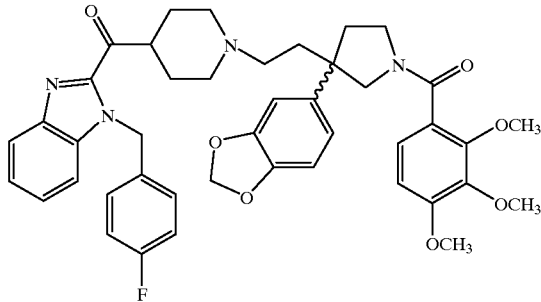

27.1.1 Synthesis of 1-(2,3,4-trimethoxy-benzoyl)-3-(benzo[1,3]dioxol-5-yl)-3-(2-hydroxy-ethyl)-pyrrolidine Prepare by the method of Example 1.4.1 using 3-(benzo[1,3]dioxol-5-yl)-3-(2-hydroxy-ethyl)-pyrrolidine and 2,3,4-trimethoxy-benzoyl chloride to obtain the title compound: $R_f$=0.27 (silica gel, ethyl acetate).

27.1.2 Synthesis of 1-(2,3,4-trimethoxy-benzoyl)-3-(benzo[1,3]dioxol-5-yl)-3-(2-hydroxy-ethyl)-pyrrolidine Combine 3-(benzo[1,3]dioxol-5-yl)-3-(2-hydroxy-ethyl)-pyrrolidine 0.33 g, 1.4 mmol), sodium carbonate (0.80 g, 0.76 mmol), and 4/1 tetrahydrofuran/water (5 mL). Cool to –5° C. using a salt-ice bath. Add dropwise a solution of 2,3,4-trimethoxy-benzoyl chloride (1.5 mmol) in dichloromethane (1 mL). After 25 minutes, dilute the reaction mixture with ethyl acetate (50 mL) and extract with 1 M hydrochloric acid solution, water, and saturated sodium chloride solution. Dry the organic layer over $Na_2SO_4$, filter, and evaporate in vacuo to give a residue. Chromatograph the residue on silica gel eluting with 5% methanol/ethyl acetate to obtain the title compound: mp; 58–62° C.

27.2 Synthesis of 1-(2,3,4-trimethoxy-benzoyl)-3-(benzo[1,3]dioxol-5-yl)-3-(2-methanesulfonyl-ethyl)-pyrrolidine Prepare by the method of Example 1.5 using 1-(2,3,4-trimethoxy-benzoyl)-3-(benzo[1,3]dioxol-5-yl)-3-(2-hydroxy-ethyl)-pyrrolidine to give the title compound.

27.3 Synthesis of 1-(2,3,4-trimethoxy-benzoyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine Combine 1-(2,3,4-trimethoxy-benzoyl)-3-(benzo[1,3]dioxol-5-yl)-3-(2-methanesulfonyl-ethyl)-pyrrolidine (0.44 g, 0.87 mmol), diisopropylethylamine (0.22 g, 1.73 mmol), 4-[1-(4-fluoro-benzyl)-1 H-benzoimidazole-2-carbonyl]-piperidine (0.45 g 1.3 mmol), and chlorobenzene (7 mL). Heat to 110° C. After 6 hours, partition the reaction mixture between ethyl acetate and water. Extract with water, a saturated sodium bicarbonate solution, and a saturated sodium chloride solution. Dry the organic layer over $Na_2SO_4$, filter, and evaporate in vacuo to give a residue. Chromatograph the residue on silica gel eluting with 7% methanol/ethyl acetate containing 0.1% of a concentrated aqueous ammonia solution to give a residue. Partition the residue between dichloromethane and water. Dry the organic layer over $Na_2SO_4$, filter, and evaporate in vacuo at 56° C. to give the title compound: $R_f$=0.07 (silica gel, ethyl acetate).

27.4 Synthesis of 1-(2,3,4-trimethoxy-benzoyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine p-toluenesulfonate salt Combine 1-(2,3,4-trimethoxy-benzoyl)-3-[2-[4-[1-(4-fluoro-benzyl)-1 H-benzoimidazole-2-carbonyl]-piperidin-1-yl]-ethyl]-3-(benzo[1,3]dioxol-5-yl)-pyrrolidine (0.40 mmol) and p-toluenesulfonic acid (78 mg, 0.40 mmol) in 5/1 dichloromethane/methanol (8 mL). Heat to reflux. After 10 minutes, cool to ambient temperature and evaporate in vacuo to give a residue. Triturate the residue with diethyl ether, filter and dry at 82° C. to give the title compound: mp 125–128° C. (dec). Elemental Analysis calculated for $C_{50}H_{53}FN_4O_{10}S$·1.69 $H_2O$: C 63.38; H 5.85; N 5.94; Found: C 63.12; H 5.97; N 5.89.

EXAMPLE 28

1-(3,4,5-Triethoxy-benzoyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine

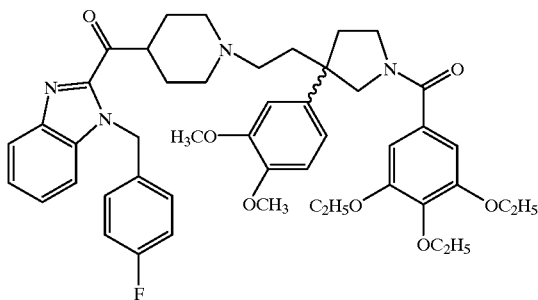
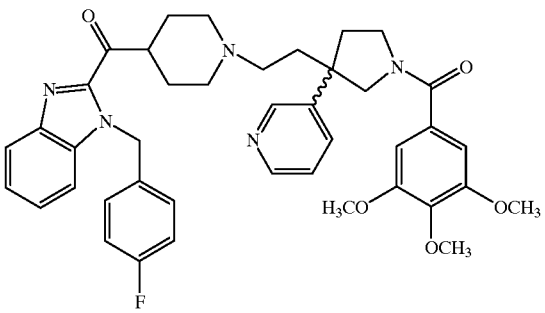

28.1 Synthesis of 1-(3,4,5-triethoxy-benzoyl)-3-(3,4-dimethoxy-phenyl)-3-(2-hydroxy-ethyl)-pyrrolidine Prepare by the method of Example 6.4 using 3-(3,4-dimethoxy-phenyl)-3-(2-hydroxy-ethyl)-pyrrolidine (0.41 g, 1.61 mmol) and 3,4,5-triethoxy-benzoyl chloride (0.46 g, 1.69 mmol) to give the title compound: mp; 139–141° C.; $R_f$=0.31 (silica gel, 20/1 ethyl acetate/methanol). Elemental Analysis calculated for $C_{27}H_{37}NO_7$: C 66.51; H 7.65; N 2.87; Found: C 66.43; H 7.67; N 2.69.

28.2 Synthesis of 1-(3,4,5-triethoxy-benzoyl)-3-(3,4-dimethoxy-phenyl)-3-(2-methanesulfonyl-ethyl)-pyrrolidine Prepare by the method of Example 1.5 using 1-(3,4,5-triethoxy-benzoyl)-3-(3,4-dimethoxy-phenyl)-3-(2-hydroxy-ethyl)-pyrrolidine to give the title compound: $R_f$=0.34 (silica gel, 20/1 ethyl acetate/methanol).

28.3 Synthesis of 1-(3,4,5-triethoxy-benzoyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine Combine 1-(3,4,5-triethoxy-benzoyl)-3-(3,4-dimethoxy-phenyl)-3-(2-methanesulfonyl-ethyl)-pyrrolidine (0.31 g, 0.55 mmol), diisopropylethylamine (0.14 g, 1.1 mmol), chlorobenzene (5 mL), and 4-[1-(4-fluoro-benzyl)-1 H-benzoimidazole-2-carbonyl]-piperidine (0.28 g, 0.83 mmol) Heat to 120° C. After 4 hours, partition the reaction mixture between ethyl acetate and water. Extract 2 times with water and a 5% sodium bicarbonate solution. Dry the organic layer over $Na_2SO_4$, filter, and evaporate in vacuo to give a residue. Chromatograph the residue on silica gel eluting sequentially with 3/1 ethyl acetate/hexane and then 10/1/0.1 ethyl acetate/methanol/concentrated aqueous ammonia to give the title compound: $R_f$=0.60 (silica gel, 10/1/0.1 ethyl acetate/methanol/concentrated aqueous ammonia); mp; 155–160° C.

28.4 Synthesis of 1-(3,4,5-triethoxy-benzoyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine maleic acid salt Prepare by the method of Example 1.7 using 1-(3,4,5-triethoxy-benzoyl)-3-[2-[4-[1-(4-fluoro-benzyl)-1 H-benzoimidazole-2-carbonyl]-piperidin-1-yl]-ethyl]-3-(3,4-dimethoxy-phenyl)-pyrrolidine (0.08 g, 0.1 mmol and maleic acid (0.011 g, 0.1 mmol) to give the title compound: mp; 111–113° C. HRMS (FAB+): calculated 807.416084. Found 807.413304.

EXAMPLE 29 s1-(3,4,5-Trimethoxy-benzoyl)-3-[2-[4-[1-(4-fluoro-benzyl)-1 H-benzoimidazole-2-carbonyl]-piperidin-1-yl]-ethyl]-3-(pyridin-3-yl)-pyrrolidine 29.1 Synthesis of 3-cyano-3-(pyridin-3-yl)-pentanedioic acid diethyl ester Prepare by the method of Example 1.1 using 3-pyridineacetonitrile to give the title compound.

29.2 Synthesis of [3-(pyridin-3-yl)-5-oxo-pyrrolidin-3-yl]-acetic acid ethyl ester Prepare by the method of Example 1.2 using 3-cyano-3-(pyridin-3-yl)-pentanedioic acid diethyl ester to give the title compound.

29.3 Synthesis of 3-(pyridin-3-yl)-3-(2-hydroxy-ethyl)-pyrrolidine

Prepare by the method of Example 1.3 using [3-(pyridin-3-yl)-5-oxo-pyrrolidin-3-yl]-acetic acid ethyl ester to give the title compound.

29.4 Synthesis of 1-(3,4,5-trimethoxy-benzoyl)-3-(pyridin-3-yl)-3-(2-hydroxy-ethyl)-pyrrolidine Prepare by the method of Example 1.4.1 using 3-(pyridin-3-yl)-3-(2-hydroxy-ethyl)-pyrrolidine to give the title compound.

29.5 Synthesis of 1-(3,4,5-trimethoxy-benzoyl)-3-(pyridin-3-yl)-3-(2-methanesulfonyl-ethyl)-pyrrolidine Prepare by the method of example 1.5 using 1-(3,4,5-trimethoxy-benzoyl)-3-(pyridin-3-yl)-3-(2-hydroxy-ethyl)-pyrrolidine to give the title compound.

29.6 Synthesis of 1-(3,4,5-trimethoxy-benzoyl)-3-[2-[4-[1-(4-fluoro-benzyl)-1 H-benzoimidazole-2-carbonyl]-piperidin-1-yl]-ethyl]-3-(pyridin-3-yl)-pyrrolidine Prepare by the method of Example 6.6.2 using 1-(3,4,5-trimethoxy-benzoyl)-3-(pyridin-3-yl)-3-(2-methanesulfonyl-ethyl)-pyrrolidine to give the title compound.

EXAMPLE 30

1-(3,4,5-Trimethoxy-benzoyl)-3-[2-[4-benzhydrylidene-piperidin-1-yl]-ethyl]-3-(3,4-dichloro-phenyl)-pyrrolidine

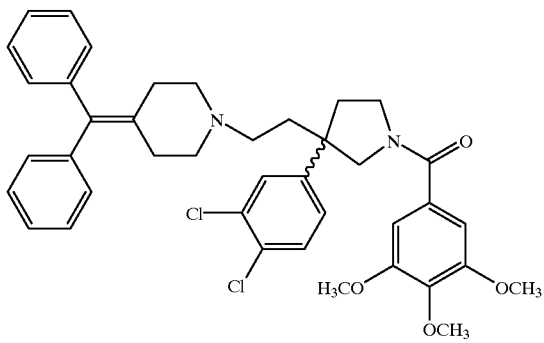

30.1 Synthesis of 1-(3,4,5-Trimethoxy-benzoyl)-3-[2-[4-benzhydrylidene-piperidin-1-yl]-ethyl]-3-(3,4-dichloro-phenyl)-5pyrrolidine Prepare by the method of Example 6.6.2 using 1-(3,4,5-trimethoxy-benzoyl)-3-(3,4-(dichloro-phenyl)-3-(2-methanesulfonyl-ethyl)-pyrrolidine (0.32 g, 0.6 mmol), diisopropylethylamine (0.15 g, 1.20 mmol), 4-benzhydrylidene-piperidine (0.22 g, 0.90 mmol). Purify by chromatography on silica gel eluting with 5% methanol/ethyl acetate to give the title compound: $R_f$=0.40 (silica gel, 20/1 ethyl acetate/methanol); mp; 90–94° C.

30.2 Synthesis of 1-(3,4,5-Trimethoxy-benzoyl)-3-[2-[4-benzhydrylidene-piperidin-1-yl]-ethyl]-3-(3,4-dichloro-phenyl)-pyrrolidine maleic acid salt Prepare by the method of Example 1.7 using 1-(3,4,5-trimethoxy-benzoyl)-3-[2-[4-benzhydrylidene-piperidin-1-yl]-ethyl]-3-(3,4-dichloro-phenyl)-pyrrolidine (031 g, 0.45 mmol) and maleic acid (0.052 g, 0.45 mmol) to give the title compound: mp; 120–122° C. HRMS (FAB+): calculated 685.258408. Found 685.259989.

PREPARATION 2

Synthesis of 4-(1H-Benzoimidazole-2-carbonyl)-piperidine hydroiodide salt

Combine piperidine-4-carboxylic acid (500 g), water (4.2 L), t-butanol (4 L), and 50% aqueous sodium hydroxide solution (386 g). Add portionwise, di-t-butyldicarbonate (930 g). After 20 hours, concentrate the reaction mixture in vacuo to about one half the volume. Slowly add 10% aqueous hydrochloride solution until the pH is about 4. Extract with diethyl ether (3×4L). Dry the organic layer over $MgSO_4$, filter and evaporate on a steam bath to a volume of about 4 L. Add ethyl acetate (4 L) and evaporate on a steam bath to a volume of about 4 L. Filter and continue to evaporate on a steam bath to a volume of about 2 L. Cool and filter to obtain 1-(t-butoxycarbonyl)-piperidine-4-carboxylic acid.

Combine 1-(t-butoxycarbonyl)-piperidine-4-carboxylic acid (813.7 g) and dichloromethane (6 L). Add portionwise, carbonyldiimidazole (633.1 g). After 1 hour, add N-methyl-O-methylhydroxylamine hydrochloride (380.5). After 56 hours, extract the reaction mixture with 5% aqueous hydrochloric acid solution and 5% aqueous sodium bicarbonate solution. Dry the organic layer over $MgSO_4$, filter, and evaporate in vacuo to obtain 1-(t-butoxycarbonyl)-piperidine-4-(N-methyl-O-methyl)-hydroxamic acid.

Combine benzimidazole (57.8 g, 490 mmol) and dimethylformamide (570 mL). Cool using an ice bath to about 20° C. Add portionwise, sodium hydride (20.2 g., 60% in oil, 500 mmol) at such a rate that the temperature of the reaction mixture remains at about 20° C. After the addition of sodium hydride is complete allow to stir for 1 hour. Add a solution of 2-(trimethylsilyl)ethoxymethyl chloride (60 g, 360 mmol) in dimethylformamide (60 mL) at such a rate that the temperature of the reaction mixture remains below 20° C. After 18 hours, add dropwise, water (50 mL). When the addition is complete, pour the reaction mixture into water (2 L). Extract repeatedly with diethyl ether. Combine the organic layers and extract with water. Dry the organic layer over $MgSO_4$, filter, and evaporate in vacuo to obtain 1-((2-trimethylsilyl)ethoxymethyl)-1 H-benzimidazole.

Combine 1-((2-trimethylsilyl)ethoxymethyl)-1 H-benzimidazole (91.2 g, 367 mmol) and tetrahydrofuran (500 mL). Cool to −78° C. using a dry-ice/acetone bath. Add a solution of n-butyl]ithium (146 mL, 2.5 M in hexane, 367 mmol) at such a rate that the temperature of the reaction mixture remains at about −70° C. After the addition of n-butyllithium is complete allow to stir for 30 minutes at −78° C. Add a solution of 1-(t-butoxycarbonyl)-piperidine-4-(N-methyl-O-methyl)-hydroxamic acid (99.9 g, 367 mmol) in tetrahydrofuran (100 mL). Warm to ambient temperature. After 18 hours, add dropwise a saturated aqueous ammonium chloride solution (100 mL). Add water (300 mL) and extract with diethyl ether. Dry the organic layer over $MgSO_4$, filter, and evaporate in vacuo to obtain a residue. Chromatograph the residue on silica gel eluting with 10% ethyl acetone/hexane to give a residue. Recrystallize the residue from methanol/water to give (1-(t-butoxycarbonyl)-4-(1-((2-trimethylsilyl)ethoxymethyl)-1 H-benzoimidazole-2-carbonyl)-piperidine.

Add portionwise, (1-(t-butoxycarbonyl)-4-(1-((2-trimethylsilyl)ethoxymethyl)-1 H-benzoimidazole-2-carbonyl)-piperidine (20.0 g, 43.5 mmol) to aqueous hydroiodic acid (48%, 140 mL). After the addition is complete, heat to 50° C. After 1.5 hours, cool to ambient temperature. After 2.5 hours, extract twice with diethyl ether. Add diethyl ether (300 mL) and isopropanol (60 mL) to the aqueous layer to give a solid. Collect the solid by filtration and rinse with diethyl ether to give, after drying, the title compound. Elemental Analysis calculated for $C_{13}H_{15}N_3O \cdot 2$ HI: C 32.19; H 3.53; N 8.66; Found: C 32.34; H 3.37; N 8.48.

EXAMPLE 31

1-(3,4,5-Trimethoxy-benzoyl)-3-[2-[4-[1 H-benzoimidazole-2-carbonyl]-piperidin-1-yl]-ethyl]-3-(3,4-dichloro-phenyl)-pyrrolidine

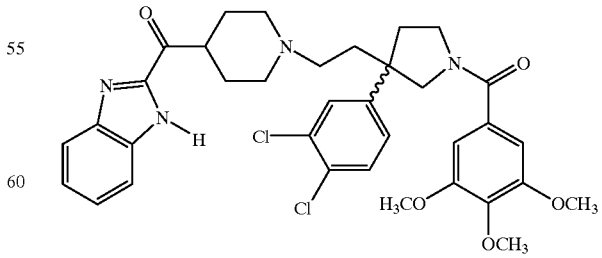

31.1 Synthesis of 1-(3,4,5-trimethoxy-benzoyl)-3-[2-[4-[1 H-benzoimidazole-2-carbonyl]-piperidin-1-yl]-ethyl]-3-(3,4-dichloro-phenyl)-pyrrolidine Prepare by the method of Example 6.6.2 using 1-(3,4,5-trimethoxy-benzoyl)-3-(3,4-dichloro-phenyl)-3-(2-methanesulfonyl-ethyl)-pyrrolidine and 4-(1 H-benzoimidazole-2-carbonyl)-piperidine hydroiodide salt to give the title compound: R$_f$=0.35 (silica gel, 10% methanol/ethyl acetate containing 0.1% concentrated aqueous ammonia solution).

31.2 Synthesis of 1-(3,4,5-trimethoxy-benzoyl)-3-[2-[4-[1 H-benzoimidazole-2-carbonyl]-piperidin-1-yl]-ethyl]-3-(3, 4-dichloro-phenyl)-pyrrolidine methanesulfonate salt Combine 1-(3,4,5-trimethoxy-benzoyl)-3-[2-[4-[1 H-benzoimidazole-2-carbonyl]-piperidin-1-yl]-ethyl]-3-(3, 4-dichloro-phenyl)-pyrrolidine (4.0 g) and ethyl acetate (70 mL). Add a solution of methanesulfonic acid (1.18 g) in ethyl acetate (50 mL) to give a solid. Collect the solid by filtration and dry in vacuo at 82° C. to give the title compound: mp; 130–140° C.

EXAMPLE 32

1-(3,4,5-Trimethoxy-benzoyl)-3-[2-[4-[1- (2-(morpholin-4-yl)-ethyl)-1 H-benzoimidazole-2-carbonyl]-piperidin-1-yl]-ethyl]-3-(3,4-dichlororphenyl)-pyrrolidine

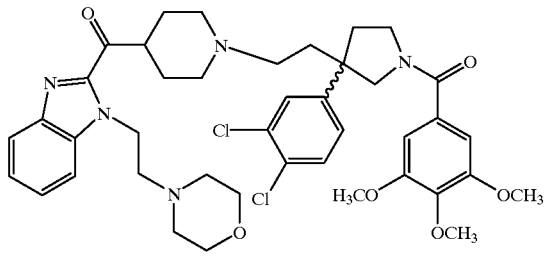

32.1 Synthesis of 1-(3,4,5-trimethoxy-benzoyl)-3-[2-[4-[1-(2-(morpholin-4-yl)-ethyl)-1 H-benzoimidazole-2-carbonyl]-piperidin-1-yl]-ethyl]-3-(3,4-dichloro-phenyl)-pyrrolidine Combine 1-(3,4,5-trimethoxy-benzoyl)-3-[2-[4-[1H-benzoimidazole-2-carbonyl]-piperidin-1-yl]-ethyl]-3-(3,4-dichloro-phenyl)-pyrrolidine methanesulfonate salt (0.60 g, 0.70 mmol) and 4-(2-chloroethyl)morpholine hydrochloride (0.156 g, 0.84 mmol), and potassium carbonate (0.464 g, 3.36 mmol) in acetone (10 mL) , water (4 mL), and dichloromethane (5 mL). Heat to reflux. After 24 hours, add more 4-(2-chloroethyl)morpholine hydrochloride (0.100 g) and continue to heat at reflux. After 20 hours, cool to ambient temperature and concentrate the reaction mixture in vacuo and dilute with ethyl acetate. Extract with saturated aqueous ammonium chloride solution, water, saturated aqueous sodium bicarbonate solution, and saturated aqueous sodium chloride solution. Dry the organic layer over MgSO$_4$, filter, and concentrate in vacuo to give a residue. Chromatograph the residue on silica gel eluting with 10/1/0.1 dichloromethane/methanol/ammonium hydroxide to give the title compound.

32.2 Synthesis of 1-(3,4,5-trimethoxy-benzoyl)-3-[2-[4-[1-(2-(morpholin-4-yl)ethyl)-1 H-benzoimidazole-2-carbonyl]-piperidin-1-yl]-ethyl]-3-(3,4-dichloro-phenyl)-pyrrolidine methanesulfonate salt Combine 1-(3,4,5-trimethoxy-benzoyl)-3-[2-[4-[1-(2-(morpholin-4-yl)ethyl)-1 H-benzoimidazole-2-carbonyl]-piperidin-1-yl]-ethyl]-3-(3,4-dichloro-phenyl)-pyrrolidine (0.4 g) and methanesulfonic acid in ethyl acetate (60 mL).

Add diethyl ether (180 mL) and cool to 5° C. to form a solid. Collect the solid by filtration and dry to give the title compound: mp; 144–149° C.

EXAMPLE 33

1-(3,4,5-Trimethoxy-benzoyl)-3-[2-[4-[1-(pyrid-2-ylmethyl)-1 H-benzoimidazole-2-carbonyl]-piperidin-1-yl]-ethyl]-3-(3,4-dichloro-phenyl)-pyrrolidine

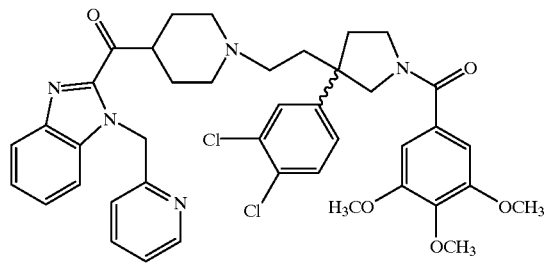

33.1 Synthesis of 1-(3,4,5-trimethoxy-benzoyl)-3-[2-[4-[1-(pyrid-2-ylmethyl)-1 H-benzoimidazole-2-carbonyl]-piperidin-1-yl]-ethyl]-3-(3,4-dichloro-phenyl)-pyrrolidine Combine 1-(3,4,5-trimethoxy-benzoyl)-3-[2-[4-[1 H-benzoimidazole-2-carbonyl]-piperidin-1-yl]-ethyl]-3-(3, 4-dichloro-phenyl)-pyrrolidine methanesulfonate salt (0.60 g, 0.70 mmol) and 2-(chloromethyl)pyridine hydrochloride (0.46 g, 2.8 mmol), and potassium carbonate (1.14 g, 8.25 mmol) in acetone (12 mL) and water (4 mL). Heat to reflux. After 24 hours, cool to ambient temperature and concentrate the reaction mixture in vacuo and dilute with ethyl acetate. Extract with water, saturated aqueous sodium bicarbonate solution, and saturated aqueous sodium chloride solution. Dry the organic layer over MgSO$_4$, filter, and concentrate in vacuo to give a residue. Chromatograph the residue on silica gel eluting with 10/1/0.1 dichloromethane/methanol/ammonium hydroxide to give the title compound: R$_f$=0.58 (silica gel, 10/1/0.1 dichloromethane/methanol/ammonium hydroxide).

33.2 Synthesis of 1-(3,4,5-trimethoxy-benzoyl)-3-[2-[4-[1-(pyrid-2-ylmethyl)-1 H-benzoimidazole-2-carbonyl]-piperidin-1-yl]-ethyl]-3-(3,4-dichloro-phenyl)-pyrrolidine methanesulfonate salt Combine 1-(3,4,5-trimethoxy-benzoyl)-3-[2-[4-[1-(pyrid-2-ylmethyl)-1 H-benzoimidazole-2-carbonyl]-piperidin-1-yl]-ethyl]-3-(3,4-dichloro-phenyl)-pyrrolidine (0.072 g) and methanesulfonic acid (0.133 g) in ethyl acetate (60 mL). Add diethyl ether (180 mL) and cool to 5° C. to form a solid. Collect the solid by filtration and dry to give the title compound: mp; 110–115° C.

EXAMPLE 34

1-(3,4,5-Trimethoxy-benzoyl)-3-[2-[4-[1-(3-ethoxycarbonyl-propyl)-1 H-benzoimidazole-2-carbonyl]-piperidin-1-yl]-ethyl]-3-(3,4-dichloro-phenyl)-pyrrolidine

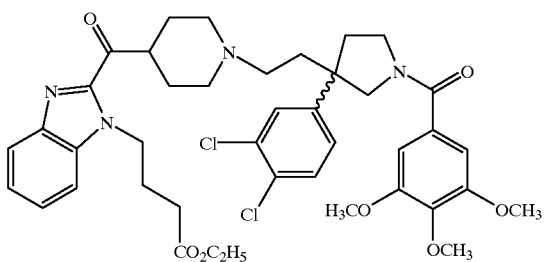

34.1 Synthesis of 1-(3,4,5-trimethoxy-benzoyl)-3-[2-[4-[1-(3-ethyoxycarbonyl-propyl)-1 H-benzoimidazole-2-carbonyl]-piperidin-1-yl]-ethyl]-3-(3,4-dichloro-phenyl)-pyrrolidine Combine 1-(3,4,5-trimethoxy-benzoyl)-3-[2-[4-[1 H-benzoimidazole-2-carbonyl]-piperidin-1-yl]-ethyl]-3-(3,4-dichloro-phenyl)-pyrrolidine methanesulfonate salt (0.90 g, 1.35 mmol), ethyl 4-bromobutyrate (1.06 g, 5.4 mmol), and potassium carbonate (2.24 g, 16.2 mmol) in 13/1 acetone/water (25 mL). Heat to reflux. After 38 hours, cool to ambient temperature and dilute with ethyl acetate. Extract with saturated aqueous ammonium chloride solution and saturated aqueous sodium chloride solution. Dry the organic layer over $MgSO_4$, filter, and concentrate in vacuo to give a residue. Chromatograph the residue on silica gel eluting with 5/1/0.1 dichloromethane/methanol/ammonium hydroxide to give the title compound: mp; 58–65° C.

EXAMPLE 35
1-(3,4,5-Trimethoxy-benzoyl)-3-[2-[4-[1-(3-carboxy-propyl)-1 H-benzoimidazole-2-carbonyl]-piperidin-1-yl]-ethyl]-3-(3,4-dichloro-phenyl)-pyrrolidine

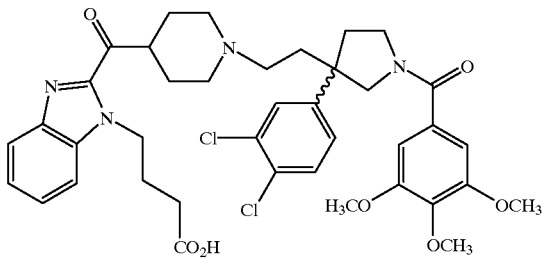

35.1 Synthesis of 1-(3,4,5-trimethoxy-benzoyl)-3-[2-[4-[1-3-carboxy-pronyl(2-(morpholin-4-yl)ethyl)-1 H-benzoimidazole-2-carbonyl]-piperidin-1-yl]-ethyl]-3-(3,4-dichloro-phenyl)-pyrrolidine hydrochloride salt Combine 1-(3,4,5-trimethoxy-benzoyl)-3-[2-[4-[1-(3-ethoxycarbonyl-propyl)-1 H-benzoimidazole-2-carbonyl]-piperidin-1-yl]-ethyl]-3-(3,4-dichloro-phenyl)-pyrrolidine (0.32 g, 0.41 mmol) and lithium hydroxide hydrate (0.052 g, 1.23 mmol) in 4/1 tetrahydrofuran/water (20 mL). After 20 hours, dilute the reaction mixture with water and evaporate in vacuo to remove most of the tetrahydrofuran. Acidify to pH 2 using 1 M hydrochloric acid solution and cool to 5° C. to obtain a solid. Collect the solid by filtration. Suspend the solid in diethyl ether (150 mL) and stir. After 18 hours, collect the solid by filtration and dry to give the title compound: mp; 125–140° C. Elemental Analysis calculated for $C_{39}H_{44}Cl_2N_4O_7 \cdot HCl$: C 59.43; H 5.75; N 7.11; Found: C 59.55; H 5.81; N 6.94.

EXAMPLE 36
1-(3,4,5-Trimethoxy-benzoyl)-3-[2-[4-[1 H-benzoimidazole-2-carbonyl]-piperidin-1-yl]-ethyl]-3-phenyl-pyrrolidine

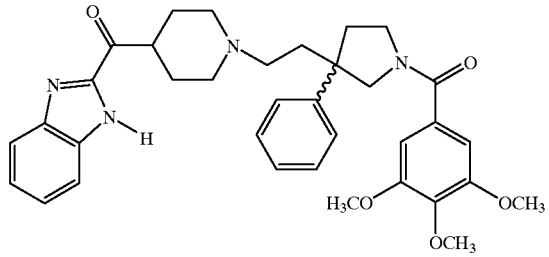

36.1 Synthesis of 1-(3,4,5-trimethoxy-benzoyl)-3-[2-[4-[1 H-benzoimidazole-2-carbonyl]-piperidin-1-yl]-ethyl]-3-phenyl-pyrrolidine Prepare by the method of Example 6.6.2 using 1-(3,4,5-trimethoxy-benzoyl)-3-phenyl-3-(2-methanesulfonyl-ethyl)-pyrrolidine and 4-(1 H-benzoimidazole-2-carbonyl)-piperidine hydroiodide salt to give the title compound: mp; 108.0–111.0° C.; $R_f$=0.28 (silica gel, 5/1 ethyl acetate/methanol) Elemental Analysis calculated for $C_{35}H_{40}N_4O_5 \cdot 0.30\ H_2O$: C 69.82; H 6.80; N 9.30; Found: C 69.90; H 6.79; N 9.22.

EXAMPLE 37
1-(3,4,5-Trimethoxy-benzoyl)-3-[2-[4-[1-(pyrid-2-ylmethyl)-1 H-benzoimidazole-2-carbonyl]-piperidin-1-yl]-ethyl]-3-phenyl-pyrrolidine

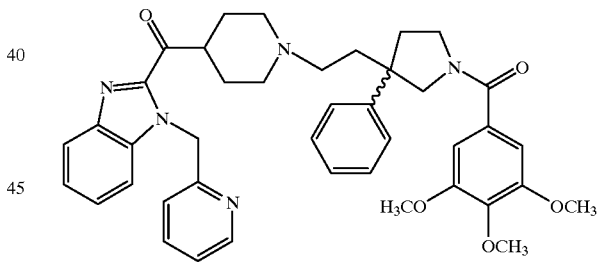

37.1 Synthesis of 1-(3,4,5-trimethoxy-benzoyl)-3-[2-[4-[1-(pyrid-2-ylmethyl) -1 H-benzoimidazole-2-carbonyl]-piperidin-1-yl]-ethyl]-3-phenyl-pyrrolidine Prepare by the method of Example 33.1 using 1-(3,4,5-trimethoxy-benzoyl)-3-[2-[4-[1 H-benzoimidazole-2-carbonyl]-piperidin-1-yl]-ethyl]-3-phenyl-pyrrolidine to obtain the title compound: mp; 84.0–89.0° C.; $R_f$=0.15 (silica gel, 5/1 ethyl acetate/methanol). Elemental Analysis calculated for $C_{41}H_{45}N_5O_5$: C 71.59; H 6.59; N 10.18; Found: C 71.34; H 6.72; N 10.17.

EXAMPLE 38
1-(3,4,5-Trimethoxy-benzoyl)-3-[2-[4-[1-(4-methoxycarbonyl-benzyl)-1 H-benzoimidazole-2-carbonyl]-piperidin-1-yl]-ethyl]-3-phenyl-pyrrolidine

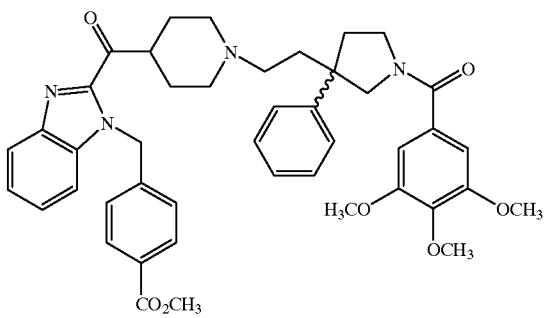

38.1 Synthesis of 1-(3,4,5-trimethoxy-benzoyl)-3-[2-[4-[1-(4-methoxycarbonyl-benzyl)-1 H-benzoimidazole-2-carbonyl]-piperidin-1-yl]-ethyl]-3-phenyl-pyrrolidine Combine 1-(3,4,5-trimethoxy-benzoyl)-3-[2-[4-[1 H-benzoimidazole-2-carbonyl]-piperidin-1-yl]-ethyl]-3-phenyl-pyrrolidine (1.0 g, 1.69 mmol), methyl (4-bromomethyl)benzoate (1.55 g, 6.76 mmol), and 1,8-diazabicyclo[5.4.0]undec-7-ene (2.06 g, 13.52 mmol) in acetonitrile (20 mL). Heat to reflux. After 72 hours, dilute the reaction mixture with ethyl acetate and extract three times with saturated aqueous ammonium chloride solution, saturated aqueous sodium bicarbonate solution, water, and saturated aqueous sodium chloride solution. Dry the organic layer over Na$_2$SO$_4$, filter, and concentrate in vacuo to give a residue. Chromatograph the residue on silica gel eluting with 5/1 ethyl acetate/methanol to give an oil. Combine the oil with dichloromethane and extract with 5% sodium bicarbonate solution. Dry the organic layer over Na$_2$SO$_4$, filter, and concentrate in vacuo to obtain a residue. Dry the residue in vacuo at 82° C. to give the title compound: mp; 92.0–96.0° C.; R$_f$=0.43 (silica gel, 5/1 ethyl acetate/methanol). Elemental Analysis calculated for C$_{44}$H$_{48}$N$_4$O$_7$: C 70.95; H 6.50; N 7.52; Found: C 70.78; H 6.56; N 7.48.

EXAMPLE 39

1-(3,4,5-Trimethoxy-benzoyl)-3-[2-[4-[1-(4-carboxy-benzyl)-1 H-benzoimidazole-2-carbonyl]-piperidin-1-yl]-ethyl]-3-phenyl-pyrrolidine

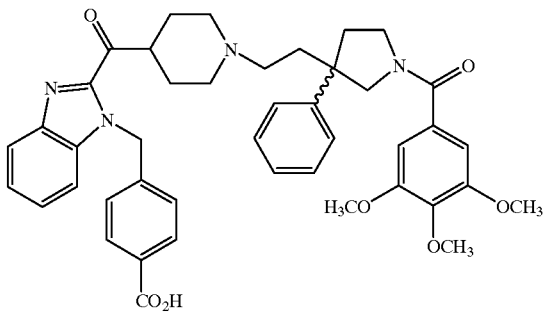

39.1 Synthesis of 1-(3,4,5-trimethoxy-benzoyl)-3-[2-[4-[1-(4-carboxy-benzyl)-1 H-benzoimidazole-2-carbonyl]-piperidin-1-yl]-ethyl]-3-phenyl-pyrrolidine hydrochloride salt Combine 1-(3,4,5-trimethoxy-benzoyl)-3-[2-[4-[1-(4-methoxycarbonyl-benzyl)-1 H-benzoimidazole-2-carbonyl]-piperidin-1-yl]-ethyl]-3-phenyl-pyrrolidine (0.68 g, 0.92 mmol) and lithium hydroxide hydrate (0.12 g, 2.75 mmol) in 4/1 tetrahydrofuran/water (45 mL). After 72 hours, dilute the reaction mixture with water and evaporate in vacuo to remove most of the tetrahydrofuran. Acidify to pH 2 using 1 M hydrochloric acid solution to obtain a solid. Collect the solid by filtration. Suspend the solid in diethyl ether (150 mL) and stir. Collect the solid by filtration and dry to give the title compound: mp; 173.0–190.0° C.

EXAMPLE 40

1-(3,4,5-Trimethoxy-benzoyl)-3-[2-[4-[1-(2-ethoxy-ethyl)-1 H-benzoimidazole-2-carbonyl]-piperidin-1-yl]-ethyl]-3-phenyl-pyrrolidine

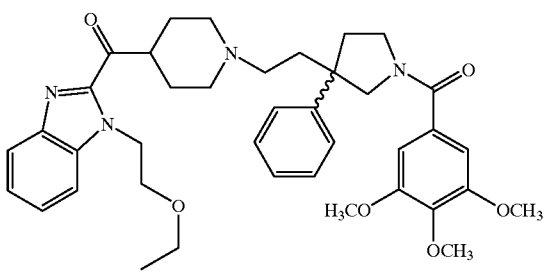

40.1 Synthesis of 1-(3,4,5-trimethoxy-benzoyl)-3-[2-[4-[1-(2-ethoxy-ethyl)-1 H-benzoimidazole-2-carbonyl]-piperidin-1-yl]-ethyl]-3-phenyl-pyrrolidine Combine 1-(3,4,5-trimethoxy-benzoyl)-3-[2-[4-[1 H-benzoimidazole-2-carbonyl]-piperidin-1-yl]-ethyl]-3-phenyl-pyrrolidine (0.81 g, 1.36 mmol), 2-chloroethyl ethyl ether (0.59 g, 5.44 mmol), and 1,8-diazabicyclo[5.4.0] undec-7-ene (1.66 g, 10.88 mmol) in acetonitrile (16 mL). Heat to reflux. After 18 hours, cool to ambient temperature and dilute the reaction mixture with ethyl acetate. Extract twice with saturated aqueous solution of ammonium chloride, 5% aqueous solution of sodium bicarbonate, water, and saturated aqueous solution of sodium chloride. Dry the organic layer over Na$_2$SO$_4$, filter, and concentrate in vacuo to obtain a residue. Chromatograph the residue on silica gel eluting with 1/5 methanol/ethyl acetate to give the title compound: mp; 65–70° C.; R$_f$=0.28 (silica gel, 1/5 methanol/ethyl acetate). Elemental Analysis calculated for C$_{39}$H$_{48}$N$_4$O$_6$·0.70 H$_2$O: C 68.74; H 7.31; N 8.22; Found: C 68.93; H 7.18; N 8.22.

40.2 Synthesis of 1-(3,4,5-trimethoxy-benzoyl)-3-[2-[4-[1-(2-ethoxy-ethyl)-1 H-benzoimidazole-2-carbonyl]-piperidin-1-yl]-ethyl]-3-phenyl-pyrrolidine methanesulfonate salt Combine 1-(3,4,5-trimethoxy-benzoyl)-3-[2-[4-[1-(2-ethoxy-ethyl)-1 H-benzoimidazole-2-carbonyl]-piperidin-1-yl]-ethyl]-3-phenyl-pyrrolidine (0.49 g, 0.73 mmol) and ethyl acetate (100 mL). Add a solution of methanesulfonic acid (0.176 g, 1.83 mmol) in ethyl acetate (2.38 mL). After 18 hours, add diethyl ether (100 mL) to form a solid. Collect the solid by filtration and dry to give the title compound: mp; 118.0–120.0° C.

EXAMPLE 41

(+)-1-(3,4,5-Trimethoxy-benzoyl)-3-[2-[4-[1-(2-ethoxy-ethyl)-1 H-benzoimidazole-2-carbonyl]-piperidin-1-yl]-ethyl]-3-phenyl-pyrrolidine

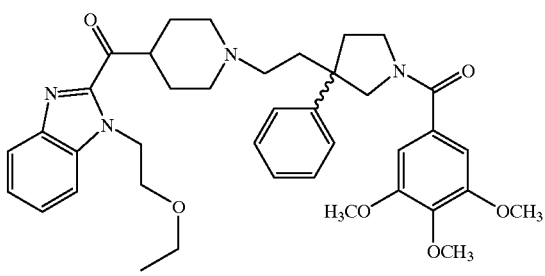

41.1.1 Resolution of (+)-3-phenyl-3-(2-hydroxy-ethyl)-pyrrolidine (R, R)-di-p-anisoyltartaric acid-hydrochloric acid salt and (−)-3-phenyl-3-(2-hydroxy-ethyl)-pyrrolidine (R, R)-di-p-anisoyltartaric acid-hydrochloric acid salt Combine (R, R)-di-p-anisoyltartaric acid (1.10 g, 2.62 mmol) in water/methanol (13.6 mL/13.6 mL). Add 12 M hydrochloric acid solution (0.217 mL, 2.63 mmol). Add a hot solution of 3-phenyl-3-(2-hydroxy-ethyl)-pyrrolidine (1.0 g, 5.23 mmol) in methanol (13.6 mL). Heat to reflux. After 30 minutes, slowly cool to ambient temperature to give a solid. Collect the solid by filtration and recrystallize the solid twice from methanol/water, once from methanol/2-butanone, and once from ethanol to give (+)-3-phenyl-3-(2-hydroxy-ethyl)-pyrrolidine (R, R)-di-p-anisoyltartaric acid-hydrochloric acid salt. After conversion of a sample to the 3,4,5-trimethoxybenzamide using sodium carbonate and 3,4,5-trimethoxybenzoyl chloride in acetone/water, analysis on HPLC using a CHIRALPAK AD (10 μm×4.6 cm×250 cm) column eluting with pentane/ethanol/methanol/triethylamine (80/15/5/0.1) with a flow rate of 1.5 mL/minute indicates an enantiomeric excess of 98%, (98% ee), retention time 22.30 minutes for the 3,4,5-trimethoxybenzamide of the (+)-isomer.

41.1.2 Resolution of (+)-3-phenyl-3-(2-hydroxy-ethyl)-pyrrolidine (R, R)-di-p-anisoyltartaric acid salt and (−)-3-phenyl-3-(2-hydroxy-ethyl)-pyrrolidine (R, R)-di-p-anisoyltartaric acid salt Add a hot solution of 3-phenyl-3-(2-hydroxy-ethyl)-pyrrolidine (5.0 g, 20.2 mmol) in ethanol (100 mL) to a refluxing solution of (R, R)-di-p-anisoyltartaric acid (8.46 g, 20.2 mmol, containing a small amount of acetone) in ethanol (200 mL). After the addition is complete, slowly cool to ambient temperature to give a solid. Collect the solid by filtration and recrystallize the solid three times from ethanol to give (+)-3-phenyl-3-(2-hydroxy-ethyl)-pyrrolidine (R, R)-di-p-anisoyltartaric acid salt: mp; 178.0–179.0° C. Elemental Analysis calculated for $C_{12}H_{17}NO \cdot C_{20}H_{18}O_{10}$: C 63.05; H 5.79; N 2.30; Found: C 62.72; H 5.80; N 2.33. After conversion of a sample to the 3,4,5-trimethoxybenzamide using sodium carbonate and 3,4,5-trimethoxybenzoyl chloride in acetone/water, analysis on HPLC using a CHIRALPAK AD (10 μm×4.6 cm×250 cm) column eluting with pentane/ethanol/methanol/triethylamine (80/15/5/0.1) with a flow rate of 1.5 mL/minute indicates an enantiomeric excess of 99.9%, (99.9% ee), retention time 22.30 minutes for the 3,4,5-trimethoxybenzamide of the (+)-isomer.

Upon standing, the mother liquors from above give a solid. Collect the solid by filtration and recrystallize twice from ethanol to give (−)-3-phenyl-3-(2-hydroxy-ethyl)-pyrrolidine (R, R)-di-p-anisoyltartaric acid salt: mp; 175.0–176.0° C. Elemental Analysis calculated for $C_{12}H_{17}NO \cdot C_{20}H_{18}O_{10} \cdot 0.8\ C_3H_6O$: C 62.98; H 6.11; N 2.13; Found: C 62.86; H 5.94; N 2.33. After conversion of a sample to the 3,4,5-trimethoxybenzamide using sodium carbonate and 3,4,5-trimethoxybenzoyl chloride in acetone/water, analysis on HPLC using a CHIRALPAK AD (10 μm×4.6 cm×250 cm) column eluting with pentane/ethanol/methanol/triethylamine (80/15/5/0.1) with a flow rate of 1.5 mL/minute indicates an enantiomeric excess of 99.9%, (99.9% ee), retention time 10.26 minutes for the 3,4,5-trimethoxybenzamide of the (−)-isomer.

41.2 Synthesis of (+)-1-(3,4,5-trimethoxy-benzoyl)-3-phenyl-3-(2-hydroxy-ethyl)-pyrrolidine Combine (+)-3-phenyl-3-(2-hydroxy-ethyl)-pyrrolidine (R, R)-di-p-anisoyltartaric acid salt (3.95 g, 6.48 mmol) and acetone (20 mL), water (6 mL), and potassium carbonate (2.70 g, 19.5 mmol). Cool to 0° C. in an ice bath. After 30 minutes, add dropwise a solution of trimethoxy-benzoyl chloride (1.71 g, 7.4 mmol) in acetone (20 mL). Warm to ambient temperature. After 18 hours, partition the reaction mixture between ethyl acetate and saturated aqueous sodium bicarbonate solution. Separate the organic layer and extract with saturated aqueous sodium chloride solution. Dry the organic layer over $Na_2SO_4$, filter, and evaporate in vacuo to give the title compound: $R_f$=0.23 (silica gel, ethyl acetate). Analysis on HPLC using a CHIRALPAK AD (10 μm×4.6 cm×250 cm) column eluting with pentane/ethanol/methanol/tri-ethylamine (80/15/5/0.1) with a flow rate of 1.5 mL/minute indicates an enantiomeric excess of 98%, (98% ee), retention time of the (+)-isomer 10.26 minutes.

41.3 Synthesis of (+)-1-(3,4,5-trimethoxy-benzoyl)-3-phenyl-3-(2-methanesulfonyl-ethyl)-pyrrolidine Prepare by the method of Example 6.5.2 using (+)-1-(3,4,5-trimethoxy-benzoyl)-3-phenyl-3-(2-hydroxy-ethyl)-pyrrolidine (2.21 g, 5.51 mmol) and methanesulfonyl chloride (0.7 mL, 9.0 mmol) to give the title compound: $R_f$=0.47 (silica gel, ethyl acetate).

41.4 Synthesis of (+)-1-(3,4,5-trimethoxy-benzoyl)-3-[2-[4-[1 H-benzoimidazole-2-carbonyl]-piperidin-1-yl]-ethyl]-3-phenyl-pyrrolidine Prepare by the method of Example 6.6.2 using (+)-1-(3,4,5-trimethoxy-benzoyl)-3-phenyl-3-(2-methanesulfonyl-ethyl)-pyrrolidine and 4-(1 H-benzoimidazole-2-carbonyl)-piperidine hydroiodide salt to give the title compound.

41.5 Synthesis of (+)-1-(3,4,5-trimethoxy-benzoyl)-3-[2-[4-[1-(2-ethoxy-ethyl)-1 H-benzoimidazole-2-carbonyl]-piperidin-1-yl]-ethyl]-3-phenyl-pyrrolidine Prepare by the method of Example 40.1 using (+)-1-(3,4,5-trimethoxy-benzoyl)-3-[2-[4-[1 H-benzoimidazole-2-carbonyl]-piperidin-1-yl]-ethyl]-3-phenyl-pyrrolidine to give the title compound.

EXAMPLE 42

1-(3,4,5-Trimethoxy-benzoyl)-3-[2-[4-[1-(4-carbomethoxy-phenylmethyl)-1 H-benzoimidazole-2-carbonyl]-piperidin-1-yl]-ethyl]-3-(3,4-dimethoxy-phenyl)-pyrrolidine

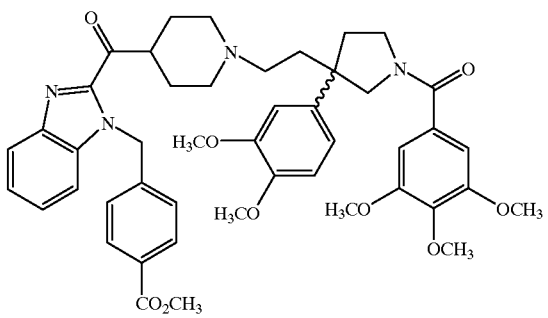

42.1 Synthesis of 1-(3,4,5-trimethoxy-benzoyl)-3-[2-[4-[1 H-benzoimidazole-2-carbonyl]-piperidin-1-yl]-ethyl]-3-(3,4-dimethoxy-phenyl)-pyrrolidine Prepare by the method of Example 6.6.2 using 1-(3,4,5-trimethoxy-benzoyl)-3-(3,4-dimethoxy-phenyl)-3-(2-methanesulfonyl-ethyl)-pyrrolidine and 4-(1 H-benzoimidazole-2-carbonyl)-piperidine hydroiodide salt to give the title compound: mp; 105.0–115.0° C.; $R_f$=0.17 (silica gel, 1/5 methanol/ethyl acetate).

42.2 Synthesis of 1-(3,4,5-trimethoxy-benzoyl)-3-[2-[4-[1-(4-carbomethoxy-phenylmethyl)-1 H-benzoimidazole-2-carbonyl]-piperidin-1-yl]-ethyl]-3-(3,4-dimethoxy-phenyl)-pyrrolidine Prepare by the method of Example 38.1 using 1-(3,4,5-trimethoxy-benzoyl)-3-[2-[4-[1 H-benzoimidazole-2-carbonyl]-piperidin-1-yl]-ethyl]-3-(3,4-dimethoxy-phenyl)-pyrrolidine to give the title compound: mp; 100.0–104.0° C.; $R_f$=0.11 (silica gel, 5/1 ethyl acetate/methanol). Elemental Analysis Calculated for $C_{46}H_{52}N_4O_9 \cdot 0.40 H_2O$: C 68.03; H 6.55; N 6.90; Found: C 68.21; H 6.55; N 7.08.

EXAMPLE 43

1-(3,4,5-Trimethoxy-benzoyl)-3-[2-[4-[1-(4-carboxy-phenylmethyl)-1 H-benzoimidazole-2-carbonyl]]-piperidin-1-yl]-ethyl]-3-(3,4-dimethoxy-phenyl)-pyrrolidine

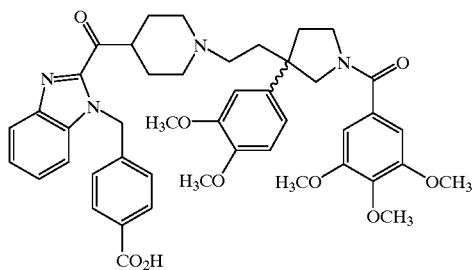

43.1 Synthesis of 1-(3,4,5-trimethoxy-benzoyl)-3-[2-[4-[1-(4-carboxy-phenylmethyl)-1 H-benzoimidazole-2-carbonyl]-piperidin-1-yl]-ethyl]-3-(3,4-dimethoxy-phenyl)-pyrrolidine hydrochloride salt Combine 1-(3,4,5-trimethoxy-benzoyl)-3-[2-[4-[1-(4-carbomethoxy-phenylmethyl)-1 H-benzoimidazole-2-carbonyl]-piperidin-1-yl]-ethyl]-3-(3,4-dimethoxy-phenyl)-pyrrolidine (0.79 g, 0.98 mmol) and lithium hydroxide hydrate (0.12 g, 2.95 mmol) in 4/1 tetrahydrofuran/water (45 mL). After 18 hours, dilute the reaction mixture with water and evaporate in vacuo to remove most of the tetrahydrofuran. Acidify to pH 2 using 1 M hydrochloric acid solution to obtain a solid. Collect the solid by filtration. Suspend the solid in diethyl ether (150 mL) and stir. Collect the solid by filtration and resuspend in diethyl ether. Collect the solid by filtration-and dry in vacuo at 82° C. to give the title compound: mp; 190.0–210.0° C.

PREPARATION 3

Synthesis of 1-(t-butoxycarbonyl)-4-(1 H-benzoimidazole-2-carbonyl)-piperidine

Combine 4-(1 H-benzoimidazole-2-carbonyl)-piperidine hydroiodide salt (3.21 g, 6.63 mmol), 1 M aqueous sodium bicarbonate solution (15 mL), and t-butanol (30 mL). Add di-t-butyldicarbonate (1.65 g, 7.54 mmol). After 20 hours, concentrate the reaction mixture in vacuo to remove most of the t-butanol. Partition the reaction mixture between ethyl acetate and water. Separate the organic layer and extract with 1 M aqueous hydrochloric acid solution, 1 M aqueous sodium bicarbonate solution, and saturated aqueous sodium chloride solution. Dry the organic layer over $Na_2SO_4$, filter, and evaporate in vacuo to give the title compound: $R_f$=0.30 (silica gel, 20% ethyl acetate/hexane).

PREPARATION 4

Synthesis of 4-(1-(Fur-2-lymethyl)-1 H-benzoimidazole-2-carbonyl)-piperidine

Combine 1-(t-butoxycarbonyl)-4-(1 H-benzoimidazole-2-carbonyl)-piperidine (0.38 g, 1.16 mmol), furfuryl alcohol (0.10 mL, 1.16 mmol), and triphenylphosphine (0.33 g, 1.28 mmol) in tetrahydrofuran (5 mL). Add diethyl azodicarboxylate (0.20 mL, 1.27 mmol). After 18 hours, evaporate the reaction mixture in vacuo to give a residue. Partition the residue between ethyl acetate and water. Separate the organic layer and extract with water and saturated aqueous sodium chloride solution. Dry the organic layer over $Na_2SO_4$, filter, and evaporate in vacuo to give the title compound. Chromatograph the residue on silica gel eluting with 5% acetone/dichloromethane to give 1-(t-butoxycarbonyl)-4-(1-(fur-2-ylmethyl)-1 H-benzoimidazole-2-carbonyl)-piperidine.

Cool 1-(t-butoxycarbonyl)-4-(1-(fur-2-ylmethyl)-1 H-benzoimidazole-2-carbonyl)-piperidine (0.38 g, 0.97 mmol) in an ice-bath. Add cold trifluoroacetic acid (5 mL) and mix. After 15 minutes, add diethyl ether and evaporate in vacuo to give a residue. Partition the residue between dichloromethane and saturated aqueous sodium bicarbonate solution. Separate the organic layer and extract with saturated aqueous sodium chloride solution. Dry the organic layer over $Na_2SO_4$, filter, and evaporate in vacuo to give the title compound.

EXAMPLE 44

1-(3,4,5-Trimethoxy-benzoyl)-3-[2-[4-[1-(fur-2-ylmethyl)-1 H-benzoimidazole-2-carbonyl]-piperidin-1-yl]-ethyl]-3-phenyl-pyrrolidine

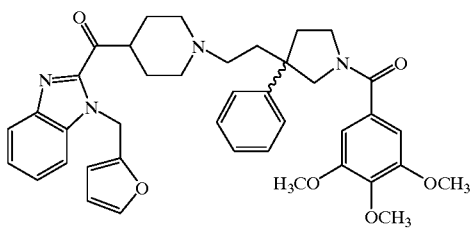

44.1 Synthesis of 1-(3,4,5-trimethoxy-benzoyl)-3-[2-[4-[1-(fur-2-ylmethyl)-1 H-benzoimidazole-2-carbonyl]-piperidin-1-yl]-ethyl]-3-phenyl-pyrrolidine Prepare by the method of Example 6.6.2 using 1-(3,4,5-trimethoxy-benzoyl)-3-phenyl-3-(2-methanesulfonyl-ethyl)-pyrrolidine and 4-(1-(fur-2-ylmethyl)-1 H-benzoimidazole-2-carbonyl)-piperidine obtain, after chromatography on silica gel eluting with 80% acetone/hexane, the title compound: Mass Spectra (CI/NH$_3$) M$^+$+H= 677.

PREPARATION 5

Synthesis of 4-(1-(2-fur-2-ylmethoxy-ethyl)-1 H-benzoimidazole-2-carbonyl)-piperidine Combine furfuryl alcohol (1 mL, 11.6 mmol) and tetrahydrofuran (20 mL). Add portionwise sodium hydride (0.57 g, 60% in oil, 14 mmol). After gas evolution ceases, add ethyl bromoacetate (1.3 mL, 11.7 mmol). Heat to reflux. After 2.5 hours cool to ambient temperature. After 18 hours, partition the reaction mixture between ethyl acetate and water. Separate the aqueous layer and extract twice with ethyl acetate. Combine the organic layers and extract with saturated aqueous sodium chloride solution, dry over Na$_2$SO$_4$, filter, and concentrate in vacuo to give a residue. Chromatograph the residue on silica gel eluting with 1% ethyl acetate/dichloromethane to give ethyl fur-2-ylmethoxyacetate: R$_f$=0.62 (silica gel, 5% ethyl acetate/dichloromethane).

Combine ethyl 2-fur-2-ylmethoxyacetate (1.2 g, 6.5 mmol) and tetrahydrofuran (10 mL). Cool in an ice-bath. Add dropwise a solution of lithium aluminum hydride (8.0 mL, 1.0 M in THF, 8.0 mmol). After 2 hours, add water (0.3 mL), add 15% sodium hydroxide solution (0.3 mL), and add water (0.9 mL). Stir vigorously. After 15 minutes, filter the reaction mixture and dry the filtrate over Na$_2$SO$_4$, filter, and concentrate in vacuo to give a residue. Chromatograph the residue on silica gel eluting with 2% ethyl acetate/dichloromethane to give fur-2-ylmethyl 2-hydroxyethyl ether: R$_f$=0.22 (silica gel, 5% acetone/dichloromethane).

Combine 1-(t-butoxycarbonyl)-4-(1 H-benzoimidazole-2-carbonyl)-piperidine (1.71 g, 5.2 mmol), fur-2-ylmethyl 2-hydroxyethyl ether (0.74 g, 5.2 mmol), and triphenylphosphine (0.31.67 g, 6.4 mmol) in tetrahydrofuran (20 mL). Add diethyl azodicarboxylate (1.0 mL, 6.35 mmol). After 21 hours, evaporate the reaction mixture in vacuo to give a residue. Chromatograph the residue on silica gel eluting with 5% acetone/dichloromethane to give 1-(t-butoxycarbonyl)-4-(1-(2-fur-2-ylmethoxy-ethyl)-1 H-benzoimidazole-2-carbonyl)-piperidine: R$_f$=0.30 (silica gel, 5% acetone/dichloromethane)

Combine 1-(t-butoxycarbonyl)-4-(1-(2-fur-2-ylmethoxy-ethyl)-1 H-benzoimidazole-2-carbonyl)-piperidine (0.43 g, 0.94 mmol) and dioxane (3 mL). Add a solution of hydrochloric acid in dioxane (4.0 mL, 4 M, 16 mmol). After 30 minutes, partition the residue between ethyl acetate and saturated aqueous sodium bicarbonate solution. Separate the organic layer and extract with saturated aqueous sodium chloride solution. Dry the organic layer over Na$_2$SO$_4$, filter, and evaporate in vacuo to give the title compound.

EXAMPLE 45

1-(3,4,5-Trimethoxy-benzoyl)-3-[2-[4-[1-(2-fur-2-ylmethoxy-ethyl)-1 H-benzoimidazole-2-carbonyl]-piperidin-1-yl]-ethyl]-3-phenyl-pyrrolidine

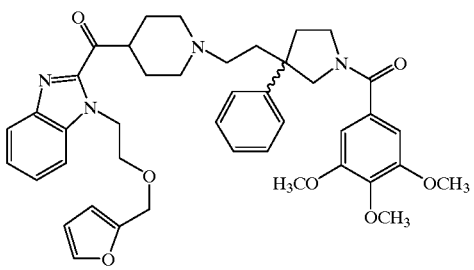

45.1 Synthesis of 1-(3,4,5-trimethoxy-benzoyl)-3-[2-[4-[1-(2-fur-2-ylmethoxy-ethyl)-1 H-benzoimidazole-2-carbonyl]-piperidin-1-yl]-ethyl]-3-phenyl-pyrrolidine Prepare by the method of Example 6.6.2 using 1-(3,4,5-trimethoxy-benzoyl)-3-phenyl-3-(2-methanesulfonyl-ethyl)-pyrrolidine and 4-(1-(2-fur-2-lymethoxy-ethyl)-1 H-benzoimidazole-2-carbonyl)-piperidine obtain, after chromatography on silica gel eluting with 5% methanol/ethyl acetate, the title compound: Mass Spectra (CI/NH$_3$) M$^+$+H=721.

PREPARATION 6

Synthesis of 4-(1-(2-allyloxy-ethyl)-1 H-benzoimidazole-2-carbonyl)-piperidine

Combine allyl hydroxyethyl ether (1.02 g, 10 mmol), and diisopropylethylamine (4.0 mL, 23 mmol), and dichloromethane (20 mL). Cool in an ice-bath. Add dropwise, methanesulfonyl chloride (1.0 mL, 13 mmol). After 1.5 hours, extract the reaction mixture with 1 M aqueous hydrochloric acid solution, saturated aqueous sodium bicarbonate solution, and saturated aqueous sodium chloride solution. Dry the organic layer over Na$_2$SO$_4$, filter, and evaporate in vacuo to obtain allyl methanesulfonylethyl ether: R$_f$=0.80 (silica gel, 20% ethyl acetate/dichloromethane).

Combine 1-(t-butoxycarbonyl)-4-(1 H-benzoimidazole-2-carbonyl)-piperidine (1.87 g, 5.68 mmol), allyl methanesulfonylethyl ether (1.83 g, 10.1 mmol), and potassium carbonate (1.60 g, 11.5 mmol) in acetone (21 mL) and water (7 mL). Heat to reflux. After 18 hours, concentrate the reaction mixture in vacuo to remove most of the acetone. Partition the concentrated reaction mixture between ethyl acetate and water. Separate the aqueous layer and extract three times with ethyl acetate. Extract the combined organic layers with saturated aqueous sodium chloride solution. Dry the organic layer over Na$_2$SO$_4$, filter, and evaporate in vacuo to obtain a residue. Chromatograph the residue on silica gel eluting with 15% ethyl acetate/dichloromethane to give 1-(t-butoxycarbonyl)-4-(1-(2-allyloxy-ethyl)-1 H-benzoimidazole-2-carbonyl)-piperidine: R$_f$=0.48 (silica gel, 20% ethyl acetate/dichloromethane).

Combine 1-(t-butoxycarbonyl)-4-(1-(2-allyloxy-ethyl)-1H-benzoimidazole-2-carbonyl)-piperidine (1.0 mmol) and dioxane (3 mL). Add a solution of hydrochloric acid in dioxane (4 mL, 4 M, 16 mmol). After 30 minutes, partition the residue between ethyl acetate and saturated aqueous sodium bicarbonate solution. Separate the organic layer and extract with saturated aqueous sodium chloride solution. Dry the organic layer over $Na_2SO_4$, filter, and evaporate in vacuo to give the title compound.

PREPARATION 7
Synthesis of 4-(1-(2-allyloxy-ethyl)-1 H-benzoimidazole-2-carbonyl)-piperidine Prepare by the method of Preparation 4 using allyl hydroxyethyl ether and 1-(t-butoxycarbonyl)-4-(1 H-benzoimidazole-2-carbonyl)-piperidine to give the title compound.

EXAMPLE 46
1-(3,4,5-Trimethoxy-benzoyl)-3-[2-[4-[1-(2-allyloxy-ethyl)-1H-benzoimidazole-2-carbonyl]-piperidin-1-yl]-ethyl]-3-phenyl-pyrrolidine

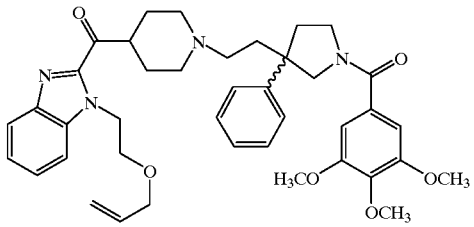

46.1 Synthesis of 1-(3,4,5-trimethoxy-benzoyl)-3-[2-[4-[1-(2-allyloxy-ethyl)-1 H-benzoimidazole-2-carbonyl]-piperidin-1-yl]-ethyl]-3-phenyl-pyrrolidine Prepare by the method of Example 6.6.2 using 1-(3,4,5-trimethoxy-benzoyl)-3-phenyl-3-(2-methanesulfonyl-ethyl)-pyrrolidine and 4-(1-(2-allyloxy-ethyl)-1 H-benzoimidazole-2-carbonyl)-piperidine to obtain the title compound.

PREPARATION 8
Synthesis of 4-(1-(2-(3,3-dimethylallyloxy)-ethyl)-1 H-benzoimidazole-2-carbonyl) -piperidine Prepare by the method of Preparation 5 using 3-methyl-2-buten-1-ol.

EXAMPLE 47
1-(3,4,5-Trimethoxy-benzoyl)-3-[2-[4-[1-(3-trifluoromethyl-benzyl)-1 H-benzoimidazole-2-carbonyl]-piperidin-1-yl]-ethyl]-3-phenyl-pyrrolidine

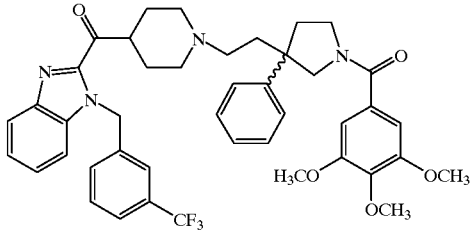

47.1 Synthesis of 1-(3,4,5-trimethoxy-benzoyl)-3-[2-[4-[1-(3-trifluoromethyl-benzyl)-1 H-benzoimidazole-2-carbonyl]-piperidin-1-yl]-ethyl1-3-phenyl-pyrrolidine Prepare by the method of Example 38.1 using 1-(3,4,5-trimethoxy-benzoyl)-3-[2-[4-[1H-benzoimidazole-2-carbonyl]-piperidin-1-yl]-ethyl]-3-phenyl-pyrrolidine and 3-trifluormethylbenzyl chloride to give the title compound.

EXAMPLE 48
1-(2,4-dichloro-benzoyl)-3-[2-[4-[1-(4-[fluoro-benzyl])-1 H-benzoimidazole-2-carbonyl]-piperidin-1-yl]-ethyl]-3-(benzo [1,3]dioxol-5-yl)-pyrrolidine

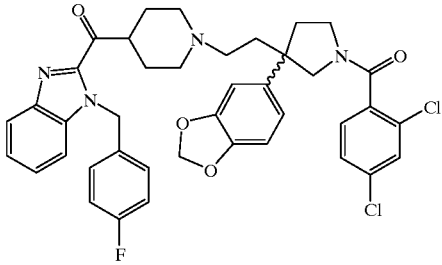

48.1 Synthesis of 1-(2,4-dichloro-benzoyl)-3-(benzo[1,3]dioxol-5-yl)-3-(2-hydroxy-ethyl)-pyrrolidine Prepare by the method of Example 1.4.1 using 3-(benzo [1,3]dioxol-5-yl)-3-(2-hydroxy-ethyl)-pyrrolidine and 2,4-dichloro-benzoyl chloride to obtain the title compound: $R_f$=0.40 (silica gel, 6/1 ethyl acetate/hexane); mp; 65.0–67.0° C. Elemental Analysis calculated for $C_{20}H_{19}Cl_2NO_4 \cdot 0.28\ H_2O$: C 58.12; H 4.77; N 3.39; Found: C 58.13; H 4.81; N 3.37.

48.2 Synthesis of 1-(2,4-dichloro-benzoyl)-3-(benzo[1,3]dioxol-5-yl)-3-(2-methanesulfonyl-ethyl)-pyrrolidine Prepare by the method of Example 6.5.2 using 1-(2,4-dichloro-benzoyl)-3-(benzo[1,3]dioxol-5-yl)-3-(2-hydroxy-ethyl)-pyrrolidine to give the title compound: $R_f$=0.60 (silica gel, 6/1 ethyl acetate/hexane).

48.3 Synthesis of 1-(2,4-dichloro-benzoyl)-3-[2-[4-[1-(4-fluoro-benzyl)-1 H-benzoimidazole-2-carbonyl]-piperidin-1-yl]-ethyl]-3-(benzo[1,3]dioxol-5-yl) -pyrrolidine Prepare by the method of Example 6.6.2 using 1-(2,4-dichloro-benzoyl)-3-(benzo[1,3]dioxol-5-yl)-3-(2-methanesulfonyl-ethyl)-pyrrolidine to give the title compound: $R_f$=0.46 (silica gel, 20/1 ethyl acetate/methanol); mp; 103.0–106.0° C. Elemental Analysis calculated for $C_{40}H_{37}Cl_2FN_4O_4$: C 66.03; H 5.13; N 7.70; Found: C 65.87; H 5.16; N 7.44.

48.4 Synthesis of 1-(2,4-dichloro-benzoyl)-3-[2-[4-[1-(4-fluoro-benzyl)-1 H-benzoimidazole-2-carbonyl]-piperidin-1-yl]-ethyl]-3-(benzo [1,3]dioxol-5-yl) -pyrrolidine methanesulfonate salt Prepare by the method of Example 6.7.3 using 1-(2,4-dichloro-benzoyl)-3-[2-[4-[1-(4-[fluoro-benzyl])-1 H-benzoimidazole-2-carbonyl]-piperidin-1-yl]-ethyl]-3-(benzo[1,3]dioxol-5-yl)-pyrrolidine and methanesulfonic acid to give the title compound: mp; 150.0–152.0° C. Elemental Analysis calculated for $C_{40}H_{37}Cl_2FN_4O_4 \cdot 2\ CH_3SO_3H \cdot 2.8\ H_2O$: C 51.99; H 5.26; N 5.77; Found: C 52.07; H 4.86; N 5.57.

EXAMPLE 49
1-(3,4,5-Trimethoxy-benzoyl)-3-[2-[4-[1-(2-ethoxy-ethyl)-1 H-benzoimidazole-2-carbonyl]-piperidin-1-yl]-ethyl]-3-(3-chloro-phenyl)-pyrrolidine

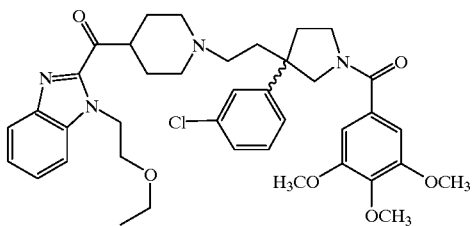

49.1 Synthesis of 3-cyano-3-(3-chloro-phenyl)-pentanedioic acid diethyl ester

Prepare by the method of Example 11.1.2 using 3-chlorophenylacetonitrile to give the title compound. Elemental Analysis calculated for $C_{16}H_{18}ClNO_4$: C 59.35; H 5.55; N 4.33; Found: C 59.47; H 5.54; N 4.51.

49.2 Synthesis of 3-(3-chloro-phenyl)-5-oxo-pyrrolidin-3-yl]-acetic acid ethyl ester Prepare by the method of Example 6.2.2 using 3-cyano-3-(3-chloro-phenyl)-pentanedioic acid diethyl ester to give the title compound.

49.3 Synthesis of 3-(3-chloro-phenyl)-3-(2-hydroxy-ethyl)-pyrrolidine

Prepare by the method of Example 6.3 using 3-(3-chloro-phenyl)-5-oxo-pyrrolidin-3-yl]-acetic acid ethyl ester to give the title compound: $R_f$=0.30 (silica gel, 85/10/5 dichloromethane/methanol/acetic acid).

49.4 Synthesis of 1-(3,4,5-trimethoxy-benzoyl)-[3-(3-chloro-phenyl)-3-(2-hydroxy-ethyl)-pyrrolidine Combine 3-(3-chloro-phenyl)-3-(2-hydroxy-ethyl)-pyrrolidine (4.5 g, 20 mmol) and sodium bicarbonate (8.4 g) in acetone (50 mL)/ water (50 mL). Add a solution of 3,4,5-trimethoxy-benzoyl chloride (4.6 g, 19.9 mmol) in acetone (50 mL). After 3 hours, extract the reaction mixture three times with ethyl acetate. Dry the organic layer over $MgSO_4$, filter, and concentrate in vacuo to give the title compound: $R_f$=0.46 (silica gel, 6% methanol/dichloromethane).

49.5 Synthesis of 1-(3,4,5-trimethoxy-benzoyl)-3-(3-chloro-phenyl)-3-(2-methanesulfonyl-ethyl)-pyrrolidine Prepare by the method of Example 6.5.2 using 1-(3,4,5-trimethoxy-benzoyl)-3-(3-chloro-phenyl)-3-(2-hydroxy-ethyl)-pyrrolidine to give the title compound: $R_f$=0.47 (silica gel, ethyl acetate).

49.6 Synthesis of 1-(3,4,5-trimethoxy-benzoyl)-3-[2-[4-[1 H-benzoimidazole-2-carbonyl]-piperidin-1-yl]-ethyl]-3-(3-chloro-phenyl)-pyrrolidine Prepare by the method of Example 6.6.2 using 1-(3,4,5-trimethoxy-benzoyl)-3-(3-chloro-phenyl)-3-(2-methanesulfonyl-ethyl)-pyrrolidine and 4-(1 H-benzoimidazole-2-carbonyl)-piperidine hydroiodide salt to give the title compound.

49.7 Synthesis of (3,4,5-trimethoxy-benzoyl)-3-[2-[4-[1-(2-ethoxy-ethyl)-1 H-benzoimidazole-2-carbonyl]-piperidin-1-yl]-ethyl]-3-(3-chloro-phenyl)-pyrrolidine Prepare by the method of Example 40.1 using 1-(3,4,5-trimethoxy-benzoyl)-3-[2-[4-[1 H-benzoimidazole-2-carbonyl]-piperidin-1-yl]-ethyl]-3-(3-chloro-phenyl)-pyrrolidine to give the title compound.

EXAMPLE 50

1-(3,4,5-Trimethoxy-benzoyl)-3-[2-[4-[1-(2-ethoxy-ethyl)-1 H-benzoimidazole-2-carbonyl]-piperidin-1-yl]-ethyl]-3-(4-chloro-phenyl)-pyrrolidine

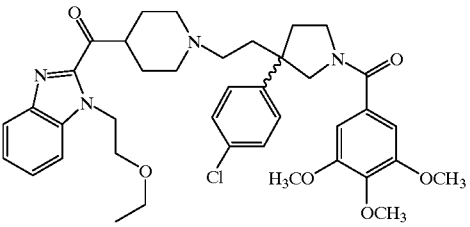

50.1 Synthesis of 3-cyano-3-(4-chloro-phenyl)-pentanedioic acid diethyl ester

Prepare by the method of Example 11.1.2 using 4-chlorophenylacetonitrile to give the title compound. Elemental Analysis calculated for $C_{16}H_{18}ClNO_4$: C 59.35; H 5.55; N 4.33; Found: C 59.27; H 5.54; N 4.33.

50.2 Synthesis of 3-(4-chloro-phenyl)-5-oxo-pyrrolidin-3-yl]-acetic acid ethyl ester Prepare by the method of Example 6.2.2 using 3-cyano-3-(4-chloro-phenyl)-pentanedioic acid diethyl ester to give the title compound.

50.3 Synthesis of 3-(4-chloro-phenyl) -3-(2-hydroxy-ethyl)-pyrrolidine

Prepare by the method of Example 6.3 using 3-(4-chloro-phenyl)-5-oxo-pyrrolidin-3-yl]-acetic acid ethyl ester to give the title compound: $R_f$=0.30 (silica gel, 85/10/5 dichloromethane/methanol/acetic acid).

50.4 Synthesis of 1-(3,4,5-trimethoxy-benzoyl)-[3-(4-chloro-phenyl)-3-(2-hydroxy-ethyl)-pyrrolidine Prepare by the method of Example 49.4 using 3-(4-chloro-phenyl)-3-(2-hydroxy-ethyl)-pyrrolidine to give the title compound: $R_f$=0.42 (silica gel, 6% methanol/dichloromethane).

50.5 Synthesis of 1-(3,4,5-trimethoxy-benzoyl)-3-(3-(4-chloro-phenyl)-3-(2-methanesulfonyl-ethyl)-pyrrolidine Prepare by the method of Example 6.5.2 using 1-(3,4,5-trimethoxy-benzoyl)-3-(4-chloro-phenyl)-3-(2-hydroxy-ethyl)-pyrrolidine to give the title compound: $R_f$=0.44 (silica gel, ethyl acetate).

50.6 Synthesis of 1-(3,4,5-trimethoxy-benzoyl)-3-[2-[4-[1 H-benzoimidazole-2-carbonyl]-piperidin-1-yl]-ethyl]-3-(4-chloro-phenyl)-pyrrolidine Prepare by the method of Example 6.6.2 using 1-(3,4,5-trimethoxy-benzoyl)-3-(4-chloro-phenyl)-3-(2-methanesulfonyl-ethyl)-pyrrolidine and 4-(1H-benzoimidazole-2-carbonyl)-piperidine hydroiodide salt to give the title compound.

50.7 Synthesis of (3,4,5-trimethoxy-benzoyl)-3-[2-[4-[1-(2-ethoxy-ethyl)-1H-benzoimidazole-2-carbonyl]-piperidin-1-yl]-ethyl]-3-(4-chloro-phenyl)-pyrrolidine Prepare by the method of Example 40.1 using 1-(3,4,5-trimethoxy-benzoyl)-3-[2-[4-[1H-benzoimidazole-2-carbonyl]-piperidin-1-yl]-ethyl]-3-(4-chloro-phenyl)-pyrrolidine to give the title compound.

EXAMPLE 51

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-piperidine

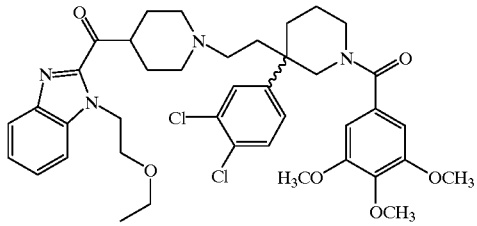

51.1 Synthesis of 2-(3,4-dichloro-phenyl)-4-(t-butyldimethylsilyloxy)-butyronitrile Combine 3,4-dichloro-phenyl-acetonitrile (10 g, 53.8 mmol) and anhydrous tetrahydrofuran (50 mL). Cool in a dry-ice/acetone bath. Add dropwise a solution of lithium bis-(trimethylsilyl)amide (64.5 mL, 1 M in THF, 64.5 mmol). Add dropwise, 2-(t-butyldimethylsilyloxy)-1-bromoethane (15.43 g, 64.5 mmol). When the addition of 2-(t-butyldimethyl-silyloxy)-1-bromoethane is complete, warm the reaction mixture to ambient temperature. After 12 hours, partition the reaction mixture between ethyl acetate and water. Extract the aqueous layer twice with ethyl acetate. Combine the organic layers and extract with 1 M hydrochloric acid solution, dry over $Na_2SO_4$, filter, and concentrate in vacuo to obtain a residue. Chromatograph the residue on silica gel eluting with 10% ethyl acetate/hexane to give the title compound: $R_f$=0.42 (silica gel, 10% ethyl acetate/hexane).

51.2 Synthesis of ethyl 4-cyano-4-(3,4-dichloro-phenyl)-6-(t-butyldimethylsilyloxy)-hexanoate Combine 2-(3,4-dichloro-phenyl)-4-(t-butyldimethylsilyloxy)-butyronitrile (13.35 g, 38.8 mmol) and anhydrous tetrahydrofuran (50 mL). Cool in a dry-ice/acetone bath. Add dropwise a solution of lithium bis-(trimethylsilyl)amide (42.6 mL, 1 M in THF, 42.6 mmol). Add dropwise, ethyl 3-bromopropionate (7.71 g, 4.26 mmol). Warm the reaction mixture to ambient temperature. After 18 hours, add water. Separate the aqueous layer and extract three times with ethyl acetate. Combine the organic layers, dry over $Na_2SO_4$, filter, and concentrate in vacuo to obtain a residue. Chromatograph the residue on silica gel eluting with 90% ethyl acetate/hexane to give the title compound: $R_f$=0.35 (silica gel, 10% ethyl acetate/hexane).

51.3 Synthesis of 3-(3,4-dichloro-phenyl)-3-(2-(t-butyldimethylsilyloxy)-ethyl)-6-oxo-piperidine Combine ethyl 4-cyano-4-(3,4-dichloro-phenyl)-6-(t-butyldimethylsilyloxy)-hexanoate (9.58 g, 21.55 mmol) and cobalt(II)chloride hexahydrate (10.25 g, 43.1 mmol) in methanol (200 mL). Cool in an ice-bath, add portionwise sodium borohydride (8.15 g, 215.5 mmol). After 18 hours, concentrate the reaction mixture in vacuo to obtain a residue. Dissolve the residue in dichloromethane and extract with 1M hydrochloric acid solution. Dry the organic layer over $Na_2SO_4$, filter, and concentrate invacuo to obtain a residue. Chromatograph the residue on silica gel eluting with 1/1 ethyl acetate/hexane to give the title compound: $R_f$=0.46 (silica gel, 1/1 ethyl acetate/hexane).

51.4 Synthesis of 3-(3,4-dichloro-phenyl)-3-(2-hydroxy-ethyl)-piperidine

Combine a solution of lithium aluminum hydride (42 mL, 1 M in THF, 42.0 mmol). Cool to about −10° C. using an isopropyl alcohol/ice bath. Slowly add a solution of sulfuric acid (1.15 mL, 21.6 mmol) in tetrahydrofuran (4 mL) at such a rate that the reaction temperature does not rise above −10° C.

Stir vigorously and warm to ambient temperature. After 2 hours, add a solution of 3-(3,4-dichloro-phenyl)-3-(2-(t-butyldimethylsilyloxy)-ethyl)-6-oxo-piperidine (5.56 g, 13.85 mmol) in tetrahydrofuran (12 mL). Heat to reflux. After 18 hours, add 1/1 tetrahydrofuran/water. After 1 hour, filter and rinse with dichloromethane. Suspend the solids removed by filtration in tetrahydrofuran (400 mL). To the tetrahydrofuran suspension add water (20 mL) and 15% aqueous sodium hydroxide solution (8 mL) and stir vigorously. After 2 hours, filter. Combine the filtrates and concentrate in vacuo to give an aqueous suspension. Extract twice with dichloromethane. Dry the organic layers over $Na_2SO_4$, filter, and concentrate in vacuo to give the title compound.

51.5 Synthesis of 1-(3,4,5-trimethoxy-benzoyl)-3-(3,4-dichloro-phenyl)-3-(2-hydroxy-ethyl)-piperidine Combine 3-(3,4-dichloro-phenyl)-3-(2-hydroxy-ethyl)-piperidine (1.08 g, 3.94 mmol) and sodium carbonate (0.21 g, 2.00 mmol) in 1/1 ethyl acetate/water (50 mL). Cool the reaction mixture to 0° C. with an ice bath. Add 3,4,5-trimethoxy-benzoyl chloride (0.83 g, 3.58 mmol). Warm to ambient temperature. After 18 hours, separate the layers and extract the aqueous layer three times with ethyl acetate. Dry the combined organic layers over $Na_2SO_4$, filter, and concentrate in vacuo to obtain a residue. Chromatograph the residue on silica gel to give the title compound: $R_f$=0.5 (silica gel, 1/1 ethyl acetate/hexane). Elemental Analysis calculated for $C_{23}H_{27}Cl_2NOS$: C 58.97; H 5.81; N 2.99; Found C 58.85; H 5.90; N 2.96.

51.6 Synthesis of 1-(3,4,5-trimethoxy-benzoyl)-3-(3,4-dichloro-phenyl)-(2-methanesulfonyl-ethyl)-piperidine Combine 1-(3,4,5-trimethoxy-benzoyl)-3-(3, 4-dichloro-phenyl)-3-(2-hydroxy-ethyl)-piperidine (0.53 g, 1.14 mmol) and diisopropylethylamine (0.40 mL, 22.3 mmol) in anhydrous dichloromethane (12.mL). Cool the reaction mixture to −5° C. with an salt-ice bath. Slowly add methanesulfonyl chloride (0.12 mL, 1.5 mmol). After 3.5 hours, dilute the reaction mixture with dichloromethane and extract with 1M hydrochloric acid and with a saturated solution of sodium bicarbonate. Dry the organic layer over $Na_2SO_4$, filter, and concentrate in vacuo to obtain the title compound.

51.7 Synthesis of 1-(3,4,5-trimethoxy-benzoyl)-3-[2-[4-[1H-benzoimidazole-2-carbonyl]-piperidin-1-yl]-ethyl]-3-(3,4-dichloro-phenyl)-piperidine Prepare by the method of Example 6.6.2 using 1-(3,4,5-trimethoxy-benzoyl)-3-(3,4-dichloro-phenyl)-(2-methanesulfonyl-ethyl)-piperidine and 4-(1H-benzoimidazole-2-carbonyl)-piperidine hydroiodide salt to give the title compound.

51.8 Synthesis of 1-(3,4,5-trimethoxy-benzoyl)-3-[2-[4-[1-(2-ethoxy-ethyl)-1H-benzoimidazole-2-carbonyl]-piperidin-1-yl]-ethyl]-3-(3 4-dichloro-phenyl)-piperidine Prepare by the method of Example 40.1 using 1-(3,4,5-trimethoxy-benzoyl)-3-[2-[4-[1H-benzoimidazole-2-carbonyl]-piperidin-1-yl]-ethyl]-3-(3,4-dichloro-phenyl)-piperidine to give the title compound.

EXAMPLE 52
1-(3-Isopropoxy-phenyl-acetyl)-3-[2-[4-[1-(2-ethoxy-ethyl)-1H-benzoimidazole-2-carbonyl]-piperidin-1-yl]-ethyl]-3-(3,4-dichloro-phenyl)-piperidine

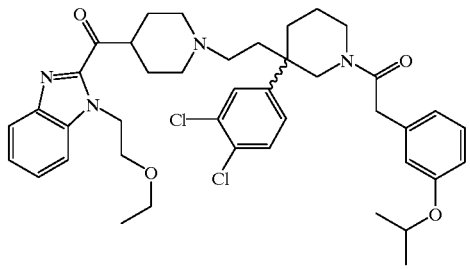

52.1 Synthesis of 1-(3-isopropoxy-phenyl-acetyl)-3-(3,4-dichloro-phenyl)-3-(2-hydroxy-ethyl)-piperidine Combine 3-(3,4-dichloro-phenyl)-3-(2-hydroxy-ethyl)-piperidine (0.81 g, 2.94 mmol), 1-ethyl-3-(3-dimethylaminopropyl)carbodiimide hydrochloride salt (0.51 g, 2.67 mmol), 1-hydroxybenzotriazole hydrate (0.36 g, 2.67 mmol) and 3-isopropoxy-phenyl-acetic acid (0.51 g, 2.67 mmol) in dichloromethane (50 mL). After 18 hours, extract the reaction mixture with 1M hydrochloric acid and with a saturated solution of sodium bicarbonate. Dry the organic layer over $Na_2SO_4$, filter, and concentrate in vacuo to give a residue. Chromatograph the residue on silica gel eluting with ethyl acetate to obtain the title compound: $R_f$=0.53 (silica gel, ethyl acetate).

52.2 Synthesis of 1-(3-isopropoxy-phenyl-acetyl)-3-(3,4-dichloro-phenyl)-(2-methanesulfonyl-ethyl)-piperidine Combine 1-(3-isopropoxy-phenyl-acetyl)-3-(3,4-dichloro-phenyl)-3-(2-hydroxy-ethyl)-piperidine (0.3 g, 0.668 mmol), diisopropylethylamine (0.26 mL, 1.51 mmol), and dichloromethane (10 mL). Cool using an salt-ice bath. Add dropwise methanesulfonyl chloride (0.11 g, 1.51 mmol) at such a rate that the reaction temperature does not rise above 0° C. After 2 hours, extract the reaction mixture twice with 1 M hydrochloric acid solution with saturated sodium bicarbonate solution. Dry the organic layer over $Na_2SO_4$, filter, and evaporate in vacuo to obtain the title compound.

52.3 Synthesis of 1-(3-isopropoxy-phenyl-acetyl)-3-[2-[4-[1H-benzoimidazole-2-carbonyl]-piperidin-1-yl]-ethyl]-3-(3,4-dichloro-phenyl)-piperidine Prepare by the method of Example 51.6 using 1-(3-isopropoxy-phenyl-acetyl)-(2-methanesulfonyl-ethyl)-piperidine and 4-(1H-benzoimidazole-2-carbonyl)-piperidine hydroiodide salt to give the title compound.

52.4 Synthesis of 1-(3-isopropoxy-phenyl-acetyl)-3-[2-[4-[1-(2-ethoxy-ethyl)-1H-benzoimidazole-2-carbonyl]-piperidin-1-yl]-ethyl]-3-(3,4-dichloro-phenyl)-piperidine Prepare by the method of Example 40.1 using 1-(3-isopropoxy-phenyl-acetyl)-3-[2-[4-[1H-benzoimidazole-2-carbonyl]-piperidin-1-yl]-ethyl]-3-(3,4-dichloro-phenyl)-piperidine to give the title compound.

PREPARATION 9
Synthesis of 3,4,5-trimethoxy-benzyl mesylate

Combine 3,4,5-trimethoxy-benzyl alcohol (9.0 g, 45.4 mmol), diisopropylethylamine (12.9 g, 100 mmol), and acetonitrile (60 mL). Cool in an ice bath. Add methanesulfonyl chloride (6.76 , 49.0 mmol). After 2 hours, partition the reaction mixture between water and ethyl acetate. Separate the layers and extract the organic layer with 1 M hydrochloric acid solution and them a saturated solution of sodium bicarbonate. Dry the organic layer over $Na_2SO_4$, filter, and evaporate in vacuo to give the title compound.

EXAMPLE 53
1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine

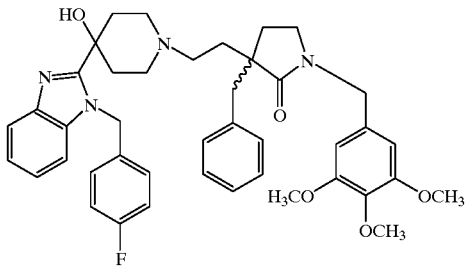

53.1 Synthesis of 1-(3,4,5-trimethoxy-benzyl)-2-oxo-pyrrolidine

Combine 2-pyrrolidinone (2.85 g, 33.5 mmol) and tetrahydrofuran (70 mL). Cool to −78° C. using a dry-ice/acetone bath. Add a solution of potassium bis-(trimethylsilyl)amide (67 mL, 0.5 M in toluene, 33.5 mmol). After 45 minutes, add a solution of 3,4,5-trimethoxy-benzyl mesylate (8.8 g, 32.02 mmol) in tetrahydrofuran (60 mL). After the addition of 3,4,5-trimethoxy-benzyl mesylate is complete, heat to reflux. After 18 hours, cool the reaction mixture and partition between water and ethyl acetate. Separate the aqueous layer and extract 4 times with ethyl acetate. Dry the combined organic layers over $Na_2SO_4$, filter, and concentrate in vacuo to obtain a residue. Chromatograph the residue on silica gel eluting with ethyl acetate to give the title compound: $R_f$=0.35 (silica gel, ethyl acetate).

53.2 Synthesis of 1-(3,4,5-trimethoxy-benzyl)-3-(phenylmethyl)-2-oxo-pyrrolidine Combine 1-(3,4,5-trimethoxy-benzyl)-2-oxo-pyrrolidine (1.0 g, 3.77 mmol) and tetrahydrofuran (5 mL). Cool to −78° C. using a dry-ice/acetone bath. Add a solution of lithium bis-(trimethylsilyl)amide (4.25 mL, 1 M in THF, 4.52 mmol). After 30 minutes, add a solution of benzyl bromide (0.77 g, 4.52 mmol) in tetrahydrofuran (1 mL). After the addition of benzyl bromide is complete, warm slowly to ambient temperature. After 15 minutes, add water and extract three times with dichloromethane. Dry the combined organic layers over $Na_2SO_4$, filter, and concentrate invacuo to obtain a residue. Chromatograph the residue on silica gel eluting with 1/1 ethyl acetate/hexane to give the title compound: $R_f$=0.69 (silica gel, 1/1 ethyl acetate/hexane).

53.3 Synthesis of 1-(3,4,5-trimethoxy-benzyl)-3-(phenylmethyl)-3-(2-t-butyldimethylsilyloxy-ethyl)-2-oxo-pyrrolidine Combine 1-(3,4,5-trimethoxy-benzyl)-3-(phenylmethyl)-2-oxo-pyrrolidine (1.0 g, 2.81 mmol) and tetrahydrofuran (10 mL). Cool to −78° C. using a dry-ice/acetone bath. Add a solution of lithium bis-(trimethylsilyl)amide (3.09 mL, 1 M in THF, 3.09 mmol). After 30 minutes, add a solution of 2-t-butyldimethylsilyloxy-ethyl bromide (0.74 g, 3.09 mmol) in tetrahydrofuran (1 mL). After the addition of 2-t-butyldimethylsilyloxy-ethyl bromide is complete, warm slowly to ambient temperature. After 2 hours, add water and extract three times with ethyl acetate. Dry the combined organic layers over $Na_2SO_4$, filter, and concentrate invacuo to obtain a residue. Chromatograph the residue on silica gel eluting with 1/3 ethyl acetate/hexane to give the title compound: $R_f$=0.58 (silica gel, 1/3 ethyl acetate/hexane).

53.4 Synthesis of 1-(3,4,5-trimethoxy-benzyl)-3-(phenylmethyl)-3-(2-hydroxy-ethyl)-2-oxo-pyrrolidine Combine 1-(3,4,5-trimethoxy-benzyl)-3-(phenylmethyl)-3-(2-t-butyldimethylsilyloxy-ethyl)-2-oxo-pyrrolidine (1.0 g, 1.95 mmol) and tetrahydrofuran (5 mL). Cool to 0° C. using a ice bath. Add a solution of tetrabutylammonium fluoride (3.90 mL, 1 M in THF, 3.90 mmol). After the addition is complete, warm to ambient temperature. After 1.5 hours, add aqueous 1 M hydrochloric acid solution (20 mL). Extract three times with ethyl acetate. Dry the combined organic layers over $Na_2So_4$, filter, and concentrate invacuo to obtain a residue. Chromatograph the residue on silica gel eluting with 1/1 ethyl acetate/hexane to give the title compound: $R_f$=0.27 (silica gel, 1/1 ethyl acetate/hexane).

53.5 Synthesis of 1-(3,4,5-trimethoxy-benzyl)-3-(phenylmethyl)-3-(2-methanesulfonyl-ethyl)-2-oxo-pyrrolidine Prepare by the method of Example 6.5.2 using 1-(3,4,5-trimethoxy-benzyl)-3-(phenylmethyl)-3-(2-hydroxy-ethyl)-2-oxo-pyrrolidine to give the title compound.

53.6 Synthesis of 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine Prepare by the method of Example 6.6.2 using 1-(3,4,5-trimethoxy-benzyl)-3-(phenylmethyl)-3-(2-methanesulfonyl-ethyl)-2-oxo-pyrrolidine and 4-[1-(4-fluoro-benzyl)-1H-benzoimidazol-2-yl]-4-hydroxy-piperidine to give the title compound: $R_f$=0.42 (silica gel, 30% methanol/ethyl acetate)

53.7 Synthesis of 1-(3,4,5-trimethoxy-benzyl)-3-[2-[4-[1-(4-fluoro-benzyl)-1H-benzoimidazol-2-yl]-1-4-hydroxy-piperidin-1-yl]-ethyl]-3-(phenylmethyl)-2-oxo-pyrrolidine methanesulfonate salt Combine 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine (0.19 g, 0.26 mmol) and ethyl acetate (5 mL). Add a solution of methanesulfonic acid (0.6 mmol) in ethyl acetate (1 mL). Heat to reflux. After 1 hour, cool to ambient temperature. After 12 hours, add diethyl ether (25 mL) to give a solid. Collect the solid by filtration and dry to give the title compound.

EXAMPLE 54

1-(3,4,5-Trimethoxy-benzvl)-3-[2-[4-[1-(4-fluoro-benzyl)-1H-benzoimidazol-2-yl]-4-hydroxy-piperidin-1-yl]-ethyl]-3-(3,4-dichloro-phenylmethyl)-2-oxo-pyrrolidine

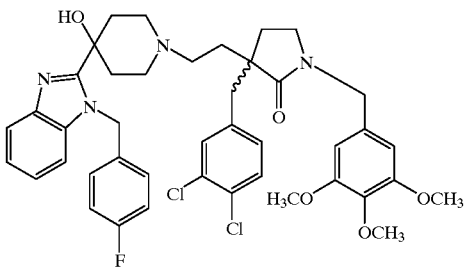

54.1 Synthesis of 1-(3,4,5-trimethoxy-benzyl)-3-(3,4-dichloro-phenylmethyl)-2-oxo-pyrrolidine Prepare by the method of Example 53.2 using 1-(3,4,5-trimethoxy-benzyl)-2-oxo-pyrrolidine and 3,4-dichlorobenzyl bromide to give the title compound: $R_f$=0.44 (silica gel,. 1/1 ethyl acetate/hexane).

54.2 Synthesis of 1-(3,4,5-trimethoxy-benzyl)-3-(3,4-dichloro-phenylmethyl)-3-(2-t-butyldimethylsilyloxy-ethyl)-2-oxo-pyrrolidine Prepare by the method of Example 53.3 using 1-(3,4,5-trimethoxy-benzyl)-3-(3,4-dichloro-phenylmethyl)-2-oxo-pyrrolidine to give the title compound: $R_f$=0.91 (silica gel, 1/1 ethyl acetate/hexane).

54.3 Synthesis of 1-(3,4.5-trimethoxy-benzyl)-3-(3,4-dichloro-phenylmethyl)-3-(2-hydroxy-ethyl)-2-oxo-pyrrolidine Prepare by the method of Example 53.4 using 1-(3,4,5-trimethoxy-benzyl)-3-(3,4-dichloro-phenylmethyl)-3-(2-t-butyldimethylsilyloxy-ethyl)-2-oxo-pyrrolidine to give the title compound: $R_f$=0.32 (silica gel, ethyl acetate).

54.4 Synthesis of 1-(3,4,5-trimethoxy-benzyl)-3-(3,4-dichloro-phenylmethyl)-3-(2-methanesulfonyl-ethyl)-2-oxo-pyrrolidine Prepare by the method of Example 6.5.2 using 1-(3,4,5-trimethoxy-benzyl)-3-(3,4-dichloro-phenylmethyl)-3-(2-hydroxy-ethyl)-2-oxo-pyrrolidine to give the title compound: $R_f$=0.87 (silica gel, ethyl acetate).

54.5 Synthesis of 1-(3,4,5-trimethoxy-benzvl)-3-[2-[4-[1-(4-fluoro-benzyl)-1H-benzoimidazol-2-yl]-4-hydroxv-piperidin-1-yl]-ethyl]-3-(3,4-dichloro-phenylmethyl)-2-oxo-pyrrolidine Prepare by the method of Example 6.6.2 using 1-(3,4,5-trimethoxy-benzyl)-3-(3,4-dichloro-phenylmethyl)-3-(2-methanesulfonyl-ethyl)-2-oxo-pyrrolidine and 4-[1-(4-fluoro-benzyl)-1H-benzoimidazol-2-yl]-4-hydroxy-piperidine to give the title compound: $R_f$=0.60 (silica gel, 10% methanol/ethyl acetate).

54.6 Synthesis of 1-(3,4,5-trimethoxy-benzyl)-3-[2-[4-[1-(4-fluoro-benzvl)-1H-benzoimidazol-2-yl]-4-hydroxy-piperidin-1-yl]-ethyl]-3-(3, 4-dichloro-phenylmethyl)-2-oxo-pyrrolidine methanesulfonate salt Prepare by the method of Example 53.7 using 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(3, 4-dichloro-phenylmethyl)-2-oxo-pyrrolidine to give the title compound.

EXAMPLE 55

1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(3,4-dimethoxy-phenylmethyl)-2-oxo-pyrrolidine

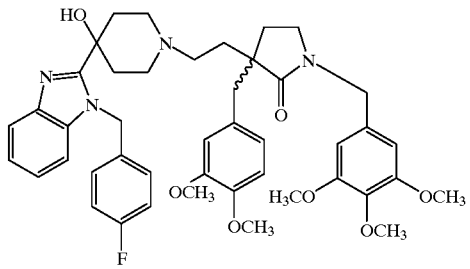
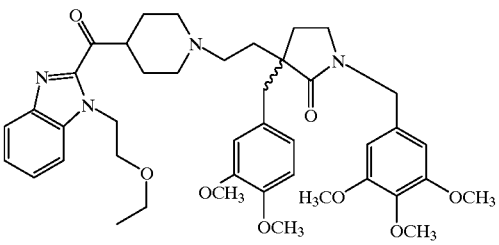

55.1 Synthesis of 1-(3,4,5-trimethoxy-benzyl)-3-(3,4-dimethoxy-phenylmethyl)-2-oxo-pyrrolidine Prepare by the method of Example 53.2 using 1-(3,4,5-trimethoxy-benzyl)-2-oxo-pyrrolidine and 3,4-dimethoxybenzyl bromide to give the title compound: $R_f$=0.34 (silica gel, 1/1 ethyl acetate/hexane).

55.2 Synthesis of 1-(3,4,5-trimethoxy-benzyl)-3-(3,4-dimethoxy-phenylmethyl)-3-(2-t-butyldimethylsilyloxy-ethyl)-2-oxo-pyrrolidine Prepare by the method of Example 53.3 using 1-(3,4,5-trimethoxy-benzyl)-3-(3,4-dimethoxy-phenylmethyl)-2-oxo-pyrrolidine to give the title compound: $R_f$=0.80 (silica gel, 1/1 ethyl acetate/hexane).

55.3 Synthesis of 1-(3,4,5-trimethoxy-benzyl)-3-(3,4-dimethoxy-phenylmethyl)-3-(2-hydroxy-ethyl)-2-oxo-pyrrolidine Prepare by the method of Example 53.4 using 1-(3,4,5-trimethoxy-benzyl)-3-(3,4-dimethoxy-phenylmethyl)-3-(2-t-butyldimethylsilyloxy-ethyl)-2-oxo-pyrrolidine to give the title compound: $R_f$=0.40 (silica gel, ethyl acetate).

55.4 Synthesis of 1-(3.4,5-trimethoxy-benzyl)-3-(3,4-dimethoxy-phenylmethyl)-3-(2-methanesulfonyl-ethyl)-2-oxo-pyrrolidine Prepare by the method of Example 6.5.2 using 1-(3,4,5-trimethoxy-benzyl)-3-(3,4-dimethoxy-phenylmethyl)-3-(2-hydroxy-ethyl)-2-oxo-pyrrolidine to give the title compound: $R_f$=0.85 (silica gel, ethyl acetate).

55.5 Synthesis of 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(3,4-dimethoxy-phenylmethyl)-2-oxo-pyrrolidine Prepare by the method of Example 6.6.2 using 1-(3,4,5-trimethoxy-benzyl)-3-(3,4-dimethoxy-phenylmethyl)-3-(2-methanesulfonyl-ethyl)-2-oxo-pyrrolidine and 4-[1-(4-fluoro-benzyl)-1H-benzoimidazol-2-yl]-4-hydroxy-piperidine to give the title compound: $R_f$=0.58 (silica gel, 10% methanol/ethyl acetate).

55.6 Synthesis of 1-(3.4,5-trimethoxy-benzyl)-3-[2-[4-[1-(4-fluoro-benzyl)-1H-benzoimidazol-2-yl]-4-hydroxy-piperidin-1-yl]-ethyl]-3-(3,4-dimethoxy-phenylmethyl)-2-oxo-pyrrolidine methanesulfonate salt Prepare by the method of Example 53.7 to give the title compound.

EXAMPLE 56

1-(3,4,5-Trimethoxy-benzyl)-3-[2-[4-[1-(2-ethoxy-ethyl)-1H-benzoimidazole-2-carbonyl]-piperidin-1-yl]-ethyl]-3-(3,4-dimethoxy-phenylmethyl)-2-oxo-pyrrolidine 56.1 Synthesis of 1-(3,4,5-trimethoxy-benzyl)-3-[2-[4-[1H-benzoimidazole-2-carbonyl]-piperidin-1-yl]-ethyl]-3-(3,4-dimethoxy-phenylmethyl)-2-oxo-pyrrolidine Prepare by the method of Example 6.6.2 using 1-(3,4,5-trimethoxy-benzoyl)-3-(3,4-dimethoxy-phenylmethyl)-3-(2-methanesulfonyl-ethyl)-pyrrolidine and 4-(1H-benzoimidazole-2-carbonyl)-piperidine hydroiodide salt to give the title compound.

56.2 Synthesis of 1-(3,4,5-trimethoxy-benzyl)-3-[2-[4-[1-(2-ethoxy-ethyl)-1H-benzoimidazole-2-carbonyl]-piperidin-1-yl]-ethyl]-3-(3,4-dimethoxy-phenylmethyl)-2-oxo-pyrrolidine Prepare by the method of Example 40.1 using 1-(3,4,5-trimethoxy-benzoyl-3-[2-[4-[1H-benzoimidazole-2-carbonyl]-piperidin-1-yl]-ethyl]-3-(3,4-dimethoxy-phenylmethyl)-2-oxo-pyrrolidine to give the title compound.

56.3 Synthesis of 1-(3,4,5-Trimethoxy-benzyl)-3-[2-[4-[1-(2-ethoxy-ethyl)-1H-benzoimidazole-2-carbonyl]-piperidin-1-yl]-ethyl]-3-(3,4-dimethoxy-phenylmethyl)-2-oxo-pyrrolidine methanesulfonate salt Prepare by the method of Example 53.7 using 1-(3,4,5-trimethoxy-benzyl)-3-[2-[4-[1-(2-ethoxy-ethyl)-1H-benzoimidazole-2-carbonyl]-piperidin-1-yl]-ethyl]-3-(3,4-dimethoxy-phenylmethyl)-2-oxo-pyrrolidine and methanesulfonic acid to give the title compound.

EXAMPLE 57

1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(4-fluoro-phenylmethyl)-2-oxo-pyrrolidine

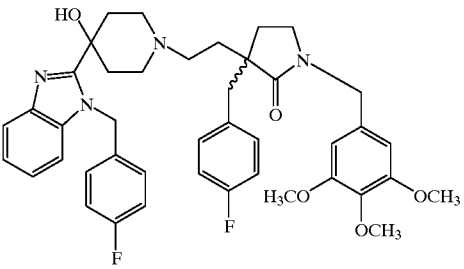

57.1 Synthesis of 1-(3,4,5-trimethoxy-benzyl)-3-(4-fluoro-phenylmethyl)-2-oxo-pyrrolidine Prepare by the method of Example 53.2 using 1-(3,4,5-trimethoxy-benzyl)-2-oxo-pyrrolidine and 4-fluorobenzyl bromide to give the title compound: $R_f$=0.58 (silica gel, 1/1 ethyl acetate/hexane).

57.2 Synthesis of 1-(3.4,5-trimethoxy-benzyl)-3-(4-fluoro-phenylmethyl)-3-(2-t-butyldimethylsilyloxy-ethyl)-2-oxo-pyrrolidine Prepare by the method of Example 53.3 using 1-(3,4,5-trimethoxy-benzyl)-3-(4-fluoro-phenylmethyl)-2-oxopyrrolidine to give the title compound: $R_f$=0.89 (silica gel, 1/1 ethyl acetate/hexane).

57.3 Synthesis of 1-(3,4,5-trimethoxy-benzyl)-3-(4-fluoro-phenylmethyl)-3-(2-hydroxy-ethyl)-2-oxo-pyrrolidine Prepare by the method of Example 53.4 using 1-(3,4,5-trimethoxy-benzyl)-3-(4-fluoro-phenylmethyl)-3-(2-t-butyldimethylsilyloxy-ethyl)-2-oxo-pyrrolidine to give the title compound: $R_f$=0.22 (silica gel, ethyl acetate)

57.4 Synthesis of 1-(3,4,5-trimethoxy-benzyl)-3-(4-fluoro-phenylmethyl)-3-(2-methanesulfonyl-ethyl)-2-oxo-pyrrolidine Prepare by the method of Example 6.5.2 using 1-(3,4,5-trimethoxy-benzyl)-3-(4-fluoro-phenylmethyl)-3-(2-hydroxy-ethyl)-2-oxo-pyrrolidine to give the title compound: $R_f$=0.92 (silica gel, ethyl acetate).

57.5 Synthesis of 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(4-fluoro-phenylmethyl)-2-oxo-pyrrolidine Prepare by the method of Example 6.6.2 using 1-(3,4,5-trimethoxy-benzyl)-3-(4-fluoro-phenylmethyl)-3-(2-methanesulfonyl-ethyl)-2-oxo-pyrrolidine and 4-[1-(4-fluoro-benzyl)-1H-benzoimidazol-2-yl]-4-hydroxy-piperidine to give the title compound: $R_f$=0.38 (silica gel, 30% methanol/ethyl acetate).

57.6 Synthesis of 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(4-fluoro-phenylmethyl)-2-oxo-pyrrolidine methanesulfonate salt Prepare by the method of Example 53.7 using 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(4-fluoro-phenylmethyl)-2-oxo-pyrrolidine to give the title compound.

EXAMPLE 58
1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(2,4-difluoro-phenylmethyl)-2-oxo-pyrrolidine

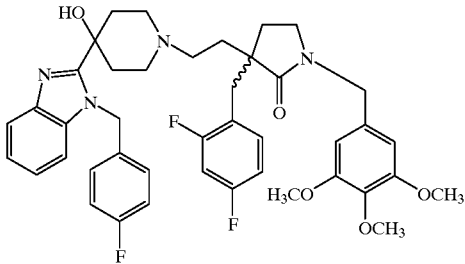

58.1 Synthesis of 1-(3,4,5-trimethoxy-benzyl)-3-(2,4-difluoro-phenylmethyl)-2-oxo-pyrrolidine Prepare by the method of Example 53.2 using 1-(3,4,5-trimethoxy-benzyl)-2-oxo-pyrrolidine and 2,4-difluorobenzyl bromide to give the title compound: $R_f$=0.30 (silica gel, 1/1 ethyl acetate/hexane).

58.2 Synthesis of 1-(3,4,5-trimethoxy-benzyl)-3-(2,4-difluoro-phenylmethyl)-3-(2-t-butyldimethylsilyloxy-ethyl)-2-oxo-pyrrolidine Prepare by the method of Example 53.3 using 1-(3,4,5-trimethoxy-benzyl)-3-(2,4-difluoro-phenylmethyl)-2-oxo-pyrrolidine to give the title compound: $R_f$=0.89 (silica gel, 1/1 ethyl acetate/hexane).

58.3 Synthesis of 1-(3,4,5-trimethoxy-benzyl)-3-(2,4-difluoro-phenylmethyl)-3-(2-hydroxy-ethyl)-2-oxo-pyrrolidine Combine 1-(3,4,5-trimethoxy-benzyl)-3-(2,4-difluoro-phenylmethyl)-3-(2-t-butyldimethylsilyloxy-ethyl)-2-oxo-pyrrolidine (0.59 g, 1.08 mmol) and ammonium fluoride (0.24 g, 6.48 mmol) in methanol (10 mL). Heat to reflux. After 2 hours, cool to ambient temperature and pour the reaction mixture into a saturated sodium chloride solution (30 mL). Extract five times with dichloromethane. Dry the combined organic layers over $Na_2SO_4$, filter, and concentrate in vacuo to give a residue. Chromatograph the residue on silica gel eluting with ethyl acetate to give the title compound: $R_f$=0.55 (silica gel, ethyl acetate)

58.4 Synthesis of 1-(3,4,5-trimethoxy-benzyl)-3-(2,4-difluoro-phenylmethyl)-3-(2-methanesulfonyl-ethyl)-2-oxo-pyrrolidine Prepare by the method of Example 6.5.2 using 1-(3,4,5-trimethoxy-benzyl)-3-(2,4-difluoro-phenylmethyl)-3-(2-hydroxy-ethyl)-2-oxo-pyrrolidine to give the title compound: $R_f$=0.91 (silica gel, ethyl acetate).

58.5 Synthesis of 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(2,4-difluoro-phenylmethyl)-2-oxo-pyrrolidine Prepare by the method of Example 6.6.2 using 1-(3,4,5-trimethoxy-benzyl)-3-(2,4-difluoro-phenylmethyl)-3-(2-methanesulfonyl-ethyl)- 2-oxo-pyrrolidine and 4-[1-(4-fluoro-benzyl)-1H-benzoimidazol-2-yl]-4-hydroxy-piperidine to give the title compound: $R_f$=0.38 (silica gel, 20% methanol/ethyl acetate).

58.6 Synthesis of 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(2,4-difluoro-phenylmethyl)-2-oxo-pyrrolidine methanesulfonate salt Prepare by the method of Example 53.7 using 1-(3,4,5-trimethoxy-benzyl)-3-[2-[4-[1-(4-fluoro-benzyl)-1H-benzoimidazol-2-yl]-4-hydroxy-piperidin-1-yl]-ethyl]-3-(2,4-difluoro-phenylmethyl)-2-oxo-pyrrolidine and methanesulfonic acid to give the title compound.

EXAMPLE 59
1-Benzyl-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine

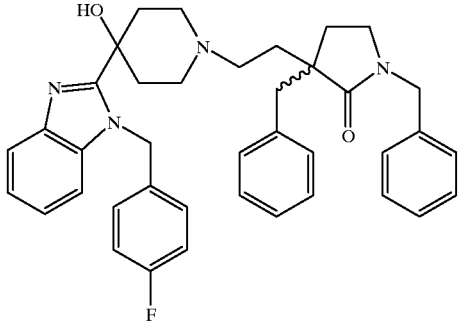

59.1 Synthesis of 1-benzyl-3-(Phenylmethyl)-2-oxo-pyrrolidine

Prepare by the method of Example 53.2 using 1-benzyl-2-oxo-pyrrolidine and benzyl bromide to give the title compound: $R_f$=0.46 (silica gel, 1/1 ethyl acetate/hexane).

59.2 Synthesis of 1-benzyl-3-(phenylmethyl)-3-(2-t-butyldimethylsilyloxy-ethyl)-2-oxo-pyrrolidine Prepare by the method of Example 53.3 using 1-benzyl-3-(phenylmethyl)-2-oxo-pyrrolidine to give the title compound: $R_f$=0.35 (silica gel, 1/4 ethyl acetate/hexane).

59.3 Synthesis of 1-benzyl-3-(phenylmethyl)-3-(2-hydroxy-ethyl)-2-oxo-pyrrolidine Prepare by the method of Example 53.4 using 1-benzyl-3-(phenylmethyl)-3-(2-t-butyldimethylsilyloxy-ethyl)-2-oxo-pyrrolidine to give the title compound: Rf=0.40 (silica gel, ethyl acetate).

59.4 Synthesis of 1-benzyl-3-(phenylmethyl)-3-(2-methanesulfonyl-ethyl)-2-oxo-pyrrolidine Prepare by the method of Example 6.5.2 using 1-benzyl-3-(phenylmethyl)-3-(2-hydroxy-ethyl)-2-oxo-pyrrolidine to give the title compound: $R_f$=0.68 (silica gel, ethyl acetate).

59.5 Synthesis of 1-benzyl-3-[2-[4-[1-(4-fluoro-benzyl)-1H-benzoimidazol-2-yl]-4-hydroxy-piperidin-1-yl1-ethyl]-3-(phenylmethyl)-2-oxo-pyrrolidine Prepare by the method of Example 6.6.2 using 1-benzyl-3-(phenylmethyl)-3-(2-methanesulfonyl-ethyl)-2-oxo-pyrrolidine and 4-[1-(4-fluoro-benzyl)-1H-benzoimidazol-2-yl]-4-hydroxy-piperidine to give the title compound: $R_f$=0.31 (silica gel, 30% methanol/ethyl acetate).

59.6 Synthesis of 1-benzyl-3-[2-[4-[1-(4-fluoro-benzyl)-1H-benzoimidazol-2-yl]-4-hydroxy-piperidin-1-yl]-ethyl-3-(phenylmethyl)-2-oxo-pyrrolidine methanesulfonate salt Prepare by the method of Example 53.7 using 1-benzyl-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine to give the title compound. Elemental Analysis calculated for $C_{39}H_{41}FN_4O_2 \cdot 2\ H_4CO_3S \cdot 1.07\ H_2O$: C 59.46; H 6.22; N 6.76; Found: C 59.22; H 6.11; N 6.76.

EXAMPLE 60

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(phenylmethyl)-pyrrolidine

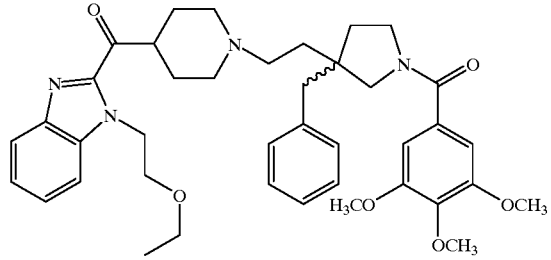

60.1 Synthesis of 1-benzyl-3-(phenylmethyl)-3-(2-hydroxy-ethyl)-pyrrolidine

Combine 1-benzyl-3-(phenylmethyl)-3-(2-t-butyldimethylsilyloxy-ethyl)-2-oxo-pyrrolidine (1.19 g, 2.81 mmol) and tetrahydrofuran (20 mL). Cool in an ice bath. Add dropwise a solution of lithium aluminum hydride (2.81 mL, 1 M in THF, 2.81 mmol). After the addition is complete, warm to ambient temperature. After 2 hours, heat to reflux. After 1 hour, cool to ambient temperature and add water (0.11 mL), a solution of 1 M sodium hydroxide (2.67 mL), and water (0.32 mL). Stir vigorously. After 2 hours, filter through celite, rinse with dichloromethane. Dry the filtrate over $Na_2SO_4$, filter, and concentrate in vacuo to give a residue. Chromatograph the residue on silica gel eluting with ethyl acetate to give the title compound: Rf=0.30 (silica gel, ethyl acetate).

60.2 Synthesis of 3-(phenylmethyl)-3-(2-hydroxy-ethyl)-pyrrolidine

Combine 1-benzyl-3-(phenylmethyl)-3-(2-hydroxy-ethyl)-pyrrolidine (0.72 g, 2.45 mmol) and methanol (20 mL). Add 20% palladium hydroxide-on-carbon (0.231 g). Hydrogenate in a Parr apparatus at an initial pressure of 50 psi. After 24 hours, filter through celite, rinse with methanol. Evaporate the filtrate invacuo to give the title compound: $R_f$=0.11 (silica gel, 20% ethyl acetate/methanol).

60.3 Synthesis of 1-(3,4,5-trimethoxy-benzoyl)-3-(phenylmethyl)-3-(2-hydroxy-ethyl)-pyrrolidine Prepare by the method of Example 51.5 using 3-(phenylmethyl)-3-(2-hydroxy-ethyl)-pyrrolidine to give the title compound: $R_f$=0.09 (silica gel, ethyl acetate).

60.4 Synthesis of 1-(3,4,5-trimethoxy-benzoyl)-3-(phenylmethyl)-3-(2-methanesulfonyl-ethyl)-pyrrolidine Prepare by the method of Example 6.5.2 using 1-(3,4,5-trimethoxy-benzoyl)-3-(phenylmethyl)-3-(2-hydroxy-ethyl)-pyrrolidine to give the title compound: $R_f$=0.74 (silica gel, ethyl acetate).

60.5 Synthesis of 1-(3,4,5-trimethoxy-benzoyl-3-[2-[4-[1H-benzoimidazole-2-carbonyl]-piperidin-1-yl]-ethyl]-3-(phenylmethyl)-pyrrolidine Prepare by the method of Example 6.6.2 using 1-(3,4,5-trimethoxy-benzoyl)-3-(phenylmethyl)-3-(2-methanesulfonyl-ethyl)-pyrrolidine and 4-(1H-benzoimidazole-2-carbonyl)-piperidine hydroiodide salt to give the title compound.

60.6 Synthesis of 1-(3,4,5-trimethoxy-benzoyl)-3-[2-[4-[-(2-ethoxy-ethyl)-1H-benzoimidazole-2-carbonyl]-piperidin-1-yl]-ethyl]-3-(phenylmethyl)-pyrrolidine Prepare by the method of Example 40.1 using 1-(3,4,5-trimethoxy-benzoyl-3-[2-[4-[1H-benzoimidazole-2-carbonyl]-piperidin-1-yl]-ethyl]-3-(phenylmethyl)-pyrrolidine to give the title compound.

EXAMPLE 61

1-(3,4,5-Trimethoxy-benzyl)-3-[2-[4-[1-(2-ethoxy-ethyl)-1H-benzoimidazole-2-carbonyl]-piperidin-1-yl]-ethyl]-3-phenyl-2-oxo-pyrrolidine

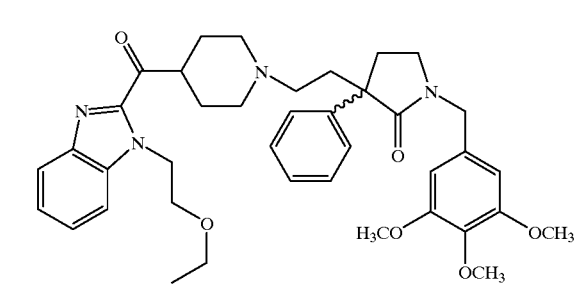

61.1 Synthesis of methyl 3-cyano-2-phenyl-propionate

Combine methyl phenylacetate (2.0 g, 13.32 mmol) and tetrahydrofuran (15 mL). Cool in a dry-ice/acetone bath. Add dropwise a solution of lithium diisopropylamide (6.66 mL, 52 M in THF, 13.32 mmol). After 1 hour, add α-bromoacetonitrile (1.6 g, 13.32 mmol). After 2 hours, warm the reaction mixture to ambient temperature and partition the reaction mixture between ethyl acetate and water. Separate the aqueous layer and extract three times with ethyl acetate. Dry the combined organic layers over Na₂SO₄, filter, and concentrate in vacuo to obtain a residue. Distill the residue bulb-to-bulb to give the title compound: bp; 150° C. at 0.5 mm Hg; R$_f$=0.72 (silica gel, 25% ethyl acetate/hexane)

61.2 Synthesis of 3-phenyl-2-oxo-pyrrolidine

Prepare by the method of Example 6.2.2 using methyl 3-cyano-2-phenyl-propionate to give the title compound R$_f$=0.20 (silica gel, ethyl acetate).

61.3 Synthesis of 1-(3,4,5-trimethoxy-benzyl)-3-phenyl-2-oxo-pyrrolidine

Prepare by the method of Example 53.1 using 3-phenyl-2-oxo-pyrrolidine to give the title compound R$_f$=0.24 (silica gel, 1/1 ethyl acetate/hexane).

61.4 Synthesis of 1-(3,4,5-trimethoxy-benzyl)-3-(2-t-butyldimethylsilyloxy-ethyl)-3-phenyl-2-oxo-pyrrolidine Prepare by the method of Example 53.3 using 1-(3,4,5-trimethoxy-benzyl)-3-phenyl-2-oxo-pyrrolidine to give the title compound: R$_f$=0.66 (silica gel, 1/1 ethyl acetate/hexane).

61.5 Synthesis of 1-(3,4,5-trimethoxy-benzyl)-3-(2-hydroxy-ethyl)-3-phenyl-2-oxo-pyrrolidine Prepare by the method of Example 58.3 using 1-(3,4,5-trimethoxy-benzyl)-3-(2-t-butyldimethylsilyloxy-ethyl)-3-phenyl-2-oxo-pyrrolidine to give the title compound: R$_f$=0.55 (silica gel, ethyl acetate).

61.6 Synthesis of 1-(3,4,5-trimethoxy-benzyl)-3-(2-methanesulfonyl-ethyl)-3-phenyl-2-oxo-pyrrolidine Prepare by the method of Example 6.5.2 using 1-(3,4,5-trimethoxy-benzyl)-3-(2-hydroxy-ethyl)-3-phenyl-2-oxo-pyrrolidine to give the title compound: R$_f$=0.74 (silica gel, ethyl acetate).

61.7 Synthesis of 1-(3,4,5-trimethoxy-benzyl)-3-[2-[4-[1H-benzoimidazole-2-carbonyl]-piperidin-1-yl]-ethyl]-3-phenyl-2-oxo-pyrrolidine Prepare by the method of Example 6.6.2 using 1-(3,4,5-trimethoxy-benzyl)-3-(2-methanesulfonyl-ethyl)-3-phenyl-2-oxo-pyrrolidine and 4-(1H-benzoimidazole-2-carbonyl)-piperidine hydroiodide salt to give the title compound.

61.8 Synthesis of 1-(3,4,5-trimethoxy-benzyl)-3-[2-[4-[1-(2-ethoxy-ethyl)-1H-benzoimidazole-2-carbonyl]-piperidin-1-yl]-ethyl]-3-phenyl-2-oxo-pyrrolidine Prepare by the method of Example 40.1 using 1-(3,4,5-trimethoxy-benzyl)-3-[2-[4-[1H-benzoimidazole-2-carbonyl]-piperidin-1-yl]-ethyl]-3-phenyl-2-oxo-pyrrolidine to give the title compound.

EXAMPLE 62

1-Benzyl-3-[2-[4-[1-(4-fluoro-benzyl)-1H-benzoimidazol-2-yl]-4-hydroxy-piperidin-1-yl]-ethyl]-3-(phenylmethyl)-2-oxo-piperidine

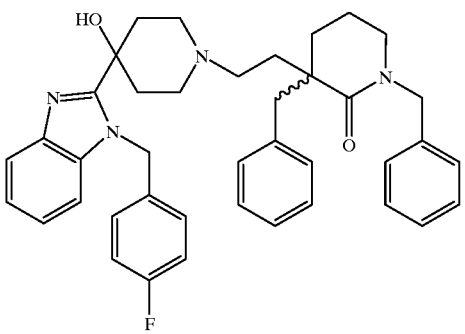

62.1 Synthesis of 1-benzyl-2-oxo-piperidine

Prepare by the method of Example 53.1 using 2-piperidinone and benzyl bromide to give the title compound: R$_f$=0.77 (silica gel, 1/1 ethyl acetate/hexane).

62.2 Synthesis of 1-benzyl-3-(phenylmethyl)-2-oxo-piperidine

Prepare by the method of Example 53.2 using 1-benzyl-2-oxo-piperidine to give the title compound: R$_f$=0.55 (silica gel, 25% ethyl acetate/hexane).

62.3 Synthesis of 1-benzyl-3-(phenylmethyl)-3-(2-t-butyldimethylsilyloxy-ethyl)-2-oxo-piperidine Prepare by the method of Example 53.3 using 1-benzyl-3-(phenylmethyl)-2-oxo-piperidine to give the title compound: R$_f$=0.92 (silica gel, 1/1 ethyl acetate/hexane).

62.4 Synthesis of 1-benzyl-3-(phenylmethyl)-3-(2-hydroxy-ethyl)-2-oxo-piperidine Prepare by the method of Example 53.4 using 1-benzyl-3-(phenylmethyl)-3-(2-t-butyldimethylsilyloxy-ethyl)-2-oxo-piperidine to give the title compound: R$_f$=0.24 (silica gel, ethyl acetate).

62.5 Synthesis of 1-benzyl-3-(phenylmethyl)-3-(2-methanesulfonyl-ethyl)-2-oxo-piperidine Prepare by the method of Example 6.5.2 using 1-benzyl-3-(phenylmethyl)-3-(2-hydroxy-ethyl)-2-oxo-piperidine to give the title compound: R$_f$=0.77 (silica gel, ethyl acetate).

62.6 Synthesis of 1-benzyl-3-[2-[4-[1-(4-fluoro-benzyl)-1H-benzoimidazol-2-yl]-4-hydroxy-piperidin-1-yl]-ethyl]-3-(phenylmethyl)-2-oxo-piperidine Prepare by the method of Example 6.6.2 using 1-benzyl-3-(phenylmethyl)-3-(2-methanesulfonyl-ethyl)-2-oxo-piperidine and 4-[1-(4-fluoro-benzyl)-1H-benzoimidazol-2-yl]-4-hydroxy-piperidine to give the title compound: R$_f$=0.66 (silica gel, 10% methanol/ethyl acetate).

EXAMPLE 63

1-(3-Isopropoxy-phenyl-acetyl)-3-[2-[4-[1-(4-fluoro-benzyl)-1H-benzoimidazole-2-carbonyl]-piperidin-1-yl]-ethyl]-3-(3,4-dichloro-phenyl)-piperidine

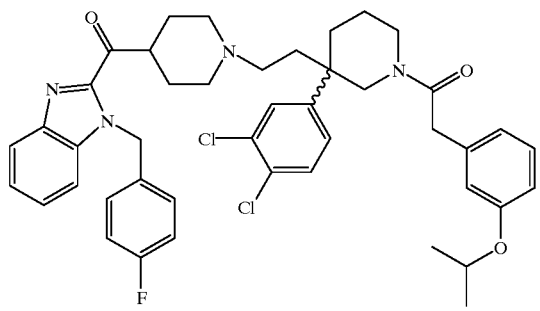

63.1 Synthesis of 1-(3-isopropoxy-phenyl-acetyl)-3-[2-[4-[1-(4-fluoro-benzyl)-1H-benzoimidazole-2-carbonyl]-piperidin-1-yl]-ethyl]-3-(3,4-dichloro-phenyl)-piperidine Prepare by the method of Example 6.6.2 using 1-(3-isopropoxy-phenyl-acetyl)-3-(3,4-dichloro-phenyl)-(2-methanesulfonyl-ethyl)-piperidine and 4-[1-(4-fluoro-benzyl)-1H-benzoimidazole-2-carbonyl]-piperidine to give the title compound: $R_f$=0.28 (silica gel, 20/1 ethyl acetate/methanol); mp; 70.0–73.0° C.

PREPARATION 10

Synthesis of 4-(ethyl acetoxy)-3,5-dimethoxybenzoic acid

Combine 4-hydroxy-3,5-dimethoxybenzoic acid (2.0 g, 12.6 mmol) and dichloromethane (200 mL). Add diphenyl diazomethane (2.67 g). After 1 hour, add an additional portion of diphenyl diazomethane (1.2 g). After 1 hour, add 4-hydroxy-3,5-dimethoxybenzoic acid (0.5 g). Concentrate in vacuo to obtain a residue. Chromatograph the residue on silica gel eluting sequentially with 20% ethyl acetate/hexane and 50% ethyl acetate/hexane to obtain the diphenylmethyl 4-hydroxy-3,5-dimethoxybenzoate: $R_f$=0.56 (silica gel, 50% ethyl acetate/hexane).

Combine diphenylmethyl 4-hydroxy-3,5-dimethoxybenzoate (12.6 mmol) and dimethylformamide (50 mL). Cool in an ice-bath. Add sodium hydride (0.52 g, 60% in oil). After 2 hours, add dimethylformamide (50 mL). Add ethyl bromoacetate (4 mL, 36 mmol). After 2 hours, partition the reaction mixture between diethyl ether and saturated aqueous ammonium chloride solution, separate the organic layer and extract with water. Dry the organic layer over $MgSO_4$, filter, and evaporate invacuo to obtain a residue. Recrystallize the residue from ethyl acetate/hexane to give diphenylmethyl 4-ethyl acetoxy-3,5-dimethoxybenzoate: $R_f$=0.22 (silica gel, 20% ethyl acetate/hexane).

Combine diphenylmethyl 4-(ethyl acetoxy)-3,5-dimethoxybenzoate (4.3 g, 9.56 mmol), 5% palladium-on-carbon (0.5 g), and ethanol/ethyl acetate/dichloromethane (200 mL/15 mL/15 mL). Hydrogenate at an initial pressure of 55 psi in a Parr apparatus. After 16 hours, filter and concentrate the filtrate to give a residue. Recrystallize the residue from diethyl ether/hexane to give the title compound: $R_f$=0.35 (silica gel, 6% methanol/dichloromethane).

PREPARATION 11

Synthesis of 4-[1-(2-Ethoxy-ethyl)-1H-benzoimidazole-2-carbonyl]-piperidine

Prepare by the method of Preparation 6 using 1-(t-butoxycarbonyl)-4-(1H-benzoimidazole-2-carbonyl)-piperidine and 2-chloroethyl ethyl ether to give the title compound.

EXAMPLE 64

1-(4-Ethyl acetoxy-3,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine

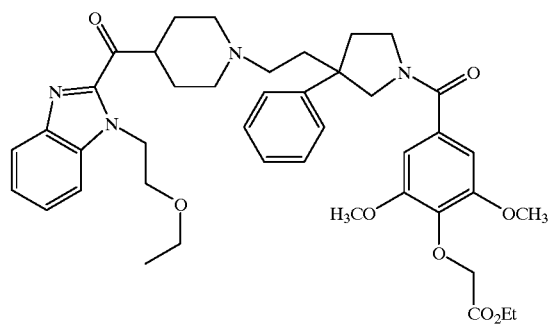

64.1 Synthesis of 1-(4-ethyl acetoxy-3,5-dimethoxy-benzoyl)-3-phenyl-3-(2-hydroxy-ethyl)-pyrrolidine Prepare by the method of Example 52.1 using 4-(ethyl acetoxy)-3,5-dimethoxybenzoic acid and 3-phenyl-3-(2-hydroxy-ethyl)-pyrrolidine to give the title compound.

64.2 Synthesis of 1-(4-ethyl acetoxy-3,5-dimethoxy-benzoyl)-3-phenyl-3-(2-methanesulfonyl-ethyl)-pyrrolidine Prepare by the method of Example 6.5.2 using 1-(4-ethyl acetoxy-3,5-dimethoxy-benzoyl)-3-phenyl-3-(2-hydroxy-ethyl)-pyrrolidine to give the title compound.

64.3 Synthesis of 1-(4-ethyl acetoxy-3,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine Prepare by the method of Example 6.6.2 using 1-(4-ethyl acetoxy-3,5-dimethoxy-benzoyl)-3-phenyl-3-(2-methanesulfonyl-ethyl)-pyrrolidine and 4-[1-(2-ethoxy-ethyl)-1H-benzoimidazole-2-carbonyl]-piperidine to give the title compound.

EXAMPLE 65

1-(4-Acetoxy-3,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine

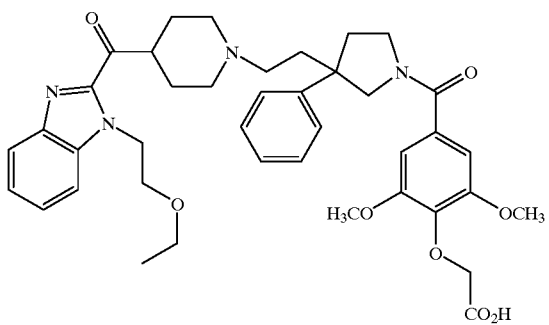

65.1 Synthesis of 1-(4-acetoxy-3,5-dimethoxy-benzoyl)-3-phenyl-3-(2-hydroxy-ethyl)-pyrrolidine Prepare by the method of Example 39.1 using 1-(4-ethyl acetoxy-3,5-dimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine to give the title compound.

EXAMPLE 66

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-dimethyl-phenyl)-pyrrolidine

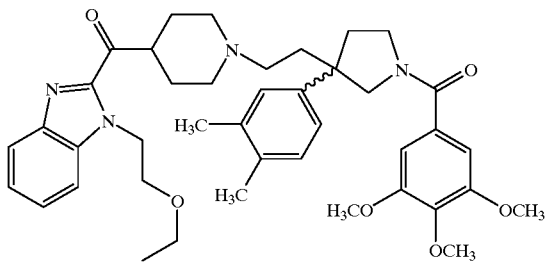

66.1 Synthesis of 3-cyano-3-(3,4-dimethyl-phenyl)-pentanedioic acid diethyl ester Prepare by the method of Example 11.1.2 using 3,4-dimethylphenylacetonitrile to give the title compound. Elemental Analysis calculated for $C_{18}H_{23}NO_4$: C 68.12; H 7.30; N 4.41; Found: C 68.11; H 7.24; N 5.18.

66.2 Synthesis of 3-(3,4-dimethyl-phenyl)-5-oxo-pyrrolidin-3-yl]-acetic acid ethyl ester Prepare by the method of Example 6.2.2 using 3-cyano-3-(3,4-dimethyl-phenyl)-pentanedioic acid diethyl ester to give the title compound.

66.3 Synthesis of 3-(3,4-dimethyl-phenyl)-3-(2-hydroxy-ethyl)-pyrrolidine

Prepare by the method of Example 6.3 using 3-(3,4-dimethyl-phenyl)-5-oxo-pyrrolidin-3-yl]-acetic acid ethyl ester to give the title compound: $R_f$=0.35 (silica gel, 85/10/5 dichloromethane/methanol/acetic acid).

66.4 Synthesis of 1-(3,4,5-trimethoxy-benzoyl)-[3-(3,4-dimethyl-phenyl)-3-(2-hydroxy-ethyl)-pyrrolidine Prepare by the method of Example 49.4 using 3-(3,4-dimethyl-phenyl)-3-(2-hydroxy-ethyl)-pyrrolidine to give the title compound: $R_f$=0.25 (silica gel, 6% methanol/dichloromethane).

66.5 Synthesis of 1-(3,4,5-trimethoxy-benzoyl)-3-(3,4-dimethyl-phenyl)-3-(2-methanesulfonyl-ethyl)-pyrrolidine Prepare by the method of Example 6.5.2 using 1-(3,4,5-trimethoxy-benzoyl)-3-(3,4-dimethyl-phenyl)-3-(2-hydroxy-ethyl)-pyrrolidine to give the title compound: $R_f$=0.44 (silica gel, ethyl acetate).

66.6 Synthesis of (3,4,5-trimethoxy-benzoyl)-3-[2-[4-[1-(2-ethoxy-ethyl)-1H-benzoimidazole-2-carbonyl]-piperidin-1-yl]-ethyl]-3-(3,4-dimethyl-phenyl)-pyrrolidine Prepare by the method of Example 6.6.2 using 1-(3,4,5-trimethoxy-benzoyl)-3-(3,4-dimethyl-phenyl)-3-(2-methanesulfonyl-ethyl)-pyrrolidine and 4-[1-(2-ethoxy-ethyl)-1H-benzoimidazole-2-carbonyl]-piperidine to give the title compound.

EXAMPLE 67

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(4-fluoro-phenyl)-pyrrolidine

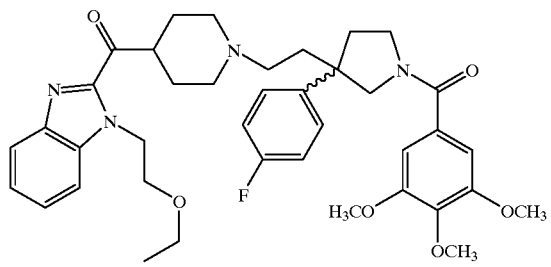

67.1 Synthesis of 3-cyano-3-(4-fluoro-phenyl)-pentanedioic acid diethyl ester

Prepare by the method of Example 11.1.2 using 4-fluorophenylacetonitrile to give the title compound.

67.2 Synthesis of 3-(4-fluoro-phenyl)-5-oxo-pyrrolidin-3-yl]-acetic acid ethyl ester Prepare by the method of Example 6.2.2 using 3-cyano-3-(4-fluoro-phenyl)-pentanedioic acid diethyl ester to give the title compound.

67.3 Synthesis of 3-(4-fluoro-phenyl)-3-(2-hydroxy-ethyl)-pyrrolidine

Prepare by the method of Example 6.3 using 3-(4-fluoro-phenyl))-5-oxo-pyrrolidin-3-yl]-acetic acid ethyl ester to give the title compound: $R_f$=0.10 (silica gel, 90/10/10 dichloromethane/methanol/acetic acid).

67.4 Synthesis of 1-(3,4,5-trimethoxy-benzoyl)-[3-(4-fluoro-phenyl)-3-(2-hydroxy-ethyl)-pyrrolidine Prepare by the method of Example 49.4 using 3-(4-fluoro-phenyl)-3-(2-hydroxy-ethyl)-pyrrolidine to give the title compound: $R_f$=0.41 (silica gel, 6% methanol/dichloromethane).

67.5 Synthesis of 1-(3,4,5-trimethoxy-benzoyl)-3-(3-(4-fluoro-phenyl)-3-(2-methanesulfonyl-ethyl)-pyrrolidine Prepare by the method of Example 6.5.2 using 1-(3,4,5-trimethoxy-benzoyl)-3-(4-fluoro-phenyl)-3-(2-hydroxy-ethyl)-pyrrolidine to give the title compound: $R_f$=0.31 (silica gel, ethyl acetate).

67.6 Synthesis of (3,4,5-trimethoxy-benzoyl)-3-[2-[4-[1-(2-ethoxy-ethyl)-1H-benzoimidazole-2-carbonyl]-piperidin-1-yl]-ethyl]-3-(4-fluoro-phenyl)-pyrrolidine Prepare by the method of Example 6.6.2 using 1-(3,4,5-trimethoxy-benzoyl)-3-(4-fluoro-phenyl)-3-(2-methanesulfonyl-ethyl)-pyrrolidine and 4-[1-(2-ethoxy-ethyl)-1H-benzoimidazole-2-carbonyl]-piperidine to give the title compound.

EXAMPLE 68

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dichloro-phenyl)-pyrrolidine

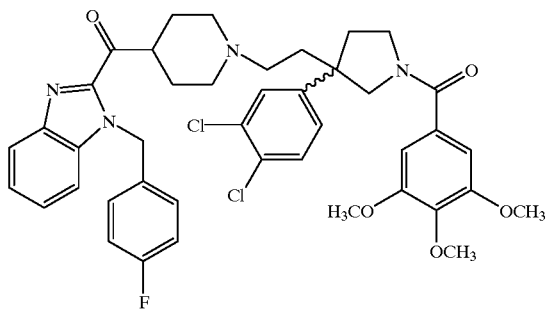
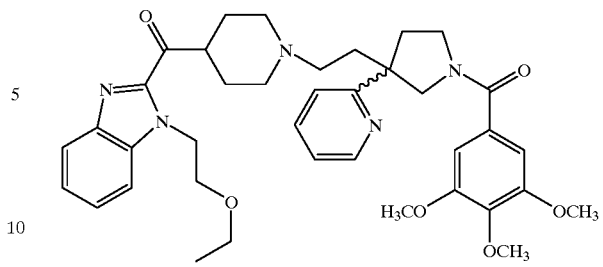

68.1 Synthesis of 1-(3.4,5-trimethoxy-benzoyl)-3-(3,4-dichloro-phenyl)-3-(2-oxo-ethyl)-pyrrolidine Combine oxalyl chloride (0.32 g, 2.27 mmol) with dichloromethane (6 mL) and cool to −60° C. Add dropwise a solution of dimethyl sulfoxide (0.39 g, 4.99 mmol) in dichloromethane (1 mL) while maintaining the temperature below −50° C. After addition is complete, stir for 5 minutes. Add a solution of 1-(3,4,5-trimethoxy-benzoyl)-3-(3,4-dichloro-phenyl)-3-(2-hydroxy-ethyl)-pyrrolidine (1.03 g, 2.27 mmol) in dichloromethane (2 mL) and stir for 15 minutes. Cool the reaction to −78° C. and add dropwise triethylamine (11.3 mmol). Allow the reaction to warm to ambient temperature and stir for 30 minutes. Pour the reaction into water. Extract this mixture with dichloromethane. Separate the organic layer and dry over $Na_2SO_4$, filter, and evaporate in vacuo to give a residue. Chromatograph the residue on silica gel eluting with ethyl acetate to give the title compound: $R_f$=0.28 (silica gel, ethyl acetate); mp; 45.0–48.0° C. Elemental Analysis Calculated for $C_{22}H_{23}Cl_2NO$.: C 58.42; H 5.13; N 3.10. Found: C 58.28; H 5.21; N 2.98.

68.2 Synthesis of (3,4,5-trimethoxy-benzoyl)-3-[2-[1-[(4-fluoro-benzyl)-1H-benzoimidazole-2-carbonyl]-piperidin-1-yl]-ethyl]-3-(3,4-dichloro-phenyl)-pyrrolidine Combine 1-(3,4,5-trimethoxy-benzoyl)-3-(3,4-dichlorophenyl)-3-(2-oxo-ethyl)-pyrrolidine (0.107 g, 0.24 mmol), (1-(4-fluoro-benzyl)-1H-benzoimidazole-2-carbonyl]-piperidine (0.1 g, 0.28 mmol), and 3A molecular sieves (about 12 g) in methanol (5 mL). After 18 hours, add silica gel (0.2 g). After 6 hours, add sodium cyanoborohydride (0.15 g, 2.4 mmol) and stir under an inert atmosphere. After 18 hours, add a solution of 2 M sodium hydroxide and dichloromethane. After 1 hour, filter, separate the layers in the filtrate, dry the organic layer over $Na_2SO_4$, filter, and evaporate invacuo to give the title compound: $R_f$=0.46 (silica gel, 5/1 ethyl acetate/methanol).

EXAMPLE 69

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(pyridin-2-yl)-pyrrolidine 69.1 Synthesis of 3-cyano-3-(pyridin-2-yl)-pentanedioic acid diethyl ester Prepare by the method of Example 1.1 using 2-pyridineacetonitrile to give the title compound: mp; 86.5–88.0° C.; $R_f$=0.46 (silica gel, 1/2 ethyl acetate/hexane). Elemental Analysis calculated for $C_{15}H_8N_2O_4$: C 62.06; H 6.25; N 9.65; Found: C 62.23; H 6.27; N 9.66.

69.2 Synthesis of 3-(pyridin-2-yl)-5-oxo-pyrrolidin-3-yl-acetic acid ethyl ester Prepare by the method of Example 1.2 using 3-cyano-3-(pyridin-2-yl)-pentanedioic acid diethyl ester to give the title compound: $R_f$=0.31 (silica gel, 20/1 ethyl acetate/methanol). Elemental Analysis calculated for $C_{13}H_{16}N_2O_3$: C 62.89; H 6.50; N 11.28; Found: C 62.54; H 6.50; N 11.18.

69.3 Synthesis of 3-(pyridin-2-yl)-3-(2-hydroxy-ethyl)-pyrrolidine

Prepare by the method of Example 1.3 using 3-(pyridin-2-yl)-5-oxo-pyrrolidin-3-yl]-acetic acid ethyl ester to give the title compound: mp; 50–55° C.

69.4 Synthesis of 1-(3,4,5-trimethoxy-benzoyl)-[3-(pyridin-2-yl)-3-(2-hydroxy-ethyl)-pyrrolidine Prepare by the method of Example 20.4.2 using 3-(pyridin-2-yl)-3-(2-hydroxy-ethyl)-pyrrolidine to give the title compound: mp; 52.0–55.0; $R_f$=0.23 (silica gel, 3% methanol/ dichloromethane). Elemental Analysis calculated for $C_{21}H_{26}N_2O_5 \cdot 0.30 H_2O$: C 64.37; H 6.84; N 7.15; Found: C 64.71; H 6.87; N 7.05.

69.5 Synthesis of 1-(3,4.5-trimethoxy-benzoyl)-3-(3-(pvridin-2-yl)-3-(2-oxo-ethyl)-pyrrolidine Prepare the method of Example 68.1 using 1-(3,4,5-trimethoxy-benzoyl)-[3-(pyridin-2-yl)-3-(2-hydroxy-ethyl)-pyrrolidine to give the title compound.

69.6 Synthesis of (3,4,5-trimethoxy-benzoyl)-3-[2-[4-[1-(2-ethoxy-ethyl)-1H-benzoimidazole-2-carbonyl]-piperidin-1-yl]-ethyl]-3-(pyridin-2-yl)-pyrrolidine Prepare by the method of Example 68.2 using 1-(3,4,5-trimethoxy-benzoyl)-3-(pyridin-2-yl)-3-(2-oxo-ethyl)-pyrrolidine and 4-[1-(2-ethoxy-ethyl)-1H-benzoimidazole-2-carbonyl]-piperidine to give the title compound

PREPARATION 12

Synthesis of methyl 2-(3-iodopropoxy)-benzoate

Combine salicylic acid (19.4 g, 140.5 mmol), sulfuric acid (20 mL), and methanol (100 mL). Heat to reflux. After 18 hours, pour the reaction mixture into dichloromethane. Separate the layers and extract the aqueous layer twice with dichloromethane. Combine the organic layers and extract three times with 5%.aqueous sodium bicarbonate solution. Dry the organic layer over $MgSO_4$, filter and evaporate invacuo to give methyl salicylate: $R_f$=0.60 (silica gel, 1/10 ethyl acetate/hexane).

Combine methyl salicylate (5.09 g, 33.2 mmol), sodium carbonate (10.56 g, 99.67 mmol), and 1,3-diiodopropane (29.49 g, 99.67 mmol) in acetone (200 mL). Heat to reflux. After 18 hours, add sodium carbonate (10.56 g, 99.67 mmol) and continue to heat at reflux. After 18 hours, add 1,3-diiodopropane (29.49 g, 99.67 mmol) and continue to heat at reflux. After 18 hours. filter the reaction mixture and concentrate the filtrate in vacuo to give a residue. Chromatograph the residue on silica gel eluting with 1/10 ethyl acetate/hexane to give the title compound: $R_f$=0.29 (silica gel, 1/10 ethyl acetate/hexane).

EXAMPLE 70

1-(3,4,5-Trimethoxy-benzoyl)-3-[2-[4-[1-(3-(2-carbomethoxy-phenoxy)-propyl)-1H-benzoimidazole-2-carbonyl]-piperidin-1-yl]-ethyl]-3-phenyl-pyrrolidine

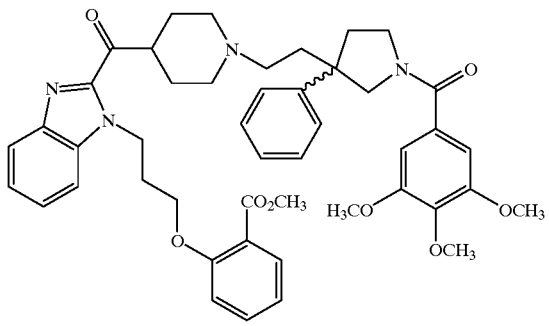

70.1 Synthesis of 1-(3,4,5-trimethoxy-benzoyl)-3-[2-[4-[1-(3-(2-carbomethoxy-phenoxy)-propyl)-1H-benzoimidazole-2-carbonyl]-piperidin-1-yl]-ethyl]-3-phenyl-pyrrolidine Prepare by the method of Example 38.1 using methyl 2-(3-iodopropoxy)-benzoate to give the title compound: mp; 74.0–80.0° C.; $R_f$=0.34 (silica gel, 5/1 ethyl acetate/methanol) Elemental Analysis calculated for $C_{46}H_{52}N_4O_8 \cdot 0.50\ H_2O$: C 69.24; H 6.69; N 7.02; Found: C 69.41; H 6.68; N 7.07.

EXAMPLE 71

1-(3,4.5-Trimethoxy-benzoyl)-3-[2-[4-[1-(3-(2-carboxy-phenoxy)-propyl)-1H-benzoimidazole-2-carbonyl]-piperidin-1-yl]-ethyl-3-phenyl-pyrrolidine

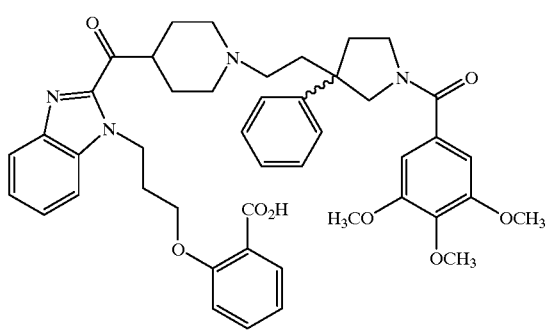

71.1 Synthesis of 1-(3,4,5-trimethoxy-benzoyl)-3-[2-[4-[1-(3-(2-carboxy-phenoxy)-propyl)-1H-benzoimidazole-2-carbonyl]-piperidin-1-yl]-ethyl]-3-phenyl-pyrrolidine hydrochloride salt Prepare by the method of Example 39.1 using 1-(3,4,5-trimethoxy-benzoyl)-3-[2-[4-[1-(3-(2-carbomethoxy-phenoxy)-propyl)-1H-benzoimidazole-2-carbonyl]-piperidin-1-yl]-ethyl]-3-phenyl-pyrrolidine to give the title compound: mp; 140.0–146.0° C.

EXAMPLE 72

1-(3,4.5-Trimethoxy-benzoyl)-3-[2-[4-[1-(2-oxo-propyl)-1H-benzoimidazole-2-carbonyl]-piperidin-1-yl]-ethyl]-3-phenyl-pyrrolidine

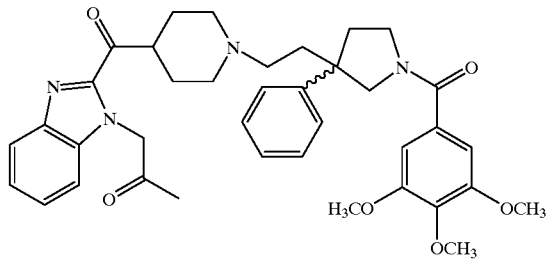

72.1 Synthesis of 1-(3,4,5-trimethoxy-benzoyl)-3-[2-[4-[1-(2-oxo-propyl)-1H-benzoimidazole-2-carbonyl]-piperidin-1-yl]-ethyl]-3-phenyl-pyrrolidine Prepare by the method of Example 38.1 using chloroacetone to give the title compound.

EXAMPLE 73

1-(3,4,5-Trimethoxy-benzoyl)-3-[2-[4-[1-(N,N-dimethylacetamido)-1H-benzoimidazole-2-carbonyl]-piperidin-1-yl]-ethyl]-3-phenyl-pyrrolidine

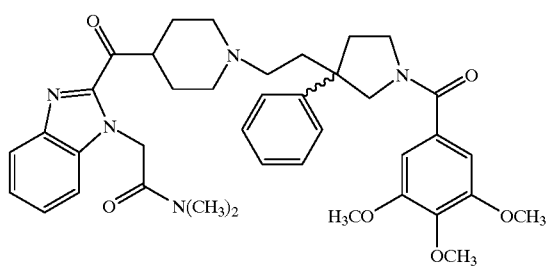

73.1 Synthesis of 1-(3,4,5-trimethoxy-benzoyl)-3-[2-[4-[1-(N,N-dimethylacetamido)-1H-benzoimidazole-2-carbonyl]-piperidin-1-yl]-ethyl]-3-phenyl-pyrrolidine Prepare by the method of Example 38.1 using N,N-dimethyl chloroacetamide to give the title compound.

EXAMPLE 74

1-(3,4,5-Trimethoxy-benzoyl)-3-[2-[4-[1-(2-acetamido-ethyl)-1H-benzoimidazole-2-carbonyl]-piperidin-1-yl]-ethyl]-3-phenyl-pyrrolidine

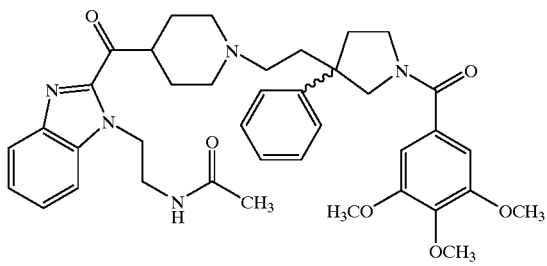

74.1 Synthesis of 1-(3,4,5-trimethoxy-benzoyl)-3-[2-[4-[1-(2-acetamido-ethyl)-1H-benzoimidazole-2-carbonyl]-piperidin-1-yl]-ethyl]-3-phenyl-pyrrolidine Prepare by the method of Example 38.1 using N-(2-chloroethyl)-acetamide to give the title compound.

EXAMPLE 75
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(4-methoxy-phenyl)-pyrrolidine

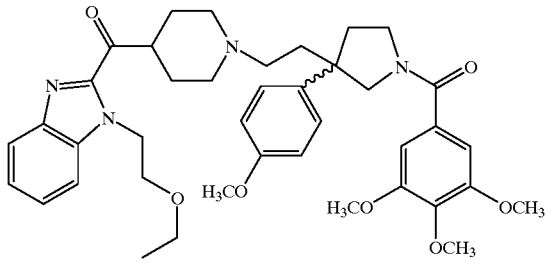

75.1 Synthesis of 3-cyano-3-(4-methoxy-phenyl)-pentanedioic acid diethyl ester

Combine 4-methoxyphenylacetonitrile (200 g, 1.36 mol) and tetrahydrofuran (500 mL). Cool to about −5° C. Add dropwise a solution of sodium bis-(trimethylsilyl)amide (2900 mL, 1 M in tetrahydrofuran, 2.90 mol). When the addition is complete warm the reaction mixture to ambient temperature and allow to stir for 1 hour. Transfer the above solution via cannula into a cooled (−12° C.) solution of ethyl bromoacetate (459.9 g) in tetrahydrofuran (1800 mL) at such a rate that the temperature of the reaction mixture does not rise above about 15° C. Allow to stir at ambient temperature. After 18 hours, dilute with diethyl ether and extract with water, 10% hydrochloric acid solution, and saturated aqueous solution of sodium bicarbonate. Dry the organic layer over MgSO$_4$, filter, and concentrate invacuo to obtain a residue. Distill the residue by bulb-to-bulb distillation to give the title compound: bp; 175–185° C. at 1.0 mm Hg.

75.2 Synthesis of 3-(4-methoxy-phenyl)-5-oxo-pyrrolidin-3-yl]-acetic acid ethyl ester Prepare by the method of Example 6.2.2 using 3-cyano-3-(4-methoxy-phenyl)-pentanedioic acid diethyl ester to give the title compound.

75.3 Synthesis of 3-(4-methoxy-phenyl)-3-(2-hydroxy-ethyl)-pyrrolidine

Prepare by the method of Example 6.3 using 3-(4-methoxy-phenyl)-5-oxo-pyrrolidin-3-yl]-acetic acid ethyl ester to give the title compound: R$_f$=0.35 (silica gel, 85/10/5 dichloromethane/methanol/acetic acid).

75.4 Synthesis of 1-(3,4,5-trimethoxy-benzoyl)-[3-(4-methoxy-phenyl)-3-(2-hydroxy-ethyl)-pyrrolidine Prepare by the method of Example 49.4 using 3-(4-methoxy-phenyl)-3-(2-hydroxy-ethyl)-pyrrolidine to give the title compound: Rf=0.25 (silica gel, 6% methanol/dichloromethane).

75.5 Synthesis of 1-(3,4,5-trimethoxy-benzoyl)-3-(4-methoxy-phenyl)-3-(2-methanesulfonyl-ethyl)-pyrrolidine Prepare by the method of Example 6.5.2 using 1-(3,4,5-trimethoxy-benzoyl)-3-(4-methoxy-phenyl)-3-(2-hydroxy-ethyl)-pyrrolidine to give the title compound: Rf=0.44 (silica gel, ethyl acetate).

75.6 Synthesis of (3,4,5-trimethoxy-benzoyl)-3-[2-[4-[1-(2-ethoxy-ethyl)-1H-benzoimidazole-2-carbonyl]-piperidin-1-yl]-ethyl]-3-(4-methoxy-phenyl)-pyrrolidine Prepare by the method of Example 6.6.2 using 1-(3,4,5-trimethoxy-benzoyl)-3-(4-methoxy-phenyl)-3-(2-methanesulfonyl-ethyl)-pyrrolidine and 4-[1-(2-ethoxy-ethyl)-1H-benzoimidazole-2-carbonyl]-piperidine to give the title compound.

EXAMPLE 76
1-(3,4,5-Trimethoxy-benzyl)-3-[3-[4-[1-(2-ethoxy-ethyl)-1H-benzoimidazole-2-carbonyl]-piperidin-1-yl]-propyl]-3-(4-fluoro-phenylmethyl)-2-oxo-pyrrolidine

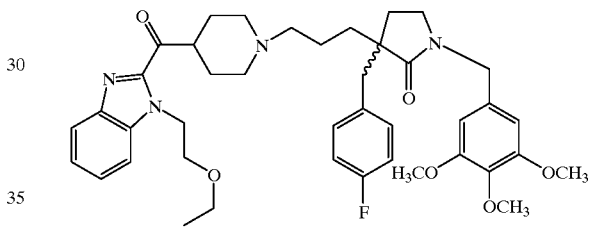

76.1 Synthesis of 1-(3,4,5-trimethoxy-benzyl)-3-(4-fluoro-phenylmethyl)-3-(3-t-butyldimethylsilyloxy-propyl)-2-oxo-pyrrolidine Prepare by the method of Example 53.3 using 1-(3,4,5-trimethoxy-benzyl)-3-(4-fluoro-phenylmethyl)-2-oxo-pyrrolidine and 3-t-butyldimethylsilyloxy-propyl bromide to give the title compound: R$_f$=0.52 (silica gel, 1/4 ethyl acetate/hexane).

76.2 Synthesis of 1-(3.4,5-trimethoxy-benzyl)-3-(4-fluoro-phenylmethyl)-3-(2-hydroxy-ethyl)-2-oxo-pyrrolidine Prepare by the method of Example 58.3 using 1-(3,4,5-trimethoxy-benzyl)-3-(4-fluoro-phenylmethyl)-3-(3-t-butyldimethylsilyloxy-propyl)-2-oxo-pyrrolidine to give the title compound: R$_f$=0.30 (silica gel, ethyl acetate)

76.3 Synthesis of 1-(3,4,5-trimethoxy-benzyl)-3-(4-fluoro-phenylmethyl)-3-(3-methanesulfonyl-propyl)-2-oxo-pyrrolidine Prepare by the method of Example 10.5 using 1-(3,4,5-trimethoxy-benzyl)-3-(4-fluoro-phenylmethyl)-3-(2-hydroxy-ethyl)-2-oxo-pyrrolidine to give the title compound: R$_f$=0.71 (silica gel, ethyl acetate).

76.4 Synthesis of 1-(3,4,5-trimethoxy-benzyl)-3-[3-[4-[1H-benzoimidazole-2-carbonyl]-4-hydroxy-piperidin-1-yl]-propyl]-3-(4-fluoro-phenylmethyl)-2-oxo-pyrrolidine Prepare by the method of Example 6.6.2 using 1-(3,4,5-trimethoxy-benzyl)-3-(4-fluoro-phenylmethyl)-3-(3-methanesulfonyl-propyl)-2-oxo-pyrrolidine and 4-(1H-benzoimidazole-2-carbonyl)-piperidine hydroiodide salt to give the title compound: $R_f$=0.53 (silica gel, 2/10/88 triethylamine/methanol/ethyl acetate).

76.5 Synthesis of 1-(3,4,5-trimethoxy-benzyl)-3-[3-[4-[1-(2-ethoxy-ethyl)-1H-benzoimidazole-2-carbonyl]-piperidin-1-yl]-propyl]-3-(4-fluoro-phenylmethyl)-2-oxo-pyrrolidine Prepare by the method of Example 40.1 using 1-(3,4,5-trimethoxy-benzyl)-3-[3-[4-[1H-benzoimidazole-2-carbonyl]-piperidin-1-yl]-propyl]-3-(4-fluoro-phenylmethyl)-2-oxo-pyrrolidine to give the title compound: $R_f$=0.53 (silica gel, 2/10/88 triethylamine/methanol/ethyl acetate).

EXAMPLE 77

1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-difluoro-phenyl)-pyrrolidine

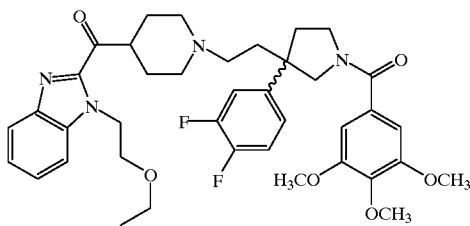

77.1 Synthesis of 3-cyano-3-(3,4-difluoro-phenyl)-pentanedioic acid diethyl ester Prepare by the method of Example 11.1.2 using 3,4-difluorophenylacetonitrile to give the title compound.

77.2 Synthesis of 3-(3,4-difluoro-phenyl)-5-oxo-pyrrolidin-3-yl]-acetic acid ethyl ester Prepare by the method of Example 6.2.2 using 3-cyano-3-(3,4-difluoro-phenyl)-pentanedioic acid diethyl ester to give the title compound.

77.3 Synthesis of 3-(3,4-difluoro-phenyl)-3-(2-hydroxy-ethyl)-pyrrolidine

Prepare by the method of Example 6.3 using 3-(3,4-difluoro-phenyl)-5-oxo-pyrrolidin-3-yl]-acetic acid ethyl ester to give the title compound: $R_f$=0.26 (silica gel, 85/10/5 dichloromethane/methanol/acetic acid).

77.4 Synthesis of 1-(3,4,5-trimethoxy-benzoyl)-[3-(3,4-difluoro-phenyl)-3-(2-hydroxy-ethyl)-pyrrolidine Prepare by the method of Example 49.4 using 3-(3,4-difluoro-phenyl)-3-(2-hydroxy-ethyl)-pyrrolidine to give the title compound: $R_f$=0.25 (silica gel, ethyl acetate).

77.5 Synthesis of 1-(3,4,5-trimethoxy-benzoyl)-3-(3,4-difluoro-phenyl)-3-(2-methanesulfonyl-ethyl)-pyrrolidine Prepare by the method of Example 6.5.2 using 1-(3,4,5-trimethoxy-benzoyl)-3-(3,4-difluoro-phenyl)-3-(2-hydroxy-ethyl)-pyrrolidine to give the title compound: $R_f$=0.44 (silica gel, ethyl acetate).

77.6 Synthesis of (3,4,5-trimethoxy-benzoyl)-3-[2-[4-[1-(2-ethoxy-ethyl)-1H-benzoimidazole-2-carbonyl]-piperidin-1-yl]-ethyl]-3-(3,4-difluoro-phenyl)-pyrrolidine Prepare by the method of Example 6.6.2 using 1-(3,4,5-trimethoxy-benzoyl)-3-(3,4-difluoro-phenyl)-3-(2-methanesulfonyl-ethyl)-pyrrolidine and 4-[1-(2-ethoxy-ethyl)-1H-benzoimidazole-2-carbonyl]-piperidine to give the title compound.

EXAMPLE 78

(−)-1-(3,4,5-Trimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine

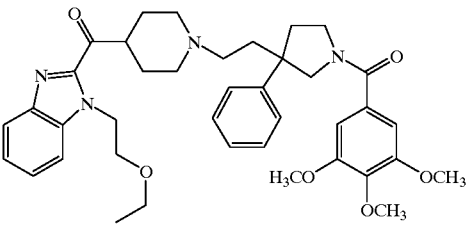

78.1 Synthesis of (−)-1-(3,4,5-trimethoxy-benzoyl)-3-phenyl-3-(2-hydroxy-ethyl)-pyrrolidine Prepare by the method of Example 41.2 using (−)-3-phenyl-3-(2-hydroxy-ethyl)-pyrrolidine (R, R)-di-p-anisoyltartaric acid salt to give the title compound: $R_f$=0.23 (silica gel, ethyl acetate).

78.2 Synthesis of (−)-1-(3,4,5-trimethoxy-benzoyl)-3-phenyl-3-(2-methanesulfonyl-ethyl)-pyrrolidine Prepare by the method of Example 6.5.2 using (−)-1-(3,4,5-trimethoxy-benzoyl)-3-phenyl-3-(2-hydroxy-ethyl)-pyrrolidine to give the title compound: $R_f$=0.47 (silica gel, ethyl acetate).

78.3 Synthesis of (−)-1-(3,4,5-trimethoxy-benzoyl)-3-[2-[4-1H-benzoimidazole-2-carbonyl]-piperidin-1-yl]-ethyl]-3-phenyl-pyrrolidine Prepare by the method of Example 6.6.2 using (−)-1-(3,4,5-trimethoxy-benzoyl)-3-phenyl-3-(2-methanesulfonyl-ethyl)-pyrrolidine and 4-(1H-benzoimidazole-2-carbonyl)-piperidine hydroiodide salt to give the title compound.

78.4 Synthesis of (−)-1-(3,4,5-trimethoxy-benzoyl)-3-[2-[4-[1- (2-ethoxy-ethyl)-1H-benzoimidazole-2-carbonyl]-piperidin-1-yl]-ethyl]-3-phenyl-pyrrolidine Prepare by the method of Example 40.1 using (−)-1-(3,4,5-trimethoxy-benzoyl)-3-[2-[4-[1H-benzoimidazole-2-carbonyl]-piperidin-1-yl]-ethyl]-3-phenyl-pyrrolidine to give the title compound.

EXAMPLE 79

1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dichloro-phenyl)-piperidine

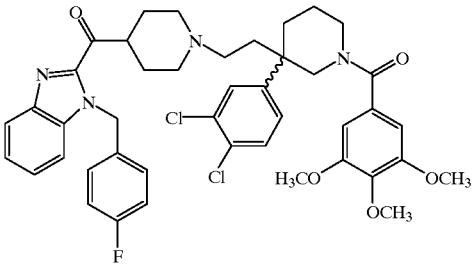

79.1 Synthesis of 1-(3,4,5-trimethoxy-benzoyl)-3-[2-[4-[1-(4-fluoro-benzyl)-1H-benzoimidazole-2-carbonyl]-piperidin-1-yl]-ethyl]-3-(3,4-dichloro-phenyl)-piperidine Combine 1-(3,4,5-trimethoxy-benzoyl)-3-(3,4-(dichloro-phenyl)-3-(2-methanesulfonyl-ethyl)-piperidine (0.30 g, 0.55 mmol), diisopropylethylamine (0.19 mL, 1.10 mmol), 4-[1-(4-fluoro-benzyl)-1H-benzoimidazole-2-carbonyl]-piperidine (0.28 g, 0.82 mmol), and acetonitrile (4 mL). Heat to reflux. After 84 hours, cool and partition the reaction mixture between ethyl acetate and water. Extract the organic layer with a saturated sodium bicarbonate solution and a saturated sodium chloride solution. Dry the organic layer over Na₂SO₄, filter, and concentrate invacuo to obtain a residue. Chromatograph the residue on silica gel eluting with 5/1 ethyl acetate/methanol to give a residue. Dissolve the residue in dichloromethane and extract with 5% sodium bicarbonate solution. Dry the organic layer over Na₂SO₄, filter, and concentrate in vacuo to obtain the title compound after drying: R$_f$=0.45 (silica gel, 5/1 ethyl acetate/methanol); mp; 93.0–95.0° C. Elemental Analysis calculated for C$_{43}$H$_{45}$Cl$_2$N$_4$O$_5$: C 65.56; H 5.76; N 7.11; Found: C 65.84; H 5.86; N 7.17.

EXAMPLE 80

1-(3,4,5-Trimethoxy-benzoyl)-3-[2-[4-[1-(imidazol-2-ylmethyl)-1H-benzoimidazole-2-carbonyl]-piperidin-1-yl]-ethyl]-3-phenyl-pyrrolidine

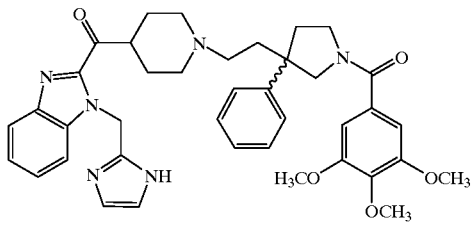

80.1 Synthesis of 1-(3,4,5-trimethoxy-benzoyl)-3-[2-[4-[1-(1-benzyl-imidazol-2-ylmethyl)-1H-benzoimidazole-2-carbonyl]-piperidin-1-yl]-ethyl]-3-phenyl-pyrrolidine Prepare by the method of Example 38.1 using 1-(3,4,5-trimethoxy-benzoyl)-3-[2-[4-[1H-benzoimidazole-2-carbonyl]-piperidin-1-yl]-ethyl]-3-phenyl-pyrrolidine and 1-benzyl-imidazol-2-ylmethylchloride hydrochloride to give the title compound.

80.2 Synthesis of 1-(3,4,5-trimethoxy-benzoyl)-3-[2-[4-[1-(imidazol-2-ylmethyl)-1H-benzoimidazole-2-carbonyl]-piperidin-1-yl]-ethyl]-3-phenyl-pyrrolidine Combine 1-(3,4,5-trimethoxy-benzoyl)-3-[2-[4-[1-(1-benzyl-imidazol-2-ylmethyl)-1H-benzoimidazole-2-carbonyl]-piperidin-1-yl]-ethyl]-3-phenyl-pyrrolidine (5 mmol) and 10% palladium-on-carbon (1.5 g) in methanol (50 mL). Add anhydrous ammonium formate (25 mmol). Heat to reflux. After 18 hours, filter, rinse with dichloromethane, and evaporate the filtrate in vacuo to give the title compound.

PREPARATION 13

4-[1-(2-ethoxy-ethyl)-1H-benzoimidazole]-4-hydroxy-piperidine

Combine 1-(2-ethoxy-ethyl)-1H-benzoimidazole (2.0 g, 10.51 mmol) and tetrahydrofuran (20 mL). Cool to −78° C. using a dry-ice/acetone bath. Add dropwise a solution of lithium diisopropylamide (4.62 mL, 2.5 M in hexane, 11.56 mmol). After 1 hour, add dropwise a solution of 1-(t-butoxycarbonyl)-piperidin-4-one (2.09 g, 10.51 mmol) in tetrahydrofuran (10 mL). Warm to ambient temperature over 3 hours. Add water and separate the layers. Extract the aqueous layer three times with ethyl acetate. Dry the combined organic layers over Na₂SO₄, filter, and evaporate in vacuo to give a residue. Chromatograph the residue on silica gel eluting with 1/1 ethyl acetate/hexane to 1-(t-butoxycarbonyl)-4-[1-(2-ethoxy-ethyl)-1H-benzoimidazole]-4-hydroxy-piperidine: R$_f$=0.25 (silica gel, 1/1 ethyl acetate/hexane).

Cool 1-(t-butoxycarbonyl)-4-[1-(2-ethoxy-ethyl)-1H-benzoimidazole]-4-hydroxy-piperidine (2.05 g) using an ice bath. Add dropwise trifluoroacetic acid (25 mL). After 1 hour, add diethyl ether (100 mL) and evaporate in vacuo to give a residue. Add dichloromethane and a 5% potassium carbonate solution. Stir vigorously. After 3 hours, separate the layers and extract the aqueous layer three times with dichloromethane. Combine the organic layers and dry over K₂CO₃, filter, and evaporate in vacuo to give the title compound: R$_f$=0.18 (silica gel, 2% triethylamine/ethyl acetate).

EXAMPLE 81

(+)-1-(3,4,5-Trimethoxy-benzoyl)-3-[2-[4-[1-(2-ethoxy-ethyl)-1H-benzoimidazole]-4-hydroxy-piperidin-1-yl]-ethyl]-3-(3,4-dichloro-phenyl)-pyrrolidine

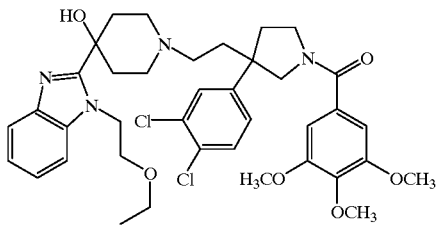

81.1 Synthesis of (+)-1-(3,4.5-trimethoxy-benzoyl)-3-[2-[4-[1- (2-ethoxy-ethyl)-1H-benzoimidazole]-4-hydroxy-piperidin-1-yl]-ethyl]-3-(3,4-dichloro-phenyl)-pyrrolidine Prepare by the method of Example 6.6.2 using (+)-1-(3,4,5-trimethoxy-benzoyl)-3-(3,4-dichloro-phenyl)-3-(2-methanesulfonyl-ethyl)-pyrrolidine and 4-[1-(2-ethoxy-ethyl)-1H-benzoimidazole]-4-hydroxy-piperidine to give the title compound: R$_f$=0.32 (silica gel 10% methanol/ethyl acetate). Elemental Analysis calculated for C$_{38}$H$_{46}$Cl$_2$N$_4$O$_6$·0.80 H$_2$O: C 62.77; H 6.40; N 7.70; Found: C 62.43; H 6.57; N 7.58.

81.2 Synthesis of (+)-1-(3,4.5-trimethoxy-benzoyl)-3-[2-[4-1-(2-ethoxy-ethyl)-1H-benzoimidazole1-4-hydroxy-piperidin-1-yl]-ethyl]-3-(3,4-dichloro-phenyl)-pyrrolidine methanesulfonate salt Prepare by the method of Example 6.7.3 using (+)-1-(3, 4,5-trimethoxy-benzoyl)-3-[2-[4-[1-(2-ethoxy-ethyl)-1H-benzoimidazole]-4-hydroxy-piperidin-1-yl]-ethyl]-3-(3,4-dichloro-phenyl)-pyrrolidine to give the title compound.

EXAMPLE 82

1-(3,4, 5-Trimethoxy-benzyl)-3-[2-[4-[1-(pyrid-2-ylmethyl)-1H-benzoimidazole-2-carbonyl]-piperidin-1-yl]-ethyl]-3-(4-fluoro-phenylmethyl)-2-oxo-pyrrolidine

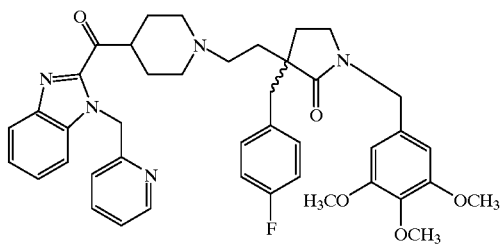

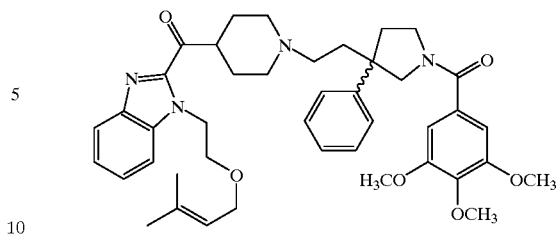

82.1 Synthesis of 1-(3,4,5-trimethoxy-benzyl)-3-[2-[4-[1H-benzoimidazole-2-carbonyl]-piperidin-1-yl]-ethyl]-3-(4-fluoro-phenylmethyl)-2-oxo-pyrrolidine Prepare by the method of Example 6.6.2 using 1-(3,4,5-trimethoxy-benzyl)-3-(4-fluoro-phenylmethyl)-3-(2-methanesulfonyl-ethyl)-2-oxo-pyrrolidine and 4-[1H-benzoimidazole-2-carbonyl]-piperidine to give the title compound.

82.6 Synthesis of 1-(3,4,5-trimethoxy-benzyl)-3-[2-[4-[1-(pryid-2-ylmethyl)-1H-benzoimidazole-2-carbonyl]-piperidin-1-yl]-ethyl]-3-(4-fluoro-phenylmethyl)-2-oxo-pyrrolidine methanesulfonate salt Prepare by the method of Example 33.1 using 1-(3,4,5-trimethoxy-benzyl)-3-[2-[4-[1H-benzoimidazole-2-carbonyl]-piperidin-1-yl]-ethyl]-3-(4-fluoro-phenylmethyl)-2-oxo-pyrrolidine to give the title compound.

EXAMPLE 83
1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine

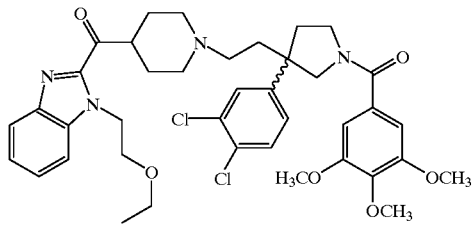

83.1 Synthesis of 1-(3,4,5-trimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine Prepare by the method of 6.6.2 using 1-(3,4,5-trimethoxy-benzoyl)-3-(3,4-dichloro-phenyl)-3-(2-methanesulfonyl-ethyl)-pyrrolidine and 4-[1-(2-ethoxy-ethyl)-1H-benzoimidazole-2-carbonyl]-piperidine to give the title compound.

83.2 Synthesis of 1-(3,4,5-trimethoxy-benzoyl)-3-[2-[4-[1-(2-ethoxy-ethyl)-1H-benzoimidazole-2-carbonyl]-piperidin-1-yl]-ethyl]-3-(3.4-dichloro-phenyl)-pyrrolidine methanesulfonate salt Prepare by the method of Example 53.7 using 1-(3,4,5-trimethoxy-benzoyl)-3-[2-[4-[1-(2-ethoxy-ethyl)-1H-benzoimidazole-2-carbonyl]-piperidin-1-yl]-ethyl]-3-(3,4-dichloro-phenyl)-pyrrolidine to give the title compound.

EXAMPLE 84
1-(3,4,5-Trimethoxy-benzoyl)-3-[2-[4-[1-(2-(3,3-dimethylallyloxy)-ethyl)-1H-benzoimidazole-2-carbonyl]-piperidin-1-yl]-ethyl]-3-phenyl-pyrrolidine 84.1 Synthesis of 1-(3,4,5-trimethoxy-benzoyl)-3-[2-[4-[1-(2-allyloxy-ethyl)-1H-benzoimidazole-2-carbonyl]-piperidin-1-yl]-ethyl]-3-phenyl-pyrrolidine Combine 1-(3,4,5-trimethoxy-benzoyl)-3-[2-[4-[1H-benzoimidazole-2-carbonyl]-piperidin-1-yl]-ethyl]-3-phenyl-pyrrolidine (0.62 g, 1.0 mmol), and 2-(3,3-dimethylallyloxy)-ethanol (0.14 g, 1.0 mmol), triphenylphosphine (0.33 g, 1.27 mmol) in tetrahydrofuran (2 mL). Add dropwise diethyl azodicarboxylate ((0.2 mL, 1.27.mmol). After 18 hours, evaporate in vacuo to give a residue. Chromatograph the residue on silica gel eluting with 10% methanol/ethyl acetate to give the title compound: $R_f$=0.35 (silica gel, 10% methanol/ethyl acetate).

EXAMPLE 85
1-(34, 5-Trimethoxy-benzoyl)-3-[2-[4-[1-(5-methylfur-2-ylmethyl)-1H-benzoimidazole-2-carbonyl]-piperidin-1-yl]-ethyl]-3-phenyl-pyrrolidine

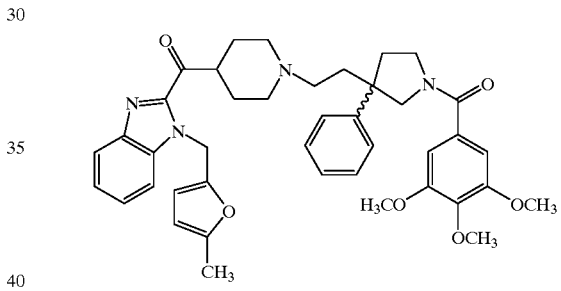

85.1 Synthesis of 1-(3,4,5-trimethoxy-benzoyl)-3-[2-[4-[1-(5-methylfur-2-ylmethyl)-1H-benzoimidazole-2-carbonyl]-piperidin-1-yl]-ethyl]-3-phenyl-pyrrolidine Prepare by the method of Example 84.1 using 5-methyl-2-hydroxymethyl-furan to give the title compound.

EXAMPLE 86
1-(3,4,5-Trimethoxy-benzoyl)-3-[2-[4-[1-(5-hydroxymethylfur-2-ylmethyl)-1H-benzoimidazole-2-carbonyl]-piperidin-1-yl]-ethyl]-3-phenyl-pyrrolidine

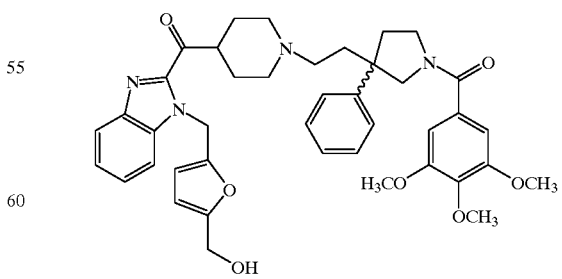

86.1 Synthesis of 1-(3,4,5-trimethoxy-benzoyl)-3-[2-[4-[1-(5-methylfur-2-ylmethyl)-1H-benzoimidazole-2-carbonyl]-piperidin-1-yl]-ethyl]-3-phenyl-pyrrolidine Prepare by the method of Example 84.1 using 1-(3,4,5-trimethoxy-benzoyl)-3-[2-[4-[1H-benzoimidazole-2-carbonyl]-piperidin-1-yl]-ethyl]-3-phenyl-pyrrolidine (1 mmol) and 2,5-di(hydroxymethyl)furan (10 mmol) to give the title compound.

EXAMPLE 87

1-(3,4,5-Trimethoxy-benzoyl)-3-[2-[4-[1-(pyrid-2-methyl)-1H-benzoimidazole-2-carbonyl]-piperidin-1-yl]-ethyl]-3-(4-methoxy-phenyl)-pyrrolidine

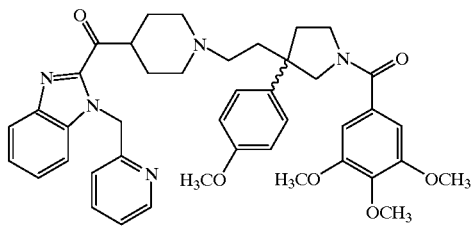

87.1 Synthesis of 1-(3,4,5-trimethoxy-benzoyl)-3-[2-[4-[1H-benzoimidazole-2-carbonyl]-piperidin-1-yl]-ethyl]-3-(4-methoxy-phenyl)-pyrrolidine Prepare by the method of Example 6.6.2 using 1-(3,4,5-trimethoxy-benzoyl)-3-(4-methoxy-phenyl)-3-(2-methanesulfonyl-ethyl)-pyrrolidine and 4-[1H-benzoimidazole-2-carbonyl]-piperidine hydroiodide salt to give the title compound: $R_f$=0.14 (silica gel, 5/95/0.1 methanol/dichloromethane/concentrated ammonium hydroxide); mp; 105–110° C.

87.2 Synthesis of 1-(3,4,5-trimethoxy-benzoyl)-3-[2-[4-[1-(pyrid-2-methyl)-1H-benzoimidazole-2-carbonyl]-piperidin-1-yl]-ethyl]-3-(4-methoxy-phenyl)-pyrrolidine Prepare by the method of Example 33.1 using 1-(3,4,5-trimethoxy-benzoyl)-3-[2-[4-[1H-benzoimidazole-2-carbonyl]-piperidin-1-yl]-ethyl]-3-(4-methoxy-phenyl)-pyrrolidine to give the title compound: $R_f$=0.20 (silica gel, 5/95/0.1 methanol/dichloromethane/concentrated ammonium hydroxide).

87.3 Synthesis of 1-(3,4,5-Trimethoxy-benzoyl)-3-[2-[4-[1-(pyrid-2-methyl)-1H-benzoimidazole-2-carbonyl]-piperidin-1-yl]-ethyl]-3-(4-methoxy-phenyl)-pyrrolidine maleic acid salt Combine 1-(3,4,5-trimethoxy-benzoyl)-3-[2-[4-[1-(pyrid-2-methyl)-1H-benzoimidazole-2-carbonyl]-piperidin-1-yl]-ethyl]-3-( 4-methoxy-phenyl)-pyrrolidine (232 mg, 0.323 mmol) and maleic acid (75.0 mg, 0.646 mmol) in dichloromethane (25 mL). Heat gently until solids dissolve. Evaporate the solvent in vacuo and triturate the residue with ether (50 mL). Filter the resulting solid and dry at 82° C. at 0.2 torr to obtain title compound. Elemental Analysis calculated for $C_{42}H_{47}N_5O_6 \cdot C_4H_4O_4 \cdot 1.62 \ H_2O$: C 64.01; H 6.33; N 8.11; Found: C 63.65; H 6.40; N 7.86.

EXAMPLE 88

1-Benzyl-3-[2-[4-[1-(4-fluoro-benzyl)-1H-benzoimidazole-2-carbonyl]-piperidin-1-yl]-ethyl]-3-(4-trifluoromethyl-phenylmethyl)-2-oxo-pyrrolidine

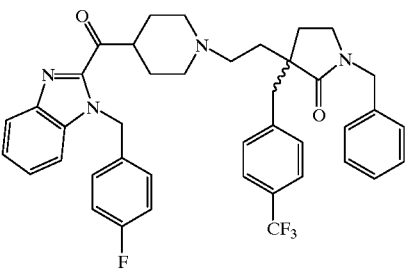

88.1 Synthesis of 1-Benzyl-3-(4-trifluoromethyl-phenylmethyl)-3-(allyl)-2-oxo-pyrrolidine Combine 1-benzyl-2-pyrrolidinone (7.10 g, 40.0 mmol) in anhydrous tetrahydrofuran at −78° C. Add dropwise a solution of sec-butyllithium (33.8 mL, 44.0 mmol) in cylcohexane. After stirring 30 minutes, add a solution of 4-(trifluoromethyl)-benzyl bromide (9.75 g, 40.8 mmol) in THF (30 mL). Stir an additional 10 minutes, transfer the reaction flask to an ice bath and warm to 0° C. Cool the solution to −78° C., and add dropwise a solution of sec-butyl lithium (33.8 mL, 44.0 mmol) in cylcohexane. Stir for 30 minutes and add allyl bromide (4.15 mL, 5.81 g, 48.0 mmol). Stir the reaction mixture an additional 10 minutes, transfer to an ice bath and warm to 0° C. Quench the reaction mixture by cautious addition of saturated aqueous $NH_4Cl$ solution. Dilute the mixture with ethyl acetate (200 mL) and extract successively with saturated aqueous $NH_4Cl$ (2×75 mL), $H_2O$ (2×75 mL), saturated aqueous $NaHCO_3$ (75 mL) and brine (75 mL). Dry the organic layer over $MgSO_4$ and evaporate the solvent in vacuo. Chromatograph the residue on silica gel initially with 30% ethyl acetate/hexane, and gradually increasing to 70% ethyl acetate/hexane. Combine the product-containing fractions and chromatograph on silica gel initially with 10% ethyl acetate/hexane, and gradually increasing to 20% ethyl acetate/hexane to give the title compound: $R_f$=0.22 (silica gel, 40% ethyl acetate/hexane, with $I_2$ development); Elemental Analysis calculated for $C_{22}H_{22}F_3NO$: C 70.76; H 5.94; N 3.75; Found: C 69.98; H 5.94; N 3.94.

88.2 Synthesis of 1-Benzyl-3-(4-trifluoromethyl-phenylmethyl)-3-(2-oxo-ethyl)-2-oxo-pyrrolidine Cool a solution of 1-benzyl-3-(4-trifluoromethyl-phenylmethyl)-3-(allyl)-2-oxo-pyrrolidine (1.55 g, 4.15 mmol) in $CH_2Cl_2$ (100 mL) to −78° C. Add methanol (10 mL), then add $O_3$ (6.0 p.s.i., 90 volts, 4.0 SLPM) via a carrius tube until a pale blue color persists (approximately 10 minutes). Purge the solution with $O_2$ for 10 minutes until the blue color is eliminated. Add dimethyl sulfide (10 mL) and stir overnight. Remove the solvent in vacuo to yield the title compound.

88.3 Synthesis of 1-Benzyl-3-[2-[4-[1-(4-fluoro-benzyl)-1H-benzoimidazole-2-carbonyl]-piperidin-1-yl]-ethyl]-3-(4-trifluoromethyl-phenylmethyl)-2-oxo-pyrrolidine Combine 1-benzyl-3-(4-trifluoromethyl-phenylmethyl)-3-(2-oxo-ethyl)-2-oxo-pyrrolidine (1.70 g, 4.15 mmol) and [1-(4-fluoro-benzyl)-1H-benzoimidazole-2-carbonyl]-piperidine trifluoroacetic acid salt (1.40 g, 3.11 mmol) in methanol (30 mL). Stir in freshly crushed 3 Å sieves. Cool the reaction mixture to 0–5° C. and add citric acid until pH=5. Add sodium cyanoborohydride (393 mg, 5.60 mmol)

in portions. Stir overnight, allowing the reaction mixture to warm to room temperature. Pour solution into saturated NH₄Cl, stir vigorously and extract with CH₂Cl₂. Separate the organic layer, extract with 1N NaOH, dry over Na₂SO₄, filter and concentrate in vacuo. Chromatograph the residue on silica gel eluting sequentially with 10% methanol/dichloromethane (with 0.1% concentrated NH₄OH), then with 40% methanol. Further purify by chromatographing the residue on silica gel eluting sequentially with 20% ethyl acetate/hexane, then with methanol/ethyl acetate/hexane(20/20/60, with 0.1% concentrated NH₄OH). Recrystallize from hexane to obtain the title compound as a white solid: mp; 104.5–106.0° C.; R$_f$=0.16 (silica gel, 10% MeOH/CH₂Cl₂ with 0.1% concentrated NH₄OH). Elemental Analysis calculated for C₄₁H₄₀F₆N₄O₂: C 65.98; H 4.72; N 2.85; Found: C 66.16; H 4.61; N 2.80.

88.4 Synthesis of 1-Benzyl-3-[2-[4-[1-(4-fluoro-benzyl)-1H-benzoimidazole-2-carbonyl]-piperidin-1-yl]-ethyl]-3-(4-trifluoromethyl-phenylmethyl)-2-oxo-pyrrolidine maleic acid salt Dissolve 1-benzyl-3-[2-[4-[1-(4-fluoro-benzyl)-1H-benzoimidazole-2-carbonyl]-piperidin-1-yl]-ethyl]-3-(4-trifluoromethyl-phenylmethyl)-2-oxo-pyrrolidine (112 mg, 0.16 mmol) in 5 mL anhydrous tetrahydrofuran (THF) and add maleic acid (18.7 mg, 0.16 mmol). Heat to 50° C., then stir at room temperature. Remove THF under reduced pressure, add diethyl ether (20 mL) and stir for 6 h. Filter the resulting solid and dry overnight at 82° C. at 2 torr, to give the title compound: mp; 103.0–107.0° C. Elemental Analysis calculated for C₄₁H₄₀F₄N₄O₂·C₄H₄O₄: C 66.49; H 5.46; N 6.89; Found: C 66.09; H 5.38; N 6.86.

EXAMPLE 89

1-(3,4,5-Trimethoxy-benzoyl)-3-[2-[4-[1H-benzoimidazole-2-carbonyl]-piperidin-1-yl]-ethyl]-3-(3,4-dimethoxy-phenyl)-pyrrolidine

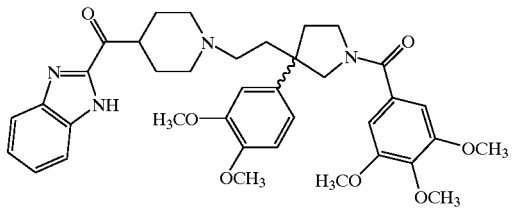

Combine 1-(3,4,5-trimethoxy-benzoyl)-3-(3,4-dimethoxy-phenyl)-3-(2-methanesulfonyl-ethyl)-pyrrolidine (1.19 g, 2.27 mmol), 4-[1H-benzoimidazole-2-carbonyl]-piperidine (1.65 g, 3.41 mmol) and diisopropylethylamine (1.47 g, 11.35 mmol) and acetonitrile (11 mL). Reflux the reaction mixture overnight, dilute with ethyl acetate and extract successively with a saturated aqueous NH₄Cl solution, 5% aqueous NaHCO₃ solution, water and saturated aqueous NaCl solution. Separate the organic layer, dry over anhydrous Na₂SO₄, filter and remove the solvent in vacuo. Chromatograph the residue on silica gel eluting with ethyl acetate/methanol (5/1), evaporate the solvent and dry overnight at 82° C. at 0.20 torr to yield title compound: mp; 113.0–116.0° .C, R$_f$=0.23 (silica gel, 5/1 ethyl acetate/methanol). Elemental Analysis calculated for C₃₇H₄₄N₄O₇: C 67.66; H 6.75; N 8.53; Found: C 67.00; H 6.77; N 8.39.

EXAMPLE 90

1-(3,4,5-Trimethoxy-benzoyl)-3-[2-[4-[1-(pyrid-4-ylmethyl)-1H-benzoimidazole-2-carbonyl]-piperidin-1-yl]-ethyl]-3-phenyl-pyrrolidine

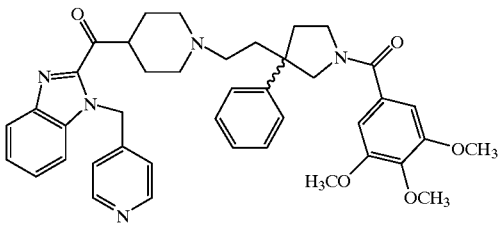

Combine 1-(3,4,5-trimethoxy-benzoyl)-3-[2-[4-[1H-benzoimidazole-2-carbonyl]-piperidin-1-yl]-ethyl]-3-phenyl-pyrrolidine (710 mg, 1.19 mmol), 4-(chloromethyl) pyridine hydrochloride (794 mg, 4.84 mmol), potassium carbonate (1.337 g, 9.67 mmol) in acetone (21 mL) and water (7 mL). Stir and heat at reflux for 24 h. Allow reaction mixture to cool to room temperature, and remove the acetone under vacuum. Add ethyl acetate, separate the organic layer and extract with saturated aqueous NaCl solution. Dry the organic layer over anhydrous Na₂SO₄, filter and concentrate in vacuo. Chromatograph the residue on silica gel eluting with 30% methanol/ethyl acetate to give the title compound: R$_f$=0.16 (silica gel, 20% methanol/ethyl acetate).

EXAMPLE 91

(+)-1-(3,4,5-Trimethoxy-benzoyl)-3-[2-[4-[1-(pyrid-2-methyl)-1H-benzoimidazole-2-carbonyl]-piperidin-1-yl]-ethyl]-3-(4-fluoro-phenyl)-pyrrolidine

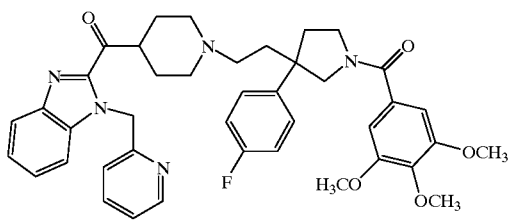

Combine (+)-1-(3,4,5-trimethoxy-benzoyl)-3-(4-fluoro-phenyl)-3-(2-methanesulfonyl-ethyl)-pyrrolidine (834 mg, 1.18 mmol), 4-[1(pyrid-2-methyl)-1H-benzoimidazole-2-carbonyl]-piperidine (382 mg, 0.790 mmol) and diisopropylethylamine (1.23 mL, 7.08 mmol) in acetonitrile (15 mL) and heat to reflux under argon for 48 hours. Add ethyl acetate and separate the organic layer. Extract successively with 5% aqueous NaHCO₃ and brine, dry over Na₂SO₄, filter and evaporate the solvent. Chromatograph the residue on silica gel eluting with 10% methanol/dichloromethane containing 0.1% NH₄OH solution. Combine product-containing fractions, evaporate the solvent in vacuo and dry at 80° C. at 0.2 torr to obtain the title compound: mp; 103.0–107.0° C, R$_f$=0.45 (silica gel, 5% methanol/dichloromethane/0.1% concentrated NH₄OH solution), [α]$_D^{20}$=+4.9(c=0.399, chloroform).

EXAMPLE 92

1-(3,4,5-Trimethoxy-benzoyl)-3-[2-[4-[1-(pyrid-3-ylmethyl)-1H-benzoimidazole-2-carbonyl]-piperidin-1-yl]-ethyl]-3-phenyl-pyrrolidine

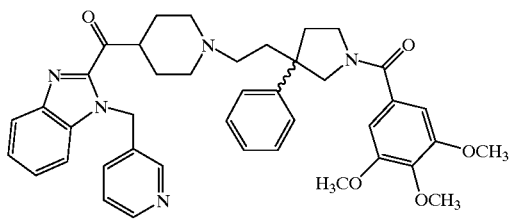

Combine 1-(3,4,5-trimethoxy-benzoyl)-3-[2-[4-[1H-benzoimidazole-2-carbonyl]-piperidin-1-yl]-ethyl]-3-phenyl-pyrrolidine (710 mg, 1.19 mmol), 3-(chloromethyl) pyridine hydrochloride (794 mg, 4.84 mmol), potassium carbonate (1.337 g, 9.67 mmol) in acetone (21 mL) and water (7 mL). Stir and heat at reflux for 24 h. Allow reaction mixture to cool to room temperature, and remove the acetone under vacuum. Add ethyl acetate to the reaction mixture and separate the organic layer. Extract the organic layer with saturated aqueous NaCl solution, dry over anhydrous $Na_2SO_4$, filter and concentrate in vacuo. Chromatograph the residue on silica gel eluting with 30% methanol/ethyl acetate to give the title compound: $R_f$=0.16 (silica gel, 20% methanol/ethyl acetate)]. Elemental Analysis calculated for $C_{41}H_{44}N_5O_5$: C 71.59; H 6.59; N 10.18; Found: C 69.84; H 6.75; N 9.82.

Immediate hypersensitivity can occur when an IgE antibody response is directed against innocuous antigens, such as pollen. During such a response there is generally a subsequent release of pharmacological mediators, such as histamine, by IgE-sensitized mast cells resulting in an acute inflammatory reaction. The characteristics of the response are determined by the tissue in which the reaction occurs and gives rise to allergic diseases including: allergic rhinitis, seasonal rhinitis, sinusitis; pulmonary diseases, such as asthma and cough; allergic dermatosis, such as urticaria, angioedema, eczema, atopic dermatitis, and contact dermatitis; gastrointestinal allergies, such as those caused by food or drugs, cramping, nausea, vomiting, and diarrhea; and ophthalmic allergies.

Histamine, producing its effects via activation of the $H_1$ receptor, is an important mediator of the above responses involved in immediate hypersensitivity. In the acute phase of allergic rhinitis, $H_1$ receptor antagonists have been shown to effectively inhibit the nasal itchiness, rhinorrhea, and sneezing associated with that condition. However, $H_1$ receptor antagonists are less effective in relieving nasal congestion. The acute response to allergen in rhinitis is often followed by a chronic inflammatory response during which the inflamed mucosa becomes hypersensitive to both antigens and nonspecific irritants. $H_1$ receptor antagonists are also ineffective in attenuating the symptoms of the chronic phase of the response.

Tachykinins are also important contributors to the allergic response and produce some symptoms distinct from those produced by a histamine response. This occurs because sensory nerves of trigeminal origin, located around blood vessels and within the nasal mucosal lining, upon stimulation by irritants or inflammatory mediators, such as histamine, will release tachykinins. The tachykinins are a class of neuropeptides which share a common C-terminus sequence, Phe-Xaa-Gly-Leu-Met-$NH_2$. The tachykinins are widely distributed in the peripheral and central nervous systems where they bind to at least three receptors types. The $NK_1$, $NK_2$, and $NK_3$ receptors are defined by the preferred binding affinity of substance P (SP), neurokinin A (NKA), and neurokinin B (NKB), respectively.

Patients with allergic rhinitis have been shown to have higher nasal levels of substance P when their rhinitis symptoms are present. Mosimann et al. *J. Allergy Clin. Immunol.* 92, 95 (1993); Takeyama et al.,*J. Pharm. Pharmacol.* 46, 41 (1994); and Wantanabe et al., *Ann. Otol. Rhinol. and Laryngol.*, 102, 16 (1993). In humans, topical or intravenous administration of tachykinins induces nasal obstruction, recruitment of inflammatory cells, glandular secretion, and microvascular leakage in allergic rhinitics. The nasal obstruction produced by substance P was found to be $NK_1$ receptor mediated. Braunstein et al., *Am. Rev. Respir. Dis.*, 144, 630 (1991); Devillier et al., Eur. Respir. J. 1, 356 (1988). Furthermore, sensory nerve-mediated effects, such as nasal irritability and hyperresponsivenesss which occurs in late phase allergic reactions, also result from tachykinin release. Anggard,*Acta Otolaryngol.* 113, 394 (1993). Depletion of tachykinins from nasal sensory nerves after chronic capsaicin administration improved rhinitic symptoms in affected individuals. Lacroix et al., *Clin. and Exper. Allergy*, 21, 595 (1991).

The use of tachykinin antagonists is indicated as therapy for a variety of tachykinin-mediated diseases and conditions, including: hypersensitivity reactions; adverse immunological reactions; asthma; bronchitis; allergic rhinitis, including seasonal rhinitis and sinusitis; allergies; contact dermatitis; atopic dermatitis; inflammatory bowel diseases, including Crohn's disease and ulcerative colitis; and emesis.

It is understood that tachykinin-mediated diseases and conditions are those diseases and conditions in which the tachykinins are involved, either in whole or in part, in their clinical manifestation(s). Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1) or stereoisomers or pharmaceutically acceptable salts thereof.

In a further embodiment, as tachykinin antagonists the present invention provides a method of treating tachykinin-mediated diseases and conditions, including: hypersensitivity reactions; adverse immunological reactions; asthma; bronchitis; allergic rhinitis, including seasonal rhinitis and sinusitis; allergies; contact dermatitis; atopic dermatitis; inflammatory bowel diseases, including Crohn's disease and ulcerative colitis; and emesis in a patient in need thereof comprising administering to said patient a therapeutically effective amount of a compound of formula (1).

Antagonism of the effects of histamine on the $H_1$ receptor is useful in the treatment of allergic diseases, such as rhinitis. Likewise, antagonism of the effects of the tachykinins, particularly substance P on its preferred receptor, is useful in the treatment of symptoms which are concurrent with allergic diseases. Therefore, the potential benefits of an antagonist with affinity at both the $H_1$ and $NK_1$ receptors would be to reduce or prevent clinical manifestations of allergic diseases which are mediated through both receptors.

The present invention provides new and useful histamine antagonists of formula (1) or stereoisomers or pharmaceutically acceptable salts thereof. The present invention also provides new and useful tachykinin antagonists of formula (1) or stereoisomers or pharmaceutically acceptable salts thereof. More particularly, the present invention provides new and useful compounds of formula (1) or stereoisomers or pharmaceutically acceptable salts thereof which are both $H_1$ and $NK_1$ receptor antagonists.

In a further embodiment, the present invention provides a method of treating allergic diseases, including: allergic rhinitis, including seasonal rhinitis and sinusitis; pulmonary diseases, such as asthma; allergic dermatosis, such as urticaria, angioedema, eczema, atopic dermatitis, and contact dermatitis; allergic conjuctivitis; gastrointestinal allergies, such as those caused by food or drugs; cramping; nausea; vomiting; cough; diarrhea;-and ophthalmic allergies and uveitis; and inflammatory bowel diseases, including Crohn's diseases and ulcerative colitis; in a patient in need thereof comprising administering to said patient a therapeutically effective amount of a compound of formula (1).

Various diseases and conditions described to be treated herein, are well known and appreciated by those skilled in the art. It is also recognized that one skilled in the art may affect the associated diseases by treating a patient presently afflicted with the diseases or by prophylactically treating a patient afflicted with the diseases with a therapeutically effective amount of the compounds of formula (1).

As used herein, the term "patient" refers to a warm blooded animal such as a mammal which is afflicted with a particular allergic disease. It is understood that guinea pigs, dogs, cats, rats, mice, horses, cattle, sheep, and humans are examples of animals within the scope of the meaning of the term.

As used herein, the term "therapeutically effective amount" of a compound of formula (1) refers to an amount which is effective in controlling the diseases described herein. The term "controlling" is intended to refer to all processes wherein there may be a slowing, interrupting, arresting, or stopping of the progression of the diseases described herein, but does not necessarily indicate a total elimination of all disease symptoms, and is intended to include prophylactic treatment of the diseases.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with diseases described above, a compound of formula (1) can be administered in any form or mode which makes the compound bioavailable in an effective amount, including oral, inhalation, and parenteral routes. For example, compounds of formula (1) can be administered orally, by inhalation of an aerosol or dry powder, subcutaneously, intramuscularly, intravenously, transdermally, intranasally, rectally, topically, and the like. Oral or inhalation administration is generally preferred for treatment of allergic diseases. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility, and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (1) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE 93

Histamine ($H_1$) antagonism in guinea pig ileum

One skilled in the art can determine that the compounds of the present invention are Hi receptor antagonists in vitro by evaluating the compound's ability to inhibit histamine mediated smooth muscle contraction. Male Hartley guinea pigs, weighing 200–450 grams, are sacrificed by $CO_2$ asphyxiation. A piece of ileum, about 20 cm in length, is removed and cut into 2 cm pieces. Each ileum piece is placed in an organ bath at 37° C. containing Tyrode's solution and is constantly aerated with 95% $O_2$/5%$CO_2$. Tyrode's solution has the composition: NaCl 136.9 mM, KCl 2.68 nM, $CaCl_2$ 1.8 mM, $NaH_2PO_4$ 0.42 mM, $NaHCO_3$ 11.9 mM, and dextrose 5.55 mM. Contractions are measured with an isometric transducer (Grass FTO3C), and are recorded on a polygraph recorder and/or a computer. The ileum strips are loaded with 1.0 grams of tension and allowed to equilibrate for a minimum of 30 minutes before starting the experiments. Tissue are preincubated with vehicle or varying concentrations of test compound followed by histamine challenge.

A competitive $H_1$ receptor antagonist produces a parallel shift of the histamine dose-response curve to the right without a depression of the maximal response. The potency of the antagonism is determined by the magnitude of the shift and is expressed as a $pA_2$ value which is the negative logarithm of the molar concentration of antagonist which produces a two-fold shift of the dose response curve to the right. The $pA_2$ value is calculated by using Schild analysis. O. Arunlakshana and H. O. Schild, *Br. J. Pharmacol Chemother.* 14, 48–58 (1958). When the slope of the lines obtained by a Schild analysis are not significantly different from one (1) the compound is acting as a competitive antagonist.

EXAMPLE 94

Evaluation of $H_1$ (or $NK_1$) antagonism in vivo

One skilled in the art can determine that the compounds of the present invention mediate the immediate hypersensitivity response in vivo by evaluating the ability of the compounds to inhibit the formation of histamine (or substance P) induced wheals in guinea pigs. Animals are anesthetized with pentobarbitol (i.p.). Dorsal skin is shaved and intradermal injections of histamine (or substance P) are given in the shaved area at appropriate times after the administration of the test compounds. Doses, routes, and times of administration may vary according to experimental design. The design of such experiments is well known and appreciated in the art. Immediately after the intradermal challenges, the animal is given an intravenous injection of 1% Evan's blue dye to make the wheals visible. At an appropriate time after the challenge the animals are sacrificed by $CO_2$ inhalation. The skin is removed and the diameter of each wheal is measured in two perpendicular directions.

The wheal response is used an the index of the edema response. The percent of inhibition of the wheal response is calculated by comparing the drug-treated group to a vehicle treated group. Linear regression of the dose-response inhibition curve is used to determine an $ED_{50}$ value, expressed in mg/kg.

EXAMPLE 95

Antagonism of iodinated tachykinin binding to $NK_1$ receptors by putative antagonists One skilled in the art can measure the $NK_1$ receptor affinity of proposed tachykinin antagonists as evaluated in guinea pig lungs (Keystone Biologicals, Cleveland, Ohio). Tissues or cells are homogenized with a Polytron in 15 volumes of 50 mM Tris-HCl buffer (pH 7.4, 40C) and centrifuged. The pellet is resuspended in Tris-HCl buffer and centrifuged; the pellet is washed twice by resuspension. The final pellet is resuspended at a concentration of 40 mg/ml incubation buffer and remains at room temperature for at least 15 min prior to use. Receptor binding is initiated by addition of 250 µl membrane preparation in duplicate to 0.1 nM of $^{125}$I-Bolton Hunter Lys-3 labeled substance P in a final volume of 500 µl of buffer containing 50 mM Tris-HCl (pH 7.4 at room temperature), 0.1% bovine serum albumin, 2 mM $MnCl_2$, 40 µg/ml bacitracin, 4 µg/ml leupeptin and chymostatin, 1 µM thiorphan and various doses of the putative tachykinin antagonists. Incubations are performed at room temperature for 90 min; binding is terminated by addition of 50 mM Tris-HCl buffer (pH 7.4, 40° C.) and filtration under vacuum through GF/B filters presoaked with 0.1% polyethyleneimine. Filter bound radioactivity is quantitated in a gamma counter. Nonspecific binding is defined as binding in the presence of 1 µM substance P. Specific binding is calculated by subtracting nonspecific binding from total binding. Competition of iodinated Substance P binding by test compounds or standards is expressed as a percentage of this maximum competition. $IC_{50}$ values (concentration required to inhibit 50% of receptor binding) are generated for each of the test compounds by nonlinear regression using an iterative curve fitting program (GraphPAD Inplot, San Diego, Calif.).

EXAMPLE 96

Antagonism of tachykinin-induced phosihatidylinositol (PI) turnover in vitro by putative antagonists One skilled in the art can determine $NK_1$ receptor antagonism by measuring the substance P-induced phosphatidylinositol (PI, inositol phosphate) accumulation in UC11 cells in the presence and absence of $NK_1$ receptor antagonists. Cells are seeded onto 24-well plates at 125,000 cells/well, two or three days prior to the assay. Cells are loaded with 0.5 mL of 0.2 µM myo-[2-$^3$H(N)] (American Radiolabeled Chemicals Inc., specific activity; 20 µCi/mmol) 20–24 hours prior to the assay. Cultured cells are maintained at 37° C. in 5% $CO_2$ environment. On the day of the assay, media is aspirated and the cells incubated in RPMI-1640 media containing 40 µg/ml bacitracin, 4 µg/ml each of leupeptin and chymostatin, 0.1% bovine serum albumin, 10 µM thiorphan, and 10 mM LiCl. After 15 minutes, the test compound is added to the cells in a volume of 0.1 mL. After another 15 min, substance P is added to UC11 cells at various concentrations to start the reaction followed by incubation for 60 min at 37° C. in 5% $CO_2$ environment in a final volume of 1 mL. To terminate the reaction, the media is aspirated and methanol (0.1 mL) is added to each well. Two aliquots of methanol (0.5 mL) are added to the wells to harvest the cells into chloroform resistant tubes. Chloroform (1 mL) is added to each tube followed by doubly distilled water (0.5 mL). Samples are vortexed for 15 seconds and centrifuged at 1700×g for 10 minutes. An aliquot (0.9 mL) of the aqueous (top) phase is removed and added to doubly distilled water (2 mL). The mixture is vortexed and loaded onto a 50% Bio-Rad AG 1-X8 (formate form, 100–200 mesh) exchange column (Bio-Rad Laboratories, Hercules, Calif.). The columns are washed, in order, with: 1) 10 ml doubly distilled water, 2) 5 mL of 5 mM disodium tetraborate/60 mM sodium formate, and 3) 2 mL of 1 M ammonium formate/0.1 M formic acid. The third elution is collected and counted in 9 mL scintillation fluid. A 50 µl aliquot of the organic (bottom) phase is removed, dried in a scintillation vial and counted in 7 mL scintillation fluid.

The ratio of DPM in the aqueous phase aliquot (total inositol phosphates) to the DPM in the 50 µl organic phase aliquot (total [$^3$H]inositol incorporated) is calculated for each sample. Data are expressed as a percent of agonist-induced accumulation of [$^3$H]-inositol phosphates over basal levels. The ratios in the presence of test compound and/or standards are compared to the ratios for control samples (i.e. no stimulating agonist). Dose-response graphs are constructed and the ability of the test compounds to inhibit tachykinin-induced phosphatidylinositol turnover determined with the aid of a computer program. Data is expressed as percent stimulation of total inositol phosphate accumulation over basal levels and normalized to the maximum response produced by substance P. Schild analysis is performed using dose response curves to obtain a value indicative of the strength of a competitive antagonist and is expressed as the $pA_2$, which is the negative logarithm of the molar concentration of antagonist which reduces the effect of a dose of agonist to one-half of that expected at the dose of agonist. The slope of the lines obtained by a Schild analysis are not significantly different from one (1) the compound is acting as a competitive antagonist.

EXAMPLE 97

Evaluation of $NK_1$ antagonism in vivo

One skilled in the art can also determine that the compounds of the present invention are $NK_1$ receptor antagonists invivo by evaluating the compound's ability to inhibit substance P-induced plasma protein extravasation in guinea pig trachea. Substance P-induced protein leakage through postcapillary venules is assessed by measuring Evans Blue dye accumulation in guinea pig trachea. Animals are anesthetized with pentobarbitol then injected with Evans Blue dye (20 mg/kg, i.v., prepared in 0.9% NaCl solution). One minute after dye administration, the antagonist is administered (i.v.) followed by Substance P (0.3 nmole/kg, i.v.) and, after 5 min, excess dye removed from the circulation by transcardiac perfusion with 50 ml 0.9% NaCl solution. The trachea and primary bronchi are removed, blotted dry and weighed. Dye quantitation is performed spectrophotometrically (620 nm) after extracting tissues in formamide for 24 hr at 50° C. Values are subtracted from background (dye only, no agonist). $ED_{50}$ (dose of compound which inhibits Substance P-induced plasma protein extravasation by 50%) is calculated from linear regression analysis.

Table 1 presents pA$_2$ values by the method of Example 93 which indicate potency of H$_1$ receptor antagonism and IC$_{50}$ values by the method of Example 95 which indicates NK$_1$ receptor binding affinity for representative compounds of the present invention.

TABLE 1

| Compound | H$_1$ Receptor Antagonism, pA$_2$, in vitro | NK$_1$ Receptor Binding Affinity, IC$_{50}$, (nM) |
| --- | --- | --- |
| Example 1 | 7.50 | 31 |
| Example 2 | 7.57 | 611 |
| Example 3 | 7.43 | 406 |
| Example 4 | 6.8 | 2593 |
| Example 5[a] | 6.57 | 25 |
| Example 6[b] | 6.85 | 85 |
| Example 7[c] | 7.41 | 64 |
| Example 9[a] | 6.14 | 122 |
| Example 10[b] | 7.22 | 146 |
| Example 11[a] | 7.47 | 34 |
| Example 14 | 7.3 | 29 |
| Example 20 | 6.89 | 109 |
| Example 25 | 6.85 | 325 |
| Example 26[b] | 7.21 | 288 |
| Example 27[d] | 7.68 | 370 |
| Example 28[a] | 7.69 | 1239 |
| Example 32[b] | 6.29 | 15 |
| Example 33[b] | 7.38 | 38 |
| Example 37 | 7.6 | 17 |
| Example 39[e] | 6.05 | 29 |
| Example 40 | 7.38 | 24 |
| Example 43[e] | 5.17 | 48 |
| Example 44 | 7.20 | 13 |
| Example 45 | 7.45 | 9 |
| Example 53[b] | 6.69 | 191 |
| Example 54[b] | 6.32 | 269 |
| Example 55[b] | 6.04 | 385 |
| Example 57[b] | 6.81 | 114 |
| Example 58[b] | 6.82 | 345 |
| Example 63 | 7.1 | 279 |
| Example 81[b] | 6.28 | 10 |
| Example 83[b] | 6.98 | 31 | a: maleic acid salt
b: methanesulfonic acid salt
c: oxalic acid salt
d: p-toluenesulfonic acid salt
e: hydrochloride salt

What is claimed is:

1. A compound of the formula

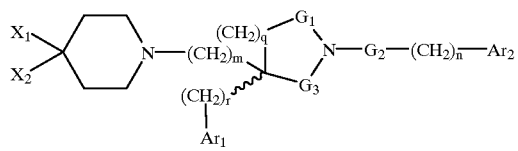

wherein
G$_1$ is —CH$_2$— or —C(O)—;
G$_2$ is —CH$_2$— or —C(O)—;
G$_3$ is —CH$_2$— or —C(O)—;
m is 2 or 3;
n is 0 or 1;
q is 1 or 2;
r is 0 or 1;

Ar$_1$ is a radical chosen from the group consisting of

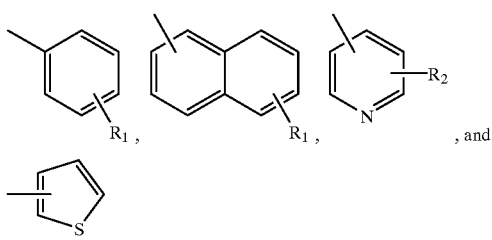

wherein
R$_1$ is from 1 to 3 substituents each independently chosen from the group consisting of hydrogen, halogen, hydroxy, CF$_3$, C$_1$–C$_6$ alkyl, and C$_1$–C$_6$ alkoxy;
R$_2$ is from 1 to 2 substituents each independently chosen from the group consisting of hydrogen, halogen, C$_1$–C$_6$ alkyl, and C$_1$–C$_6$ alkoxy;
Ar$_2$ is a radical chosen from the group consisting of

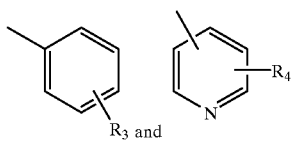

wherein
R$_3$ is from 1 to 3 substituents each independently chosen from the group consisting of hydrogen, halogen, C$_1$–C$_6$ alkyl, C$_1$–C$_6$ alkoxy, and —OCH$_2$CO$_2$R$_{21}$ wherein R$_{21}$ is chosen from the group consisting of hydrogen and C$_1$–C$_4$ alkyl;
R$_4$ is from 1 to 2 substituents each independently chosen from the group consisting of hydrogen, halogen, C$_1$–C$_6$ alkyl, and C$_1$–C$_6$ alkoxy; and
X$_1$ and X$_2$ are as defined in one of parts A), B), or C):
A) X$_1$ is hydrogen;
X$_2$ is a radical chosen from the group consisting of

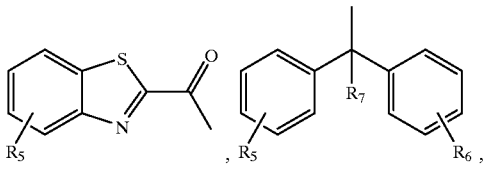

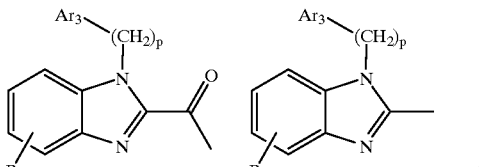

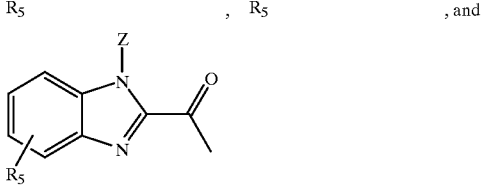

wherein
p is 1 or 2
R$_5$ is from 1 to 3 substituents each independently chosen from the group consisting of hydrogen, halogen, CF$_3$, C$_1$–C$_6$ alkyl, and C$_1$–C$_6$ alkoxy;

$R_6$ is from 1 to 3 substituents each independently chosen from the group consisting of hydrogen, halogen, $CF_3$, $C_1$–$C_6$ alkyl, and $C_1$–$C_6$ alkoxy, $R_7$ is hydrogen or hydroxy;

$Ar_3$ is a radical chosen from the group consisting of

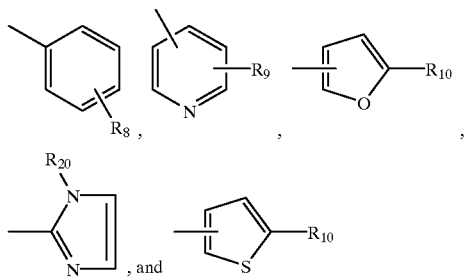

wherein $R_8$ is from 1 to 3 substituents each independently chosen from the group consisting of hydrogen, halogen, $CF_3$, $C_1$–$C_6$ alkyl, $C_1$–$C_6$ alkoxy, and —$CO_2R_{19}$ wherein $R_{19}$ is chosen from the group consisting of hydrogen and $C_1$–$C_4$ alkyl;

$R_9$ is from 1 to 2 substituents each independently chosen from the group consisting of hydrogen, halogen, $C_1$–$C_6$ alkyl, and $C_1$–$C_6$ alkoxy;

$R_{10}$ is chosen from the group consisting of hydrogen, —$CH_3$, and —$CH_2OH$;

$R_{20}$ is chosen from the group consisting of hydrogen, $C_1$–$C_4$ alkyl, and benzyl;

Z is chosen from the group consisting of hydrogen, $C_1$–$C_4$ alkyl, —$(CH_2)_w$—O—$(CH_2)_t$—$(CH_2)_f$A, —$(CH_2)_u CO_2R_{11}$, —$(CH_2)_u C(O)NR_{12}R_{13}$, —$(CH_2)_g C(O)(CH_2)_h CH_3$, —$(CH_2)_w$—O—$Ar_4$, and —$CH_2OCH_2CH_2Si(CH_3)_3$ wherein w is an integer from 2 to 5;

t is an integer from 1 to 3;

f is 2 or 3;

u is an integer from 1 to 4;

g is an integer from 1 to 3;

h is an integer from 0 to 3;

w is an integer from 2 to 4;

Y is chosen from the group consisting of hydrogen, —$CH=CH_2$, —$CH=C(CH_3)_2$, and —$CO_2R_{14}$ wherein $R_{14}$ is chosen from the group consisting of hydrogen and $C_1$–$C_4$ alkyl;

A is chosen from the group consisting of —$NR_{17}R_{18}$, acetylamino, and morpholino wherein $R_{17}$ is chosen from the group consisting of hydrogen and $C_1$–$C_4$ alkyl and $R_{18}$ is $C_1$–$C_4$ alkyl;

$R_{11}$ is chosen from the group consisting of hydrogen and $C_1$–$C_4$ alkyl;

$R_{12}$ is chosen from the group consisting of hydrogen, $C_1$–$C_4$ alkyl, and benzyl;

$R_{13}$ is chosen from the group consisting of hydrogen and $C_1$–$C_4$ alkyl;

$Ar_4$ is a radical chosen from the group consisting of

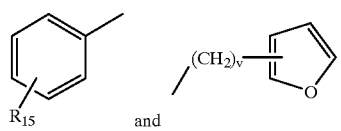

wherein v is an integer from 1 to 3;

$R_{15}$ is chosen from the group consisting of hydrogen and —$CO_2R_{16}$ wherein $R_{16}$ is chosen from the group consisting of hydrogen and $C_1$–$C_4$ alkyl;

B) $X_1$ is hydroxy; and $X_2$ is a radical chosen from the group consisting of

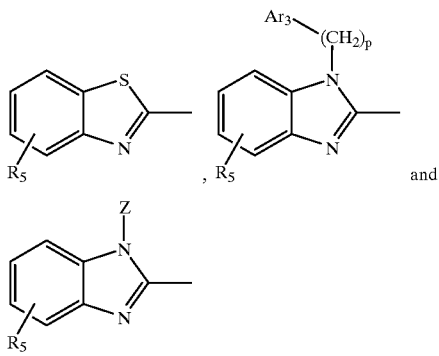

wherein p, $R_5$, Z, and $Ar_3$ are as previously defined;

C) $X_2$ is a radical of the formula;

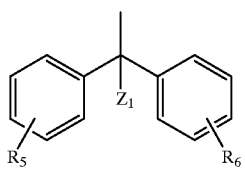

wherein $R_5$ and $R_6$ are as previously defined; and $X_1$ and $Z_1$ taken together form a second bond between the carbon atoms bearing $X_1$ and $Z_1$;

provided that when $G_1$ is —C(O)— then $G_2$ and $G_3$ are —$CH_2$—;

further provided that when $G_2$ is —C(O)— then $G_1$ and $G_3$ are —$CH_2$—;

still further provided that when $G_3$ is —C(O)— then $G_1$ and $G_2$ are —$CH_2$—;

or stereoisomers, or pharmaceutically acceptable salt thereof.

2. A compound of claim 1 wherein m is 2.

3. A compound of claim 2 wherein $G_2$ is —C(O)—.

4. A compound of claim 3 wherein $X_1$ is hydrogen.

5. A compound of claim 4 wherein $X_2$ is a radical of the formula

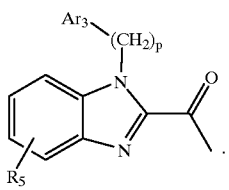

6. A compound of claim 5 wherein $R_5$ is hydrogen, p is 1, and $Ar_3$ is 4-fluoro-phenyl.

7. A compound of claim 5 wherein $R_5$ is hydrogen, p is 1, and $Ar_3$ is pyrid-2-yl.

8. A compound of claim 5 wherein $R_5$ is hydrogen, p is 1, and $Ar_3$ is fur-2-yl.

9. A compound of claim 4 wherein $X_2$ is a radical of the formula

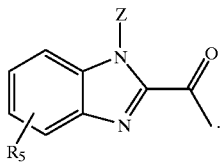

10. A compound of claim 9 wherein Z is 2-ethoxy-ethyl.
11. A compound of claim 9 wherein Z is 2-fur-2-ylmethoxy-ethyl.
12. A compound of claim 3 wherein $X_1$ is hydroxy.
13. A compound of claim 12 wherein $X_2$ is a radical of the formula

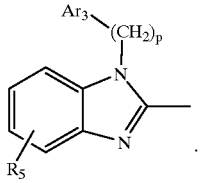

14. A compound of claim 13 wherein $R_5$ is hydrogen, p is 1, and $Ar_3$ is 4-fluoro-phenyl.

15. A compound of claim 1 wherein the compound is (+)- or (−)-1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine or a mixture thereof.

16. A compound of claim 1 wherein the compound is (+)- or (−)-1-Benzoyl-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine or a mixture thereof.

17. A compound of claim 1 wherein the compound is (+)- or (−)-1-Benzoyl-3-[2-[4-[1-(4-fluoro-benzyl)-1H-benzoimidazol-2-yl]-4-hydroxy-piperidin-1-yl]-ethyl]-3-(3,4-dimethoxy-phenyl)-pyrrolidine or a mixture thereof.

18. A compound of claim 1 wherein the compound is (+)- or (−)-1-Benzoyl-3-[2-[4-(benzothiazol-2-yl)-piperidin-1-yl]-ethyl]-3-(3,4-dimethoxy-phenyl)-pyrrolidine or a mixture thereof.

19. A compound of claim 1 wherein the compound is (+)- or (−)-1-(3,4,5-Trimethoxybenzoyl)-3-[2-[4-[1-(4-fluoro-benzyl)- 1H-benzoimidazol-2-yl]-4-hydroxy-piperidin-1-yl]-ethyl]-3-(3,4-dimethoxy-phenyl)-pyrrolidine or a mixture thereof.

20. A compound of claim 1 wherein the compound is (+)- or (−)-1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dichloro-phenyl)-pyrrolidine or a mixture thereof.

21. A compound of claim 1 wherein the compound is (+)- or (−)-1-(3,4,5-Trimethoxy-benzoyl)-3-[2-[4-[1-(4-fluoro-benzyl)-1H-benzoimidazol-2-yl(3-4-hydroxy-piperidin-1-yl]-ethyl]-3-(3,4-dichloro-phenyl)-pyrrolidine or a mixture thereof.

22. A compound of claim 1 wherein the compound is (+)- or (−)-1-Benzoyl-3-[2-[4-(benzothiazole-2-carbonyl)-piperidin-1-yl]-ethyl]-3-(3,4-dimethoxy-phenyl)-pyrrolidine or a mixture thereof.

23. A compound of claim 1 wherein the compound is (+)- or (−)-1-(3,4,5-Trimethoxybenzoyl)-3-[2-[4-(hydroxy-diphenyl-methyl)-piperidin-1-yl]-ethyl]-3-(3,4-dimethoxy-phenyl)-pyrrolidine or a mixture thereof.

24. A compound of claim 1 wherein the compound is (+)- or (−)-1-(3,4,5-Trimethoxy-benzoyl)-3-[2-[4-[1-(4-fluoro-benzyl)-1H-benzoimidazole-2-carbonyl]-piperidin-1-yl]-ethyl]-3-(benzo[1,3]dioxol-5-yl)-pyrrolidine or a mixture thereof.

25. A compound of claim 1 wherein the compound is (+)- or (−)-1-(3,4,5-Trimethoxy-benzoyl)-3-[2-[4-[1-(4-fluoro-benzyl)-1H-benzoimidazole-2-carbonyl]-piperidin-1-yl]-ethyl]-3-phenyl-pyrrolidine or a mixture thereof.

26. A compound of claim 1 wherein the compound is (+)- or (−)-1-(3,4,5-Trimethoxy-benzoyl)-3-[2-[4-[1-(4-fluoro-benzyl)-1H-benzoimidazole-2-carbonyl]-piperidin-1-yl]-ethyl]- 3-(4-trifluoromethyl-phenyl)-pyrrolidine or a mixture thereof.

27. A compound of claim 1 wherein the compound is (+)- or (−)-1-(3,4,5-Trimethoxy-benzoyl)-3-[2-[4-[1-(4-fluoro-benzyl)-1H-benzoimidazole-2-carbonyl]-piperidin-1-yl]-ethyl]-3-(2,4-difluoro-phenyl)-pyrrolidine or a mixture thereof.

28. A compound of claim 1 wherein the compound is (+)- or (−)-1-(3-Isopropoxy-phenyl-acetyl)-3-[2-[4-[1-(4-fluoro-benzyl)-1H-benzoimidazole-2-carbonyl]-piperidin-1-yl]-ethyl]-3-(benzo[1,3]dioxol-5-yl)-pyrrolidine or a mixture thereof.

29. A compound of claim 1 wherein the compound is (+)- or (−)-1-(2,3,4-Trimethoxy-benzoyl)-3-[2-[4-[1-(4-fluoro-benzyl)-1H-benzoimidazole-2-carbonyl]-piperidin-1-yl]-ethyl]-3-(benzo[1,3]dioxol-5-yl)-pyrrolidine or a mixture thereof.

30. A compound of claim 1 wherein the compound is (+)- or (−)-1-(3,4,5-Triethoxy-benzoyl)-3-[2-[4-[1-(4-fluoro-benzyl)-1H-benzoimidazole-2-carbonyl]-piperidin-1-yl]-ethyl]-3-(3,4-dimethoxy-phenyl)-pyrrolidine or a mixture thereof.

31. A compound of claim 1 wherein the compound is (+)- or (−)-1-(3,4,5-Trimethoxy-benzoyl)-3-[2-[4-benzhydrylidene-piperidin-1-yl]-ethyl]-3-(3,4-dichloro-phenyl)-pyrrolidine or a mixture thereof.

32. A compound of claim 1 wherein the compound is (+)- or (−)-1-(3,4,5-Trimethoxy-benzoyl)-3-[2-[4-[1H-benzoimidazole-2-carbonyl]-piperidin-1-yl]-ethyl]-3-(3,4-dichloro-phenyl)-pyrrolidine or a mixture thereof.

33. A compound of claim 1 wherein the compound is (+)- or (−)-1-(3,4,5-Trimethoxy-benzoyl)-3-[2-[4-[1-(2-

(morpholin-4-yl)-ethyl)-1H-benzoimidazole-2-carbonyl]-piperidin-1-yl]-ethyl]-3-(3,4-dichloro-phenyl)-pyrrolidine or a mixture thereof.

34. A compound of claim 1 wherein the compound is (+)- or (−)-1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-(3,4-dichloro-phenyl)-pyrrolidine or a mixture thereof.

35. A compound of claim 1 wherein the compound is (+)- or (−)-1-(3,4,5-Trimethoxy-benzoyl)-3-[2-[4-[1-(3-ethoxycarbonyl-propyl)-1H-benzoimidazole-2-carbonyl]-piperidin-1-yl]-ethyl]-3-(3,4-dichloro-phenyl)-pyrrolidine or a mixture thereof.

36. A compound of claim 1 wherein the compound is (+)- or (−)-1-(3,4,5-Trimethoxy-benzoyl)-3-[2-[4-[1-(3-carboxy-propyl)-1H-benzoimidazole-2-carbonyl]-piperidin-1-yl]-ethyl]-3-(3,4-dichloro-phenyl)-pyrrolidine or a mixture thereof.

37. A compound of claim 1 wherein the compound is (+)- or (−)-1-(3,4,5-Trimethoxy-benzoyl)-3-[2-[4-[1H-benzoimidazole-2-carbonyl]-piperidin-1-yl]-ethyl]-3-phenyl-pyrrolidine or a mixture thereof.

38. A compound of claim 1 wherein the compound is (+)- or (−)-1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-phenyl-pyrrolidine or a mixture thereof.

39. A compound of claim 1 wherein the compound is (+)- or (−)-1-(3,4,5-Trimethoxy-benzoyl)-3-[2-[4-[1-(4-methoxycarbonyl-benzyl)-1H-benzoimidazole-2-carbonyl]-piperidin-1-yl]-ethyl]-3-phenyl-pyrrolidine or a mixture thereof.

40. A compound of claim 1 wherein the compound is (+)- or (−)-1-(3,4,5-Trimethoxy-benzoyl)-3-[2-[4-[1-(4-carboxy-benzyl)-1H-benzoimidazole-2-carbonyl]-piperidin-1-yl]-ethyl]-3-phenyl-pyrrolidine or a mixture thereof.

41. A compound of claim 1 wherein the compound is (+)- or (−)-1-(3,4,5-Trimethoxy-benzoyl)-3-[2-[4-[1-(2-ethoxy-ethyl)-1H-benzoimidazole-2-carbonyl]-piperidin-1-yl]-ethyl]-3-phenyl-pyrrolidine or a mixture thereof.

42. A compound of claim 1 wherein the compound is (+)- or (−)-1-(3,4,5-Trimethoxy-benzoyl)-3-[2-[4-[1H-benzoimidazole-2-carbonyl]-piperidin-1-yl]-ethyl]-3-phenyl-pyrrolidine or a mixture thereof.

43. A compound of claim 1 wherein the compound is (+)- or (−)-1-(3,4,5-Trimethoxy-benzoyl)-3-[2-[4-[1H-benzoimidazole-2-carbonyl]-piperidin-1-yl]-ethyl]-3-(3,4-dimethoxy-phenyl)-pyrrolidine or a mixture thereof.

44. A compound of claim 1 wherein the compound is (+)- or (−)-1-(3,4,5-Trimethoxy-benzoyl)-3-[2-[4-[1-(4-carbomethoxy-phenylmethyl)-1H-benzoimidazole-2-carbonyl]-piperidin-1-yl]-ethyl]-3-(3,4-dimethoxy-phenyl)-pyrrolidine or a mixture thereof.

45. A compound of claim 1 wherein the compound is (+)- or −)-1-(3,4,5-Trimethoxy-benzoyl)-3-[2-[4-[1-(4-carboxy-phenylmethyl)-1H-benzoimidazole-2-carbonyl]-piperidin-1-yl]-ethyl]-3-(3,4-dimethoxy-phenyl)-pyrrolidine or a mixture thereof.

46. A compound of claim 1 wherein the compound is (+)- or (−)-1-(3,4,5-Trimethoxy-benzoyl)-3-[2-[4-[1-(fur-2-ylmethyl)-1H-benzoimidazole-2-carbonyl]-piperidin-1-yl]-ethyl]-3-phenyl-pyrrolidine or a mixture thereof.

47. A compound of claim 1 wherein the compound is (+)- or (−)-1-(3,4,5-Trimethoxy-benzoyl)-3-[2-[4-[1-(2-fur-2-ylmethoxy-ethyl)-1H-benzoimidazole-2-carbonyl]-piperidin-1-yl]-ethyl]-3-phenyl-pyrrolidine or a mixture thereof.

48. A compound of claim 1 wherein the compound is (+)- or (−)-1-(3,4,5-Trimethoxy-benzoyl)-3-[2-[4-[1-(2-allyloxy-ethyl)-1H-benzoimidazole-2-carbonyl]-piperidin-1-yl]-ethyl]-3-phenyl-pyrrolidine or a mixture thereof.

49. A compound of claim 1 wherein the compound is (+)- or (−)-1-(3,4,5-Trimethoxy-benzoyl)-3-[2-[4-[1-(2-(3,3-dimethylallyloxy)-ethyl)-1H-benzoimidazole-2-carbonyl]-piperidin-1-yl]-ethyl]-3-phenyl-pyrrolidine or a mixture thereof.

50. A compound of claim 1 wherein the compound is (+)- or (−)-1-(2,4-Dichloro-benzoyl)-3-[2-[4-[1-(4-fluoro-benzyl)-1H-benzoimidazole-2-carbonyl]-piperidin-1-yl]-ethyl]-3-(benzo[1,3]dioxol-5-yl)-pyrrolidine or a mixture thereof.

51. A compound of claim 1 wherein the compound is (+)- or (−)-1-(3-Isopropoxy-phenyl-acetyl)-3-[2-[4-[1-(2-ethoxy-ethyl)-1H-benzoimidazole-2-carbonyl]-piperidin-1-yl]-ethyl]-3-(3,4-dichloro-phenyl)-piperidine or a mixture thereof.

52. A compound of claim 1 wherein the compound is (+)- or (−)-1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine or a mixture thereof.

53. A compound of claim 1 wherein the compound is (+)- or (−)-1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(3,4-dichloro-phenylmethyl)-2-oxo-pyrrolidine or a mixture thereof.

54. A compound of claim 1 wherein the compound is (+)- or (−)-1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(3,4-dimethoxy-phenylmethyl)-2-oxo-pyrrolidine or a mixture thereof.

55. A compound of claim 1 wherein the compound is (+)- or (−)-1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(4-fluoro-phenylmethyl)-2-oxo-pyrrolidine or a mixture thereon.

56. A compound of claim 1 wherein the compound is (+)- or (−)-1-(3,4,5-Trimethoxy-benzyl)-3-[2-[4-[1-(4-fluoro-benzyl)-1H-benzoimidazol-2-yl]-4-hydroxy-piperidin-1-yl]-ethyl]-3-(2,4-difluoro-phenylmethyl)-2-oxo-pyrrolidine or a mixture thereof.

57. A compound of claim 1 wherein the compound is (+)- or (−)-1-Benzyl-3-[2-[4-[1-(4-fluoro-benzyl)-1H-benzoimidazol-2-yl]-4-hydroxy-piperidin-1-yl]-ethyl]-3-(phenylmethyl)-2-oxo-pyrrolidine or a mixture thereof.

58. A compound of claim 1 wherein the compound is (+)- or (−)-1-(3-Isopropoxy-phenyl-acetyl)-3-[2-[4-[1-(4-fluoro-benzyl)-1H-benzoimidazole-2-carbonyl]-piperidin-1-yl]-ethyl]-3-(3,4-dichloro-phenyl)-piperidine or a mixture thereof.

59. A compound of claim 1 wherein the compound is (+)- or (−)-1-(3,4,5-Trimethoxy-benzoyl)-3-[2-[4-[1-(3-(2-carbomethoxy-phenoxy)-propyl)-1H-benzoimidazole-2- carbonyl]-piperidin-1-yl]-ethyl]-3-phenyl-pyrrolidine or a mixture thereof.

60. A compound of claim 1 wherein the compound is (+)- or (−)-1-(3,4,5-Trimethoxy-benzoyl)-3-[2-[4-[1-(3-(2-carboxy-phenoxy)-propyl)-1H-benzoimidazole-2-carbonyl]-piperidin-1-yl]-ethyl]-3-phenyl-pyrrolidine or a mixture thereof.

61. A compound of claim 1 wherein the compound is (+)- or (−)-1-(3,4,5-Trimethoxy-benzoyl)-3-[2-[4-[1-(pyrid-2-ylmethyl)-1H-benzoimidazole-2-carbonyl]-piperidin-1-yl]-ethyl]-3-(4-methoxy-phenyl)-pyrrolidine or a mixture thereof.

62. A compound of claim 1 wherein the compound is (+)- or (−)-1-(3,4,5-Trimethoxy-benzoyl)-3-[3-[4-[1-(2-ethoxy-ethyl)-1H-benzoimidazole-2-carbonyl]-piperidin-1-yl]-propyl]-3-(4-fluoro-phenylmethyl)-2-oxo-pyrrolidine or a mixture thereof.

63. A compound of claim 1 wherein the compound is (+)- or (−)-1-(3,4,5-Trimethoxy-benzoyl)-3-[2-[4-[1-(2-ethoxy-ethyl)-1H-benzoimidazole-2-carbonyl]-piperidin-1-yl]-ethyl]-3-(3,4-difluoro-phenyl)-pyrrolidine or a mixture thereof.

64. A compound of claim 1 wherein the compound is (+)- or (−)-1-(3,4,5-Trimethoxy-benzoyl)-3-[2-[4-[1-(2-ethoxy-ethyl)-1H-benzoimidazole]-4-hydroxy-piperidin-1-yl]-ethyl]-3-(3,4-dichloro-phenyl)-pyrrolidine or a mixture thereof.

65. A compound of claim 1 wherein the compound is (+)- or (−)-1-(3,4,5-Trimethoxy-benzoyl)-3-[2-[4-[1-(4-fluoro-benzyl)-1H-benzoimidazole-2-carbonyl]-piperidin-1-yl]-ethyl]-3-(3,4-dichloro-phenyl)-piperidine or a mixture thereof.

66. A compound of claim 1 wherein the compound is (+)- or (−)-1-(3,4,5-Trimethoxy-benzyl)-3-[2-[4-[1-(pryid-2-ylmethyl)-1H-benzoimidazole-2-carbonyl]-piperidin-1-yl]-ethyl]-3-(4-fluoro-phenylmethyl)-2-oxo-pyrrolidine or a mixture thereof.

67. A compound of claim 1 wherein the compound is (+)- or (−)-1-(3,4,5-Trimethoxy-benzoyl)-3-[2-[4-(l-(2-ethoxy-ethyl)-1H-benzoimidazole-2-carbonyl]-piperidin-1-yl]-ethyl]-3-(3,4-dichloro-phenyl)-pyrrolidine or a mixture thereof.

68. A compound of claim 1 wherein the compound is (+)- or (−)-1-(3,4,5-Trimethoxy-benzoyl)-3-[2-[4-[1H-benzoimidazole-2-carbonyl]-piperidin-1-yl]-ethyl]-3-(4-methoxy-phenyl)-pyrrolidine or a mixture thereof.

69. A pharmaceutical composition comprising a histamic receptor inhibitory effective amount or a tachykinin receptor antagonistic effective amount of a compound of claim 1.

70. A pharmaceutical composition comprising a histamic receptor inhibitory effective amount or a tachykinin receptor antagonistic effective amount of a compound of claim 1 and one or more pharmaceutically acceptable inert carriers.

71. A method of treating allergic response or inflammatory response in a patient in need thereof, comprising administering to said patient a histamine receptor inhibitory effective amount or a tachykinin receptor antagonistic effective amount of a compound of claim 1.

72. The method of claim 71 wherein said allergic or inflammatory response is in allergic rhinitis.

73. The method of claim 71 wherein said allergic or inflammatory response is in asthma.

74. The method of claim 71 wherein said allergic or inflammatory response is in opthalmic allergies.

75. The method of claim 71 wherein said allergic or inflammatory response is in inflammatory bowel disease.

76. The method of claim 71 wherein said allergic or inflammatory response is in uveitis.

77. A method of treating emesis in a patient in need thereof comprising administering to said patient an anti-emetic effective amount of a compound of claim 1.

* * * * *